(12) United States Patent
Park et al.

(10) Patent No.: US 11,707,533 B2
(45) Date of Patent: Jul. 25, 2023

(54) ANTIBODY-DRUG CONJUGATE COMPRISING ANTIBODY AGAINST HUMAN ROR1 AND USE FOR THE SAME

(71) Applicants: LegoChem Biosciences, Inc., Youseong-Gu (KR); ABL Bio, Inc., Seongnam-Si (KR)

(72) Inventors: Yun-Hee Park, Daejeon (KR); Ho Young Song, Daejeon (KR); Hyun Min Ryu, Daejeon (KR); Sung Min Kim, Daejeon (KR); Ju Yuel Baek, Daejeon (KR); Ji Hye Oh, Daejeon (KR); Nara Han, Daejeon (KR); Hyoung Rae Kim, Daejeon (KR); Kyung Eun Park, Daejeon (KR); Hyeun Joung Lee, Daejeon (KR); Ju Young Lee, Daejeon (KR); Dae Hyuck Kang, Daejeon (KR); Young-Jae Yang, Daejeon (KR); Ji-Na You, Daejeon (KR); Yong Zu Kim, Daejeon (KR); Chang Sun Lee, Daejeon (KR); Jeiwook Chae, Daejeon (KR); Jinwon Jung, Daejeon (KR); Juhee Kim, Daejeon (KR); Bora Lee, Daejeon (KR); Daehae Song, Daejeon (KR); Byungje Sung, Daejeon (KR); Donghoon Yeom, Daejeon (KR); Jaehyun Eom, Daejeon (KR); Youngeun Hong, Daejeon (KR); Jinhyung Ahn, Daejeon (KR); Yangsoon Lee, Daejeon (KR); Kyungjin Park, Daejeon (KR); Jiseon Yoo, Daejeon (KR); Minji Park, Daejeon (KR)

(73) Assignees: LegoChem Biosciences, Inc., Youseong-Gu (KR); ABL Bio, Inc., Gyeonggi-do (KR)

( * ) Notice: Subject to any disclaimer, the term of this patent is extended or adjusted under 35 U.S.C. 154(b) by 75 days.

(21) Appl. No.: 16/940,326

(22) Filed: Jul. 27, 2020

(65) Prior Publication Data

US 2021/0069342 A1    Mar. 11, 2021

(30) Foreign Application Priority Data

Sep. 4, 2019   (KR) ........................ 10-2019-0109807
Apr. 6, 2020   (KR) ........................ 10-2020-0041527

(51) Int. Cl.
 *A61K 47/68*   (2017.01)
 *A61P 35/00*   (2006.01)
 *C07K 16/28*   (2006.01)

(52) U.S. Cl.
 CPC ...... *A61K 47/6849* (2017.08); *A61K 47/6803* (2017.08); *A61P 35/00* (2018.01); *C07K 16/2803* (2013.01)

(58) Field of Classification Search
 None
 See application file for complete search history.

(56) References Cited

U.S. PATENT DOCUMENTS 5,112,739 A    5/1992   Meneghini et al.
5,935,995 A    8/1999   Bosslet et al.
 (Continued)

FOREIGN PATENT DOCUMENTS

CA    2921707 A1    4/2015
CN    1185786 A    6/1998
 (Continued)

OTHER PUBLICATIONS

Al Qaraghuli et al Antibody-protein binding and conformational changes: identifying allosteric signaling pathways to engineer a better effector response. Sci Rep 10, 13696 (2020) (Year: 2020).*

(Continued)

*Primary Examiner* — Scarlett Y Goon
*Assistant Examiner* — Miles Joseph Delahoussaye
(74) *Attorney, Agent, or Firm* — Foley Hoag LLP; David P. Halstead; Lucas P. Watkins

(57) ABSTRACT

The present invention relates to new antibody-drug conjugates (ADCs) targeting ROR1, active metabolites of such ADCs, methods for preparation of such ADCs, uses for such ADCs in treatment and/or prevention of illnesses, and uses for such ADCs in production of drugs for treatment and/or (Continued)

prevention of diseases, more specifically diseases associated with over-expression of ROR1, for example cancer. More specifically, the present invention relates to an antibody-drug conjugate comprising an antibody that binds to ROR1 or an antigen-binding fragment thereof, and a pharmaceutical composition comprising the same.

38 Claims, 15 Drawing Sheets

Specification includes a Sequence Listing.

(56) References Cited

U.S. PATENT DOCUMENTS

| | | | |
|---|---|---|---|
| 6,218,519 | B1 | 4/2001 | Kenten et al. |
| 6,759,509 | B1 | 7/2004 | King et al. |
| 8,039,273 | B2 | 10/2011 | Jeffrey |
| 8,568,728 | B2 | 10/2013 | Jeffrey |
| 9,919,057 | B2 | 3/2018 | Kim et al. |
| 9,993,568 | B2 | 6/2018 | Kim et al. |
| 10,118,965 | B2 | 10/2018 | Kim et al. |
| 10,183,997 | B2 | 1/2019 | Kim et al. |
| 10,383,949 | B2 | 8/2019 | Kim et al. |
| 10,980,890 | B2 | 4/2021 | Kim et al. |
| 11,167,040 | B2 | 11/2021 | Kim et al. |
| 11,173,214 | B2 | 11/2021 | Kim et al. |
| 11,413,353 | B2 | 8/2022 | Kim et al. |
| 2005/0238649 | A1 | 10/2005 | Doronina et al. |
| 2006/0088522 | A1 | 4/2006 | Boghaert et al. |
| 2009/0326205 | A1 | 12/2009 | Nakamura et al. |
| 2012/0030858 | A1 | 2/2012 | Duffin |
| 2012/0058051 | A1 | 3/2012 | Rader et al. |
| 2012/0107332 | A1 | 5/2012 | Jeffrey |
| 2012/0308584 | A1 | 12/2012 | Kim et al. |
| 2013/0251723 | A1 | 9/2013 | Rohlff et al. |
| 2013/0281922 | A1 | 10/2013 | Teige |
| 2014/0031535 | A1 | 1/2014 | Jeffrey |
| 2014/0032535 | A1 | 1/2014 | Singla |
| 2014/0072558 | A1 | 3/2014 | Park et al. |
| 2014/0088292 | A1 | 3/2014 | Kim et al. |
| 2014/0161829 | A1 | 6/2014 | Kim et al. |
| 2014/0187756 | A1 | 7/2014 | Kim et al. |
| 2014/0286969 | A1 | 9/2014 | Tschoepe et al. |
| 2015/0105541 | A1 | 4/2015 | Kim et al. |
| 2016/0184451 | A1 | 6/2016 | Kim et al. |
| 2016/0256561 | A1 | 9/2016 | Howard et al. |
| 2016/0257709 | A1 | 9/2016 | Kline et al. |
| 2017/0088614 | A1 | 3/2017 | Kim et al. |
| 2017/0088621 | A1 | 3/2017 | Kim et al. |
| 2017/0095576 | A1 | 4/2017 | Kim et al. |
| 2018/0265593 | A1 | 9/2018 | Chen et al. |
| 2018/0369406 | A1 | 12/2018 | Lannutti et al. |
| 2019/0151465 | A1 | 5/2019 | Kim et al. |
| 2019/0381185 | A1 | 12/2019 | Kim et al. |
| 2020/0069816 | A1 | 3/2020 | Kim et al. |
| 2020/0095317 | A1 | 3/2020 | Song et al. |
| 2020/0297865 | A1 | 9/2020 | Kim et al. |
| 2021/0069342 | A1 | 3/2021 | Park et al. |
| 2021/0214432 | A1 | 7/2021 | Lim et al. |
| 2022/0218830 | A1 | 7/2022 | Song et al. |
| 2022/0218840 | A1 | 7/2022 | Kim et al. |
| 2022/0339291 | A1 | 10/2022 | Park et al. |

FOREIGN PATENT DOCUMENTS

| | | |
|---|---|---|
| CN | 101287500 A | 10/2008 |
| CN | 103648530 A | 3/2014 |
| CN | 105358579 A | 2/2016 |
| EP | 2913064 A1 | 9/2015 |
| EP | 3156424 A1 | 4/2017 |
| EP | 3604311 A1 | 2/2020 |
| JP | 2009501800 A | 1/2009 |
| KR | 10-2009-0088893 A | 8/2009 |
| KR | 10-2012-0113175 A | 10/2012 |
| KR | 2014/0035393 A | 3/2014 |
| KR | 10-2015-0137015 | 6/2016 |
| KR | 10-2014-0192328 | 7/2016 |
| KR | 10-2018-0110645 A | 10/2018 |
| KR | 10-2019-0018400 A | 2/2019 |
| KR | 10-2019-0028350 A | 3/2019 |
| RU | 2191021 C2 | 10/2002 |
| RU | 2218922 C2 | 12/2003 |
| RU | 2651776 C2 | 4/2018 |
| TW | 201524520 A | 7/2015 |
| WO | WO-98/19705 A1 | 5/1998 |
| WO | WO-2004050089 A1 | 6/2004 |
| WO | WO-2007/011968 A2 | 1/2007 |
| WO | WO-2008/034120 A2 | 3/2008 |
| WO | WO-2009/016647 A1 | 2/2009 |
| WO | WO-2009/054863 A2 | 4/2009 |
| WO | WO-2011066418 A1 | 6/2011 |
| WO | WO-2011/130598 A1 | 10/2011 |
| WO | WO-2011/145068 A1 | 11/2011 |
| WO | WO-2012/153193 A2 | 11/2012 |
| WO | WO-2013055990 A1 | 4/2013 |
| WO | WO-2013103707 A1 | 7/2013 |
| WO | WO-2014/096368 A1 | 6/2014 |
| WO | WO-2014/194030 A2 | 12/2014 |
| WO | WO-2015/052322 A1 | 4/2015 |
| WO | WO-2015/057699 A2 | 4/2015 |
| WO | WO-2015/095755 A1 | 6/2015 |
| WO | WO-2015/182984 A1 | 12/2015 |
| WO | WO-2016/033570 A1 | 3/2016 |
| WO | WO-2016/040684 A1 | 3/2016 |
| WO | WO-2016/094517 A1 | 6/2016 |
| WO | WO-2016108587 A1 | 7/2016 |
| WO | WO-2017/051249 A1 | 3/2017 |
| WO | WO-2017/051254 A1 | 3/2017 |
| WO | WO-2017/066136 A2 | 4/2017 |
| WO | WO-2017089890 A1 | 6/2017 |
| WO | WO-2017089894 A1 | 6/2017 |
| WO | WO-2017089895 A1 | 6/2017 |
| WO | WO-2018/069490 A1 | 4/2018 |
| WO | WO-2018/083535 A1 | 5/2018 |
| WO | WO-2018/146199 A1 | 8/2018 |
| WO | WO-2019/050362 A2 | 3/2019 |
| WO | WO-2019/215510 A2 | 11/2019 |
| WO | WO-2019/225992 A1 | 11/2019 |
| WO | WO-2020/180121 A1 | 9/2020 |
| WO | WO-2019/215510 A8 | 11/2020 |
| WO | WO-2021/044208 A1 | 3/2021 |

OTHER PUBLICATIONS

Bender et al., "A Mechanistic Pharmacokinetic Model Elucidating the Disposition of Trastuzumab Emtansine (T-DM1), an Antibody-Drug Conjugate (ADC) for Treatment of Metastatic Breast Cancer," The AAPS Journal, 16: 994-1008 (2014).

Collins et al ., "The emergence of oxime click chemistry and its utility in polymer science," Polymer Chemistry, 23: 3812-3826 (2016).

Kim et al., "A dimeric form of a small-sized protein binder exhibits enhanced anti-tumor activity through prolonged blood circulation," Journal of Controlled Release, 279: 282-191 (2018).

Kim et al., "Protein conjugation with genetically encoded unnatural amino acids," Current Opinion in Chemical Biology, 17: 412-419 (2013).

Kim et al., "Strategies and Advancement in Antibody-Drug Conjugate Optimization for Targeted Cancer Therapeutics," Biomolecular Therapeutics, 23: 493-509 (2015).

Skriec et al., "Non-immunoglobulin scaffolds: a focus on their targets," Trends in Biotechnology, 33(7): 408-418 (2015).

Behrens et al., "Methods for Site-specific Drug Conjugation to Antibodies," MAbs, 6(1): 46-53 (2014).

Bergmann, CP et al. Dental Ceramics. Microstructure, Properties, and Degradation. 2013, Chapter 2, Biomaterials, p. 9.

Carey, FA. Organic Chemistry 6th Ed. McGraw Hill. 2006, chapter 1, p. 9.

Christie et al., "Stabilization of cysteine-linked antibody drug conjugates with N-aryl maleimides," Journal of Controlled Release, 220:660-670 (2015).

(56) References Cited

OTHER PUBLICATIONS

Chu et al., "Antibody-drug Conjugates for the Treatment of B-cell Non-Hodgkin's Lymphoma and Leukemia," Future Oncol, 9(3): 355-368 (2013).
Connolly et al., "Discovery of Orally Active 4-amino-6-arylaminopyrimidine-5-carbaldehyde Oximes with Dual EGFR and HER2 Inhibitory Activity," AACR 104th Annual Meeting, Abstract 2456 (2013).
Desbene, S. et al. Doxorubicin prodrugs with reduced cytotoxicity suited for tumour-specific activation. Anti-Cancer Drug Design. 1998,vol. 13,p. 955.
Dunn, PJ. et al. Green Chemistry Principle #8. ACS What is Green Chemistry. Accessed from ACS Website on Jan. 8, 2016.
Extended European Search Report for EP Application No. 15799360.1 dated Dec. 21, 2017.
Extended European Search Report for EP Application No. 16868091.6 dated May 17, 2019.
Extended European Search Report for EP Application No. 16868095.7 dated Jul. 29, 2019.
Extended European Search Report for EP Application No. 16868096.5 dated Jun. 21, 2019.
Gaertner et al., "Chemo-enzymic Backbone Engineering of Proteins ," J. Biol. Chem., 269(10):7224-7230 (1994).
Grinda, M. et al., A Self-Immolative Dendritic Glucuronide Prodrug of Doxorubicin, Medicinal Chemistry Communications, (2012) vol. 3, No. 1, pp. 68-70.
Guan., "Metabolic Activation and Drug Targeting," Drug Delivery: Principles and Applications: 201-244 (2005).
International Search Report and Written Opinion for International Application No. PCT/IB2016/001810 dated Apr. 19, 2017.
International Search Report and Written Opinion for International Application No. PCT/IB2016/001811 dated Apr. 19, 2017.
International Search Report and Written Opinion for International Application No. PCT/IB2019/000577 dated Nov. 28, 2019.
International Search Report and Written Opinion for International Application No. PCT/KR2015/005299 dated Jul. 17, 2015.
Jeffrey et al., "Development and properties of β-glucuronide linkers for monoclonal antibody-drug conjugates," Bioconjugate Chem, 17:835 (2006).
Jeffrey et al., "Minor groove binder antibody conjugates employing a water soluable β-glucuronide linker," Bioorganic & Medicinal Chemistry Letters, 17:2278-2280 (2007).
Kim et al., "Synthesis of Bispecific Antibodies Using Genetically Encoded Unnatural Amino Acids," J Am Chem Soc, 134: 9918-9921 (2012).
Lartigue, "Antibody-Drug Conjugates: Guided Missiles Deployed Against Cancerous Cells," Oncology Live, p. 1 (2012).
Lee et al., "Enzymatic prenylation and oxime ligation for the synthesis of stable and homogeneous protein-drug conjugates for targeted therapy," Angewandte Chemie, 54(41):12020-12024 (2015).
Leong, KW. Biomaterials. El Sevier. Accessed on Sep. 26, 2016.
Lu et al., "Linkers Having a Crucial Role in Antibody-Drug Conjugates," Int J Molec Sci 17(561):1-22 (2016).
McCombs et al., "Antibody Drug Conjugates: Design and Selection of Linker, Payload and Conjugation Chemistry," AAPS J, 17(2): 339-351 (2015).
Merriam-Webster. Biomaterial Definition. Accessed on Sep. 26, 2016.
Rose et al., "Preparation of well-defined protein conjugates using enzyme-assisted reverse proteolysis," Bioconjugate Chem, 2(3):154-159 (1991).
Sagnou et al., "Design and synthesis of novel pyrrolobenzodiazepine (PBD) prodrugs for ADEPT and GDEPT," Bioorganic and Medicinal Chemistry Letters, 10(18): 2083-2086 (2000).
Schwarz et al., "[15] Enzymatic C-terminal biotinylation of proteins," Methods Enzymol 184:160-162 (1990).

Tranoy-Opalinski et al., "β-Glucuronidase-responsive prodrugs for selective cancer chemotherapy: an update," Eur J Med Chem, 74:302-313 (2014).
Translation of International Search Report for International Application No. PCT/KR2020/003100 dated Jun. 24, 2020 (4 pages).
Varvounis, "An Update on the Synthesis of Pyrrolo[1,4]benzodiazepines," Molecules, 21(154):1-55 (2016).
Wermuth, "Similarity in drugs: reflections on analogue design," Drug Discov Today, 11(Issues 7-8): 248-254 (2006).
Yewale et al., "Epidermal growth factor receptor targeting in cancer: A review of trends and strategies," Biomaterials, 34: 8690-8707 (2013).
Zimmerman et al., "Production of Site-Specific Antibody-Drug Conjugates Using Optimized Non-Natural Amino Acids in a Cell-Free Expression System," Bioconjugate Chem., 25(2):351-361 (2014).
U.S. Appl. No. 14/865,778, Issued.
U.S. Appl. No. 14/898,932, Issued.
U.S. Appl. No. 16/005,245, Issued.
U.S. Appl. No. 16/545,869, Subject to Reissue.
U.S. Appl. No. 17/475,109, Pending.
U.S. Appl. No. 15/276,231, Issued.
U.S. Appl. No. 15/276,209, Issued.
U.S. Appl. No. 15/779,444, Issued.
U.S. Appl. No. 17/525,582, Pending.
U.S. Appl. No. 15/779,450, Issued.
U.S. Appl. No. 16/408,002, Pending.
U.S. Appl. No. 16/328,256, Pending.
U.S. Appl. No. 16/964,965, Pending.
International Search Report and Written Opinion for International Application No. PCT/IB2020/000649 dated Nov. 27, 2020.
Bendig, "Humanization of Rodent Monoclonal Antibodies by CDR Grafting," Methods: A Companion to Methods in Enzymology, 8:83-93 (1995).
Colman, "Effects of Amino Acid Sequence Changes on Antibody-Antigen Interactions," Research in Immunology, 145: 33-36 (1994).
Edwards et al., "The remarkable flexibility of the human antibody repertoire; isolation of over one thousand different antibodies to a single protein, BLyS," J Mol Biol, 334(1): 103-118 (2003).
Murphy et al., "Enhancing recombinant antibody performance by optimally engineering its format," Journal of Immunological Methods, 463: 127-133 (2018).
Murphy et al., "Targeting Sema3D in pancreatic cancer: A novel therapeutic strategy," Journal of Clinical Oncology: Abstract 4129 pp. 1-2 (2015).
Paul., "Fundamental Immunology Third Edition," Raven Press New York: 292-295 (1993).
Rudikoff et al., "Single amino acid substitution altering antigen-binding specificity," PNAS, 79(6): 1979-1983(1982).
Extended European Search Report for Application No. EP 18774896 dated Dec. 15, 2020.
U.S. Appl. No. 16/545,869, Allowed.
U.S. Appl. No. 15/779,446, Pending.
U.S. Appl. No. 15/779,444, Pending.
U.S. Appl. No. 15/779,450, Pending.
U.S. Appl. No. 16/940,326, Pending.
Lockard et al., "Efficacy and toxicity of the solvent polyethylene glycol 400 in monkey model." Epilepsia 20.1: 77-84 (1979).
Mariuzza et al., "The structural basis of antigen-antibody recognition." Annual review of biophysics and biophysical chemistry 16.1: 139-159 (1987).
Qi et al., "Blocking neuropilin-1 function has an additive effect with anti-VEGF to inhibit tumor growth." Cancer cell 11.1: 53-67 (2007).
Bujak et al., "A Monoclonal Antibody to Human DLK1 Reveals Differential Expression in Cancer and Absence in Healthy Tissues." Antibodies, 4(2):71-87 (2015).
International Search Report and Written Opinion for International Application No. PCT/IB2016/001772 dated Apr. 6, 2017.

* cited by examiner

| Cancer Cell Line | | Mean Fold Ratio | Cancer Cell Line | | Mean Fold Ratio |
|---|---|---|---|---|---|
| Gastric cancer | AGS | 12.3 | Lung cancer | H460 | 10.9 |
| | NCI-N87 | 11.8 | | A549 | 6.0 |
| | MKN-28 | 4.9 | | NCI-H1975 | 4.2 |
| | SNU-1750 | 3.9 | | H1437 | 4.1 |
| | SNU-16 | 2.4 | | Calu-6 | 3.3 |
| Breast cancer | HCC1187 | 9.3 | Colon cancer | HCT116 | 18.0 |
| | MDA-MB-231 | 8.8 | | DLD-1 | 17.6 |
| | MDA-MB-468 | 6.4 | | HT29 | 3.9 |
| | HCC70 | 3.8 | ALL | 697 | 12.0 |
| | HCC1143 | 3.2 | | Kasumi-2 | 11.5 |
| | BT20 | 3.0 | MCL | Mino | 7.2 |
| | HCC1806 | 2.3 | | JeKo-1 | 4.0 |
| | HCC1937 | 2.7 | T cell leukemia | Jurkat | 1.7 |
| | BT474 | 1.7 | | | |
| | MCF7 | 1.1 | | | |

* Mean Fold Ratio : MFI of anti-ROR1 / MFI of 2nd Ab

SEQUENCE LISTING

```
<160> NUMBER OF SEQ ID NOS: 106

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      Heavy chain CDR1

<400> SEQUENCE: 1

Ser Tyr Asp Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      Heavy chain CDR1

<400> SEQUENCE: 2

Asp Tyr Tyr Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      Heavy chain CDR1

<400> SEQUENCE: 3

Asn Tyr Asp Met Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      Heavy chain CDR1

<400> SEQUENCE: 4

Asn Tyr Ala Met Ser
1               5

<210> SEQ ID NO 5
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      Heavy chain CDR1

<400> SEQUENCE: 5

Asp Tyr Asp Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      Heavy chain CDR2

<400> SEQUENCE: 6

Trp Ile Ser Pro Asp Ser Gly Ser Ile Tyr Tyr Ala Asp Ser Val Lys
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      Heavy chain CDR2

<400> SEQUENCE: 7

Ser Ile Ser Pro Asp Gly Ser Asn Thr Tyr Tyr Ala Asp Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      Heavy chain CDR2

<400> SEQUENCE: 8

Trp Ile Ser Pro Gly Gly Gly Ser Lys Tyr Tyr Ala Asp Ser Val Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      Heavy chain CDR2

<400> SEQUENCE: 9

Ala Ile Tyr His Ser Gly Ser Ser Lys Tyr Tyr Ala Asp Ser Val Lys
1               5                   10                  15

Gly

<210> SEQ ID NO 10
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      Heavy chain CDR2

<400> SEQUENCE: 10

Gly Ile Ser His Gly Ser Gly Asn Lys Tyr Tyr Ala Asp Ser Val Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      Heavy chain CDR2

<400> SEQUENCE: 11

Ser Ile Ser His Asn Ser Gly Ser Thr Tyr Tyr Ala Asp Ser Val Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      Heavy chain CDR2

<400> SEQUENCE: 12

Val Ile Ser Pro Asp Gly Gly Ser Ile Tyr Tyr Ala Asp Ser Val Lys
1               5                   10                  15

Gly

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      Heavy chain CDR2

<400> SEQUENCE: 13

Ser Ile Ser Pro Ser Ser Gly Ser Ser Ile Tyr Tyr Ala Asp Ser Val
1               5                   10                  15

Lys Gly

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      Heavy chain CDR3

<400> SEQUENCE: 14

Pro Thr Gly Arg Phe Asp Tyr
1               5

<210> SEQ ID NO 15
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      Heavy chain CDR3

<400> SEQUENCE: 15

Asn Leu Arg Ala Phe Asp Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      Heavy chain CDR3

<400> SEQUENCE: 16

Val Asn Gly Arg Phe Asp Tyr
1               5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      Heavy chain CDR3

<400> SEQUENCE: 17

Gly Gly Asn Gly Ala Trp Asp Thr Gly Phe Asp Tyr
1               5                   10

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      Heavy chain CDR3

<400> SEQUENCE: 18

Arg Leu Ser Leu Arg Arg Arg Pro Ser Tyr Tyr Ser Asp Asn Ala Met
1               5                   10                  15

Asp Val

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      Heavy chain CDR3

<400> SEQUENCE: 19

Phe Ile Ser Ala Arg Lys Ser Leu Gly Arg Ser Tyr Ser Asn Gly Met
1               5                   10                  15

Asp Val

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      Heavy chain CDR3
```

<400> SEQUENCE: 20

Asp Val Val Glu Cys Asn Met Asn Pro Cys Ser Tyr Asp Asn Ala Met
1               5                   10                  15

Asp Val

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      Heavy chain CDR3

<400> SEQUENCE: 21

Ala Pro Gly Trp Cys Gln Ala Pro Ser Cys Tyr Tyr Asp Asn Ala Met
1               5                   10                  15

Asp Val

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      Light chain CDR1

<400> SEQUENCE: 22

Ser Gly Ser Ser Ser Asn Ile Gly Asn Asn Asn Val Asn
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      Light chain CDR1

<400> SEQUENCE: 23

Ser Gly Ser Ser Ser Asn Ile Gly Ser Asn Thr Val Tyr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      Light chain CDR1

<400> SEQUENCE: 24

Ser Gly Ser Ser Ser Asn Ile Gly Asn Asn Asn Val Ser
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      Light chain CDR1

<400> SEQUENCE: 25

Ser Gly Ser Ser Ser Asn Ile Gly Ser Asn Asp Val Ser
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      Light chain CDR1

<400> SEQUENCE: 26

Thr Gly Ser Ser Ser Asn Ile Gly Asn Asn Ala Val Asn
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      Light chain CDR1

<400> SEQUENCE: 27

Thr Gly Ser Ser Ser Asn Ile Gly Ser Asn Asp Val Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      Light chain CDR1

<400> SEQUENCE: 28

Ser Gly Ser Ser Ser Asn Ile Gly Ser Asn Tyr Val Ser
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      Light chain CDR1

<400> SEQUENCE: 29

Ser Gly Ser Ser Ser Asn Ile Gly Asn Asn Asp Val Ser
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      Light chain CDR2

<400> SEQUENCE: 30

Tyr Asp Asn Lys Arg Pro Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      Light chain CDR2

<400> SEQUENCE: 31

Ala Asn Ser Gln Arg Pro Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      Light chain CDR2

<400> SEQUENCE: 32

Ala Asp Ser His Arg Pro Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      Light chain CDR2

<400> SEQUENCE: 33

Tyr Asp Asn Asn Arg Pro Ser
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      Light chain CDR2

<400> SEQUENCE: 34

Tyr Asp Ser Asn Arg Pro Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      Light chain CDR2

<400> SEQUENCE: 35

Ala Asp Ser Lys Arg Pro Ser
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      Light chain CDR2

<400> SEQUENCE: 36

Asp Asp Ser His Arg Pro Ser
1               5

<210> SEQ ID NO 37
<211> LENGTH: 7

```
<212> TYPE: PRT
<213> ORGANISM: Artificial Sequence
<220> FEATURE:
<223> OTHER INFORMATION: Description of Artificial Sequence: Synthetic
      Light chain CDR2

<400> SEQUENCE: 37

Asp Asp Ser Gln Arg Pro Ser
1               5

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      Light chain CDR3

<400> SEQUENCE: 38

Gly Thr Trp Asp Ala Ser Leu Ser Gly Tyr Val
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      Light chain CDR3

<400> SEQUENCE: 39

Gly Ser Trp Asp Tyr Ser Leu Ser Gly Tyr Val
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      Light chain CDR3

<400> SEQUENCE: 40

Ala Thr Trp Asp Tyr Ser Leu Ser Gly Tyr Val
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      Light chain CDR3

<400> SEQUENCE: 41

Gly Ala Trp Asp Asp Ser Leu Ser Gly Tyr Val
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      Light chain CDR3
```

-continued

```
<400> SEQUENCE: 42

Gly Thr Trp Asp Tyr Ser Leu Ser Gly Tyr Val
1               5                   10

<210> SEQ ID NO 43
<211> LENGTH: 116
<212> TYPE: PRT
<213> ORGANISM: Artificial Sequence
<220> FEATURE:
<223> OTHER INFORMATION: Description of Artificial Sequence: Synthetic
      Heavy chain variable region

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Pro Asp Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Thr Gly Arg Phe Asp Tyr Trp Gly Gln Gly Thr Leu Val
            100                 105                 110

Thr Val Ser Ser
        115

<210> SEQ ID NO 44
<211> LENGTH: 116
<212> TYPE: PRT
<213> ORGANISM: Artificial Sequence
<220> FEATURE:
<223> OTHER INFORMATION: Description of Artificial Sequence: Synthetic
      Heavy chain variable region

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ser Ile Ser Pro Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Arg Ala Phe Asp Tyr Trp Gly Gln Gly Thr Leu Val
            100                 105                 110

Thr Val Ser Ser
        115

<210> SEQ ID NO 45
<211> LENGTH: 116
```

```
<212> TYPE: PRT
<213> ORGANISM: Artificial Sequence
<220> FEATURE:
<223> OTHER INFORMATION: Description of Artificial Sequence: Synthetic
      Heavy chain variable region

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Pro Gly Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Gly Arg Phe Asp Tyr Trp Gly Gln Gly Thr Leu Val
            100                 105                 110

Thr Val Ser Ser
        115

<210> SEQ ID NO 46
<211> LENGTH: 121
<212> TYPE: PRT
<213> ORGANISM: Artificial Sequence
<220> FEATURE:
<223> OTHER INFORMATION: Description of Artificial Sequence: Synthetic
      Heavy chain variable region

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Ala Ile Tyr His Ser Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Gly Ala Trp Asp Thr Gly Phe Asp Tyr Trp Gly
            100                 105                 110

Gln Gly Thr Leu Val Thr Val Ser Ser
        115                 120

<210> SEQ ID NO 47
<211> LENGTH: 127
<212> TYPE: PRT
<213> ORGANISM: Artificial Sequence
<220> FEATURE:
<223> OTHER INFORMATION: Description of Artificial Sequence: Synthetic
      Heavy chain variable region
```

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Gly Ile Ser His Gly Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Leu Ser Leu Arg Arg Pro Ser Tyr Tyr Ser Asp Asn
            100                 105                 110

Ala Met Asp Val Trp Gly Gln Gly Thr Leu Val Thr Val Ser Ser
        115                 120                 125

<210> SEQ ID NO 48
<211> LENGTH: 127
<212> TYPE: PRT
<213> ORGANISM: Artificial Sequence
<220> FEATURE:
<223> OTHER INFORMATION: Description of Artificial Sequence: Synthetic
      Heavy chain variable region

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser His Asn Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ile Ser Ala Arg Lys Ser Leu Gly Arg Ser Tyr Ser Asn
            100                 105                 110

Gly Met Asp Val Trp Gly Gln Gly Thr Leu Val Thr Val Ser Ser
        115                 120                 125

<210> SEQ ID NO 49
<211> LENGTH: 127
<212> TYPE: PRT
<213> ORGANISM: Artificial Sequence
<220> FEATURE:
<223> OTHER INFORMATION: Description of Artificial Sequence: Synthetic
      Heavy chain variable region

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

```
Asp Met Ser Trp Val Arg Gln Ala Pro Gly Lys Gly Leu Glu Trp Val
            35                  40                  45

Ser Val Ile Ser Pro Asp Gly Gly Ser Ile Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Val Val Glu Cys Asn Met Asn Pro Cys Ser Tyr Asp Asn
            100                 105                 110

Ala Met Asp Val Trp Gly Gln Gly Thr Leu Val Thr Val Ser Ser
            115                 120                 125
```

<210> SEQ ID NO 50
<211> LENGTH: 128
<212> TYPE: PRT
<213> ORGANISM: Artificial Sequence
<220> FEATURE:
<223> OTHER INFORMATION: Description of Artificial Sequence: Synthetic
      Heavy chain variable region

<400> SEQUENCE: 50

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
            35                  40                  45

Ser Ser Ile Ser Pro Ser Ser Gly Ser Ser Ile Tyr Tyr Ala Asp Ser
 50                      55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                85                  90                  95

Cys Ala Lys Ala Pro Gly Trp Cys Gln Ala Pro Ser Cys Tyr Tyr Asp
            100                 105                 110

Asn Ala Met Asp Val Trp Gly Gln Gly Thr Leu Val Thr Val Ser Ser
            115                 120                 125
```

<210> SEQ ID NO 51
<211> LENGTH: 111
<212> TYPE: PRT
<213> ORGANISM: Artificial Sequence
<220> FEATURE:
<223> OTHER INFORMATION: Description of Artificial Sequence: Synthetic
      Light chain variable region

<400> SEQUENCE: 51

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Asn Asn
            20                  25                  30

Asn Val Asn Trp Tyr Gln Gln Leu Pro Gly Thr Ala Pro Lys Leu Leu
            35                  40                  45

Ile Tyr Tyr Asp Asn Lys Arg Pro Ser Gly Val Pro Asp Arg Phe Ser
 50                      55                  60

Gly Ser Lys Ser Gly Thr Ser Ala Ser Leu Ala Ile Ser Gly Leu Arg
 65                  70                  75                  80
```

```
Ser Glu Asp Glu Ala Asp Tyr Tyr Cys Gly Thr Trp Asp Ala Ser Leu
                85                  90                  95

Ser Gly Tyr Val Phe Gly Gly Gly Thr Lys Leu Thr Val Leu Gly
            100                 105                 110

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      Light chain variable region

<400> SEQUENCE: 52

Gln Ser Val Leu Thr Gln Pro Pro Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Tyr Trp Tyr Gln Gln Leu Pro Gly Thr Ala Pro Lys Leu Leu
            35                  40                  45

Ile Tyr Ala Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 53
<211> LENGTH: 111
<212> TYPE: PRT
<213> ORGANISM: Artificial Sequence
<220> FEATURE:
<223> OTHER INFORMATION: Description of Artificial Sequence: Synthetic
      Light chain variable region

<400> SEQUENCE: 53

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
                20                  25                  30

Asn Val Ser Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic
      Light chain variable region
```

<400> SEQUENCE: 54

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Tyr Asp Asn Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110

<210> SEQ ID NO 55
<211> LENGTH: 111
<212> TYPE: PRT
<213> ORGANISM: Artificial Sequence
<220> FEATURE:
<223> OTHER INFORMATION: Description of Artificial Sequence: Synthetic
      Light chain variable region

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Tyr Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic
      Light chain variable region

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Thr Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Description of Artificial Sequence: Synthetic
      Light chain variable region

<400> SEQUENCE: 57

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic
      Light chain variable region

<400> SEQUENCE: 58

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly
            100                 105                 110

<210> SEQ ID NO 59
<211> LENGTH: 446
<212> TYPE: PRT
<213> ORGANISM: Artificial Sequence -continued

```
<220> FEATURE:
<223> OTHER INFORMATION: Description of Artificial Sequence: Synthetic
      Heavy chain

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Pro Asp Ser Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Thr Gly Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 60
<211> LENGTH: 446
<212> TYPE: PRT
<213> ORGANISM: Artificial Sequence
<220> FEATURE:
<223> OTHER INFORMATION: Description of Artificial Sequence: Synthetic
      Heavy chain

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ser Ile Ser Pro Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Arg Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 61
<211> LENGTH: 446
<212> TYPE: PRT
<213> ORGANISM: Artificial Sequence
<220> FEATURE:
<223> OTHER INFORMATION: Description of Artificial Sequence: Synthetic
      Heavy chain

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Pro Gly Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Gly Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

```
Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 62
<211> LENGTH: 451
<212> TYPE: PRT
<213> ORGANISM: Artificial Sequence
<220> FEATURE:
<223> OTHER INFORMATION: Description of Artificial Sequence: Synthetic
      Heavy chain

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Ala Ile Tyr His Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Gly Gly Asn Gly Ala Trp Asp Thr Gly Phe Asp Tyr Trp Gly
                100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 63
<211> LENGTH: 457
<212> TYPE: PRT
<213> ORGANISM: Artificial Sequence
<220> FEATURE:
<223> OTHER INFORMATION: Description of Artificial Sequence: Synthetic
      Heavy chain
```

-continued

```
<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Gly Ile Ser His Gly Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Leu Ser Leu Arg Arg Pro Ser Tyr Tyr Ser Asp Asn
            100                 105                 110

Ala Met Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415
```

```
Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
            450                 455

<210> SEQ ID NO 64
<211> LENGTH: 457
<212> TYPE: PRT
<213> ORGANISM: Artificial Sequence
<220> FEATURE:
<223> OTHER INFORMATION: Description of Artificial Sequence: Synthetic
      Heavy chain

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
            35                  40                  45

Ser Ser Ile Ser His Asn Ser Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Phe Ile Ser Ala Arg Lys Ser Leu Gly Arg Ser Tyr Ser Asn
            100                 105                 110

Gly Met Asp Val Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
    290                 295                 300
```

```
Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
450                 455

<210> SEQ ID NO 65
<211> LENGTH: 457
<212> TYPE: PRT
<213> ORGANISM: Artificial Sequence
<220> FEATURE:
<223> OTHER INFORMATION: Description of Artificial Sequence: Synthetic
      Heavy chain

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Val Ile Ser Pro Asp Gly Ser Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Val Glu Cys Asn Met Asn Pro Cys Ser Tyr Asp Asn
            100                 105                 110

Ala Met Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190
```

-continued

```
Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
        210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
        450                 455

<210> SEQ ID NO 66
<211> LENGTH: 458
<212> TYPE: PRT
<213> ORGANISM: Artificial Sequence
<220> FEATURE:
<223> OTHER INFORMATION: Description of Artificial Sequence: Synthetic
      Heavy chain

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Ser Ile Ser Pro Ser Gly Ser Ser Ile Tyr Tyr Ala Asp Ser
    50                  55                  60

Val Lys Gly Arg Phe Thr Ile Ser Arg Asp Asn Ser Lys Asn Thr Leu
65                  70                  75                  80
```

```
Tyr Leu Gln Met Asn Ser Leu Arg Ala Glu Asp Thr Ala Val Tyr Tyr
                85                  90                  95

Cys Ala Lys Ala Pro Gly Trp Cys Gln Ala Pro Ser Cys Tyr Tyr Asp
            100                 105                 110

Asn Ala Met Asp Val Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 67
<211> LENGTH: 216
<212> TYPE: PRT
<213> ORGANISM: Artificial Sequence
<220> FEATURE:
```

<223> OTHER INFORMATION: Description of Artificial Sequence: Synthetic
      Light chain

<400> SEQUENCE: 67

Gln Ser Val Leu Thr Gln Pro Pro Ala Ser Gly Thr Pro Gly Gln
1               5                   10                  15

Arg Val Thr Ile Ser Cys Ser Gly Ser Ser Asn Ile Gly Asn Asn
                20                  25                  30

Asn Val Asn Trp Tyr Gln Gln Leu Pro Gly Thr Ala Pro Lys Leu Leu
            35                  40                  45

Ile Tyr Tyr Asp Asn Lys Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Ala Ser Leu
                85                  90                  95

Ser Gly Tyr Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
210                 215

<210> SEQ ID NO 68
<211> LENGTH: 216
<212> TYPE: PRT
<213> ORGANISM: Artificial Sequence
<220> FEATURE:
<223> OTHER INFORMATION: Description of Artificial Sequence: Synthetic
      Light chain

<400> SEQUENCE: 68

Gln Ser Val Leu Thr Gln Pro Pro Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Tyr Trp Tyr Gln Gln Leu Pro Gly Thr Ala Pro Lys Leu Leu
            35                  40                  45

Ile Tyr Ala Asn Ser Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly Gln
                100                 105                 110

```
Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 69
<211> LENGTH: 216
<212> TYPE: PRT
<213> ORGANISM: Artificial Sequence
<220> FEATURE:
<223> OTHER INFORMATION: Description of Artificial Sequence: Synthetic
      Light chain

<400> SEQUENCE: 69

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Asn Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 70
<211> LENGTH: 216
<212> TYPE: PRT
<213> ORGANISM: Artificial Sequence
```

```
<220> FEATURE:
<223> OTHER INFORMATION: Description of Artificial Sequence: Synthetic
      Light chain

<400> SEQUENCE: 70

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asp Val Ser Trp Tyr Gln Gln Leu Pro Gly Thr Ala Pro Lys Leu Leu
            35                  40                  45

Ile Tyr Tyr Asp Asn Asn Arg Pro Ser Gly Val Pro Asp Arg Phe Ser
50                      55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
        210                 215

<210> SEQ ID NO 71
<211> LENGTH: 216
<212> TYPE: PRT
<213> ORGANISM: Artificial Sequence
<220> FEATURE:
<223> OTHER INFORMATION: Description of Artificial Sequence: Synthetic
      Light chain

<400> SEQUENCE: 71

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Ala Val Asn Trp Tyr Gln Gln Leu Pro Gly Thr Ala Pro Lys Leu Leu
            35                  40                  45

Ile Tyr Tyr Asp Ser Asn Arg Pro Ser Gly Val Pro Asp Arg Phe Ser
50                      55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Leu
                85                  90                  95

Ser Gly Tyr Val Phe Gly Gly Gly Thr Lys Leu Thr Val Leu Gly Gln
            100                 105                 110
```

```
Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 72
<211> LENGTH: 216
<212> TYPE: PRT
<213> ORGANISM: Artificial Sequence
<220> FEATURE:
<223> OTHER INFORMATION: Description of Artificial Sequence: Synthetic
      Light chain

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Asp Val Thr Trp Tyr Gln Gln Leu Pro Gly Thr Ala Pro Lys Leu Leu
        35                  40                  45

Ile Tyr Ala Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 73
<211> LENGTH: 216
<212> TYPE: PRT
```

<213> ORGANISM: Artificial Sequence
<220> FEATURE:
<223> OTHER INFORMATION: Description of Artificial Sequence: Synthetic Light chain

<400> SEQUENCE: 73

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Ser Trp Tyr Gln Gln Leu Pro Gly Thr Ala Pro Lys Leu Leu
        35                  40                  45

Ile Tyr Asp Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215
```

<210> SEQ ID NO 74
<211> LENGTH: 216
<212> TYPE: PRT
<213> ORGANISM: Artificial Sequence
<220> FEATURE:
<223> OTHER INFORMATION: Description of Artificial Sequence: Synthetic Light chain

<400> SEQUENCE: 74

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95
```

```
Ser Gly Tyr Val Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215
```

<210> SEQ ID NO 75
<211> LENGTH: 1338
<212> TYPE: DNA
<213> ORGANISM: Artificial Sequence
<220> FEATURE:
<223> OTHER INFORMATION: Description of Artificial Sequence: Synthetic
      Heavy chain coding gene

<400> SEQUENCE: 75

| | | | | | |
|---|---|---|---|---|---|
| gaagtacaac | ttctggagtc | aggtggagga | cttgttcagc | ccggcgggtc | cctgaggctg | 60 |
| agttgcgcag | caagcgggtt | cacattctcc | tcttatgata | tgtcttgggt | aagacaggct | 120 |
| cctggtaagg | gtctggaatg | ggtatcctgg | ataagtcctg | actccggttc | aatatactac | 180 |
| gccgatagtg | tgaagggacg | tttcaccatc | agccgggaca | cagcaaaaa | taccttgtat | 240 |
| ctccaaatga | atagcctccg | ggctgaagac | actgccgtat | attactgcgc | cagacctact | 300 |
| ggtcgttttg | actattgggg | gcaaggaaca | ctggtaaccg | tttcaagcgc | ctccaccaag | 360 |
| ggccctccg | tgttcccct | ggcccctc | tccaagtcca | cctccggcgg | caccgccgcc | 420 |
| ctgggctgcc | tggtgaagga | ctacttcccc | gagcccgtga | ccgtgtcctg | gaactccggc | 480 |
| gccctgacct | ccggcgtgca | caccttcccc | gccgtgctgc | agtcctccgg | cctgtactcc | 540 |
| ctgtcctccg | tcgtgaccgt | gccctcctcc | tccctgggca | cccagaccta | catctgcaac | 600 |
| gtgaaccaca | agccctccaa | caccaaggtg | gacaagaagg | tggagcccaa | gtcctgcgac | 660 |
| aagacccaca | cctgccctcc | ctgccccgcc | cccgagctgc | tgggcggccc | ctccgtgttc | 720 |
| ctgttccctc | ctaagcccaa | ggacaccctg | atgatctccc | gaccccccga | ggtgacttgc | 780 |
| gtggtggtgg | acgtgtccca | cgaggacccc | gaggtgaagt | tcaactggta | cgtggacggc | 840 |
| gtggaggtgc | acaacgccaa | gaccaagccc | cgggaggagc | agtacaactc | cacctaccgg | 900 |
| gtggtgtccg | tgctgaccgt | gctgcaccag | gactggctga | acggcaagga | gtacaagtgc | 960 |
| aaggtgtcca | acaaggccct | gccgcccc | atcgagaaga | ccatctccaa | ggccaagggc | 1020 |
| cagccccggg | agccccaggt | gtacaccctg | ccccctccc | gggaggagat | gaccaagaac | 1080 |
| caggtgtccc | tgacctgcct | ggtgaagggc | ttctacccct | ccgacatcgc | cgtggagtgg | 1140 |
| gagtccaacg | gccagcccga | gaacaactac | aagaccaccc | ccccgtgct | ggactccgac | 1200 |

```
ggctccttct tcctgtactc caagctgacc gtggacaagt cccggtggca gcagggcaac    1260
gtgttctcct gctccgtgat gcacgaggcc ctgcacaacc actacaccca gaagtccctg    1320
tccctgtccc ccggcaag                                                  1338
```

<210> SEQ ID NO 76
<211> LENGTH: 1338
<212> TYPE: DNA
<213> ORGANISM: Artificial Sequence
<220> FEATURE:
<223> OTHER INFORMATION: Description of Artificial Sequence: Synthetic
      Heavy chain coding gene

<400> SEQUENCE: 76

```
gaagtgcagc tgctggaatc cggcggaggc ctggtgcagc ctggcggctc tctgagactg      60 tcttcgccg cctccggctt caccttctcc gactactaca tgtcctgggt gcgacaggcc     120
cctggcaagg gcctgaatg ggtgtcctcc atctcccccg acggctccaa cacctactac     180
gccgactccg tgaagggccg gttcaccatc tcccgggaca actccaagaa cacctgtac     240 ctgcagatga actccctgcg ggccgaggac accgccgtgt actactgcgc caagaacctg    300
cgggccttcg actactgggg ccagggcaca ctggtgaccg tgtcctccgc tccaccaag     360 ggcccctccg tgttcccct ggcccctcc tccaagtcca cctccggcgg caccgccgcc     420
ctgggctgcc tggtgaagga ctacttcccc gagcccgtga ccgtgtcctg aactccggc     480 gccctgacct ccggcgtgca ccttcccc gccgtgctgc agtcctccgg cctgtactcc     540
ctgtcctccg tcgtgaccgt gccctcctcc tccctgggca cccagaccta catctgcaac    600
gtgaaccaca agccctccaa caccaaggtg acaagaagg tggagcccaa gtcctgcgac     660
aagacccaca cctgccctcc ctgccccgcc ccgagctgc tgcgcgcc ctccgtgttc       720 ctgttccctc ctaagcccaa ggacaccctg atgatctcc ggaccccga ggtgacttgc      780 gtggtggtgg acgtgtccca cgaggacccc gaggtgaagt tcaactggta cgtggacggc    840
gtggaggtgc acaacgccaa gaccaagccc cgggaggagc agtacaactc cacctaccgg    900
gtggtgtccg tgctgaccgt gctgcaccag gactggctga acggcaagga gtacaagtgc    960
aaggtgtcca acaaggccct gccgccccc atcgagaaga ccatctccaa ggccaagggc   1020
cagccccggg agccccaggt gtacaccctg cccccctccc gggaggagat gaccaagaac    1080
caggtgtccc tgacctgcct ggtgaagggc ttctacccct ccgacatcgc cgtggagtgg    1140
gagtccaacg gccagcccga gaacaactac aagaccaccc cccccgtgct ggactccgac    1200
ggctccttct tcctgtactc caagctgacc gtggacaagt cccggtggca gcagggcaac    1260
gtgttctcct gctccgtgat gcacgaggcc ctgcacaacc actacaccca gaagtccctg    1320
tccctgtccc ccggcaag                                                 1338
```

<210> SEQ ID NO 77
<211> LENGTH: 1341
<212> TYPE: DNA
<213> ORGANISM: Artificial Sequence
<220> FEATURE:
<223> OTHER INFORMATION: Description of Artificial Sequence: Synthetic
      Heavy chain coding gene

<400> SEQUENCE: 77

```
gaagtgcaac ttcttgagag tggtggagga ttggtacaac ctgggggtag tttgcgtctc      60
tcctgtgctg cttctggttt cacattttcc tcctatgaca tgagctgggt acggcaagct    120
```

```
ccaggaaaag ggcttgagtg ggtctcctgg atctctcccg gtggaggcag caagtattat    180
gcagactctg taaagggtag gtttactata tcacgcgata atagtaagaa tactttgtat    240
ttgcaaatga actccctccg agctgaggac acagcagtct attattgcgc ccgagttaac    300
ggtcgcttcg attactgggg ccaaggcaca ctggttacag tgtcctcagc ctccaccaag    360
ggcccctccg tgttcccct  ggccccctcc tccaagtcca cctccggcgg caccgccgcc    420
ctgggctgcc tggtgaagga ctacttcccc gagcccgtga ccgtgtcctg gaactccggc    480
gccctgacct ccggcgtgca caccttcccc gccgtgctgc agtcctccgg cctgtactcc    540
ctgtcctccg tcgtgaccgt gccctcctcc ccctgggca  cccagaccta catctgcaac    600
gtgaaccaca agccctccaa caccaaggtg acaagaagg  tggagcccaa gtcctgcgac    660
aagacccaca cctgccctcc ctgccccgcc ccgagctgc  tgggcggccc ctccgtgttc    720
ctgttccctc ctaagcccaa ggacaccctg atgatctccc ggaccccga  ggtgacttgc    780 gtggtggtgg acgtgtccca cgaggacccc gaggtgaagt tcaactggta cgtggacggc    840
gtggaggtgc acaacgccaa gaccaagccc cgggaggagc agtacaactc cacctaccgg    900
gtggtgtccg tgctgaccgt gctgcaccag gactggctga acggcaagga gtacaagtgc    960
aaggtgtcca acaaggccct gcccgccccc atcgagaaga ccatctccaa ggccaagggc   1020
cagccccggg agccccaggt gtacaccctg cccccctccc gggaggagat gaccaagaac   1080
caggtgtccc tgacctgcct ggtgaagggc ttctacccct ccgacatcgc cgtggagtgg   1140
gagtccaacg gccagcccga gaacaactac aagaccaccc cccccgtgct ggactccgac   1200
ggctccttct tcctgtactc caagctgacc gtggacaagt cccggtggca gcagggcaac   1260
gtgttctcct gctccgtgat gcacgaggcc ctgcacaacc actacaccca gaagtccctg   1320
tccctgtccc ccggcaagtg a                                             1341
```

<210> SEQ ID NO 78
<211> LENGTH: 1353
<212> TYPE: DNA
<213> ORGANISM: Artificial Sequence
<220> FEATURE:
<223> OTHER INFORMATION: Description of Artificial Sequence: Synthetic Heavy chain coding gene

<400> SEQUENCE: 78

```
gaggtgcagc tgctggagtc cggcggcggc ctggtgcagc ccggcggctc cctgcggctg     60
tcctgcgccg cctccggctt caccttctcc aactacgaca tgtcctgggt gcggcaggcc    120
cccggcaagg gcctggagtg ggtgtccgcc atctaccact ccggctcctc caagtactac    180
gccgactccg tgaagggccg gttcaccatc tcccgggaca actccaagaa caccctgtac    240
ctgcagatga actccctgcg ggccgaggac accgccgtgt actactgcgc ccggggcggc    300
aacggcgcct gggacaccgg cttcgactac tggggccagg gcaccctggt gaccgtgtcc    360
tccgcctcca caagggccc  ctccgtgttc cccctggccc cctcctccaa gtccacctcc    420
ggcggcaccg ccgccctggg ctgcctggtg aaggactact cccccgagcc cgtgaccgtg    480
tcctggaact ccggcgccct gacctccggc gtgcacacct tccccgccgt gctgcagtcc    540
tccggcctgt actccctgtc ctccgtcgtg accgtgccct cctcctccct gggcacccag    600
acctacatct gcaacgtgaa ccacaagccc tccaacacca aggtggacaa gaaggtggag    660
cccaagtcct gcgacaagac ccacacctgc cctccctgcc ccgccccga  gctgctgggc    720 ggccctccg  tgttcctgtt ccctcctaag cccaaggaca ccctgatgat ctcccggacc    780
```

| | |
|---|---|
| cccgaggtga cttgcgtggt ggtggacgtg tcccacgagg accccgaggt gaagttcaac | 840 |
| tggtacgtgg acggcgtgga ggtgcacaac gccaagacca agccccggga ggagcagtac | 900 |
| aactccacct accgggtggt gtccgtgctg accgtgctgc accaggactg gctgaacggc | 960 |
| aaggagtaca agtgcaaggt gtccaacaag gccctgcccg cccccatcga aagaccatc | 1020 |
| tccaaggcca agggccagcc ccgggagccc caggtgtaca ccctgccccc ctcccgggag | 1080 |
| gagatgacca gaaccaggt gtccctgacc tgcctggtga agggcttcta cccctccgac | 1140 |
| atcgccgtgg agtgggagtc caacggccag cccgagaaca actacaagac caccccccc | 1200 |
| gtgctggact ccgacggctc cttcttcctg tactccaagc tgaccgtgga caagtcccgg | 1260 |
| tggcagcagg gcaacgtgtt ctcctgctcc gtgatgcacg aggccctgca caaccactac | 1320 |
| acccagaagt ccctgtccct gtcccccggc aag | 1353 |

<210> SEQ ID NO 79
<211> LENGTH: 1374
<212> TYPE: DNA
<213> ORGANISM: Artificial Sequence
<220> FEATURE:
<223> OTHER INFORMATION: Description of Artificial Sequence: Synthetic Heavy chain coding gene

<400> SEQUENCE: 79

| | |
|---|---|
| gaagttcaac tgttggaatc cgggggtggt ctggtccaac tggagggtc tcttagactg | 60 |
| agttgtgctg cttcaggctt cacatttagc tcatatgata tgtcctgggt cagacaggcc | 120 |
| cccggcaaag gtcttgaatg ggtatctggt attagtcatg gatctggcaa caagtactac | 180 |
| gctgatagtg tcaaaggacg attcaccata tctcgtgaca actctaaaaa cactttgtac | 240 |
| ttgcagatga actcactgcg tgccgaagac acagccgtgt attattgcgc taagcgtctc | 300 |
| tcactccgca ggcgaccttc ctattacagc gacaacgcta tggatgtctg ggggcagggt | 360 |
| acactcgtca ccgtgtcatc agcctccacc aagggcccct ccgtgttccc cctggccccc | 420 |
| tcctccaagt ccacctccgg cggcaccgcc gccctgggct gcctggtgaa ggactacttc | 480 |
| cccgagcccg tgaccgtgtc ctggaactcc ggcgccctga cctccggcgt gcacaccttc | 540 |
| cccgccgtgc tgcagtcctc cggcctgtac tccctgtcct ccgtcgtgac cgtgccctcc | 600 |
| tcctccctgg gcacccagac ctacatctgc aacgtgaacc acaagccctc caacaccaag | 660 |
| gtggacaaga aggtggagcc caagtcctgc gacaagaccc acacctgccc ctcctgcccc | 720 |
| gcccccgagc tgctgggcgg ccccctccgtg ttcctgttcc ctcctaagcc caaggacacc | 780 |
| ctgatgatct cccggacccc cgaggtgact tgcgtggtgg tggacgtgtc ccacgaggac | 840 |
| cccgaggtga agttcaactg gtacgtggac ggcgtggagg tgcacaacgc caagaccaag | 900 |
| ccccgggagg agcagtacaa ctccacctac cgggtggtgt ccgtgctgac cgtgctgcac | 960 |
| caggactggc tgaacggcaa ggagtacaag tgcaaggtgt ccaacaaggc cctgcccgcc | 1020 |
| cccatcgaga gaccatctc caaggccaag ggccagcccc gggagcccca ggtgtacacc | 1080 |
| ctgcccccct cccgggagga gatgaccaag aaccaggtgt ccctgacctg cctggtgaag | 1140 |
| ggcttctacc cctccgacat cgccgtggag tgggagtcca acggccagcc cgagaacaac | 1200 |
| tacaagacca ccccccccgt gctggactcc gacggctcct cttcctgta ctccaagctg | 1260 |
| accgtggaca agtcccggtg gcagcagggc aacgtgttct cctgctccgt gatgcacgag | 1320 |
| gccctgcaca accactacac ccagaagtcc ctgtccctgt ccccggcaa gtga | 1374 |

<210> SEQ ID NO 80

<211> LENGTH: 1371
<212> TYPE: DNA
<213> ORGANISM: Artificial Sequence
<220> FEATURE:
<223> OTHER INFORMATION: Description of Artificial Sequence: Synthetic
      Heavy chain coding gene

<400> SEQUENCE: 80

```
gaggtgcagc tgctggagtc cggcggcggc ctggtgcagc ccggcggctc cctgcggctg      60
tcctgcgccg cctccggctt caccttctcc aactacgcca tgtcctgggt gcggcaggcc     120
cccggcaagg gcctggagtg ggtgtcctcc atctcccaca actccggctc cacctactac     180
gccgactccg tgaagggccg gttcaccatc tcccgggaca ctccaagaa cccctgtac      240 ctgcagatga actccctgcg ggccgaggac accgccgtgt actactgcgc aagttcatc     300 tccgcccgga gtccctggg ccggtcctac tccaacggca tggacgtgtg ggggcagggc     360
accctggtga ccgtgtcctc cgcctccacc aagggcccct ccgtgttccc cctggccccc    420
tcctccaagt ccacctccgg cggcaccgcc gccctgggct gcctggtgaa ggactacttc    480
cccgagcccg tgaccgtgtc ctggaactcc ggcgccctga cctccggcgt gcacaccttc    540
cccgccgtgc tgcagtcctc cggcctgtac tccctgtcct ccgtcgtgac cgtgccctcc    600
tcctccctgg gcacccagac ctacatctgc aacgtgaacc acaagccctc caacaccaag    660
gtggacaaga aggtggagcc caagtcctgc gacaagaccc acacctgccc tcctgcccc    720 gcccccgagc tgctgggcgg cccctccgtg ttcctgttcc ctcctaagcc caaggacacc    780
ctgatgatct cccggacccc cgaggtgact tgcgtggtgg tggacgtgtc ccacgaggac    840
cccgaggtga agttcaactg gtacgtggac ggcgtggagt gcacaacgc caagaccaag    900 ccccgggagg agcagtacaa ctccacctac cgggtggtgt ccgtgctgac cgtgctgcac    960
caggactggc tgaacggcaa ggagtacaag tgcaaggtgt ccaacaaggc cctgcccgcc   1020
cccatcgaga gaccatctc caaggccaag ggccagcccc gggagcccca ggtgtacacc   1080
ctgcccccct cccgggagga gatgaccaag aaccaggtgt ccctgacctg cctggtgaag   1140
ggcttctacc cctccgacat cgccgtggag tgggagtcca acggccagcc cgagaacaac   1200
tacaagacca cccccccgt gctggactcc gacggctcct tcttcctgta ctccaagctg   1260
accgtggaca gtccggtg gcagcagggc aacgtgttct cctgctccgt gatgcacgag   1320
gccctgcaca accactacac ccagaagtcc ctgtccctgt ccccggcaa g              1371
```

<210> SEQ ID NO 81
<211> LENGTH: 1371
<212> TYPE: DNA
<213> ORGANISM: Artificial Sequence
<220> FEATURE:
<223> OTHER INFORMATION: Description of Artificial Sequence: Synthetic
      Heavy chain coding gene

<400> SEQUENCE: 81

```
gaagtacagt tgcttgaaag tggcggtggt cttgtccagc caggcggttc ccttcggctg      60
tcttgcgccg caagtggctt cactttcagc gactatgata tgtcttgggt ccgccaagca     120
ccaggaaagg gacttgaatg ggtgagtgta atcagtcctg acggagggtc aatttattat     180
gcagattcag tcaagggtcg attcactata tcccgagaca actccaaaaa tactctttat     240
cttcagatga actctttgag agctgaagac accgcagttt attactgtgc tcgggatgta     300
gtggagtgca atatgaatcc ctgctcatac gacaacgcaa tggatgtttg ggggcagggg     360
actctggtga cagtcagctc tgcctccacc aagggcccct ccgtgttccc cctggccccc    420
```

| | |
|---|---|
| tcctccaagt ccacctccgg cggcaccgcc gccctgggct gcctggtgaa ggactacttc | 480 |
| cccgagcccg tgaccgtgtc ctggaactcc ggcgccctga cctccggcgt gcacaccttc | 540 |
| cccgccgtgc tgcagtcctc cggcctgtac tccctgtcct ccgtcgtgac cgtgccctcc | 600 |
| tcctccctgg gcacccagac ctacatctgc aacgtgaacc acaagccctc caacaccaag | 660 |
| gtggacaaga aggtggagcc caagtcctgc gacaagaccc acacctgccc tccctgcccc | 720 |
| gcccccgagc tgctgggcgg ccctccgtg ttcctgttcc ctcctaagcc caaggacacc | 780 |
| ctgatgatct cccggacccc cgaggtgact gcgtggtgg tggacgtgtc ccacgaggac | 840 |
| cccgaggtga agttcaactg gtacgtggac ggcgtggagg tgcacaacgc caagaccaag | 900 |
| ccccgggagg agcagtacaa ctccacctac cgggtggtgt ccgtgctgac cgtgctgcac | 960 |
| caggactggc tgaacggcaa ggagtacaag tgcaaggtgt ccaacaaggc cctgcccgcc | 1020 |
| cccatcgaga agaccatctc caaggccaag ggccagcccc gggagcccca ggtgtacacc | 1080 |
| ctgccccct cccgggagga gatgaccaag aaccaggtgt ccctgacctg cctggtgaag | 1140 |
| ggcttctacc cctccgacat cgccgtggag tgggagtcca acggccagcc cgagaacaac | 1200 |
| tacaagacca cccccccgt gctggactcc gacggctcct tcttcctgta ctccaagctg | 1260 |
| accgtggaca gtcccggtg gcagcagggc aacgtgttct cctgctccgt gatgcacgag | 1320 |
| gccctgcaca accactacac ccagaagtcc ctgtccctgt cccccggcaa g | 1371 |

<210> SEQ ID NO 82
<211> LENGTH: 1374
<212> TYPE: DNA
<213> ORGANISM: Artificial Sequence
<220> FEATURE:
<223> OTHER INFORMATION: Description of Artificial Sequence: Synthetic
      Heavy chain coding gene

<400> SEQUENCE: 82

| | |
|---|---|
| gaagtgcagc tgcttgaatc aggaggcggc ctcgtacaac cagggggatc tctcagactg | 60 |
| tcctgcgctg ccagtggctt cactttcagc aactacgata tgtcatgggt gaggcaggca | 120 |
| cctggcaagg gtctggagtg ggtctcaagc ataagtccca gtagtggaag ctcaatttat | 180 |
| tacgccgaca gtgtaaaggg ccggttcacc attagtagag acaattctaa gaataccttg | 240 |
| taccttcaaa tgaatagtct gagagccgaa gataccgcag tttattattg cgctaaggcc | 300 |
| ccagggtggt gtcaggcccc ttcatgctat tatgataatg caatggacgt gtggggtcag | 360 |
| ggtactctgg tcacagtcag tagtgcctcc accaagggcc cctccgtgtt ccccctggcc | 420 |
| ccctcctcca gtccacctc cggcggcacc gccgccctgg gctgcctggt gaaggactac | 480 |
| ttccccgagc ccgtgaccgt gtcctggaac tccggcgccc tgacctccgg cgtgcacacc | 540 |
| ttccccgccg tgctgcagtc ctccggcctg tactccctgt cctccgtcgt gaccgtgccc | 600 |
| tcctcctccc tgggcaccca gacctacatc tgcaacgtga accacaagcc ctccaacacc | 660 |
| aaggtggaca agaaggtgga gcccaagtcc tgcgacaaga cccacacctg ccctccctgc | 720 |
| cccgccccg agctgctggg cggccctcc gtgttcctgt tcctcctaa gcccaaggac | 780 |
| accctgatga tctcccggac ccccgaggtg acttgcgtgg tggtggacgt gtcccacgag | 840 |
| gaccccgagg tgaagttcaa ctggtacgtg gacggcgtgg aggtgcacaa cgccaagacc | 900 |
| aagccccggg aggagcagta caactccacc taccgggtgg tgtccgtgct gaccgtgctg | 960 |
| caccaggact ggctgaacgg caaggagtac aagtgcaagg tgtccaacaa ggccctgccc | 1020 |
| gccccccatcg agaagaccat ctccaaggcc aagggccagc cccgggagcc ccaggtgtac | 1080 |

```
accctgcccc cctcccggga ggagatgacc aagaaccagg tgtccctgac ctgcctggtg    1140
aagggcttct accccctccga catcgccgtg gagtgggagt ccaacggcca gcccgagaac    1200
aactacaaga ccaccccccc cgtgctggac tccgacggct ccttcttcct gtactccaag    1260
ctgaccgtgg acaagtcccg gtggcagcag ggcaacgtgt tctcctgctc cgtgatgcac    1320
gaggccctgc acaaccacta cacccagaag tccctgtccc tgtcccccgg caag          1374
```

<210> SEQ ID NO 83
<211> LENGTH: 648
<212> TYPE: DNA
<213> ORGANISM: Artificial Sequence
<220> FEATURE:
<223> OTHER INFORMATION: Description of Artificial Sequence: Synthetic
      Light chain coding gene

<400> SEQUENCE: 83

```
cagtctgtgc tgacacaacc accttctgcc tctgggactc caggccagcg ggttaccatt    60
agctgttctg gtagttctag taatatcggt aacaacaatg tgaattggta tcaacaactg    120
ccaggaaccg cccctaagtt gctcatatat tatgataaca gcggccttc aggcgttcct    180 gatcgtttct ccggctctaa aagtggcaca tccgccagtc ttgctatcag cggtctcaga    240
tccgaggacg aggccgacta ttattgtggt acatgggacg cttccctgtc aggttacgtc    300
tttggcggcg gcacaaaact gacagttctt ggccagccca aggccgcccc ctccgtgacc    360
ctgttccccc cctcctccga ggagctgcag gccaacaagg ccaccctggt gtgcctgatc    420
tccgacttct accccggcgc cgtgaccgtg gcctggaagg ccgactcctc ccccgtgaag    480
gccggcgtgg agaccaccac ccctccaag cagtccaaca acaagtacgc cgcctcctcc    540
tacctgtccc tgaccccga gcagtggaag tccaccggt cctactcctg ccaggtgacc    600
cacgagggct ccaccgtgga agaccgtg gcccccgccg agtgctcc                   648
```

<210> SEQ ID NO 84
<211> LENGTH: 648
<212> TYPE: DNA
<213> ORGANISM: Artificial Sequence
<220> FEATURE:
<223> OTHER INFORMATION: Description of Artificial Sequence: Synthetic
      Light chain coding gene

<400> SEQUENCE: 84

```
cagtctgtgc tgacccagcc tccccctgct tctggcaccc ctggccagag agtgaccatc    60
tcctgctccg gctcctcctc caacatcggc tccaacaccg tgtactggta tcagcagctg    120
cccggcaccg cccccaagct gctgatctac gccaactccc agcggccctc cggcgtgccc    180
gacagattct ccggctccaa gtccggcacc tccgcctccc tggccatctc cggcctgaga    240
tctgaggacg aggccgacta ctactgcggc tcctgggact actccctgtc cggctacgtg    300
ttcggcggag gcaccaagct gaccgtgctg ggccagccta aggccgctcc ctccgtgacc    360
ctgttccccc catcctccga ggaactgcag gccaacaagg ccaccctggt ctgcctgatc    420
tccgacttct accctggcgc cgtgaccgtg gcctggaagg ccgacagctc tcctgtgaag    480
gccggcgtgg aaaccaccac cccctccaag cagtccaaca caaatacgc cgcctcctcc    540 tacctgtccc tgaccccga gcagtggaag tccaccggt cctacagctg ccaggtcaca    600
cacgagggct ccaccgtgga aaagaccgtg gcccctgccg agtgctcc                648
```

<210> SEQ ID NO 85

```
<211> LENGTH: 648
<212> TYPE: DNA
<213> ORGANISM: Artificial Sequence
<220> FEATURE:
<223> OTHER INFORMATION: Description of Artificial Sequence: Synthetic
      Light chain coding gene

<400> SEQUENCE: 85
cagagtgttt tgacccagcc tccttccgcc agcggcaccc ctgggcaacg ggttacaatc      60
agctgttccg ggagcagcag taacattggt aataataacg tctcttggta tcagcagttg     120
cctggcacag cacctaagct cctgatttac gctgactccc accggccttc cggcgtccct     180
gatcgtttct ccgggtcaaa aagtggaacc tcagcaagcc ttgcaatcag cggactgcgg     240
tccgaagatg aagctgacta ctactgcgct acctgggatt actcattgtc cggctacgtc     300 tttgggggg gaaccaaatt gacagtcttg ggtcagccca aggccgcccc ctccgtgacc      360
ctgttccccc cctcctccga ggagctgcag gccaacaagg ccaccctggt gtgcctgatc     420
tccgacttct accccggcgc cgtgaccgtg gcctggaagg ccgactcctc ccccgtgaag     480
gccggcgtgg agaccaccac ccctccaag cagtccaaca acaagtacgc cgcctcctcc      540
tacctgtccc tgacccccga gcagtggaag tcccaccggt cctactcctg ccaggtgacc     600
cacgagggct ccaccgtgga agaccgtg gccccgccg agtgctcc                     648

<210> SEQ ID NO 86
<211> LENGTH: 648
<212> TYPE: DNA
<213> ORGANISM: Artificial Sequence
<220> FEATURE:
<223> OTHER INFORMATION: Description of Artificial Sequence: Synthetic
      Light chain coding gene

<400> SEQUENCE: 86
cagtccgtgc tgacccagcc ccctccgcc tccggcaccc ccggccagcg ggtgaccatc       60
tcctgctccg gctcctcctc caacatcggc tccaacgacg tgtcctggta ccagcagctg     120
cccggcaccg cccccaagct gctgatctac tacgacaaca accggccctc cggcgtgccc     180
gaccggttct ccggctccaa gtccggcacc tccgcctccc tggccatctc cggcctgcgg     240
tccgaggacg aggccgacta ctactgcggc gcctgggacg actccctgtc cggctacgtg     300
ttcggcggcg gcaccaagct gaccgtgctg ggccagccca aggccgcccc ctccgtgacc     360
ctgttccccc cctcctccga ggagctgcag gccaacaagg ccaccctggt gtgcctgatc     420
tccgacttct accccggcgc cgtgaccgtg gcctggaagg ccgactcctc ccccgtgaag     480
gccggcgtgg agaccaccac ccctccaag cagtccaaca acaagtacgc cgcctcctcc      540
tacctgtccc tgacccccga gcagtggaag tcccaccggt cctactcctg ccaggtgacc     600
cacgagggct ccaccgtgga agaccgtg gccccgccg agtgctcc                     648

<210> SEQ ID NO 87
<211> LENGTH: 651
<212> TYPE: DNA
<213> ORGANISM: Artificial Sequence
<220> FEATURE:
<223> OTHER INFORMATION: Description of Artificial Sequence: Synthetic
      Light chain coding gene

<400> SEQUENCE: 87
caaagcgtac tcacccagcc cccatccgca tctggcactc tggtcaacg ggttacaatc       60 tcttgtactg ggtcaagttc caatattgga aataacgcag tgaactggta tcagcagctc     120
```

```
cctggcaccg cccctaaact cttgatatac tatgactcta atcggccaag tggagtcccc    180
gataggttct caggttctaa gagtggcaca agtgccagcc tggcaatctc agggctcagg    240
tccgaagatg aggctgatta ttactgcgga gcttgggatg atagcctgag tggctacgtc    300
ttcggggag gaacaaaatt gaccgtactt ggccagccca aggccgcccc ctccgtgacc     360
ctgttccccc cctcctccga ggagctgcag gccaacaagg ccaccctggt gtgcctgatc    420
tccgacttct accccggcgc cgtgaccgtg gcctggaagg ccgactcctc ccccgtgaag    480
gccggcgtgg agaccaccac ccctccaag cagtccaaca acaagtacgc cgcctcctcc     540
tacctgtccc tgaccccga gcagtggaag tcccaccggt cctactcctg ccaggtgacc     600
cacgagggct ccaccgtgga gaagaccgtg gcccccgccg agtgctcctg a             651
```

<210> SEQ ID NO 88
<211> LENGTH: 648
<212> TYPE: DNA
<213> ORGANISM: Artificial Sequence
<220> FEATURE:
<223> OTHER INFORMATION: Description of Artificial Sequence: Synthetic
    Light chain coding gene

<400> SEQUENCE: 88

```
cagtccgtgc tgacccagcc cccctccgcc tccggcaccc ccggccagcg ggtgaccatc    60
tcctgcaccg gctcctcctc caacatcggc tccaacgacg tgacctggta ccagcagctg    120
cccggcaccg cccccaagct gctgatctac gccgactcca gcggccctc cggcgtgccc     180
gaccggttct ccggctccaa gtccggcacc tccgcctccc tggccatctc cggcctgcgg    240
tccgaggacg aggccgacta ctactgcggc acctgggact actccctgtc cggctacgtg    300
ttcggcggcg gcaccaagct gaccgtgctg ggccagccca aggccgcccc ctccgtgacc    360
ctgttccccc cctcctccga ggagctgcag gccaacaagg ccaccctggt gtgcctgatc    420
tccgacttct accccggcgc cgtgaccgtg gcctggaagg ccgactcctc ccccgtgaag    480
gccggcgtgg agaccaccac ccctccaag cagtccaaca acaagtacgc cgcctcctcc     540
tacctgtccc tgaccccga gcagtggaag tcccaccggt cctactcctg ccaggtgacc     600
cacgagggct ccaccgtgga gaagaccgtg gcccccgccg agtgctcc                 648
```

<210> SEQ ID NO 89
<211> LENGTH: 648
<212> TYPE: DNA
<213> ORGANISM: Artificial Sequence
<220> FEATURE:
<223> OTHER INFORMATION: Description of Artificial Sequence: Synthetic
    Light chain coding gene

<400> SEQUENCE: 89

```
caaagtgtat tgactcaacc tccctccgct tccggtacac agggcagcg agtaaccatc      60
agttgcagtg gcagcagctc caatatcgga agcaattatg taagttggta tcaacagttg    120
ccagggaccg ctccaaaact gttgatctat gacgacagtc accgtccttc aggtgtgccc    180
gaccgatttt caggcagcaa gagcggcaca tccgcctccc tcgctatctc cggcctccga    240
tccgaagatg aggccgacta ctattgtgga gcctgggacg actcccttag tggctatgtg    300
tttggggag ggacaaagtt gaccgtactt ggccagccca aggccgcccc ctccgtgacc     360
ctgttccccc cctcctccga ggagctgcag gccaacaagg ccaccctggt gtgcctgatc    420
tccgacttct accccggcgc cgtgaccgtg gcctggaagg ccgactcctc ccccgtgaag    480
gccggcgtgg agaccaccac ccctccaag cagtccaaca acaagtacgc cgcctcctcc     540
```

```
tacctgtccc tgaccccga gcagtggaag tcccaccggt cctactcctg ccaggtgacc    600
cacgagggct ccaccgtgga gaagaccgtg gcccccgccg agtgctcc               648
```

<210> SEQ ID NO 90
<211> LENGTH: 648
<212> TYPE: DNA
<213> ORGANISM: Artificial Sequence
<220> FEATURE:
<223> OTHER INFORMATION: Description of Artificial Sequence: Synthetic
      Light chain coding gene

<400> SEQUENCE: 90

```
cagtcagttc ttacacaacc cccatccgct tctggcactc ccggccagcg cgtaactata    60
tcttgctctg ggagtagtag caatatcggt aataatgatg tctcatggta ccaacagctg   120
cctggaacag cccccaaact cctcatttat gatgactctc aaaggccaag tggtgtgcca   180
gacagatttt ccggtagcaa gagtggaaca tcagcaagtc ttgctataag tggcttgcgt   240
tccgaggacg aggccgacta ttattgtggc gcatgggatg actcactgag cggctacgtt   300 ttcggggggcg gtactaagtt gaccgttttg gacagcccca aggccgcccc ctccgtgacc   360
ctgttccccc cctcctccga ggagctgcag gccaacaagg ccaccctggt gtgcctgatc   420
tccgacttct accccggcgc cgtgaccgtg gcctggaagg ccgactcctc ccccgtgaag   480
gccggcgtgg agaccaccac ccctccaag cagtccaaca caagtacgc cgcctcctcc    540 tacctgtccc tgaccccga gcagtggaag tcccaccggt cctactcctg ccaggtgacc   600
cacgagggct ccaccgtgga gaagaccgtg gcccccgccg agtgctcc               648
```

<210> SEQ ID NO 91
<211> LENGTH: 330
<212> TYPE: PRT
<213> ORGANISM: Artificial Sequence
<220> FEATURE:
<223> OTHER INFORMATION: Description of Artificial Sequence: Synthetic
      Heavy chain constant region

<400> SEQUENCE: 91

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 92
<211> LENGTH: 993
<212> TYPE: DNA
<213> ORGANISM: Artificial Sequence
<220> FEATURE:
<223> OTHER INFORMATION: Description of Artificial Sequence: Synthetic
      Heavy chain constant region coding gene

<400> SEQUENCE: 92

```
gcctccacca agggcccctc cgtgttcccc ctggccccct cctccaagtc cacctccggc    60
ggcaccgccg ccctgggctg cctggtgaag gactacttcc ccgagcccgt gaccgtgtcc   120
tggaactccg gcgccctgac ctccggcgtg cacaccttcc cggccgtgct gcagtcctcc   180
ggcctgtact ccctgtcctc cgtcgtgacc gtgccctcct cctccctggg cacccagacc   240
tacatctgca acgtgaacca caagccctcc aacaccaagg tggacaagaa ggtggagccc   300
aagtcctgcg acaagaccca cacctgccct cctgccccg ccccgagct gctgggcggc   360
ccctccgtgt tcctgttccc tcctaagccc aaggacaccc tgatgatctc ccggacccc   420
gaggtgactt gcgtggtggt ggacgtgtcc cacgaggacc ccgaggtgaa gttcaactgg   480
tacgtggacg gcgtggaggt gcacaacgcc aagaccaagc ccgggagga gcagtacaac   540
tccacctacc gggtggtgtc cgtgctgacc gtgctgcacc aggactggct gaacggcaag   600
gagtacaagt gcaaggtgtc caacaaggcc ctgcccgccc catcgagaa gaccatctcc   660
aaggccaagg ccagccccg ggagcccag gtgtacaccc tgcccccctc ccgggaggag   720
atgaccaaga accaggtgtc cctgacctgc ctggtgaagg cttctaccc ctccgacatc   780
gccgtggagt gggagtccaa cggccagccc gagaacaact acaagaccac cccccccgtg   840
ctggactccg acggctcctt cttcctgtac tccaagctga ccgtggacaa gtcccggtgg   900
cagcagggca acgtgttctc ctgctccgtg atgcacgagg ccctgcacaa ccactacacc   960
cagaagtccc tgtccctgtc ccccggcaag tga                                993
```

<210> SEQ ID NO 93
<211> LENGTH: 105
<212> TYPE: PRT
<213> ORGANISM: Artificial Sequence
<220> FEATURE:
<223> OTHER INFORMATION: Description of Artificial Sequence: Synthetic
      Light chain constant region

<400> SEQUENCE: 93

Gln Pro Lys Ala Ala Pro Ser Val Thr Leu Phe Pro Pro Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Ala Glu Cys Ser
            100                 105

<210> SEQ ID NO 94
<211> LENGTH: 318
<212> TYPE: DNA
<213> ORGANISM: Artificial Sequence
<220> FEATURE:
<223> OTHER INFORMATION: Description of Artificial Sequence: Synthetic
      Light chain constant region coding gene

<400> SEQUENCE: 94
cagcccaagg ccgcccccctc cgtgaccctg ttccccccct cctccgagga gctgcaggcc    60
aacaaggcca ccctggtgtg cctgatctcc gacttctacc ccggcgccgt gaccgtggcc   120
tggaaggccg actcctcccc cgtgaaggcc ggcgtggaga ccaccacccc ctccaagcag   180
tccaacaaca agtacgccgc ctcctcctac ctgtccctga cccccgagca gtggaagtcc   240
caccggtcct actcctgcca ggtgacccac gagggctcca ccgtggagaa gaccgtggcc   300
cccgccgagt gctcctga                                                 318

<210> SEQ ID NO 95
<211> LENGTH: 318
<212> TYPE: DNA
<213> ORGANISM: Artificial Sequence
<220> FEATURE:
<223> OTHER INFORMATION: Description of Artificial Sequence: Synthetic
      Light chain constant region coding gene

<400> SEQUENCE: 95
cagcctaagg ccgctcccctc cgtgaccctg ttcccccccat cctccgagga actgcaggcc    60
aacaaggcca ccctggtctg cctgatctcc gacttctacc ctggcgccgt gaccgtggcc   120
tggaaggccg acagctctcc tgtgaaggcc ggcgtggaaa ccaccacccc ctccaagcag   180
tccaacaaca aatacgccgc ctcctcctac ctgtccctga cccccgagca gtggaagtcc   240
caccggtcct acagctgcca ggtcacacac gagggctcca ccgtggaaaa gaccgtggcc   300
cctgccgagt gctcctga                                                 318

<210> SEQ ID NO 96

```
<211> LENGTH: 17
<212> TYPE: PRT
<213> ORGANISM: Artificial Sequence
<220> FEATURE:
<223> OTHER INFORMATION: Description of Artificial Sequence: Synthetic
      Heavy chain CDR2

<400> SEQUENCE: 96

Ser Ile Ser Pro Asp Ala Ser Asn Thr Tyr Tyr Ala Asp Ser Val Lys
1               5                   10                  15
Gly

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      Heavy chain CDR3

<400> SEQUENCE: 97

Gly Gly Asn Ala Ala Trp Asp Thr Gly Phe Asp Tyr
1               5                   10

<210> SEQ ID NO 98
<211> LENGTH: 116
<212> TYPE: PRT
<213> ORGANISM: Artificial Sequence
<220> FEATURE:
<223> OTHER INFORMATION: Description of Artificial Sequence: Synthetic
      Heavy chain variable region

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Val Arg Gln Ala Pro Gly Lys Gly Leu Glu Trp Val
            35                  40                  45

Ser Ser Ile Ser Pro Asp Ala Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Arg Ala Phe Asp Tyr Trp Gly Gln Gly Thr Leu Val
            100                 105                 110

Thr Val Ser Ser
        115

<210> SEQ ID NO 99
<211> LENGTH: 121
<212> TYPE: PRT
<213> ORGANISM: Artificial Sequence
<220> FEATURE:
<223> OTHER INFORMATION: Description of Artificial Sequence: Synthetic
      Heavy chain variable region

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30
```

Asp Met Ser Trp Val Arg Gln Ala Pro Gly Lys Gly Leu Glu Trp Val
            35                  40                  45

Ser Ala Ile Tyr His Ser Gly Ser Ser Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Asn Ala Ala Trp Asp Thr Gly Phe Asp Tyr Trp Gly
            100                 105                 110

Gln Gly Thr Leu Val Thr Val Ser Ser
        115                 120

<210> SEQ ID NO 100
<211> LENGTH: 446
<212> TYPE: PRT
<213> ORGANISM: Artificial Sequence
<220> FEATURE:
<223> OTHER INFORMATION: Description of Artificial Sequence: Synthetic
      Heavy chain

<400> SEQUENCE: 100

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
            35                  40                  45

Ser Ser Ile Ser Pro Asp Ala Ser Asn Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asn Leu Arg Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 101
<211> LENGTH: 451
<212> TYPE: PRT
<213> ORGANISM: Artificial Sequence
<220> FEATURE:
<223> OTHER INFORMATION: Description of Artificial Sequence: Synthetic
      Heavy chain

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Ala Ile Tyr His Ser Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Ala Ala Trp Asp Thr Gly Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 102
<211> LENGTH: 1338
<212> TYPE: DNA
<213> ORGANISM: Artificial Sequence
<220> FEATURE:
<223> OTHER INFORMATION: Description of Artificial Sequence: Synthetic
      Heavy chain coding gene

<400> SEQUENCE: 102
gaagtgcagc tgctggaatc cggcggaggc ctggtgcagc ctggcggctc tctgagactg      60
tcttgcgccg cctccggctt caccttctcc gactactaca tgtcctgggt gcgacaggcc     120
cctggcaagg gcctggaatg ggtgtcctcc atctcccccg acgcctccaa cacctactac     180
gccgactccg tgaagggccg gttcaccatc tcccggacaa ctccaagaa cacccctgtac     240 ctgcagatga actccctgcg ggccgaggac accgccgtgt actactgcgc caagaacctg     300

| | |
|---|---|
| cgggccttcg actactgggg ccagggcaca ctggtgaccg tgtcctccgc ctccaccaag | 360 |
| ggccctccg tgttccccct ggccccctcc tccaagtcca cctccggcgg caccgccgcc | 420 |
| ctgggctgcc tggtgaagga ctacttcccc gagcccgtga ccgtgtcctg gaactccggc | 480 |
| gccctgacct ccggcgtgca caccttcccc gccgtgctgc agtcctccgg cctgtactcc | 540 |
| ctgtcctccg tcgtgaccgt gccctcctcc tccctgggca cccagaccta catctgcaac | 600 |
| gtgaaccaca gcccctccaa caccaaggtg gacaagaagg tggagcccaa gtcctgcgac | 660 |
| aagacccaca cctgccctcc ctgccccgcc cccgagctgc tgggcggccc ctccgtgttc | 720 |
| ctgttccctc ctaagcccaa ggacaccctg atgatctccc ggaccccga ggtgacttgc | 780 |
| gtggtggtgg acgtgtccca cgaggacccc gaggtgaagt tcaactggta cgtggacggc | 840 |
| gtggaggtgc acaacgccaa gaccaagccc cgggaggagc agtacaactc cacctaccgg | 900 |
| gtggtgtccg tgctgaccgt gctgcaccag gactggctga acggcaagga gtacaagtgc | 960 |
| aaggtgtcca acaaggccct gcccgccccc atcgagaaga ccatctccaa ggccaagggc | 1020 |
| cagccccggg agcccaggt gtacaccctg cccccctccc gggaggagat gaccaagaac | 1080 |
| caggtgtccc tgacctgcct ggtgaagggc ttctacccct ccgacatcgc cgtggagtgg | 1140 |
| gagtccaacg gccagcccga gaacaactac aagaccaccc cccccgtgct ggactccgac | 1200 |
| ggctccttct cctgtactc caagctgacc gtggacaagt cccggtggca gcagggcaac | 1260 |
| gtgttctcct gctccgtgat gcacgaggcc ctgcacaacc actacaccca gaagtccctg | 1320 |
| tccctgtccc ccggcaag | 1338 |

<210> SEQ ID NO 103
<211> LENGTH: 1353
<212> TYPE: DNA
<213> ORGANISM: Artificial Sequence
<220> FEATURE:
<223> OTHER INFORMATION: Description of Artificial Sequence: Synthetic Heavy chain coding gene

<400> SEQUENCE: 103

| | |
|---|---|
| gaggtgcagc tgctggagtc cggcggcggc ctggtgcagc ccggcggctc cctgcggctg | 60 |
| tcctgcgccg cctccggctt caccttctcc aactacgaca tgtcctgggt gcggcaggcc | 120 |
| cccggcaagg gcctggagtg ggtgtccgcc atctaccact ccggctcctc caagtactac | 180 |
| gccgactccg tgaagggccg gttcaccatc tcccgggaca actccaagaa caccctgtac | 240 |
| ctgcagatga actccctgcg ggccgaggac accgccgtgt actactgcgc ccggggcggc | 300 |
| aacgccgcct gggacaccgg cttcgactac tggggccagg gcaccctggt gaccgtgtcc | 360 |
| tccgcctcca ccaagggccc ctccgtgttc cccctggccc cctcctccaa gtccacctcc | 420 |
| ggcggcaccg ccgccctggg ctgcctggtg aaggactact cccccgagcc cgtgaccgtg | 480 |
| tcctggaact ccggcgccct gacctccggc gtgcacacct tccccgccgt gctgcagtcc | 540 |
| tccggcctgt actccctgtc ctcgtcgtg accgtgccct cctcctccct gggcacccag | 600 |
| acctacatct gcaacgtgaa ccacaagccc tccaacacca aggtggacaa gaaggtggag | 660 |
| cccaagtcct gcgacaagac ccacacctgc cctccctgcc cgccccga gctgctgggc | 720 |
| ggccctccg tgttcctgtt ccctcctaag cccaaggaca cctgatgat ctcccggacc | 780 |
| cccgaggtga cttgcgtggt ggtggacgtg tcccacgagg accccgaggt gaagttcaac | 840 |
| tggtacgtgg acggcgtgga ggtgcacaac gccaagacca gcccggga ggagcagtac | 900 |
| aactccacct accgggtggt gtccgtgctg accgtgctgc accaggactg gctgaacggc | 960 |

```
aaggagtaca agtgcaaggt gtccaacaag gccctgcccg ccccatcga gaagaccatc   1020 tccaaggcca agggccagcc ccgggagccc caggtgtaca ccctgccccc ctcccgggag   1080
gagatgacca agaaccaggt gtccctgacc tgcctggtga agggcttcta ccctccgac    1140 atcgccgtgg agtgggagtc caacggccag cccgagaaca actacaagac cacccccccc   1200
gtgctggact ccgacggctc cttcttcctg tactccaagc tgaccgtgga caagtcccgg   1260
tggcagcagg gcaacgtgtt ctcctgctcc gtgatgcacg aggccctgca caaccactac   1320
acccagaagt ccctgtccct gtccccggc aag                                1353

<210> SEQ ID NO 104
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Cys Val Ile Met
1

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Val Leu Leu
1

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Gly Gly Gly Gly Gly Gly Cys Val Ile Met
1               5                   10
```

ANTIBODY-DRUG CONJUGATE COMPRISING ANTIBODY AGAINST HUMAN ROR1 AND USE FOR THE SAME

RELATED APPLICATIONS

This application claims priority to Korean Republic Application No. 10-2019-0109807, filed Sep. 4, 2019, and Korean Republic Application No. 10-2020-0041527, filed Apr. 6, 2020; the contents of each of which is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 28, 2020, is named LCH-01201_SL.txt and is 123,812 bytes in size.

TECHNICAL FIELD

The present invention relates to new antibody-drug conjugates (ADCs) targeting ROR1, active metabolites of such ADCs, methods for preparation of such ADCs, uses for such ADCs in treatment and/or prevention of illnesses, and uses for such ADCs in production of drugs for treatment and/or prevention of diseases, more specifically diseases associated with over-expression of ROR1, for example cancer. More specifically, the present invention relates to an antibody-drug conjugate comprising an antibody binding with ROR1 or an antigen-binding fragment thereof, and a pharmaceutical composition comprising the same.

BACKGROUND

Cancer is a disease caused by abnormal and uncontrolled cell growth in the tissues of the body, and is the result of uncontrolled cell growth in a variety of tissues. Tumors in early stage cancers can be removed through surgical and radiotherapeutic measures, and metastasized tumors are generally treated palliatively using chemotherapy.

Most chemotherapy agents administered non-orally may induce unwanted adverse effects or serious toxicity as a result of systemic administration. Accordingly, the focus of development has been on developing novel chemotherapy agents to achieve increased efficacy and minimal toxicity/adverse effects through improved and selective action of chemotherapy agents on tumor cells or immediately adjacent tissues.

An antibody-drug conjugate (ADC) is a targeted technology where a toxin or drug is bonded to an antibody which in turn binds to an antigen, the toxin or drug released into a tumor cell, etc., to cause cell death. The technology has superior efficacy over antibody drugs, is able to substantially reduce the risk of adverse effects compared to conventional anti-cancer agents, as it specifically delivers drugs to the target cancer cells with minimum impact to healthy cells, and only releases drugs under specific conditions.

The basic structure of an antibody-drug conjugate is "antibody linker small molecule drug (toxin)". Here, the linker needs to play not only the functional role of linking the antibody and drug, but also ensure that the drug is released properly through antibody-drug dissociation (e.g. as a result of hydrolysis by enzyme) after being circulated through the body and reaching the target cells, and exhibits efficacy against the target cancer cells. That is, the stability of the linker plays a very important role in the efficacy and systemic toxicity of an antibody-drug conjugate (Discovery Medicine 2010, 10(53): 329-39) 85-8 2018-08-14).

The use of monoclonal antibodies for cancer treatment is having substantial success. Monoclonal antibodies are suitable for target-oriented addressing of tumor tissue and tumor cells. Antibody-drug conjugates have become a novel and powerful option for therapy of lymphomas and solid tumors, and recently, immunoregulatory antibodies are seeing significant success in clinical trials. Development of therapeutic antibodies is based on a profound understanding of cancer serology, protein engineering technology, mechanisms of action and resistance, and interactions between immune systems and cancer cells.

Antigens which are expressed on the surface of human cancer cells encompass a broad range of targets which are over-expressed compared to normal tissues, mutated or selectively expressed. The key problem is identifying the appropriate antigens for antibody-based therapies. These therapeutic agents mediate changes in antigen or receptor function (i.e., as a stimulant or antagonist), regulate the immune system through Fc and T cell activation, and exhibit efficacy through the delivery of specific drugs that bind to antibodies targeting specific antigens. Molecular techniques that can alter antibody pharmacokinetics, function, size and immune stimulation are emerging as key elements in the development of novel antibody-based therapies. Evidence from clinical trials of therapeutic antibodies in cancer patients highlights the importance of approaches for selecting optimized antibodies, including affinity and binding of the target antigen and antibodies, selection of antibody structure, and therapeutic approaches (blocking signaling or immune function).

ROR1 is expressed in the process of embryo and fetal development, and controls cell polarity, cell migration and neurite growth, etc. The expression is gradually reduced as development progresses, and it is hardly expressed in adults. It is temporarily expressed in the process of development of B cells, and only little expression has been reported in adipocytes (Hudecek et al., 2010, Blood 116:4532, Matsuda et al., 2001, Mech. Dev. 105:153).

However, as the overexpression of ROR1 is observed in various cancer cells, it is classified as an oncofetal gene. In particular, ROR1 has received attention as an anticancer antibody target, upon discovery that ROR1 is overexpressed in chronic lymphocytic leukemia (CLL) (Klein et al., 2001, J. Exp. Med 194:1625). It has been reported as overexpressed in not only blood cancers such as B-cell leukemia, lymphoma, acute myeloid leukemia (AML), Burkitt lymphoma, mantle cell lymphoma (MCL), acute lymphoblastic leukemia (ALL), chronic lymphocytic leukemia (CLL), Diffuse large B-cell lymphoma (DLBCL), follicular lymphoma (FL) and marginal zone lymphoma (MZL), etc. but also solid cancers including breast cancer, renal cancer, ovarian cancer, gastric cancer, liver cancer, lung cancer, colorectal cancer, pancreatic cancer, skin cancer, bladder cancer, testicular cancer, uterine cancer, prostate cancer, non-small cell lung cancer (NSCLC), neuroblastoma, brain cancer, colon cancer, squamous cell carcinoma, melanoma, myeloma, cervical cancer, thyroid cancer, head and neck cancer and adrenal cancer, etc. It is reported that the expression of ROR1 in such cancers is correlated to poor prognosis in cancer patients and affects cancer metastasis.

Such cancer cell-specific expression of ROR1 indicates that ROR1 can be an effective cancer target, and necessitates the development of an antibody able to specifically recognize the same.

U.S. Pat. No. 9,316,646 relates to an anti-ROR1 antibody, and discloses a monoclonal antibody specifically recognizing a human extracellular domain ROR1.

U.S. Pat. No. 9,266,952 relates to an antibody to ROR1 and its use, and discloses an antibody inducing CLL death by specifically binding to a CLL cell.

Since various anti-cancer antibodies to the same ROR1 antigen may be developed according to the properties or uses of each antibody, when considering cancer-specific expression of ROR1, and its expression in various cancers, it is necessary to develop various antibodies that can replace or complement existing antibodies.

DESCRIPTION

To this technical background, the inventors of the present application have worked to develop antibodies which bind specifically to ROR1, as a result developing anti-ROR1 antibodies exhibiting superior binding to ROR1. By applying a linker including an effective self-immolative group, which is stable in the plasma and in circulation, yet allows a drug to be easily released and exhibit efficacy in a cancer cell, to the anti-ROR1 antibody to further reinforce the effect of the antibody, it is possible to provide a useful antibody-drug conjugate (ADC) which targets ROR1 and is effective at treating and/or preventing cancer illnesses.

The present invention provides novel antibody-drug conjugates targeting ROR1, or a salt thereof.

In certain embodiments, the present invention provides a drug-antibody conjugate includes an antibody that binds specifically to ROR1 and a drug linked thereto, as well as pharmaceutical compositions including the same.

Furthermore, the present invention provides an antibody-linker-drug (toxin) system, which allows a drug and/or toxin to reach a target cell and effectively exhibit efficacy while substantially reducing toxicity, by grafting technology for a linker including a self-immolative group which is stable in the plasma and in circulation, yet allows a drug to be easily released in a cancer cell to exhibit efficacy.

Technical Solution

One aspect of the present invention provides an antibody conjugate of the General Formula I, or a pharmaceutically acceptable salt or solvate thereof.

Ab-(X)y      [General Formula I]

Where:

Ab is an antibody specifically binding to the extracellular domain of ROR1, the antibody including a heavy chain variable region and a light chain variable region, or an antigen-binding fragment thereof.

wherein the antibody or antigen-binding fragment thereof comprises:

a heavy chain variable region comprising a CDRH1 comprising the amino acid sequence of any one of SEQ ID NOs. 1 through 5;

a CDRH2 comprising the amino acid sequence of any one of SEQ ID NOs. 6 through 13 and 96; and a CDRH3 comprising the amino acid sequence of any one of SEQ ID NOs. 14 through 21 and 97; and a light chain variable region comprising a CDRL1 comprising the amino acid sequence of any one of SEQ ID NOs. 22 through 29;

a CDRL2 comprising the amino acid sequence of any one of SEQ ID NOs. 30 through 37; and a CDRL3 comprising the amino acid sequence of any one of SEQ ID NOs. 38 through 42;

X is a chemical residue which independently includes at least one active agent and a linker;

the linker links Ab and the at least one active agent; and y is an integer from 1 to 20.

In some embodiments, the antibody specifically recognizes the extracellular domain of, for example, human ROR1, and exhibits cross-reactivity to mouse ROR1.

Included in the scope of the present invention is not only a complete antibody form which specifically binds to ROR1, but also antigen-binding fragments of the antibody molecule.

In some embodiments, the antibody or antigen-binding fragment according to the present invention comprises (i) complementarity determining regions of CDRH1, CDRH2 and CDRH3, and/or (ii) complementarity determining regions of CDRL1, CDRL2 and CDRL3, where the CDRH1 comprises the amino acid sequence of any one of SEQ ID NOs 1 through 5; the CDRH2 comprises the amino acid sequence of any one of SEQ ID NOs 6 through 13 and 96; the CDRH3 comprises the amino acid sequence of any one of SEQ ID NOs 14 through 21 and 97; the CDRL1 comprises the amino acid sequence of any one of SEQ ID NOs 22 through 29; the CDRL2 comprises the amino acid sequence of any one of SEQ ID NOs 30 through 37; and the CDRL3 comprises the amino acid sequence of any one of SEQ ID NOs 38 through 42. CDRH indicates a CDR included in a heavy chain variable region, and CDRL indicates a CDR included in a light chain variable region.

From this perspective, in other embodiments, the antibody or antigen-binding fragment according to the present invention includes (i) complementarity determining regions of CDRH1, CDRH2 and CDRH3, and/or (ii) complementarity determining regions of CDRL1, CDRL2 and CDRL3, where the CDRH1 comprises the amino acid sequence of any one of SEQ ID NOs 1 through 5; the CDRH2 comprises the amino acid sequence of any one of SEQ ID NOs 6 through 13 and 96; the CDRH3 comprises the amino acid sequence of any one of SEQ ID NOs 14 through 21 and 97; the CDRL1 comprises the amino acid sequence of any one of SEQ ID NOs 22 through 29; the CDRL2 comprises the amino acid sequence of any one of SEQ ID NOs 30 through 37; and the CDRL3 comprises the amino acid sequence of any one of SEQ ID NOs 38 through 42.

In other embodiments, the CDRH1, CDRH2 and CDRH3 comprise the amino acid sequence of SEQ ID NOs 1, 6, and 14, respectively; SEQ IDs NO 2, 7 and 15 respectively; SEQ ID NOs 1, 8 and 16, respectively; SEQ ID NOs 3, 9 and 17, respectively; SEQ ID NOs 1, 10 and 18, respectively; SEQ ID NOs 4, 11 and 19, respectively; SEQ ID NOs 5, 12 and 20, respectively; SEQ ID NOs 3, 13 and 21, respectively; SEQ ID NOs 2, 96 and 15, respectively; or SEQ ID NOs 3, 9 and 97, respectively.

In other embodiments, the CDRL1, CDRL2 and CDRL3 comprise the amino acid sequence of SEQ ID NOs 22, 30 and 38, respectively; SEQ ID NOs 23, 31 and 39, respectively; SEQ ID NOs 24, 32 and 40, respectively; SEQ ID NOs 25, 33 and 41, respectively; SEQ ID NOs 26, 34 and 41, respectively; SEQ ID NOs 27, 35 and 42, respectively; SEQ ID NOs 28, 36 and 41, respectively; or SEQ ID NOs 29, 37 and 41, respectively.

In other embodiments, the antibody comprises a set of CDRs: CDRH1, CDRH2, CDRH3, CDRL1, CDRL2, and CDRL3 in which:

(a) CDRH1, CDRH2 and CDRH3 of SEQ ID NO 1, 6 and 14, respectively, and CDRL1, CDRL2 and CDRL3 of SEQ ID NO 22, 30 and 38, respectively;

(b) CDRH1, CDRH2 and CDRH3 comprise the amino acid sequence of SEQ ID NOs 2, 7 and 15, respectively, and CDRL1, CDRL2 and CDRL3 comprise the amino acid sequence of SEQ ID NOs 23, 31 and 39, respectively;

(c) CDRH1, CDRH2 and CDRH3 comprise the amino acid sequence of SEQ ID NOs 1, 8 and 16, respectively, and CDRL1, CDRL2 and CDRL3 comprise the amino acid sequence of SEQ ID NOs 24, 32 and 40, respectively;

(d) CDRH1, CDRH2 and CDRH3 comprise the amino acid sequence of SEQ ID NOs 3, 9 and 17, respectively, and CDRL1, CDRL2 and CDRL3 comprise the amino acid sequence of SEQ ID NOs 25, 33 and 41, respectively;

(e) CDRH1, CDRH2 and CDRH3 comprise the amino acid sequence of SEQ ID NOs 1, 10 and 18, respectively, and CDRL1, CDRL2 and CDRL3 comprise the amino acid sequence of SEQ ID NOs 26, 34 and 41, respectively;

(f) CDRH1, CDRH2 and CDRH3 comprise the amino acid sequence of SEQ ID NOs 4, 11 and 19, respectively, and CDRL1, CDRL2 and CDRL3 comprise the amino acid sequence of SEQ ID NOs 27, 35 and 42, respectively;

(g) CDRH1, CDRH2 and CDRH3 comprise the amino acid sequence of SEQ ID NOs 5, 12 and 20, respectively, and CDRL1, CDRL2 and CDRL3 comprise the amino acid sequence of SEQ ID NOs 28, 36 and 41, respectively;

(h) CDRH1, CDRH2 and CDRH3 comprise the amino acid sequence of SEQ ID NOs 3, 13 and 21, respectively, and CDRL1, CDRL2 and CDRL3 comprise the amino acid sequence of SEQ ID NOs 29, 37 and 41, respectively;

(i) CDRH1, CDRH2 and CDRH3 comprise the amino acid sequence of SEQ ID NOs 2, 96 and 15, respectively, and CDRL1, CDRL2 and CDRL3 comprise the amino acid sequence of SEQ ID NOs 23, 31 and 39, respectively, or;

(j) CDRH1, CDRH2 and CDRH3 comprise the amino acid sequence of SEQ ID NOs 3, 9 and 97, respectively, and CDRL1, CDRL2 and CDRL3 comprise the amino acid sequence of SEQ ID NOs 25, 33 and 41, respectively.

In some embodiments, the antibody or antigen-binding fragment according to the present invention comprises a heavy chain variable region i comprising: the amino acid sequence of any one of SEQ ID NOs 43 through 50, 98 and 99; at least 90% sequence identity to the amino acid sequence of any one of SEQ ID NOs 43 through 50, 98 and 99, or; at least 95% sequence identity to the amino acid sequence of any one of SEQ ID NOs 43 through 50, 98 and 99.

In some embodiments, the antibody or antigen-binding fragment according to the present invention comprises a light chain variable region comprising: the amino acid sequence of any one of SEQ ID NOs 51 through 58; at least 90% sequence identity to the amino acid sequence of any one of SEQ ID NOs 51 through 58, or; at least 95% sequence identity to the amino acid sequence of any one of SEQ ID NOs 51 through 58.

In some embodiments, the antibody or antigen-binding fragment according to the present invention comprises a combination of heavy chain and light chain variable regions comprising the amino acid sequence of: sequences indicated by SEQ ID NOs 43 and 51, respectively; SEQ ID NOs 44 and 52, respectively; SEQ ID NOs 45 and 53, respectively; SEQ ID NOs 46 and 54, respectively; SEQ ID NOs 47 and 55, respectively; SEQ ID NOs 48 and 56, respectively; SEQ ID NOs 49 and 57, respectively; SEQ ID NOs 50 and 58, respectively; SEQ ID NOs 98 and 52, respectively, or SEQ ID NOs 99 and 54, respectively; at least 90% complementarity with these amino acid sequences, or; at least 95% complementarity with these amino acid sequences.

In some embodiments, the antibody or antigen-binding fragment according to the present invention is a human antibody, a full human antibody, or an antigen-binding fragment, having cross-reactivity with mouse ROR1.

In some embodiments, the antibody according to the present invention is a monoclonal antibody, in particular a human monoclonal antibody, having cross-reactivity with mouse ROR1.

In some embodiments, the antibody or antigen-binding fragment according to the present invention specifically recognizes and/or binds to human and mouse ROR1.

In some embodiments, the antibody according to the present invention is of the IgG1, IgG2, IgG3 or IgG4 type.

In some embodiments, the antibody according to the present invention comprises a combination of a heavy chain and a light chain comprising the amino acid sequence of: SEQ ID NOs 59 and 67, respectively; SEQ ID NOs 60 and 68, respectively; SEQ ID NOs 61 and 69, respectively; SEQ ID NOs 62 and 70, respectively; SEQ ID NOs 63 and 71, respectively; SEQ ID NOs 64 and 72, respectively; SEQ ID NOs 65 and 73, respectively, or SEQ ID NOs 66 and 74, respectively.

In some embodiments, the antibody or antigen-binding fragment according to the present invention may include, but is not limited to: a monoclonal antibody, a domain antibody (dAb), a single chain antibody (scab), a Fab fragment, a Fab' fragment, a F(ab')2 fragment, an scFab fragment, an Fv fragment, a dsFv fragment, a single chain variable fragment (scFv), an ScFv-Fc fragment, a single domain heavy chain antibody, a single domain light chain antibody, a variant antibody, a multimeric antibody, a minibody, a diabody, a bispecific antibody or a multispecific antibody.

In some embodiments, the antibody or antigen-binding fragment has specificity to at least one more antigen in addition to the ROR1 antigen. In some embodiments, the at least one more antigen is different from ROR1, and may include, for example, cancer antigen, in which case the antibody may have bi-specificity. A skilled person would be able to select a suitable cancer antigen depending on the specific purpose of the bi-specific antibody.

In another aspect, the present invention provides an isolated polynucleotide encoding the antibody or antigen-binding fragment according to the present invention.

In some embodiments, the polynucleotide according to the present invention is a polynucleotide encoding a CDR disclosed in the present invention.

In some embodiments, the polynucleotide according to the present invention is a polynucleotide encoding a heavy chain or light chain variable region disclosed in the present invention.

In yet other embodiments, the polynucleotide according to the present invention is a polynucleotide encoding a heavy chain or light chain disclosed in the present invention.

In some embodiments, the polynucleotide according to the present invention comprises the sequence of any one of SEQ ID NOs 75 through 82, 102 and 103 which encode a whole-length heavy chain disclosed in the present invention.

In some embodiments, the polynucleotide according to the present invention comprises the sequence of any one of SEQ ID NOs 83 through 90 which encode a whole-length light chain disclosed in the present invention.

The polynucleotide encoding a CDR and variable region according to the present invention may be readily determined from among the above nucleic acid sequences encoding heavy chain and light chain, based on the CDR and variable region amino acid sequences disclosed in the present invention.

In another aspect, a vector including the polynucleotide according to the present invention is provided. In some embodiments, the vector according to the present invention includes an expression vector for antibody production or a vector for CAR-T cells (Chimeric Antigen receptor redirected T cells) or CAR-NK (Natural killer) cells.

In another aspect, a cell line transformed by the vector according to the present invention is provided.

In yet another aspect, the present invention provides a method for preparing an isolated antibody which binds specifically to ROR1 or an antigen-binding fragment thereof, the method comprising a step of isolating an antigen or an antigen-binding fragment thereof from the cell line according to the present invention.

In certain embodiments, the antibody drug conjugate has a structure represented by General Formula IIa:

[Chemical Formula (IIa)]

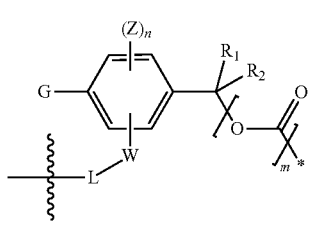

or a pharmaceutically acceptable salt thereof, wherein

G is a sugar, a sugar acid or a sugar derivative;

W is —C(O)—, —C(O)NR'—, —C(O)O—, SO$_2$NR'—, —P(O)R"NR'—, —SONR'— or —PO$_2$NR'—; wherein the C, S or P is directly bound to the phenyl ring;

each Z is independently C$_1$-C$_8$ alkyl, halogen, cyano or nitro;

n is an integer from 0 to 3; and m is 0 or 1;

L is absent, C$_1$-C$_{50}$ alkylene or 1-50 atom heteroalkylene, or L contains at least one branching unit (BR) and at least one connection unit;

R$^1$ and R$^2$ are independently hydrogen, C$_1$-C$_8$ alkyl or C$_3$-C$_8$ cycloalkyl; or R$_1$ and R$_2$, combine to complete a (C$_3$-C$_8$) cycloalkyl ring;

* represents a connection point to the active agent; and

⤳ represents a connection point to the antibody.

In certain preferred embodiments, the antibody drug conjugate has a structure represented by General Formula II:

[General Formula II]

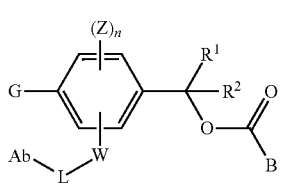

or a pharmaceutically acceptable salt thereof, wherein

G is a glucuronic acid moiety or

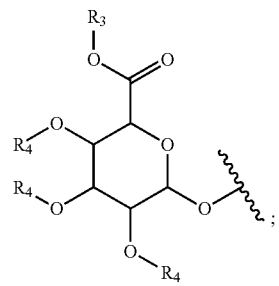

R$^3$ is a hydrogen or carboxyl protecting group;

each of the R$_4$ are independently a hydrogen or hydroxyl protecting group;

B is an active agent;

R$^1$ and R$^2$ are respectively and independently hydrogen, C$_1$-C$_8$ alkyl or C$_3$-C$_8$ cycloalkyl;

W is —C(O)—, —C(O)NR'—, —C(O)O—, SO$_2$NR'—, —P(O)R"NR'—, —SONR'— or —PO$_2$NR'—; wherein the C, S or P is directly bound to a phenyl ring;

R' and R" are each independently are hydrogen, C$_1$-C$_8$ alkyl, C$_3$-C$_8$ cycloalkyl, C$_1$-C$_8$ alkoxy, C$_1$-C$_8$ alkylthio, mono- or di-C$_1$-C$_8$ alkylamino, C$_3$-C$_{20}$ heteroaryl or C$_6$-C$_{20}$ aryl;

each Z is independently C$_1$-C$_8$ alkyl, halogen, cyano or nitro;

n is an integer of 0 to 3; and

L comprises:
A) a C$_1$-C$_{50}$ alkylene or 1-50 atom heteroalkylene satisfying at least one of the following:
  (i) L includes at least one unsaturated bond;
  (ii) L is substituted by a bivalent substituent where 2 atoms in L are the same as in a substituent, thus completing a heteroarylene;
  (iii) L is interrupted by a divalent heteroarylene group;
  (iv) L is a 1 to 50 atom heteroalkylene;
  (v) L is substituted by at least one C$_{1-20}$ alkyl; or
B) at least one isoprenyl derivative unit of General Formula III below which can be recognized by an isoprenoid transferase:

[General Formula III]

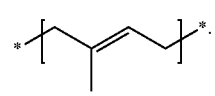

In certain embodiments, G is

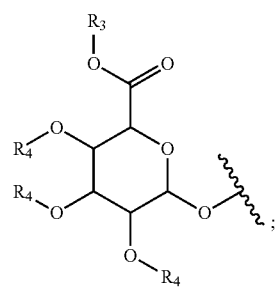

R$^3$ is a hydrogen or a carboxyl protective group; and each R$^4$ is, respectively and independently, a hydrogen or a hydroxyl protective group.

In certain preferred embodiments, R$^3$ is hydrogen, and each R$^4$ is hydrogen.

In certain embodiments, $R^1$ and $R^2$ are hydrogen.

In certain embodiments, Z is independently $C_1$-$C_8$ alkyl, halogen, cyano or nitro.

In certain embodiments, n is 0.

In certain embodiments, W is —C(O)—, —C(O)NR'—, —C(O)O—, $SO_2NR'$—, —P(O)R"NR'—, —SONR'— or —$PO_2NR'$—; the C, S or P is directly bound to the phenyl ring; the R' and R" are respectively and independently compounds which are hydrogen, $C_1$-$C_8$ alkyl, $C_3$-$C_8$ cycloalkyl, $C_1$-$C_8$ alkoxy, $C_1$-$C_8$ alkylthio, mono- or di-$C_1$-$C_8$ alkylamino, $C_3$-$C_{20}$ heteroaryl or $C_6$-$C_{20}$ aryl.

In certain embodiments, W is —C(O)—, —C(O)NR'—, or —C(O)O—. In certain preferred embodiments, W is —C(O)NR'—; and the C(O) is directly bound to a phenyl ring, and NR' binds to L.

In certain embodiments, G is

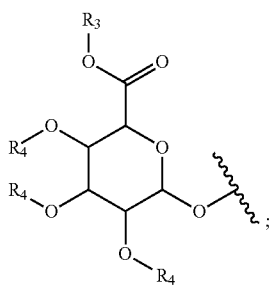

W is —C(O)NR'—, the C(O) is bound to the phenyl ring, NR' binds to L; and $R_3$ and $R_4$ are hydrogen.

In certain embodiments, L is $C_1$-$C_{50}$ alkylene or a 1-50 atom heteroalkylene comprising at least one of:
(i) an unsaturated bond;
(ii) a bivalent substituent where 2 atoms in L are the same as in a substituent, this completing a heteroarylene;
(iii) a divalent heteroarylene group interrupting L;
(iv) a 1 to 50 atom heteroalkylene; or
(v) at least one $C_{1-20}$ alkyl substituent.

In certain embodiments, L is $C_1$-$C_{50}$ alkylene or a 1-50 atom heteroalkylene comprising at least one of:
(i) an unsaturated bond;
(ii) a heteroarylene (e.g., interrupting L);
(iii) a 1 to 50 atom heteroalkylene; or
(iv) at least one $C_{1-20}$ alkyl substituent.

In certain embodiments, L is a nitrogen-comprising 1-50 atom hetero alkylene, the linker includes at least 2 atoms of a hydrophilic amino acid; and the nitrogen forms a peptide bond with a carbonyl of a hydrophilic amino acid. In certain embodiments, W is —C(O)NR'—, and the nitrogen of W is a nitrogen atom of a hydrophilic amino acid. In certain preferred embodiments, the hydrophilic amino acid any one selected from a group comprising arginine, aspartate, asparagine, glutamate, glutamine, histidine, lysine, ornithine, proline, serine and threonine. In certain embodiments, the amino acid covalently bonds an oxime of a linker to a polyethylene glycol unit of the linker. In certain embodiments, the amino acid is selected from arginine, aspartate, asparagine, glutamate, glutamine, histidine, lysine, ornithine, proline, serine and threonine. In certain embodiments, the hydrophilic amino comprises a side chain having a moiety which has electric charge in aqueous solution at a neutral pH. In certain embodiments, the hydrophilic amino acid is aspartate or glutamate. In other embodiments, the hydrophilic amino acid is ornithine or lysine. In yet other embodiments, the hydrophilic amino acid is arginine.

In certain embodiments, L further comprises a peptide, and the peptide comprises at least once hydrophilic amino acid and includes a side chain having a moiety which has electric charge in aqueous solution at a neutral pH. In certain embodiments, each amino acid of the peptide is independently selected from alanine, aspartate, asparagine, glutamate, glutamine, glycine, lysine, ornithine, proline, serine and threonine. In certain preferred embodiments, the peptide comprises at least one aspartate or glutamate. In certain preferred embodiments, W is —C(O)NR'—, and in that the nitrogen of W is a nitrogen atom of an N-terminal amino acid of a peptide. In certain embodiments, the peptide covalently bonds an oxime of a linker to a polyethylene glycol unit of the linker. In certain embodiments, the peptide comprises 2 to 20 amino acids.

In certain embodiments, L is covalently bonded to an antibody by a thioether bond, and the thioether bond includes a sulfur atom of the cysteine of the antibody. In certain embodiments, the amino acid motif is a CYYX sequence; C is cysteine; Y is an aliphatic amino acid; X is any one selected from glutamine, glutamate, serine, cysteine, methionine, alanine and leucine; and the thioether bond includes a sulfur atom of the cysteine of the antibody. In certain embodiments, the amino acid motif is a CYYX sequence; and Y is any one selected from alanine, isoleucine, leucine, methionine and valine. In certain embodiments, the amino acid motif is a CVIM (SEQ ID NO: 104) or CVLL (SEQ ID NO: 105) sequence. In certain embodiments, at least one of the 1 to 20 amino acids preceding the amino acid motif is glycine. In certain embodiments, at least three of the 1 to 20 amino acids preceding the amino acid motif is glycine or proline. In certain embodiments, at least one of the 1 to 20 amino acids preceding the amino acid motif is selected from glycine, aspartic acid, arginine and serine. In certain embodiments, at least 1, 2, 3, 4, 5, 6, 7, 8, 9 or 10 amino acids preceding the amino acid motif is (are) respectively glycine.

In certain embodiments, L further comprises the amino acid sequence GGGGGGGCVIM (SEQ ID NO: 106) at the C-terminus.

In certain embodiments, L further comprises at least one isoprenyl derivative unit of General Formula III:

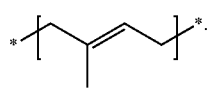

[General Formula III]

In certain embodiments, L further comprises at least one isoprenyl derivative unit of General Formula III which is recognized by an isoprenoid transferase:

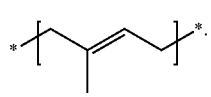

[General Formula III]

In certain embodiments, L is a 3 to 50 heteroalkylene comprising oxime and the oxygen atom of the oxime is on the side of L linked to W and the carbon atom of the oxime is on the side of L linked to Ab; or the carbon atom of the oxime is on the side of L linked to W and the oxygen atom of the oxime is on the side of L linked to Ab.

In certain embodiments, L further comprises an oxime and at least one isoprenyl unit covalently binds the oxime to Ab.

In certain embodiments, L further comprises a connecting unit represented by General Formula VIII or General Formula IX:

—(CH$_2$)$_r$(V(CH$_2$)$_p$)$_q$—      [General Formula VIII]

—(CH$_2$CH$_2$X)$_w$—      [General Formula IX]

wherein

V is a single bond, —O—, —S—, —NR$^{21}$—, —C(O)NR$^{22}$—, NR$^{23}$C(O)—, NR$^{24}$SO$_2$—, or —SO$_2$NR$^{25}$—;

X is —O—, C$_1$-C$_8$ alkylene or —NR$^{21}$—;

R$^{21}$ to R$^{25}$ are, independently and respectively hydrogen, (C$_1$-C$_6$) alkyl, (C$_1$-C$_6$) alkyl (C$_6$-C$_{20}$) aryl, or (C$_1$-C$_6$) alkyl (C$_3$-C$_{20}$) heteroaryl;

r is an integer of 0 to 10;

p is an integer of 0 to 10;

q is an integer of 1 to 20; and w is an integer of 1 to 20.

In certain embodiments, q is an integer of 4 to 20. In certain embodiments, q is an integer of 2 to 12. In certain embodiments, q is an integer of 6 to 20. In certain preferred embodiments, q is an integer of 2, 5 or 11.

In certain embodiments, r is an integer of 2.

In certain embodiments, p is an integer of 2.

In certain preferred embodiments, V is —O—.

In certain embodiments, r is an integer of 2; p is an integer of 2; q is an integer of 2, 5 or 11; and V is —O—.

In certain preferred embodiments, X is —O—.

In certain embodiments, w is an integer of 6 to 20.

In certain embodiments, L further comprises at least one polyethylene glycol unit represented by or .

In certain embodiments, L further comprises 1 to 12 —OCH$_2$CH$_2$— units. In certain embodiments, L further comprises 3 to 12 —OCH$_2$CH$_2$— units. In certain embodiments, 5 to 12 —OCH$_2$CH$_2$— units. In certain embodiments, L comprises 6 to 12 —OCH$_2$CH$_2$— units. In certain preferred embodiments, L further comprises 3 —OCH$_2$CH$_2$- units.

In certain embodiments, L further comprise an oxime and at least one polyethylene glycol unit covalently bonds the oxime to an active agent.

In certain embodiments, L further comprises a unit formed by 1,3-dipolar cycloaddition reactions, hetero-diels reactions, nucleophilic substitution reactions, nonaldol type carbonyl reactions, additions to carbon-carbon multiple bonds, oxidation reactions or click reactions. In certain preferred embodiments, the binding units are formed through reaction of acetylene and azide, or through reaction of an aldehyde or ketone group with hydrazine or hydroxylamine.

In certain embodiments, L further comprises a binding unit represented by General Formulae IV, V, VI or VII below:

[General Formula IV]

[General Formula V]

[General Formula VI]

[General Formula VII]

wherein

L$^1$ is a single bond or an alkylene of C$_1$-C$_{30}$; and

R$^{11}$ is a hydrogen or an alkyl of C$_1$-C$_{10}$.

In certain embodiments, L$^1$ is a single bond. In other embodiments, L$^1$ is a C$_{11}$-alkylene. In other embodiments, L$^1$ is a C$_{12}$-alkylene.

In certain embodiments, L further comprises or

;

wherein

V is a single bond, —O—, —S—, —NR$^{21}$—, —C(O)NR$^{22}$—, NR$^{23}$C(O)—, NR$^{24}$SO$_2$—, or —SO$_2$NR$^{25}$—;

R$^{21}$ to R$^{25}$ are, independently and respectively hydrogen, C$_1$-C$_6$ alkyl, C$_1$-C$_6$ alkyl C$_6$-C$_{20}$ aryl, or C$_1$-C$_6$ alkyl C$_3$-C$_{20}$ heteroaryl;

r is an integer of 1 to 10;
p is an integer of 0 to 10;
q is an integer of 1 to 20; and
L$^1$ is a single bond.

In certain embodiments, r is an integer of 2 or 3.
In certain embodiments, p is an integer of 1 or 2.
In certain embodiments, q is an integer of 1 to 6.
In certain embodiments, r is an integer of 2 or 3; p is an integer of 1 or 2; and q is an integer of 1 to 6.

In certain embodiments, the isoprenoid transferase is a farnesyl protein transferase (FTase) or a geranylgeranyl transferase (GGTase).

In certain embodiments, L further comprises one or more branched linkers covalently coupled to Ab, wherein i) each branched linker comprises a branching unit (BR) covalently coupled to Ab by a primary linker (PL);
ii) each branched linker comprises a first branch (B1), in which a first active agent is covalently coupled to the branching unit by a secondary linker (SL) and a cleavage group (CG); and
iii) each branched linker further comprises a second branch (B2), in which either a) a second active agent is covalently coupled to the branching unit by a secondary linker (SL) and a cleavage group (CG) or b) a polyethylene glycol moiety is covalently coupled to the branching unit, wherein each cleavage group can be hydrolyzed to release the active agent from the antibody-drug conjugate.

In certain embodiments, the branching unit is represented by:

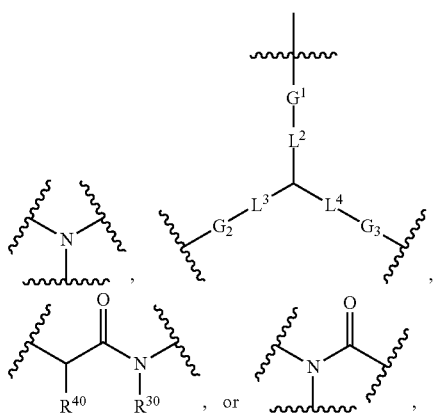

L$^2$, L$^3$ and L$^4$ are each independently a bond or —C$_n$H$_{2n}$—;
n is an integer of 1 to 30;
G$^1$, G$^2$ and G$^3$ are each independently, a bond,

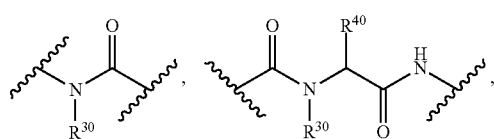

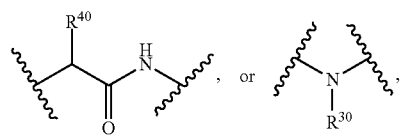

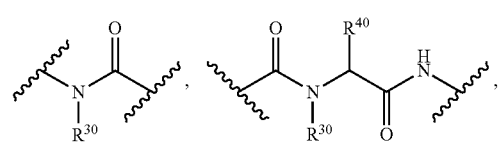

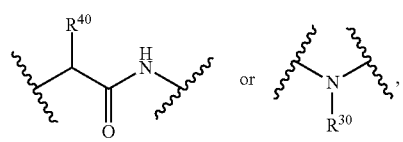

R$^{30}$ is hydrogen or C$_{1-30}$ alkyl;
L$^5$ is a direct bond or C$_{1-10}$ alkylene; and
R$^{50}$ is hydrogen C$_{1-30}$ alkyl.

In certain embodiments, the antibody conjugate comprises at least one branched linker covalently bonded to Ab; and at least two active agents covalently linked to the branched linker. In certain embodiments, the antibody conjugate comprises at two or more branched linker covalently bonded to Ab; and the branched linkers bind to at least two active agents. In certain embodiments, the antibody conjugate comprises 3 branched linkers. In other embodiments, the antibody conjugate comprises 4 branched linkers. In yet other embodiments, the antibody conjugate comprises 1 branched linker. In certain embodiments, the respective branched linkers each bind to two active agents. In certain embodiments, the conjugate comprises at least two different active agents. In certain embodiments, the branched linker is bonded to at least two active agents. In certain embodiments, the active agents bind to a branching unit through a second linker; and the branching units are bonded to an anti-ROR1 antibody by a first linker.

In certain preferred embodiments, the branching unit is a nitrogen atom. In certain even further preferred embodiments, the branching unit is an amide, and the first linker comprises a carbonyl of the amide. In the most preferred embodiments, the branching unit is a lysine unit.

In certain embodiments, the antibody conjugate comprises a structure represented by:

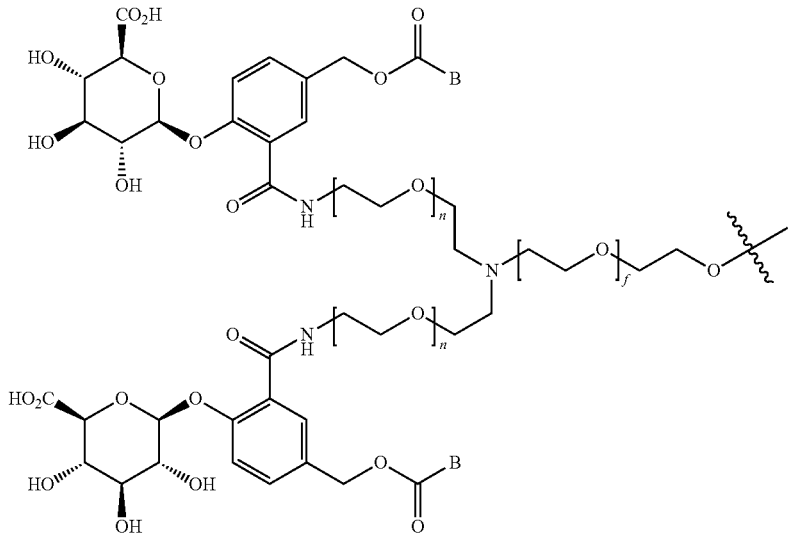

wherein
each B is an active agent;
each n is independently an integer of 0 to 30; and
each n is independently an integer of 0 to 30.

In certain embodiments, n is an integer of 1 to 10. In other embodiments, n is an integer of 4 to 20.

In certain embodiments, comprises oxime, and at least one polyethylene glycol unit covalently binds the oxime to an active agent.

In certain embodiments, the cleavable bond is cleavable within a target cell. In certain embodiments, the cleavable bond is cleavable by an activator (e.g., radiation, acid, base, or an enzyme).

In certain embodiments, the conjugate is represented by the following structure or a pharmaceutically acceptable salt thereof:

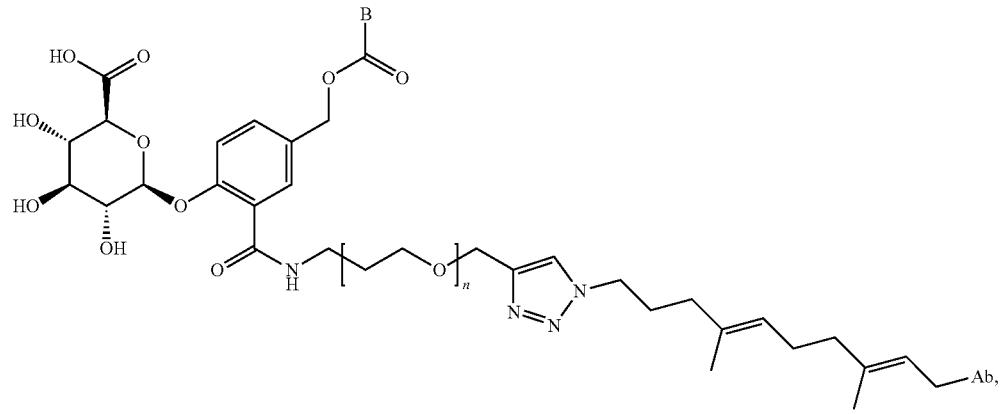

wherein Ab is an anti-ROR1 antibody; B is an active agent and; n is an integer of 1 to 20.

In certain embodiments, the conjugate is represented by the following structure or a pharmaceutically acceptable salt thereof:

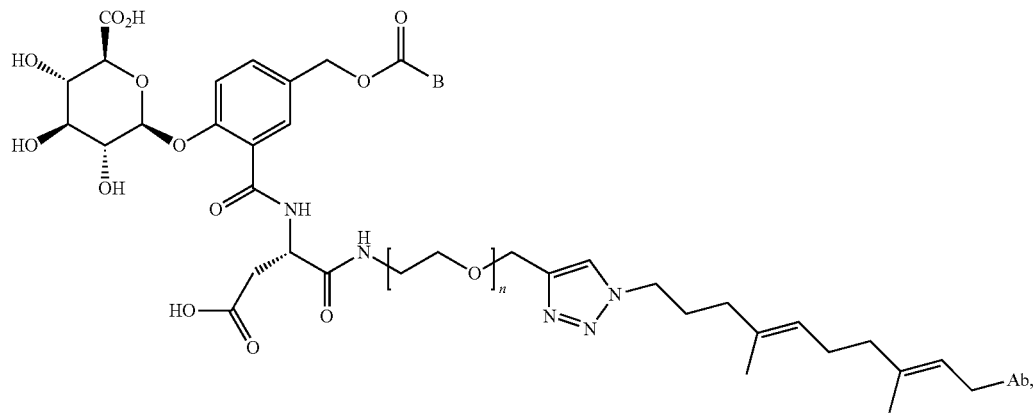

wherein Ab is an anti-ROR1 antibody; B is an active agent and; n is an integer of 1 to 20.

In certain embodiments, the conjugate is represented by the following structure or a pharmaceutically acceptable salt thereof:

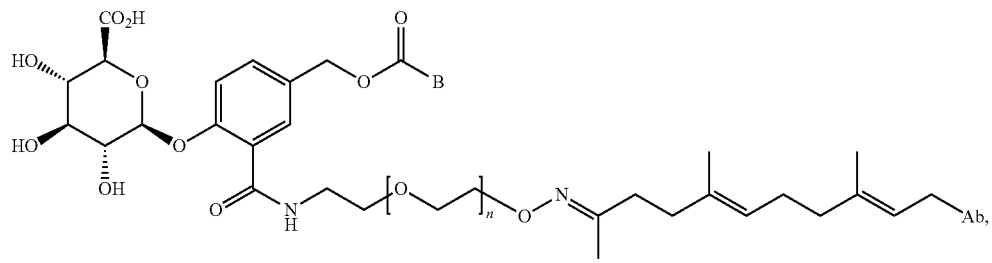

wherein Ab is an anti-ROR1 antibody; B is an active agent and; n is an integer of 1 to 20.

In certain embodiments, the conjugate is represented by the following structure or a pharmaceutically acceptable salt thereof:

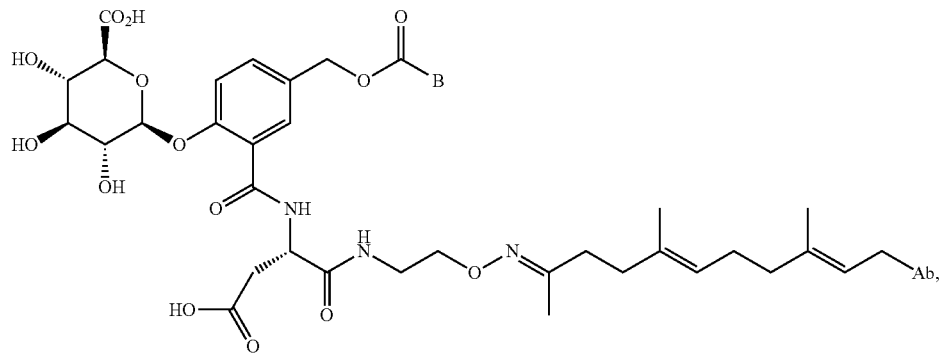

wherein Ab is an anti-ROR1 antibody; B is an active agent and; n is an integer of 1 to 20.

In some embodiments, the linker has the structure of Chemical Formula (IIa) below.

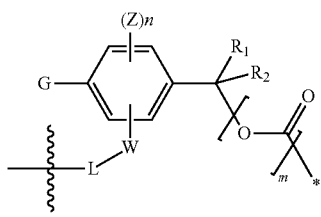

[Chemical Formula (IIa)]

Wherein

G is a sugar, a sugar acid or a sugar derivative;

W is —C(O)—, —C(O)NR'—, —C(O)O—, —S(O)$_2$NR'—, —P(O)R"NR'—, —S(O)NR'—, or —PO$_2$NR'—; wherein C(O), S or P is linked directly with the phenyl ring, R' and R" are, respectively and independently, hydrogen, (C$_1$-C$_8$) alkyl, (C$_3$-C$_8$) cycloalkyl, (C$_1$-C$_8$) alkoxy, (C$_1$-C$_8$) alkylthio, mono- or di-(C$_1$-C$_8$) alkylamino, (C$_3$-C$_{20}$) heteroaryl, or (C$_6$-C$_{20}$) aryl;

each Z is, respectively and independently, (C$_1$-C$_8$) alkyl, halogen, cyano or nitro;

n is an integer of 1 through 3;

m is 0 or 1;

L is absent, or contains at least one branching unit (BR) and at least one connection unit;

R$_1$ and R$_2$ are, respectively and independently, hydrogen, (C$_1$-C$_8$) alkyl or (C$_3$-C$_8$) cycloalkyl, or the R$_1$ and R$_2$, together with the carbon atoms to which they are bound, form a (C$_3$-C$_8$) cycloalkyl ring; and In the above formula, * denotes a region which binds to an antibody or an antigen-binding fragment thereof, and ⌇ denotes a region which binds to a drug or a toxin.

In some embodiments, the sugar or sugar acid is a monosaccharide.

In some embodiments, G is a compound of the structure of Chemical Formula (IIIa) below:

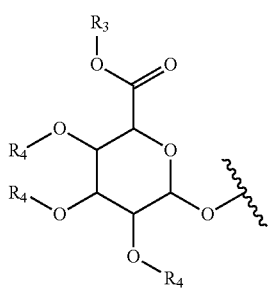

[Chemical Formula (IIIa)]

wherein

R$_3$ is a hydrogen or carboxyl protective group; and each R$_4$ is, respectively and independently, a hydrogen or hydroxyl protecting group.

In some embodiments, R$_3$ is hydrogen, and each R$_4$ is hydrogen.

In some embodiments, W is —C(O)NR'—, where C(O) is linked to a phenyl ring, and NR' is linked to L.

In some embodiments, Z is hydrogen, and n is 3.

In some embodiments, R$_1$ and R$_2$ are respectively hydrogen.

In some embodiments, G is a compound of the structure of Chemical Formula (IIIa) below:

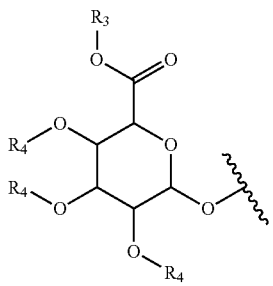

[Chemical Formula (IIIa)]

wherein

R$_3$ is a hydrogen or carboxyl protective group;

each R$_4$ is, respectively and independently, a hydrogen or hydroxyl protecting group; and W is —C(O)NR'—, where C(O) is linked to a phenyl ring, and NR' is linked to L, each Z is hydrogen, n is 3, m is 1, and R$_1$ and R$_2$ are respectively hydrogen.

In some embodiments, at least one branching unit is an alkylene having 1 to 100 carbon atoms, where the carbon atoms of the alkylene may be substituted by one or more heteroatoms selected from N, O and S, and the alkylene may further be substituted with one or more alkyls having 1 to 20 carbon atoms.

In some embodiments, at least one branching unit is a hydrophilic amino acid.

In some embodiments, the hydrophilic amino acid may be arginine, aspartate, asparagine, glutamate, glutamine, histidine, lysine, ornithine, proline, serine or threonine.

In some embodiments, the hydrophilic amino acid may be an amino acid including a side chain having residues which have electric charge in aqueous solution at a neutral pH.

In some embodiments, the hydrophilic amino acid is aspartate or glutamate.

In some embodiments, the hydrophilic amino acid is ornithine or lysine.

In some embodiments, the hydrophilic amino acid is arginine.

In some embodiments, at least one branching unit is —C(O)—, —C(O)NR'—, —C(O)O—, —S(O)$_2$NR'—, —P(O)R"NR'—, —S(O)NR'—, or —PO$_2$NR'—, and R' and R" are, respectively and independently, hydrogen, (C$_1$-C$_8$) alkyl, (C$_3$-C$_8$) cycloalkyl, (C$_1$-C$_8$) alkoxy, (C$_1$-C$_8$) alkylthio, mono- or di-(C$_1$-C$_8$) alkylamino, (C$_3$-C$_{20}$) heteroaryl, or (C$_6$-C$_{20}$) aryl.

In some embodiments, at least one branching unit is —C(O)NR'—, and R' is hydrogen.

In some embodiments, at least one connection unit is —(CH$_2$)$_r$(V(CH$_2$)$_p$)$_q$—, where r is an integer or 0 to 10, p is an integer of 0 to 12, q is an integer of 1 to 20, V is a single bond, —O— or —S—.

In some embodiments, r is 2.

In some embodiments, p is 2.

In some embodiments, q is an integer of 6 to 20.

In some embodiments, r is 2, p is 2, q is 2, 4, 5 or 11, and V is —O—.

In some embodiments, at least one connection unit is at least one polyethylene glycol unit, and has a structure of

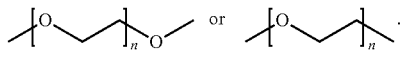

In some embodiments, at least one connection unit is 1 to 12 —OCH$_2$CH$_2$— units, or 5 to 12 —OCH$_2$CH$_2$— units, or 6 to 12 —OCH$_2$CH$_2$— units.

In some embodiments, at least one connection unit is —(CH$_2$CH$_2$X)$_w$—,

Where X is a single bond, —O—, (C$_1$-C$_8$) alkylene, or —NR$_{21}$—;

R$_{21}$ is hydrogen, (C$_1$-C$_6$) alkyl, (C$_1$-C$_6$) alkyl (C$_6$-C$_{20}$) aryl, or (C$_1$-C$_6$) alkyl (C$_3$-C$_{20}$) heteroaryl; and w is an integer of 1 to 20, specifically 1, 3, 6 or 12.

In some embodiments, X is —O—, and w is an integer of 6 to 20.

In some embodiments, the linker additionally includes a binding unit formed by a 1,3-dipolar cycloaddition reaction, a hetero-Diels-Alder reaction, a nucleophilic substitution reaction, a non-aldol carbonyl reaction, an addition to carbon-carbon multiple bond, oxidation reaction or click reaction.

In some embodiments, the binding unit is formed by a reaction between acetylene and azide, or a reaction between aldehyde or a ketone group and hydrazine or alkoxyamin.

In some embodiments, the binding unit is represented by:

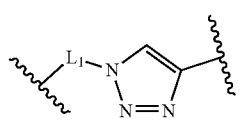

[General Formula IV]

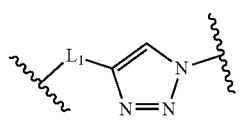

[General Formula V]

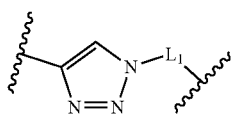

[General Formula VI]

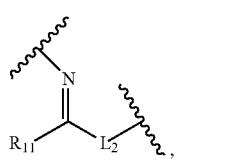

[General Formula VII]

wherein

L$_1$ is a single bond or an alkylene having 1 to 30 carbon atoms;

R$_{11}$ is hydrogen or an alkyl having 1 to 10 carbon atoms, specifically methyl; and L$_2$ is an alkylene having 1 to 30 carbon atoms.

In some embodiments, the linker may additionally contain at least one isoprenyl unit having the structure

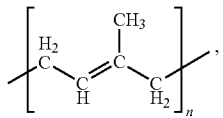

where n is at least 2.

In some embodiments, at least one isoprenyl unit is an isoprenoid transferase substrate or a product of isoprenoid transferase.

In some embodiments, the isoprenyl unit of the linker is covalently linked to the antibody through a thioether bond, and the thioether bond includes a sulfur atom of cysteine. In some embodiments, the antibody includes an amino acid motif recognized by isoprenoid transferase, and the thioether bond includes a sulfur atom of the cysteine of the amino acid motif.

In some embodiments, the antibody binding to ROR1 or antigen-binding fragment thereof includes an amino acid motif recognized by isoprenoid transferase, and the thioether bond includes a sulfur atom of the cysteine of the amino acid motif.

In some embodiments, the amino acid motif is a sequence selected from a group comprised of CXX, CXC, XCXC, XXCC and CYYX, where C denotes cysteine; Y in each case independently denotes an aliphatic amino acid; X in each case independently denotes glutamine, glutamate, serine, cysteine, methionine, alanine or leucine; and the thioether bond includes a sulfur atom of the cysteine of the amino acid motif.

In some embodiments, the amino acid motif is a CYYX sequence, and Y in each case is independently alanine, isoleucine, leucine, methionine or valine.

In some embodiments, the amino acid motif is a CVIM (SEQ ID NO: 104) or CVLL (SEQ ID NO: 105) sequence.

In some embodiments, at least one of the 1 to 20 amino acids preceding the amino acid motif is glycine.

In some embodiments, at least one of the 1 to 20 amino acids preceding the amino acid motif may, respectively and independently, be selected from glycine, arginine, aspartic acid and serine.

In some embodiments, 1 to 20 amino acids preceding the amino acid motif are glycine. More specifically, at least 1, 2, 3, 4, 5, 6, 7, 8, 9, 10, 11, 12, 13, 14, 15, 16, 17, 18, 19 of 20 amino acids preceding the amino acid motif is (are) glycine.

In some embodiments, the antibody may include the amino acid sequence GGGGGGGCVIM (SEQ ID NO: 106).

In some embodiments, the linker may include:

(a) at least one branching unit; (b) at least one connection unit; (c) at least one binding unit (BU); and (d) at least one trigger unit (TU).

Here, the connection unit connects the trigger unit and binding unit, the trigger unit and the branching unit, or the branching unit and the binding unit;

the at least one trigger unit may release at least one drug or toxin; and the branching unit links a connection unit and trigger unit, or a connection unit and another connection unit.

In some embodiments, the trigger unit has the structure of Chemical Formula (IIb) below:

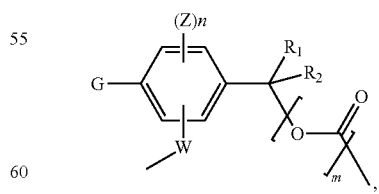

[Chemical Formula (IIb)]

Wherein

G is a sugar, a sugar acid or a sugar derivative;

W is —C(O)—, —C(O)NR'—, —C(O)O—, —S(O)$_2$NR'—, —P(O)R"NR'—, —S(O)NR'—, or —PO$_2$NR'—; wherein C(O), S or P is linked directly to the phenyl ring, R' and R" are, respectively and independently, hydrogen, ($C_1$-$C_8$) alkyl, ($C_3$-$C_8$) cycloalkyl, ($C_1$-$C_8$) alkoxy, ($C_1$-$C_8$) alkylthio, mono- or di-($C_1$-$C_8$) alkylamino, ($C_3$-$C_{20}$) heteroaryl, or ($C_6$-$C_{20}$) aryl, and W is linked to a connection unit or a branching unit;

each Z is, respectively and independently, ($C_1$-$C_5$) alkyl, halogen, cyano or nitro;

n is an integer of 1 through 3;

m is 0 or 1; and $R_1$ and $R_2$ are, respectively and independently, hydrogen, ($C_1$-$C_8$) alkyl or ($C_3$-$C_8$) cycloalkyl, or the $R_1$ and $R_2$, together with the carbon atoms to which they are bound, form a ($C_3$-$C_8$) cycloalkyl ring.

In some embodiments, the sugar or sugar acid is a monosaccharide.

In some embodiments, G is a compound having the structure of Chemical Formula (IIIa) below:

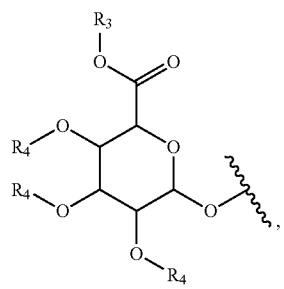

[Chemical Formula (IIIa)]

wherein $R_3$ is a hydrogen or carboxyl protective group; and each $R_4$ is, respectively and independently, a hydrogen or hydroxyl protective group.

In some embodiments, $R_3$ is hydrogen, and each $R_4$ is hydrogen.

In some embodiments, W is —C(O)NR'—, where C(O) is linked to the phenyl ring, and NR' is linked to L.

In some embodiments, Z is hydrogen.

In some embodiments, $R_1$ and $R_2$ are respectively hydrogen.

In some embodiments, the connection unit is represented as —($CH_2$)$_r$(V($CH_2$)$_p$)$_q$—, —(($CH_2$)$_p$V)$_q$—, —($CH_2$)$_r$(V($CH_2$)$_p$)$_q$Y—, —(($CH_2$)$_p$V)$_q$($CH_2$)$_r$—, —Y(($CH_2$)$_p$V)$_q$— or ($CH_2$)$_r$(V($CH_2$)$_p$)$_q$YCH$_2$—, wherein:

r is an integer of 0 to 10;

p is an integer of 1 to 10;

q is an integer of 1 to 20;

V and Y are, independently and respectively a single bond, —O—, —S—, —$NR_{21}$—, —C(O)$NR_{22}$—, $NR_{23}$C(O)—, $NR_{24}SO_2$—, or —$SO_2NR_{25}$— and;

$R_{21}$ to $R_{25}$ are, independently and respectively hydrogen, ($C_1$-$C_6$) alkyl, ($C_1$-$C_6$) alkyl ($C_6$-$C_{20}$) aryl, or ($C_1$-$C_6$) alkyl ($C_3$-$C_{20}$) heteroaryl.

In some embodiments, r is 2.

In some embodiments, p is 2.

In some embodiments, q is an integer of 6 to 20.

In some embodiments, q is 2, 5 or 11.

In some embodiments, V and Y are, respectively and independently, —O—.

In some embodiments, the branching unit is:

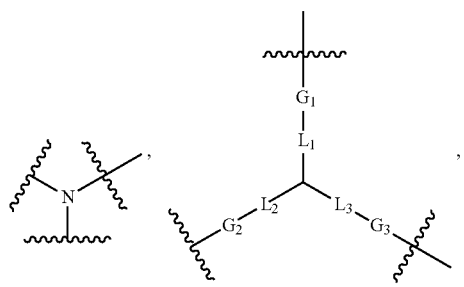

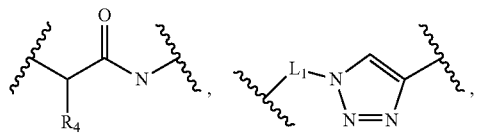

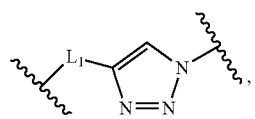, or

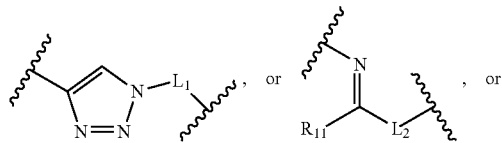

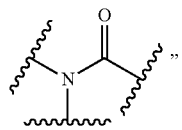

wherein $L_1$, $L_2$ and $L_3$ are, respectively and independently, a direct bond or —$C_nH_{2n}$—;

n is an integer of 1 through 30;

$G_1$, $G_2$ and $G_3$ are, respectively and independently, a direct bond,

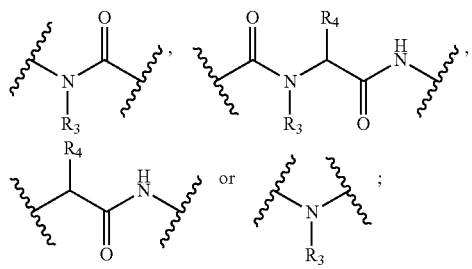

$R_3$ is hydrogen or $C_1$-$C_{30}$ alkyl;

$R_4$ is hydrogen or $L_4$-$COOR_5$; $L_4$ is a direct bond or —$C_nH_{2n}$—; n is an integer of 1 to 10, and $R_5$ is hydrogen or $C_1$-$C_{30}$ alkyl.

In some embodiments, the branching unit is:

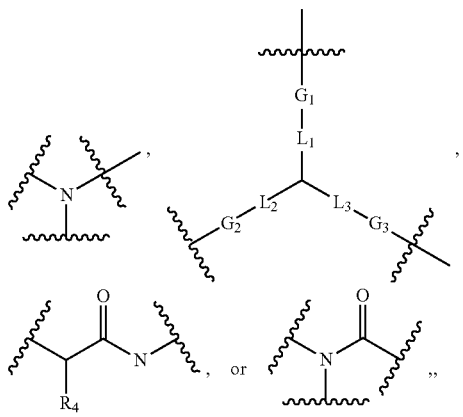

wherein

L$_1$, L$_2$ and L$_3$ are, respectively and independently, a direct bond or —C$_n$H$_{2n}$—;

n is an integer of 1 through 30;

G$_1$, G$_2$ and G$_3$ are, respectively and independently, a direct bond,

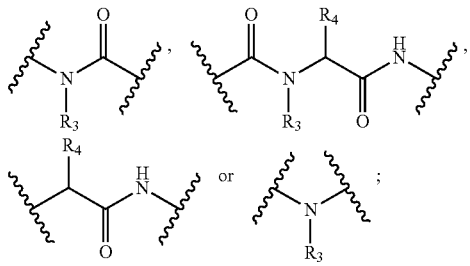

R$_3$ is hydrogen or C$_1$-C$_{30}$ alkyl;

R$_4$ is hydrogen or L$_4$-COOR$_5$; L$_4$ is a direct bond or —C$_n$H$_{2n}$—; n is an integer of 1 to 10, and R$_5$ is hydrogen or C$_1$-C$_{30}$ alkyl.

In some embodiments, the branching unit is

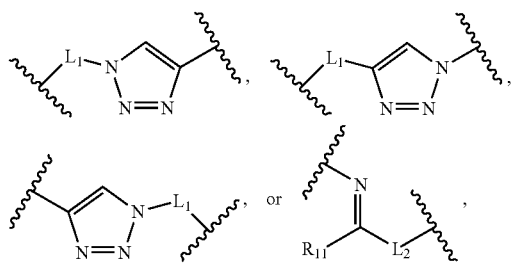

where L$_1$ is a direct bond or an alkylene having 1 to 30 carbon atoms;

R$_{11}$ is hydrogen or an alkyl having 1 to 10 carbon atoms, specifically methyl;

L$_2$ is an alkylene having 1 to 30 carbon atoms; and the branching unit links a connection unit and an antibody.

In some embodiments, L$_1$ is an alkylene having 12 carbon atoms.

In some embodiments, R$_{11}$ is methyl.

In some embodiments, L$_2$ is an alkylene having 11 carbon atoms.

In some embodiments, the binding unit is covalently bound to the antibody through a thioether bond, and the thioether bond includes a sulfur atom of cysteine. In some such embodiments, the antibody includes an amino acid motif recognized by isoprenoid transferase, and the thioether bond includes a sulfur atom of the cysteine of the amino acid motif.

In some embodiments, the amino acid motif is a sequence selected from a group comprised of CXX, CXC, XCXC, XXCC and CYYX, where C denotes cysteine; Y in each case independently denotes an aliphatic amino acid; X in each case independently denotes glutamine, glutamate, serine, cysteine, methionine, alanine or leucine; and the thioether bond includes a sulfur atom of the cysteine of the amino acid motif.

In some embodiments, the amino acid motif is a CYYX sequence, and Y in each case is independently alanine, isoleucine, leucine, methionine or valine.

In some embodiments, the amino acid motif is a CVIM (SEQ ID NO: 104) or CVLL (SEQ ID NO: 105) sequence.

In some embodiments, at least one of the 1 to 20 amino acids preceding the amino acid motif is glycine.

In some embodiments, at least one of the 1 to 20 amino acids preceding the amino acid motif may, respectively and independently, be selected from glycine, arginine, aspartic acid and serine.

In some embodiments, 1 to 20 amino acids preceding the amino acid motif are glycine. More specifically, at least 1, 2, 3, 4, 5, 6, 7, 8, 9, 10, 11, 12, 13, 14, 15, 16, 17, 18, 19 of 20 amino acids preceding the amino acid motif is (are) glycine.

In some embodiments, the antibody may include the amino acid sequence GGGGGGGCVIM (SEQ ID NO: 106).

In certain embodiments, the active agent is an immunoregulatory compound, anti-cancer agent, antiviral, antibacterial, antifungal, antiparasitic or a combination of these.

In certain embodiments, the active agent is selected from:
(a) erlotinib, bortezomib, fulvestrant, sutent, letrozole, imatinib mesylate, PTK787/ZK 222584, oxaliplatin, 5-fluorouracil, leucovorin, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethylenimine, altretamine, triethylenemelamine, triethylenephosphoramide, triethylenethiophosphoramide, teimethylolomelamine, bullatacin, bullataciionone, camptothecin, topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, melphalan, novembichin, phenesterine, prednimustine, trofosfamide, uracil mustard, carmustine, chlorozotoxin, fotemustine, lomustine, nimustine, ranimustine, calicheamicin, calicheamicin gamma 1, calicheamicin omega 1, dynemicin, dynemicin A, clodronate, esperamicin, neocarzinostatin chromophore, aclacinomysins, actinomycin, antrymycin, azaserine, bleomycins, catcinomycin, carabicin, carninomycin, carzinophilin, chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tudercidin, ubenimex, zinostatin, zorubicin, 5-fluororacil, denopterin, methotrexate, pteropterin, trimetrexate, fludarabine, 6-mercaptopurine, thiamiprine, thiguianine, ancitabine, azacytidine, 6-azauridine, carmofur, cytarabine, dideoxyuridine, doxifluridine, enocitabine, floxuridine, calusterone, dromostanolone, propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatrexate, defofamine, democolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaqizuone, 2,2', 2"-trichlorotriethylamine, T-2 toxin, verracurin A, roridin A, anguidine, urethane, vindesine, dacarbazine, mannomustine, mitobronitol, mitolactol, pipobroman, gacytosine, arabinoside, cyclophosphamide, thiotepa, paclitaxel, albumin-engineered nanoparticle formulation of paclitaxel, docetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, xeloda, ibandronate, CPT-11, topoisomerase inhibitor RFS 2000, difluoromethylornithine, retinoic acid, capecitabine, or pharmaceutically acceptable salts, solvates or acids thereof;
- (b) monokine, lympokine, traditional polypeptide hormone, parathyroid hormone, thyroxine, relaxin, prorelaxin, glycoprotein hormone, follicle stimulating hormone, thyroid stimulating hormone, luteinizing hormone, hepatic growth factor fibroblast growth factor, prolactin, placental lactogen, tumor necrosis factor, tumor necrosis factor-α, tumor necrosis factor-β, Mullerian inhibiting substance, mouse gonadotropin associated peptide, inhibin, activin, vascular endothelial growth factor, thrombopoietin, erythropoietin, osteoinductive factor, interferon, interferon-α, interferon-β, interferon-γ, colony stimulating factor (CSF), macrophage-CSF, granulocyte-macrophage-CSF, granulocyte-CSF, interleukin (IL), IL-1, IL-1α, IL-2, IL-3, IL-4, IL-5, IL-6, IL-7, IL-8, IL-9, IL-10, IL-11, IL-12, tumor necrosis factor, polypeptide factor, LIF, kit ligand, or mixtures thereof;
- (c) diphtheria toxin, botulinum toxin, tetanus toxin, dysentery toxin, cholera toxin, amanitin, α-amatinin, pyrrolobenzodiazepine, pyrrolobenzodiazepine derivative, indolinobenzodiazepine, pyridobenzodiazepine, tetrodotoxin, brevetoxin, ciguatoxin, ricin, AM toxin, auristatin, tubulysin, geldanamycin, maytansinoid, calicheamicin, daunomycin, doxorubicin, methotrexate, vindesine, SG2285, dolastatin, dolastatin analog, auristatin, cryptophycin, camptothecin, rhizoxin, rhizoxin derivatives, CC-1065, CC-1065 analogs or derivatives, duocarmycin, enediyne antibiotic, esperamicin, epothilone, toxoid, or mixtures thereof;
- (d) affinity ligand, where the affinity ligand is a substrate, inhibitor, active agent, neurotransmitter, radioactive isotope, or mixtures thereof;
- (e) radioactive label, 32P, 35S, fluorescent dye, electron dense reagent, enzyme, biotin, streptavidin, dioxigenin, hapten, immunogenic protein, nucleic acid molecule with a sequence complementary to a target, or mixtures thereof;
- (f) immunomodulatory compound, anti-cancer agent, anti-viral agent, anti-bacterial agent, anti-fungal agent, anti-parasitic agent, or mixtures thereof;
- (g) tamoxifen, raloxifene, droloxifene, 4-hydroxytamoxifen, trioxifene, keoxifene, LY117018, onapristone or toremifene;
- (h) 4(5)-imidazole, aminoglutethimide, megestrol acetate, exemestane, letrozole or anastrozole
- (i) flutamide, nilutamide, bicalutamide, leuprolide, goserelin, or troxacitabine;
- (j) aromatase inhibitor;
- (k) protein kinase inhibitor;
- (l) lipid kinase inhibitor;
- (m) antisense oligonucleotide;
- (n) ribozyme;
- (o) vaccine; and
- (p) anti-angiogenic agent.

In certain preferred embodiments, Ab is an anti-ROR1 antibody;

the active agent is a pyrrolobenzodiazepine dimer;

the linker links Ab to the N10 or N'10 position of the pyrrolobenzodiazepine dimer; and y is an integer of 1 to 20.

In certain embodiments, the active agent is a pyrrolobenzodiazepine dimer;

the pyrrolobenzodiazepine dimer is substituted by X at the N10 position or by X' at the N'10 position, where X or X' links the pyrrolobenzodiazepine dimer to the linker;

X and X' are, respectively and independently, —C(O)O*, —S(O)O—*, —C(O)—*, —C(O)NR$^X$—*, —S(O)$_2$NR$^X$—*, —P(O)R'NR$^X$—*, —S(O)NR$^X$—*, or —PO$_2$NR$^X$—*;

R$^X$ is $C_{1-8}$ alkyl, $C_{3-8}$ cycloalkyl, $C_{3-20}$ heteroaryl or $C_{5-20}$ aryl;

R$^{X'}$ is OH, N$_3$, CN, SH, $C_{1-8}$ alkyl, $C_{3-8}$ cycloalkyl, $C_{1-8}$ alkoxy, $C_{1-8}$ alkylthio, $C_{3-20}$ heteroaryl, $C_{5-20}$ aryl or amino; and

* is a binding site between the pyrrolobenzodiazepine dimer and the linker.

In certain embodiments, X and X' are each independently —C(O)O*, —C(O)—*, or —C(O)NR$^X$—*.

In certain embodiments, the pyrrolobenzodiazepine dimer is represented by General Formula X or General Formula XI below:

[General Formula X]

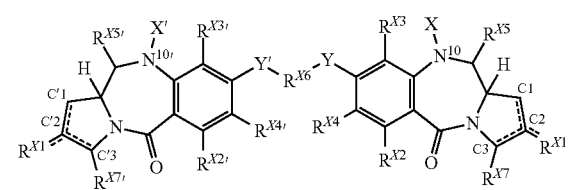

[General Formula XI]

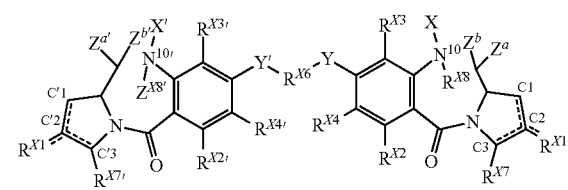

wherein:

a dotted line represents an optional double bond as permitted by valency;

$R^{X1}$ and $R^{X1'}$ are independently selected from H, OH, =O, =$CH_2$ CN, $R^m$, $OR^m$, =CH—$R^{m'}$, =C($R^{m'}$)$_2$, $OSO_2$—$R^m$, $CO_2R^m$, $COR^m$, halo and dihalo;

$R^{m'}$ is selected from $R^m$, $CO_2R^m$, $COR^m$, CHO, $CO_2H$ and halo;

each $R^m$ is independently selected from of $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3-7 membered heterocyclyl, 3-7 membered heterocycloalkyl and 5 to 7 heteroaryl; or $R^m$ is X or X';

$R^{X2}$, $R^{X2'}$, $R^{X3}$, $R^{X3'}$, $R^{X5}$ and $R^{X5'}$ are independently selected from H, $R^m$, OH, $OR^m$, SH, $SR^m$, $NH_2$, $NHR^m$, $NR^m{}_2$, $NO_2$, $Me_3SN$ and halo;

$R^{X4}$ and $R^{X4'}$ are independently selected from H, $R^m$, OH, $OR^m$, SH, $SR^m$, $NH_2$, $NHR^m$, $NR^m{}_2$, $NO_2$, $Me_3SN$, halo, $C_{1-6}$ alkyl $C_{1-6}$ alkoxy, $C_{2-6}$ alkenyl, $C_{2-6}$ alkynyl, $C_{3-6}$ cycloalkyl, 3-7 membered heterocycloalkyl, $C_{5-12}$ aryl, 5 to 7 heteroaryl, —CN, —NCO, —$OR''$, —OC(O)$R''$, —OC(O)N$R''R'$, —OS(O)$R''$, —OS(O)$_2R''$, —$SR''$, —S(O)$R''$, —S(O)$_2R''$, —S(O)N$R''R'$, —S(O)$_2$N$R''R'$, —OS(O)N$R''R'$, —OS(O)$_2$N$R''R'$, —N$R''R'$, —N$R''$C(O)$R^o$, —N$R''$C(O)O$R^o$, —N$R''$C(O)N$R^oR^{o'}$, —N$R''$S(O)$R^o$, —N$R''$S(O)$_2R^o$, —N$R''$S(O)N$R^oR^{o'}$, —N$R''$S(O)$_2$N$R^oR^{o'}$, —C(O)$R''$, —C(O)O$R^o$ and —C(O)N$R''R'$;

$R^X$ and $R^{X'}$ are each independently selected from H, OH, $N_3$, CN, $NO_2$, SH, $NH_2$, $ONH_2$, $NHNH_2$, halo, $C_{1-8}$ alkyl, $C_{3-8}$ cycloalkyl, $C_{1-8}$ alkoxy, $C_{1-8}$ alkylthio, $C_{3-20}$ heteroaryl, $C_{5-20}$ aryl or mono- or di-$C_{1-8}$ alkylamino;

Y and Y' are each independently selected from O, S and N(H);

each $R^{x6}$ is independently selected from $C_{3-12}$ alkylene, $C_{3-12}$ alkenylene, or $C_{3-12}$ heteroalkylene;

$R^{X7}$ and $R^{X7'}$ are independently selected from H, $C_{1-6}$ alkyl, $C_{2-6}$ alkenyl, $C_{2-6}$ alkynyl, $C_{3-6}$ cycloalkyl, 3-7 membered heterocycloalkyl, $C_{6-10}$ aryl, 5 to 7 heteroaryl, —$OR^r$, —OC(O)$R^r$, —OC(O)N$R'R''$, —OS(O)$R^r$, —OS(O)$_2R^r$, —$SR^r$, —S(O)$R^r$, —S(O)$_2R^r$, —S(O)N$R'R''$, —S(O)$_2$N$R'R''$, —OS(O)N$R'R''$, —OS(O)$_2$N$R'R''$, —N$R'R''$, —N$R'$C(O)$R^s$, —N$R'$C(O)O$R^s$, —N$R'$C(O)N$R^sR^{s'}$, —N$R'$S(O)$R^s$, —N$R'$S(O)$_2R^s$, —N$R'$S(O)N$R^sR^{s'}$, —N$R'$S(O)$_2$N$R^sR^{s'}$, —C(O)$R^r$, —C(O)O$R^s$ or —C(O)N$R'R''$;

each $R^r$, $R^{r'}$, $R^s$ and $R^{s'}$ is independently selected from H, $C_{1-7}$ alkyl, $C_{2-7}$ alkenyl, $C_{2-7}$ alkynyl, $C_{3-13}$ cycloalkyl, 3-7 membered heterocycloalkyl, $C_{5-10}$ aryl and 5 to 7 heteroaryl;

each $R^{X8}$ and $R^{X8'}$ is independently selected from H, $C_{1-6}$ alkyl, $C_{2-6}$ alkenyl, $C_{2-6}$ alkynyl, $C_{3-6}$ heteroalkyl, 3-7 membered heterocycloalkyl, $C_{5-10}$ aryl, 5 to 7 heteroaryl, —S(O)$R^m$, —S(O)$_2R^m$, —S(O)N$R'''R^m$, —S(O)$_2$N$R'''R^m$, —N$R'''R^m$, —N$R'''$C(O)$R^m$, N$R'''$C(O)O$R^m$, —N$R'''$C(O)N$R''R'$, —N$R'''$S(O)$R^m$, —N$R'''$S(O)$_2R^m$, —N$R'''$S(O)N$R''R'$, —N$R'''$S(O)$_2$N$R''R'$, —C(O)$R^m$, —C(O)O$R^m$ and —C(O)N$R'''R^m$;

$Z^a$ is selected from $OR^{X12a}$, $NR^{X12a}R^{X12a}$, or $SR^{X12a}$;

$Z^b$ is selected from $OR^{X13a}$, $NR^{X13a}R^{X13a}$, or $SR^{X13a}$;

$Z^{a'}$ is selected from $OR^{X12a}$, $NR^{X12a}R^{X12a}$, or $SR^{X12a}$;

$Z^{b'}$ is selected from $OR^{X13a'}$, $NR^{X13a'}R^{X13a'}$, or $SR^{X13a'}$;

each $R^{X12a}$, $R^{X12a'}$, $R^{X13a'}$ and $R^{X13a'}$ is independently selected from H, $C_{1-6}$ alkyl, $C_{2-6}$ alkenyl, $C_{2-6}$ alkynyl, $C_{3-6}$ cycloalkyl, 3 to 7 membered heterocycloalkyl, $C_{5-10}$ aryl, 5 to 7 heteroaryl, —C(O)$R^{X15a}$, —C(O)O$R^{X15a}$ and —C(O)N$R^{X15a}R^{X15a'}$;

each $R^{X15a}$ and $R^{X15a'}$ is independently selected from $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3-7 membered heterocyclyl, 3-7 membered heterocycloalkyl, and 5 to 7 heteroaryl; o each $R^{X13a}$ and $R^{X14a}$ is independently H or alkyl; or $R^{X13a}$ and $R^{X14a}$, together with the atom to which it is connected, form 3-7 membered heterocyclyl, form 3-7 membered heterocycloalkyl, or form 3-7 membered heteroaryl, and the $R^{X13a'}$ and $R^{X14a'}$ arbitrarily bind to the atoms to which they are attached to form 3-7 membered heterocyclyl, 3-7 membered heterocycloalkyl, or 3-7 membered heteroaryl; and each of $R''$, $R'''$, $R^o$, $R^{o'}$, $R^p$ and $R^{p'}$ is independently selected from H, $C_{1-7}$ alkyl, $C_{2-7}$ alkenyl, $C_{2-7}$ alkynyl, $C_{3-13}$ cycloalkyl, 3-7 membered heterocycloalkyl, $C_{5-10}$ aryl, and 5 to 7 heteroaryl.

In certain embodiments, $R^m$ is independently selected from of $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3-7 membered heterocyclyl, 3-7 membered heterocycloalkyl and 5 to 7 heteroaryl; and $R^m$ is substituted $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3-7 membered heterocyclyl, 3-7 membered heterocycloalkyl or 5 to 7 heteroaryl.

In certain embodiments, $R^{X4}$ and $R^{X4'}$ are independently selected from H, $R^m$, OH, $OR^m$, SH, $SR^m$, $NH_2$, $NHR^m$, $NR^mR^{m'}$, $NO_2$, $Me_3SN$, halo, $C_{1-6}$ alkyl, $C_{1-6}$ alkoxy, $C_{2-6}$ alkenyl, $C_{2-6}$ alkynyl, $C_{3-6}$ cycloalkyl, 3-7 membered heterocycloalkyl, $C_{5-12}$ 5 to 7 heteroaryl, —CN, —NCO, —$OR''$, —OC(O)$R''$, —OC(O)N$R''R'$, —OS(O)$R''$, —OS(O)$_2R''$, —$SR''$, —S(O)$R''$, —S(O)$_2R''$, —S(O)N$R''R'$, —S(O)$_2$N$R''R'$, —OS(O)N$R''R'$, —OS(O)$_2$N$R''R'$, —N$R''R'$, —N$R''$C(O)$R^o$, —N$R''$C(O)O$R^o$, —N$R''$C(O)N$R^oR^{o'}$, —N$R''$S(O)$R^o$, —N$R''$S(O)$_2R^o$, —N$R''$S(O)N$R^oR^{o'}$, —N$R''$S(O)$_2$N$R^oR^{o'}$, —C(O)$R''$, —C(O)O$R^o$ and —C(O)N$R''R'$; and $R^{X4}$ or $R^{X4'}$ is $C_{1-6}$ alkyl, $C_{1-6}$ alkoxy, $C_{2-6}$ alkenyl, $C_{2-6}$ alkynyl, $C_{3-6}$ cycloalkyl, 3-7 membered heterocycloalkyl, $C_{5-12}$ aryl or 5 to 7 heteroaryl, and additionally is substituted with at least one $C_{1-6}$ alkyl, $C_{1-6}$ alkoxy, $C_{2-6}$ alkenyl, $C_{2-6}$ alkynyl, $C_{3-6}$ cycloalkyl, 3-7 membered heterocycloalkyl, $C_{5-10}$ aryl, 5 to 7 heteroaryl, —$OR^p$, —OC(O)$R^p$, —C(O)N$R^pR^{p'}$, —OS(O)$R^p$, —OS(O)$_2R^p$, —$SR^p$, —S(O)$R^p$, —S(O)$_2R^p$, —S(O)N$R^pR^{p'}$, —S(O)$_2$N$R^pR^{p'}$, —OS(O)N$R^pR^{p'}$, —OS(O)$_2$N$R^pR^{p'}$, —N$R^pR^{p'}$, —N$R^p$C(O)$R^q$, —N$R^p$C(O)O$R^q$, —N$R^p$C(O)N$R^qR^{q'}$, —N$R^p$S(O)$R^q$, —N$R^p$S(O)$_2R^q$, —N$R^p$S(O)N$R^qR^{q'}$, —N$R^p$S(O)$_2$N$R^qR^{q'}$, —C(O)$R^p$, —C(O)O$R^p$ or —C(O)N$R^pR^p$.

In certain embodiments, $R^{X1}$ and $R^{X1'}$ are both $R^m$; and $R^m$ is $C_{1-6}$ alkyl, $C_{2-6}$ alkenyl, $C_{5-7}$ aryl, or $C_{3-6}$ heteroaryl.

In certain embodiments, $R^{X2}$, $R^{X2'}$, $R^{X3}$, $R^{X3'}$, $R^{X5}$ and $R^{X5'}$ are independently selected from H or OH.

In certain embodiments, $R^{X4}$ and $R^{X4'}$ are both $R^m$; and $R^m$ is $C_{1-6}$ alkoxy. In certain preferred embodiments, $R^{X4}$ and $R^{X4'}$ are each independently selected from methoxy, ethoxy and butoxy.

In certain embodiments, Y and Y' are O.

In certain embodiments, $R^{x6}$ is $C_{3-12}$ alkylene, $C_{3-12}$ alkenylene or $C_{3-12}$ heteroalkylene, where $R^{x6}$ is substituted with —$NH_2$, —$NHR^m$, —NHC(O)$R^m$, —NHC(O)$R^m$, —NHC(O)$CH_2$—[OCH$_2$CH$_2$]$_n$—$R^{XX}$, or —[CH$_2$CH$_2$O]$^n$—$R^{XX}$;

$R^{XX}$ is H, OH, $N_3$, CN, $NO_2$, SH, $NH_2$, $ONH_2$, $NHNH_2$, halo, $C_{1-8}$ alkyl, $C_{3-8}$ cycloalkyl, $C_{1-8}$ alkoxy, $C_{1-8}$ alkylthio, $C_{3-20}$ heteroaryl, $C_{5-20}$ aryl or mono- or di-$C_{1-8}$ alkyl amino; and n is an integer of 1 through 6.

In certain embodiments, the active agent has a structure represented by General Formula XII or General Formula XIII;

[General Formula XII]

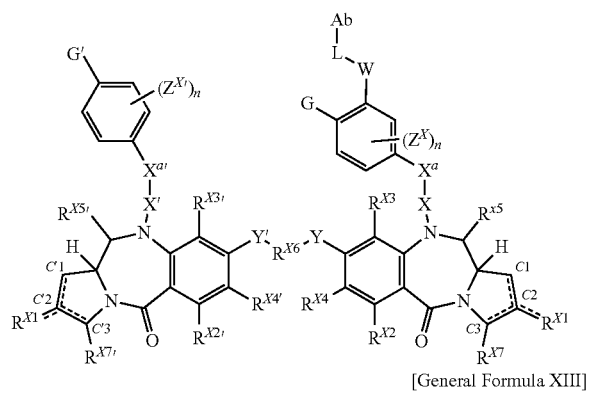

[General Formula XIII]

wherein
X$^a$ and X$^{a'}$ are each independently a bond or C$_{1-6}$ alkylene;
Z$^{X'}$ and Z$^X$ are each independently selected from hydrogen, C$_{1-8}$ alkyl, halogen, cyano, nitro

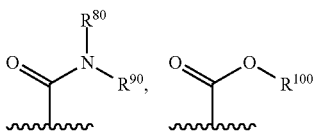

and —(CH$_2$)$_m$—OCH$_3$;
each R$^{80}$, R$^{90}$ and R$^{100}$ is independently selected from hydrogen, C$_{1-8}$ alkyl, C$_{2-6}$ alkenyl and C$_{1-6}$ alkoxy; and
m is an integer of 0 to 12.

In certain embodiments, Z$^{X'}$ and Z$^X$ are each independently selected from hydrogen,

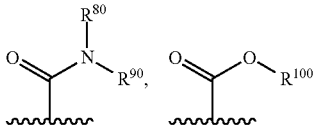

and —(CH$_2$)$_m$—OCH$_3$;
R$^{80}$, R$^{90}$ and R$^{100}$ are each independently selected from hydrogen, C$_{1-3}$ alkyl and C$_{1-3}$ alkoxy;
and
m is an integer of 1 to 6.

In certain preferred embodiments, the active agent is selected from:

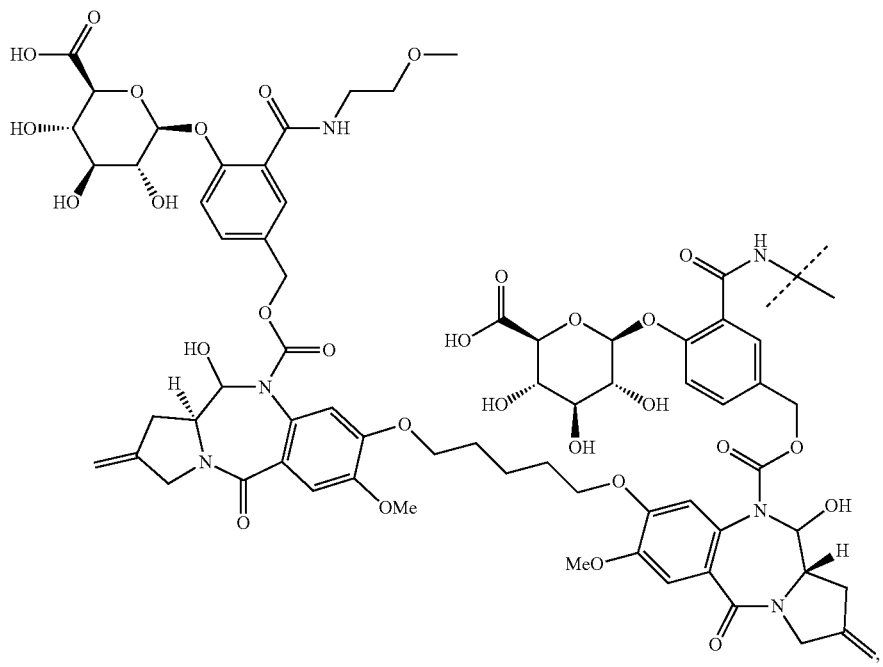

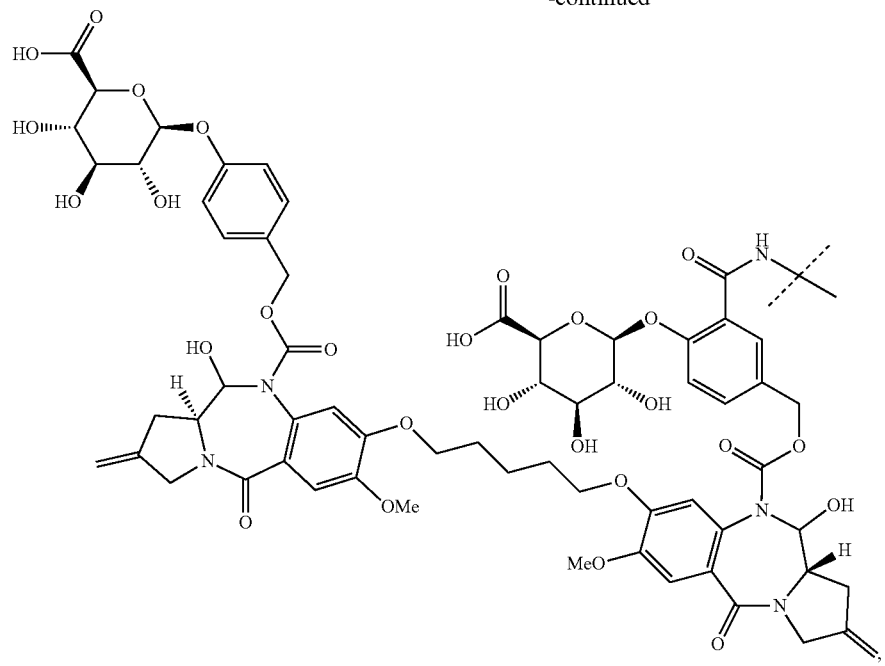
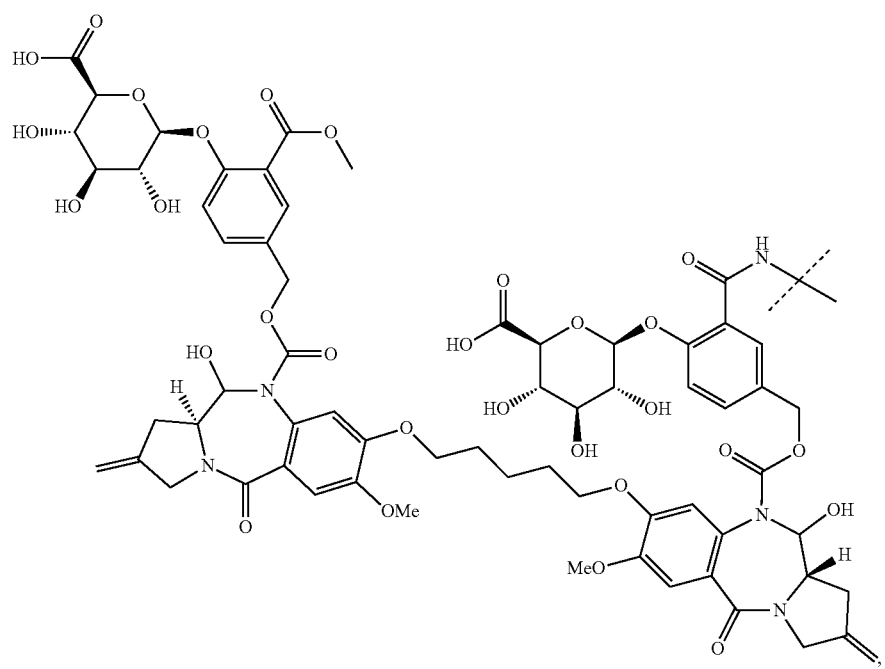

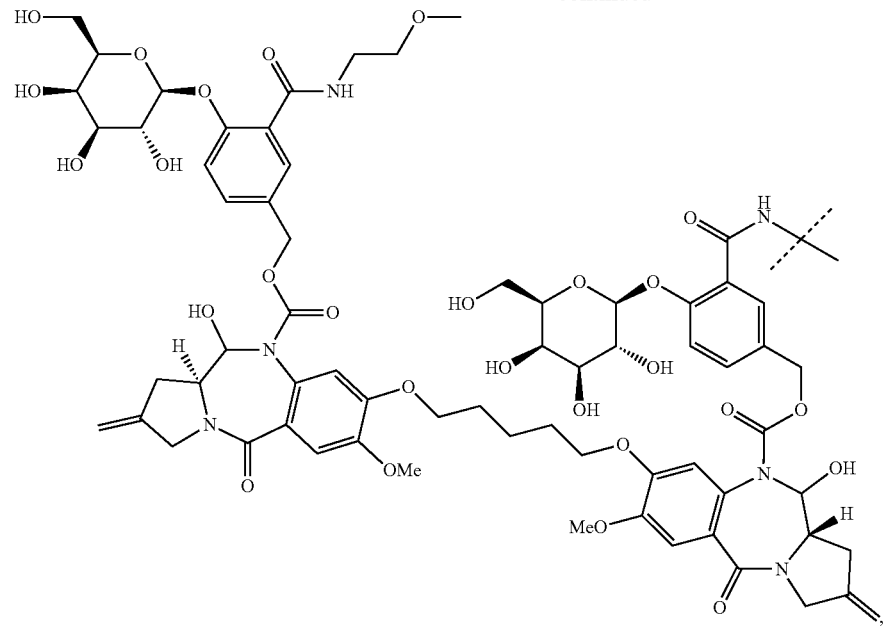
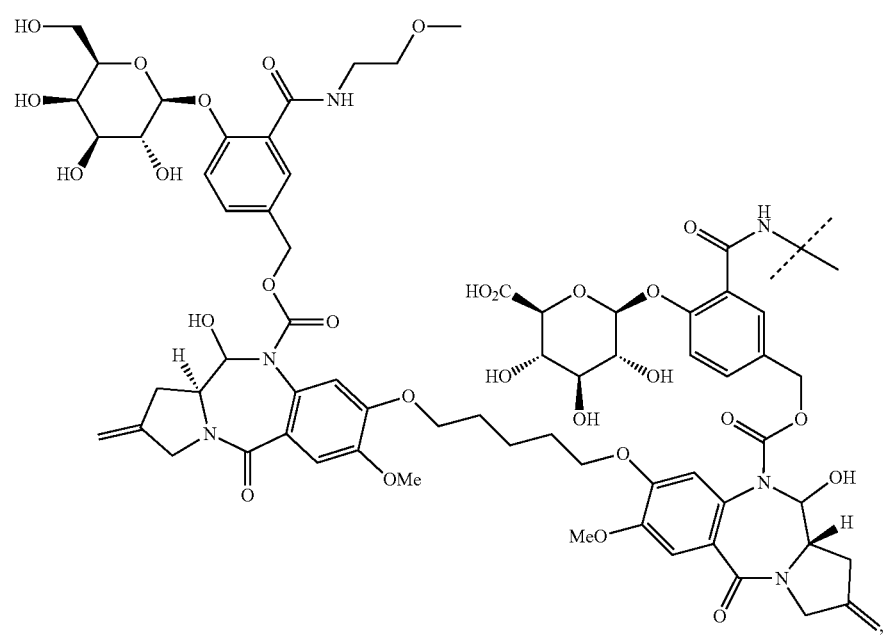

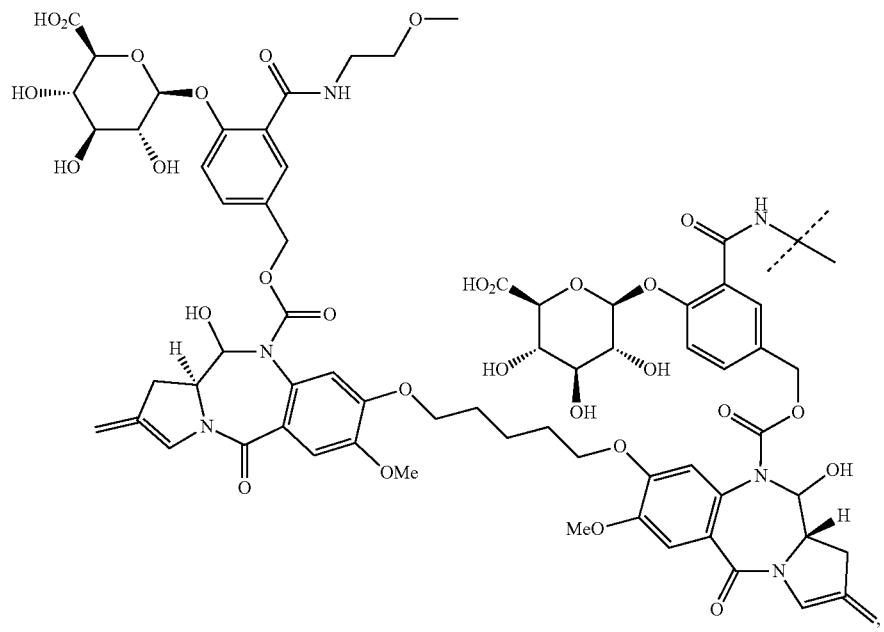
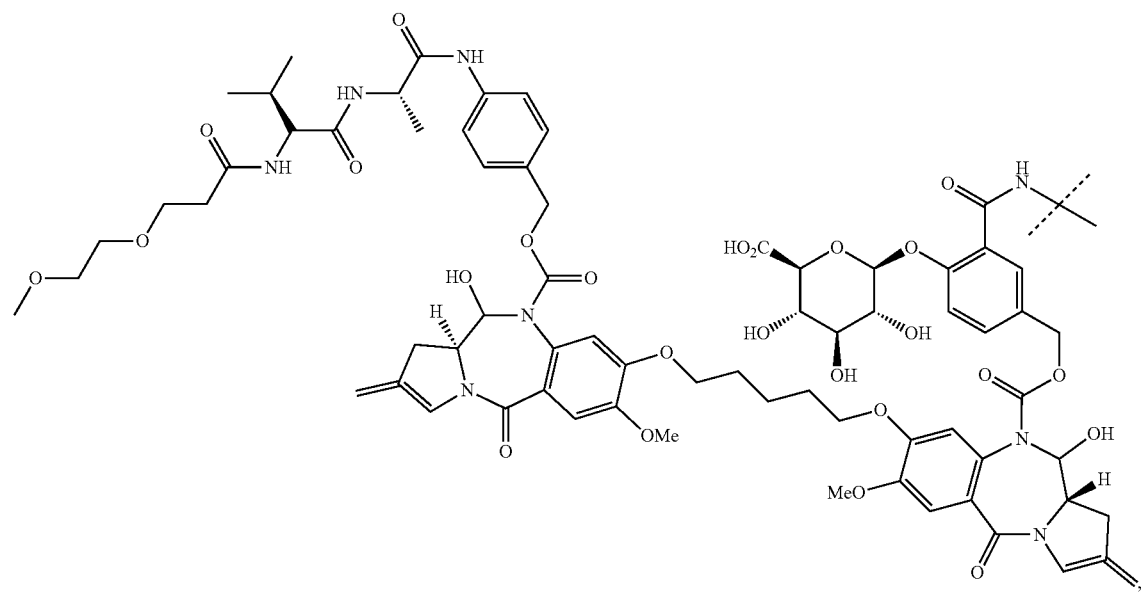

-continued
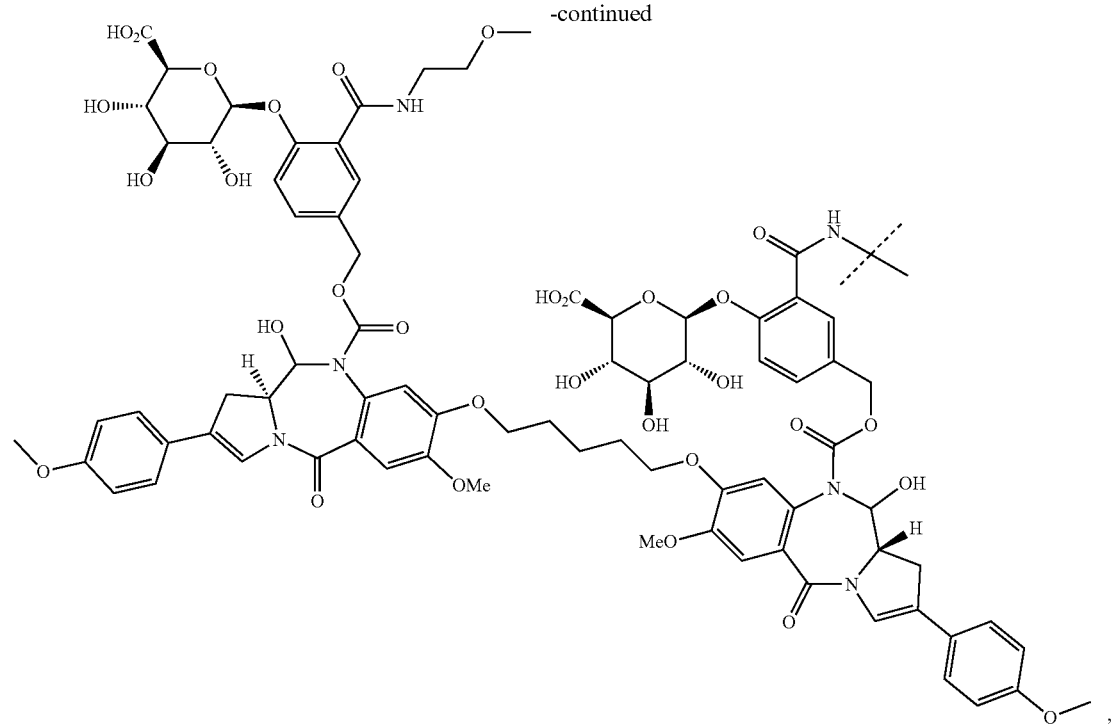
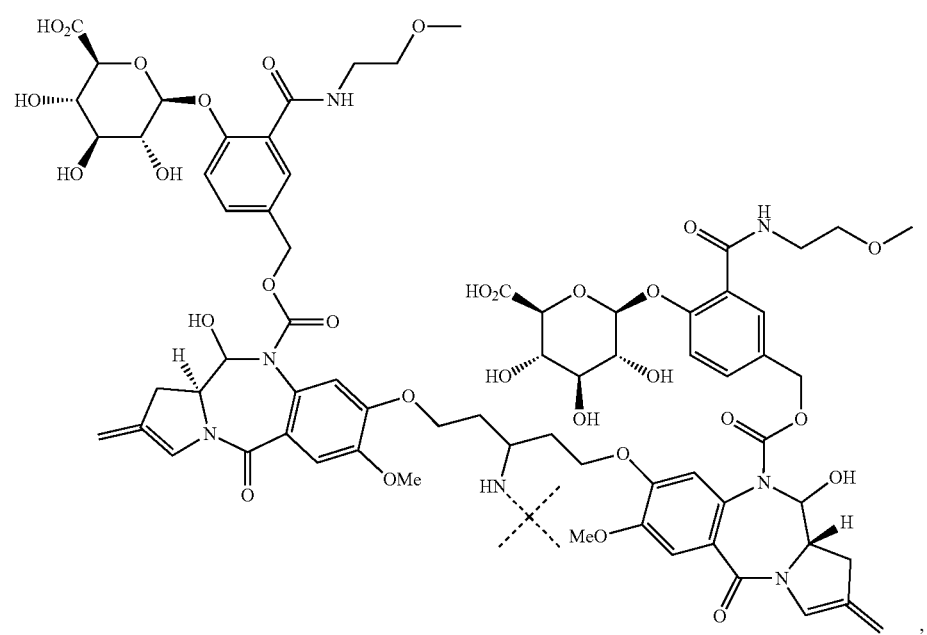

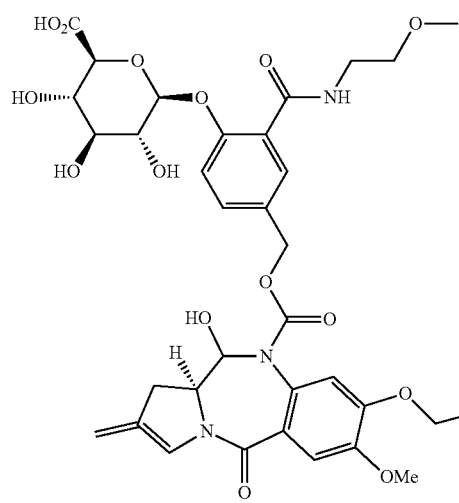
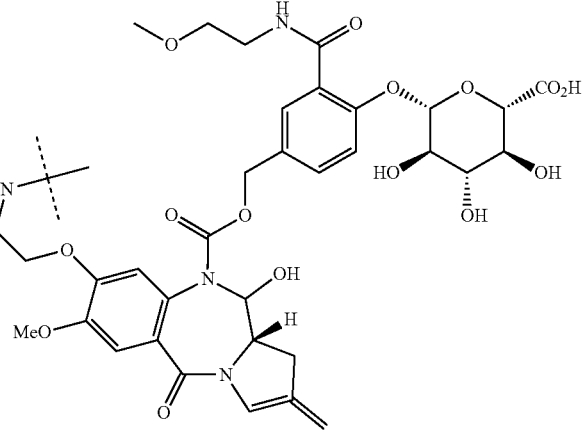

and

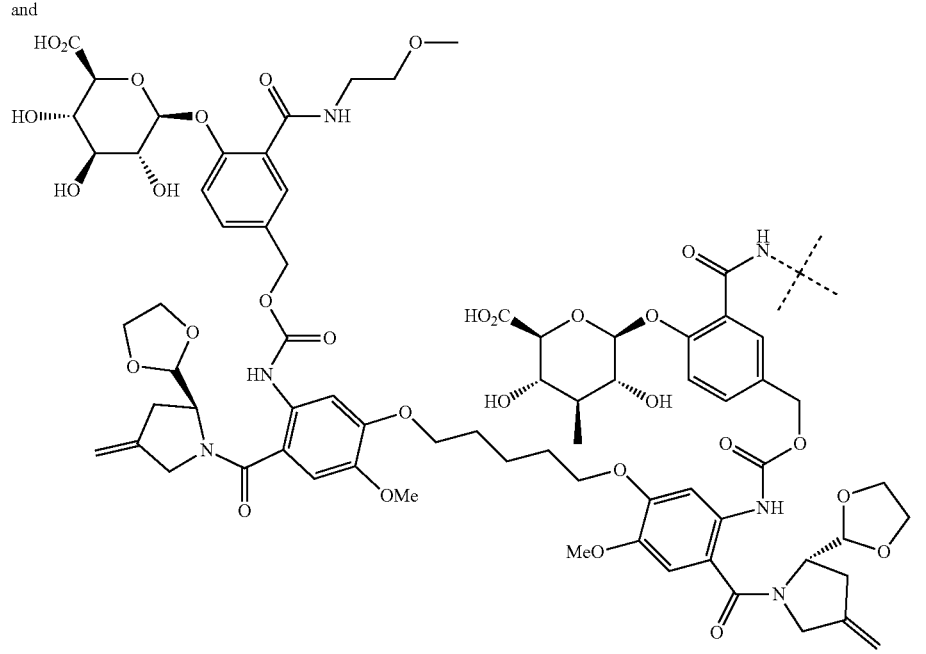

or a pharmaceutically acceptable salt thereof; and the bond overlaid with a dashed line represents a connection point to L.

In a further aspect, the present disclosure provides methods of treating a disease or disorder associated with the over-expression of ROR1 in a subject, comprising administering an antibody drug conjugate of the disclosure or a pharmaceutically acceptable salt thereof. In certain embodiments, the disease or disorder associated with the over-expression of ROR1 is cancer. In certain embodiments, the cancer is selected from chronic lymphocytic leukemia (CLL), B-cell leukemia, lymphoma, acute myeloid leukemia (AML), Burkitt lymphoma, mantle cell lymphoma (MCL), acute lymphoblastic leukemia (ALL), Diffuse large B-cell lymphoma (DLBCL), follicular lymphoma (FL) and marginal zone lymphoma (MZL), breast cancer, renal cancer, ovarian cancer, gastric cancer, liver cancer, lung cancer, colorectal cancer, pancreatic cancer, skin cancer, bladder cancer, testicular cancer, uterine cancer, prostate cancer, non-small cell lung cancer (NSCLC), neuroblastoma, brain cancer, colon cancer, squamous cell carcinoma, melanoma, myeloma, cervical cancer, thyroid cancer, head and neck cancer and adrenal cancer.

In a further aspect, the present disclosure provides methods of cancer in a subject, comprising administering an antibody drug conjugate of the disclosure or a pharmaceutically acceptable salt thereof. In certain embodiments, the cancer is selected from chronic lymphocytic leukemia (CLL), B-cell leukemia, lymphoma, acute myeloid leukemia (AML), Burkitt lymphoma, mantle cell lymphoma (MCL), acute lymphoblastic leukemia (ALL), Diffuse large B-cell lymphoma (DLBCL), follicular lymphoma (FL) and marginal zone lymphoma (MZL), breast cancer, renal cancer, ovarian cancer, gastric cancer, liver cancer, lung cancer, colorectal cancer, pancreatic cancer, skin cancer, bladder cancer, testicular cancer, uterine cancer, prostate cancer, non-small cell lung cancer (NSCLC), neuroblastoma, brain cancer, colon cancer, squamous cell carcinoma, melanoma, myeloma, cervical cancer, thyroid cancer, head and neck cancer and adrenal cancer.

In another aspect, the present invention provides an antibody-drug conjugate of general formula Ia below:

Ab-(Linker-D)$_n$,     [General Formula Ia]

Where:
Ab is an anti-ROR1 antibody;
Linker is a linker;
D is a pyrrolobenzodiazepine dimer as an active agent; and
The linker and the antibody are linked through the N10 or N10' position of the pyrrolobenzodiazepine dimer.

Here, a pyrrolobenzodiazepine dimer prodrug wherein at the N10 and N10' positions of the pyrrolobenzodiazepine dimer, respectively and independently, are attached any one selected from the group comprised of —C(O)O—*, —S(O)O—*, —C(O)—*, —C(O)NR—*, —S(O)$_2$NR—*, —(P(O)R')NR—*, —S(O)NR—* and —PO$_2$NR—* groups;

$R^X$ and $R^{X'}$ are independently selected from H, OH, N$_3$, CN, NO$_2$, SH, NH$_2$, ONH$_2$, NHNH$_2$, halo, C$_{1-8}$ alkyl, C$_{3-8}$ cycloalkyl, C$_{1-8}$ alkoxy, C$_{1-8}$ alkylthio, C$_{3-20}$ heteroaryl, C$_{5-20}$ aryl or mono- or (di)-C$_{1-8}$ alkylamino,
where * is a region where a linker is attached;

R and R' are respectively and independently H, OH, N$_3$, CN, NO$_2$, SH, NH$_2$, ONH$_2$, NHNH$_2$, halo, substituted or unsubstituted C$_{1-8}$ alkyl, substituted or unsubstituted C$_{3-8}$ cycloalkyl, substituted or unsubstituted C$_{1-8}$ alkoxy, substituted or unsubstituted C$_{1-8}$ alkylthio, substituted or unsubstituted C$_{3-20}$ heteroaryl, substituted or unsubstituted C$_{5-20}$ aryl, or mono- or di-C$_{1-8}$ alkylamino; and where, in a case where the C$_{1-8}$ alkyl, C$_{3-8}$ cycloalkyl, C$_{1-8}$ alkoxy, C$_{1-8}$ alkylthio, C$_{3-20}$ heteroaryl or C$_{5-20}$ aryl is substituted, the substitution is by a substitution group selected from a group comprising H, OH, N$_3$, CN, NO$_2$, SH, NH$_2$, ONH$_2$, NNH$_2$, halo, C$_{1-6}$ alkyl, C$_{1-6}$ alkoxy and C$_{6-12}$ aryl, or a pharmaceutically acceptable salt or solvate thereof may be used as an active agent.

More specifically, substitution occurs with X at the N10 position or with X' at the N'10 position of pyrrolobenzodiazepine dimer, where X or X' links the pyrrolobenzodiazepine dimer to a linker;

X and X' are selected, respectively and independently, from among —C(O)O*, —S(O)O—*, —C(O)—*, —C(O)NR$^X$—*, —S(O)$_2$NR$^X$—*, —P(O)R'NR$^X$—*, —S(O)NR$^X$—*, or —PO$_2$NR$^X$—*; and $R^X$ and $R^{X'}$ are independently selected from H, OH, N$_3$, CN, NO$_2$, SH, NH$_2$, ONH$_2$, NHNH$_2$, halo, C$_{1-8}$ alkyl, C$_{3-8}$ cycloalkyl, C$_{1-8}$ alkoxy, C$_{1-8}$ alkylthio, C$_{3-20}$ heteroaryl, C$_{5-20}$ aryl or mono- or di-C$_{1-8}$ alkylamino, In some embodiments, a pyrrolobenzodiazepine dimer precursor is provided. In a case of administering in the form of the precursor according to the present invention, there are advantages over conventional PBD drugs in that: additional reactions are necessary for conversion to an efficacious drug upon exposure to blood, preventing the potential for adverse reactions which may arise when the linker is cleaved prematurely; in that toxicity to normal cells is reduced, and in that the drug is more stable.

Further, when preparing antibody-drug conjugates, whereas antibody-drug conjugate prepared using conventional methods has high impurity content, and the exposed imine group is subject to nucleophile attack, posing a risk of a drug of an undesirable structure being generated. On the other hand, an antibody-drug conjugate prepared using the method according to the present invention has an advantage of ease of isolation due to high purity, and further improved physical properties over conventional PBD or PBD dimer.

In some embodiments, the pyrrolobenzodiazepine dimer precursor is a pyrrolobenzodiazepine dimer precursor wherein it has the structure of General Formula X or General Formula XI below, or a pharmaceutically acceptable salt or solvate thereof:

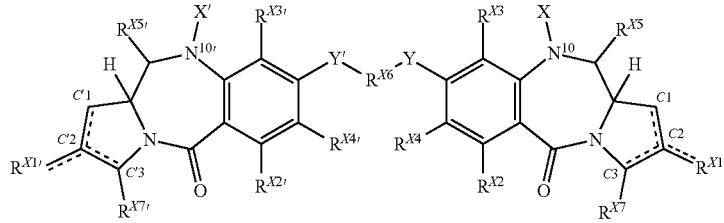

[General Formula X]

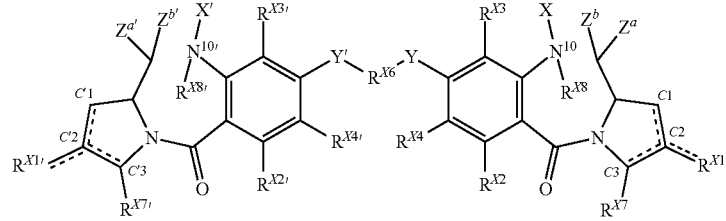

[General Formula XI]

In the above formulae:

the dotted lines denote the selective existence of double bonds between C1 and C2, between C2 and C3, between C'1 and C'2, or between C'2 and C'3;

$R^{X1}$ and $R^{X1'}$ are independently selected from H, OH, =O, =CH$_2$, CN, R''' OR''', =CH—R''',
=C(R''')$_2$, O—SO$_2$—R''', CO$_2$R''', COR''', halo and dihalo;

R''' is selected from R''', CO$_2$R''', COR''', CHO, CO$_2$H and halo;

each R''' is independently selected from $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3-7 membered heterocyclyl, 3-7 membered heterocycloalkyl and 5 to 7 heteroaryl;

$R^{X2}$, $R^{X2'}$, $R^{X3}$, $R^{X3'}$, $R^{X5}$ and $R^{X5'}$ are independently selected from H, R''', OH, OR''', SH, SR''', NH$_2$, NHR''', NR'''$_2$, NO$_2$, Me$_3$SN and halo;

$R^{X4}$ and $R^{X4'}$ are independently selected from H, R''', OH, OR''', SH, SR''', NH$_2$, NHR''', NR'''$_2$, NO$_2$, Me$_3$SN, halo, $C_{1-6}$ alkyl $C_{1-6}$ alkoxy, $C_{2-6}$ alkenyl, $C_{2-6}$ alkynyl, 3-7 membered heterocyclyl, $C_{5-12}$ aryl, 5 to 7 heteroaryl,
—CN, —NCO, —OR'', —OC(O)R'', —OC(O)NR''R''', —OS(O)R'', —OS(O)$_2$R$^o$, —SR'', —S(O)R'', —S(O)$_2$R'', —S(O)NR''R''', —S(O)$_2$NR''R''', —OS(O)NR''R''', —OS(O)$_2$NR''R''', —NR''R'''—NR''C(O)R$^o$, —NR''C(O) OR$^o$, —NR''C(O)NR$^o$R$^{o'}$, —NR''S(O)R$^o$, —NR''S(O)$_2$R$^o$, —NR''S(O)NR$^o$R$^{o'}$, —NR''S(O)$_2$NR$^o$R$^{o'}$, —C(O)R'', —C(O)OR$^o$ and —C(O)NR''R''';

X and X' are independently selected from —C(O)O*, —S(O)O—*, —C(O)—*, —C(O)NR$^X$—*, —S(O)$_2$NR$^X$—*, —P(O)R$^9$NR$^X$—*, —S(O)NR$^X$—*, or —PO$_2$NR$^X$—*;

$R^X$ and $R^{X'}$ are independently selected from H, OH, N$_3$, CN, NO$_2$, SH, NH$_2$, ONH$_2$, NHNH$_2$, halo, $C_{1-8}$ alkyl, $C_{3-8}$ cycloalkyl, $C_{1-8}$ alkoxy, $C_{1-8}$ alkylthio, $C_{3-20}$ heteroaryl, $C_{5-20}$ aryl or mono- or di-$C_{1-8}$ alkylamino;

Y and Y' are independently selected from O, S and N(H);

$R^{x6}$ is independently selected from $C_{3-12}$ alkylene, $C_{3-12}$ alkenylene, or $C_{3-12}$ heteroalkylene;

$R^{X7}$ and $R^{X7'}$ are independently selected from H, $C_{1-6}$ alkyl, $C_{2-6}$ alkenyl, $C_{2-6}$ alkynyl, $C_{3-6}$ cycloalkyl, 3-7 membered heterocycloalkyl, $C_{6-10}$ aryl, 5 to 7 heteroaryl, —OR$^r$, —OC(O)R$^r$, —OC(O)NR'R''', —OS(O)R$^r$, —OS(O)$_2$R$^r$, —SR$^r$, —S(O)R$^r$, —S(O)$_2$R$^r$, —S(O)NR'R''', —S(O)$_2$NR'R''', —OS(O)NR'R''', —OS(O)$_2$NR'R''', —NR'R''', —NR'C(O)R$^s$, —NR'C(O)OR$^s$, —NR'C(O)NR$^s$R$^{s'}$, —NRr$^S$(O)R$^s$, —NRr$^S$(O)$_2$R$^s$, —NRr$^S$(O)NR$^s$R$^{s'}$, —NRr$^S$(O)$_2$NR$^s$R$^s$, —C(O)R$^r$, —C(O)OR$^s$ or —C(O)NR'R''';

each R$^r$, R$^{r'}$, R$^s$ and R$^{s'}$ is independently selected from H, $C_{1-7}$ alkyl, $C_{2-7}$ alkenyl, $C_{2-7}$ alkynyl, $C_{3-13}$ cycloalkyl, 3-7 membered heterocyclyl, 3-7 membered heterocycloalkyl, $C_{5-10}$ aryl and 5 to 7 heteroaryl;

each $R^{X8}$ and $R^{X8'}$ is independently selected from H, $C_{1-6}$ alkyl, $C_{2-6}$ alkenyl, $C_{2-6}$-alkynyl, $C_{3-6}$ heteroalkyl, 3-7 membered heterocycloalkyl, $C_{5-10}$ aryl, 5 to 7 heteroaryl, —S(O)R''', —S(O)$_2$R''', —S(O)NR'''R''', —S(O)$_2$NR'''R'''—NR'''R''', —NR'''C(O)R''', —NR'''C(O) OR'', —NR''C(O)NR''R''', —NR''S(O)R'', —NR'''S(O)$_2$R'', —NR''S(O)NR''R''', —NR'''S(O)$_2$NR''R''', —C(O)R''', —C(O)OR''' and —C(O)NR'''R''';

$Z^a$ is selected from OR$^{X12a}$, NR$^{X12a}$R$^{X12a}$, or SR$^{X12a}$;

$Z^b$ is selected from OR$^{X13a}$, NR$^{X13a}$R$^{X13a}$, or SR$^{X13a}$;

$Z^{a'}$ is selected from OR$^{X12a}$, NR$^{X12a}$R$^{X12a}$, or SR$^{X12a}$;

$Z^{b'}$ is selected from OR$^{X13a'}$, NR$^{X13a'}$R$^{X13a'}$, or SR$^{X13a'}$;

each $R^{X12a}$, $R^{X12a'}$, $R^{X13a}$ and $R^{X13a'}$ is independently selected from H, $C_{1-6}$ alkyl, $C_{2-6}$ alkenyl, $C_{2-6}$ alkynyl, $C_{3-6}$ cycloalkyl, 3-7 membered heterocycloalkyl, $C_{5-10}$ aryl, 5 to 7 heteroaryl, —C(O)R$^{X15a}$, —C(O)OR$^{X15a}$ and —C(O)NR$^{X15a}$R$^{X15a'}$; and each $R^{X15a}$ and $R^{X15a'}$ is independently selected from $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3-7 membered heterocyclyl, 3-7 membered heterocycloalkyl, and 5 to 7 heteroaryl, and:

$R^{X13a}$ and $R^{X14a}$ arbitrarily bind to the atoms to which they are attached to form 3-7 membered heterocyclyl, 3-7 membered heterocycloalkyl, or 3-7 membered heteroaryl, and the $R^{X13a'}$ and $R^{X14a'}$ arbitrarily bind to the atoms to which they are attached to form 3-7 membered heterocyclyl, 3-7 membered heterocycloalkyl, or 3-7 membered heteroaryl; and each of R'', R''', R$^o$, R$^{o'}$, R$^p$ and R$^{p'}$ is independently selected from H, $C_{1-7}$ alkyl, $C_{2-7}$ alkenyl, $C_{2-7}$ alkynyl, $C_{3-13}$ cycloalkyl, 3-7 membered heterocycloalkyl, $C_{5-10}$ aryl, and 5 to 7 heteroaryl.

Further, R''' is independently selected from $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3-7 membered heterocyclyl, 3-7 membered heterocycloalkyl and 5 to 7 heteroaryl; and R''' is additionally substituted with of $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3-7 membered heterocyclyl, 3-7 membered heterocycloalkyl or 5 to 7 heteroaryl.

Further, $R^{x4}$ and $R^{x4'}$ are independently selected from H, R''', OH, OR''', SH, SR''', NH$_2$, NHR''', NR'''R''', NO$_2$, Me$_3$Sn, halo, $C_{1-6}$ alkyl $C_{1-6}$ alkoxy, $C_{2-6}$ alkenyl, $C_{2-6}$ alkynyl, $C_{3-6}$ cycloalkyl, 3-7 membered heterocycloalkyl, $C_{5-12}$ aryl, 5 to 7 heteroaryl, —CN, —NCO, —OR'', —OC(O)R$^o$, —OC(O)NR''R''', —OS(O)R'', —OS(O)$_2$R$^o$, —SR'', —S(O)R'', —S(O)$_2$R$^o$, —S(O)NR''R''', —S(O)$_2$NR''R''', —OS(O)NR''R''', —OS(O)$_2$NR''R''', —NR''R''', —NR''C(O) R$^o$, —NR''C(O)OR$^o$, —NR''C(O)NR$^o$R$^{o'}$, —NR''S(O)R$^o$, —NR''S(O)$_2$R$^o$, —NR''S(O)NR$^o$R$^{o'}$, —NR''S(O)$_2$NR$^o$R$^{o'}$, —C(O)R'', —C(O)OR$^o$ and —C(O)NR''R'''; and $R^{X4}$ or $R^{X4'}$ is $C_{1-6}$ alkyl, $C_{1-6}$ alkoxy, $C_{2-6}$ alkenyl, $C_{2-6}$ alkynyl, $C_{3-6}$ cycloalkyl, 3-7 membered heterocycloalkyl, $C_{5-12}$ aryl or 5 to 7 heteroaryl, and additionally is substituted with at least one $C_{1-6}$ alkyl, $C_{1-6}$ alkoxy, $C_{2-6}$ alkenyl, $C_{2-6}$ alkynyl, $C_{3-6}$ cycloalkyl, 3-7 membered heterocycloalkyl, $C_{5-10}$ aryl, 5 to 7 heteroaryl, —OR$^p$, —OC(O)R$^p$, —OC(O)NR$^p$R$^{p'}$, —OS(O)R$^p$, —OS(O)$_2$R$^p$, —SR$^p$, —S(O)R$^p$, —S(O)$_2$R$^p$, —S(O)NR$^p$R$^{p'}$, —S(O)$_2$NR$^p$R$^{p'}$, —OS(O)NR$^p$R$^{p'}$, —OS(O)$_2$NR$^p$R$^{p'}$, —NR$^p$R$^{p'}$, —NR$^p$C(O)R$^q$, —NR$^p$C(O)OR$^q$, —NR$^p$C(O)NR$^q$R$^{q'}$, —NR$^p$S(O)R$^q$, —NR$^p$S(O)$_2$R$^q$, —NR$^p$S(O)NR$^q$R$^{q'}$, —NR$^p$S(O)$_2$NR$^q$R$^{q'}$, —C(O)R$^p$, —C(O)OR$^p$ or —C(O)NR$^p$R$^p$.

Further, $R^{X7}$ and $R^{X7'}$ are independently selected from H, $C_{1-6}$ alkyl, $C_{2-6}$ alkenyl, $C_{2-6}$ alkynyl, $C_{3-6}$ cycloalkyl, 3-7 membered heterocycloalkyl, $C_{6-10}$ aryl, 5 to 7 heteroaryl, —OR$^r$, —OC(O)R$^r$, —OC(O)NR'R'', —OS(O)R$^r$, —OS(O)$_2$R$^r$, —S(O)R$^r$, —S(O)$_2$R$^r$, —S(O)NR'R'', —S(O)$_2$NR'R'', —OS(O)NR'R'', —OS(O)$_2$NR'R'', —NR'R$^{r'}$, —NR'C(O)R$^s$, —NR'C(O)OR$^s$, —NR'C(O)NR$^s$R$^{s'}$, —NR'S(O)R$^s$, —NR'S(O)$_2$R$^s$, —NR'S(O)NR$^s$R$^{s'}$, —NR'S(O)$_2$NR$^s$R$^s$, —C(O)R$^r$, —C(O)OR$^s$ or —C(O)NR'R$^{r'}$;

$R^{X7}$ and $R^{X7'}$ are independently selected from $C_{1-6}$ alkyl, $C_{2-6}$ alkenyl, $C_{2-6}$ alkynyl, $C_{3-6}$ cycloalkyl, 3-7 membered heterocycloalkyl, $C_{6-10}$ aryl, 5 to 7 heteroaryl, as well as $C_{1-6}$ alkyl, $C_{2-6}$ alkenyl, $C_{2-6}$ alkynyl, $C_{3-6}$ cycloalkyl, 3-7 membered heterocycloalkyl, $C_{6-10}$ aryl, 5 to 7 heteroaryl, —OR$^t$, —OC(O)R$^t$, —OC(O)NR$^t$R$^{t'}$, —OS(O)R$^t$, —OS(O)$_2$R$^t$, —SR$^t$, —S(O)R$^t$, —S(O)$_2$R$^t$, —S(O)NR$^t$R$^{t'}$, —S(O)$_2$NR$^t$R$^{t'}$, —OS(O)NR$^t$R$^{t'}$, —OS(O)$_2$NR$^t$R$^{t'}$, —NR$^t$R$^{t'}$, —NR$^t$C(O)R$^u$, —NR$^t$C(O)OR$^u$, —NR$^t$C(O)NR$^u$R$^{u'}$, —NR'S(O)R", —NR'S(O)₂R", —NR'S(O)NR"R"', —NR'S(O)₂NR"R"', —C(O)R', —C(O)OR' or —C(O)NR'R''; and R', R'', R$^s$, R$^{s'}$, R$^t$, R$^{t'}$, R" and R"' are independently selected from H, $C_{1-7}$ alkyl, $C_{2-7}$ alkenyl, $C_{2-7}$ alkynyl, $C_{3-13}$ cycloalkyl, 3-7 membered heterocycloalkyl, $C_{5-10}$ aryl, and 5 to 7 heteroaryl.

Further, $R^{X1}$ and $R^{X1'}$ are independently selected from R'''; and

R''' is selected from $C_{1-6}$ alkyl, $C_{2-6}$ alkenyl, $C_{5-7}$ aryl and $C_{3-6}$ heteroaryl.

Further, $R^{X2}$, $R^{X2'}$, $R^{X3}$, $R^{X3'}$, $R^{X5}$ and $R^{X5'}$ are independently selected from H or OH.

Further, $R^{X4}$ and $R^{X4'}$ are independently selected from R'''; and

R''' is $C_{1-6}$ alkoxy.

Further, $R^{X4}$ and $R^{X4'}$ are independently any one selected from methoxy, ethoxy and butoxy-.

Further, Y and Y' are O.

Further, the $R^{x6}$ is $C_{3-12}$ alkylene, $C_{3-12}$ alkenylene or $C_{3-12}$ heteroalkylene, with the $R^{x6}$ substituted by —NH₂, —NHR''', —NHC(O)R''', —NHC(O)CH₂—[OCH₂CH₂]$_n$—$R^{XX}$, or —[CH²CH²O]$_n$—$R^{XX}$;

$R^{XX}$ is H, OH, N₃, CN, NO₂, SH, NH₂, ONH₂, NHNH₂, halo, $C_{1-8}$ alkyl, $C_{3-8}$ cycloalkyl, $C_{1-8}$ alkoxy, $C_{1-8}$ alkylthio, $C_{3-20}$ heteroaryl, $C_{5-20}$ aryl or mono- or di-$C_{1-8}$ alkyl amino; and n is an integer of 1 through 6.

Further, in some embodiments, the active agent is a pyrrolobenzodiazepine dimer denoted by General Formula XII or General Formula XIII;

[General Formula XII]

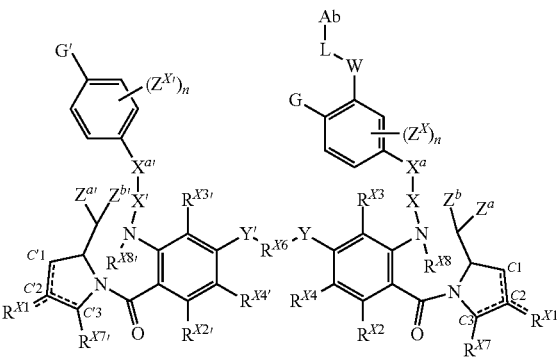

[General Formula XIII]

$X^a$ and $X^{a'}$ are independently selected from between a bond or $C_{1-6}$ alkylene;

$Z^{X'}$ and $Z^X$ are independently selected from hydrogen, $C_{1-8}$ alkyl, halogen, cyano, nitro,

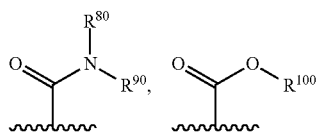

or —(CH₂)$_m$—OCH₃;

$R^{80}$, $R^{90}$ and $R^{100}$ are each independently selected from hydrogen, $C_{1-8}$ alkyl, $C_{2-6}$ alkenyl and $C_{1-6}$ alkoxy; and m is an integer of 0 to 12.

$Z^{X'}$ and $Z^X$ are independently any one selected from hydrogen and —(CH₂)$_m$—OCH₃;

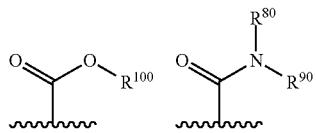

$R^{80}$, $R^{90}$ and $R^{100}$ are each independently selected from hydrogen, $C_{1-3}$ alkyl and $C_{1-3}$ alkoxy;

m is an integer of 1 to 6; and the active agent is any one selected from:

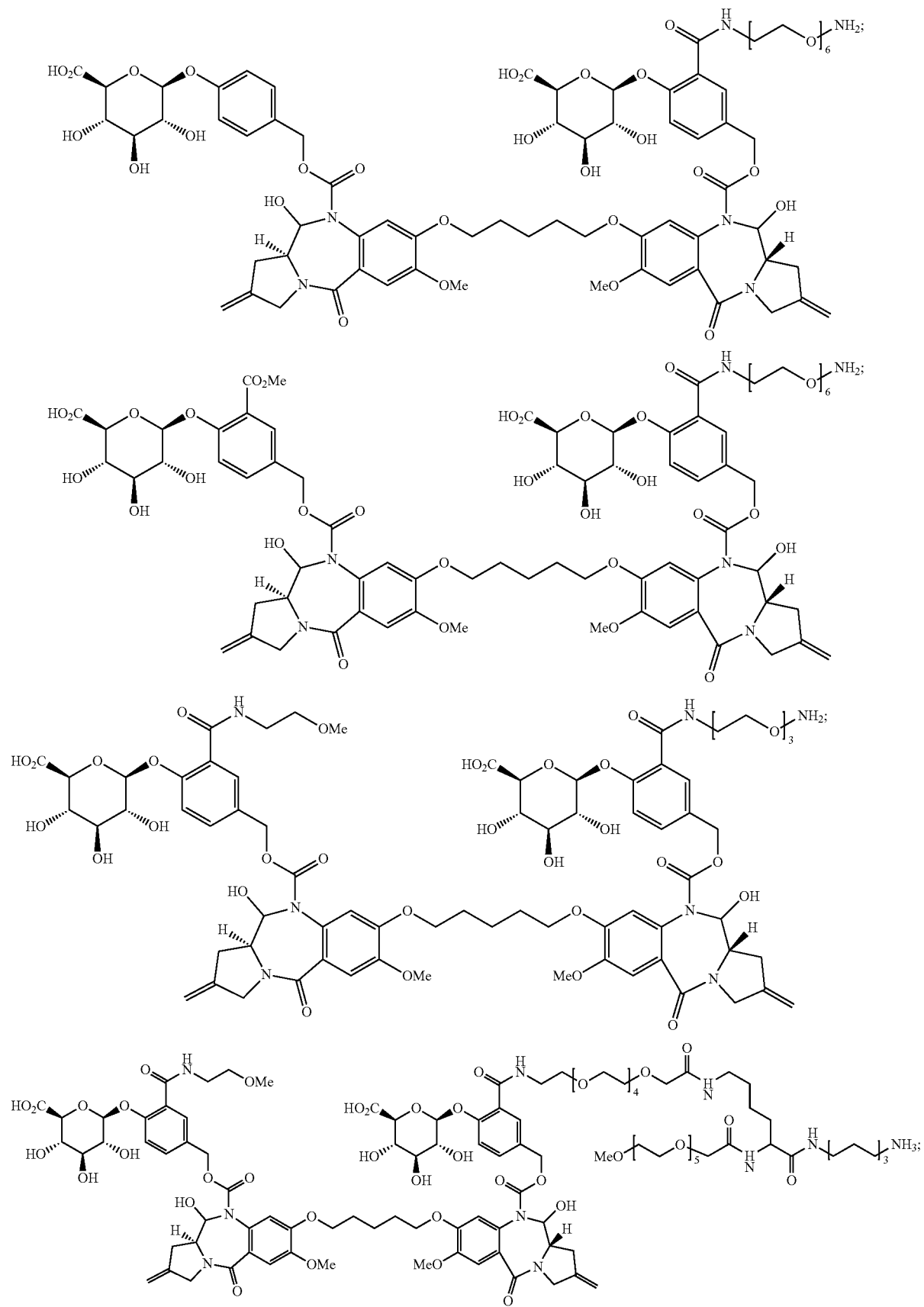

-continued
51
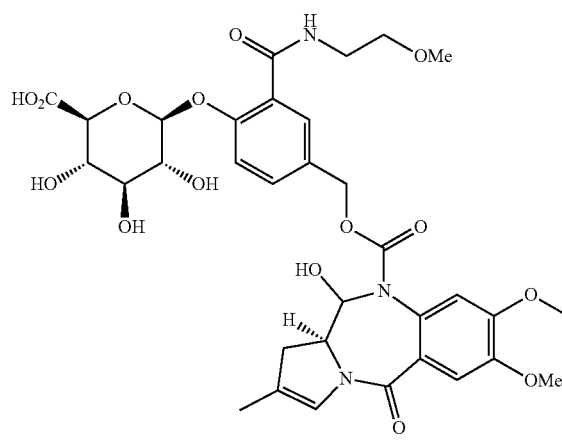
52
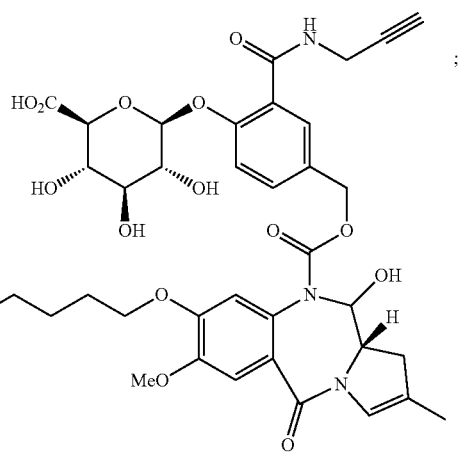
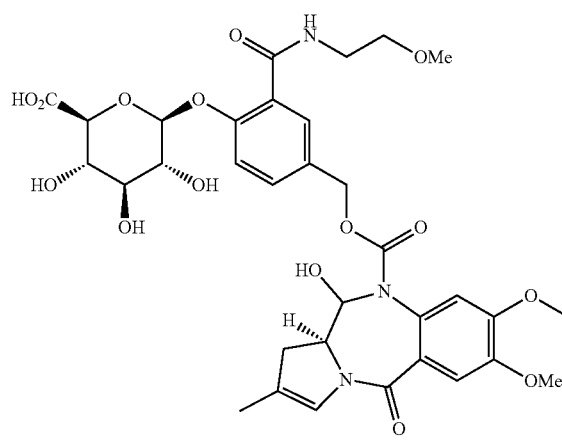
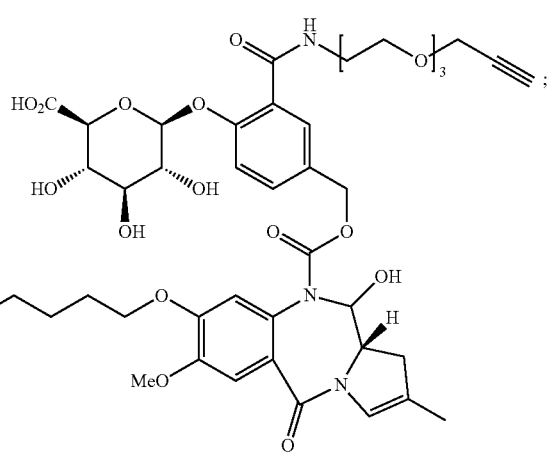
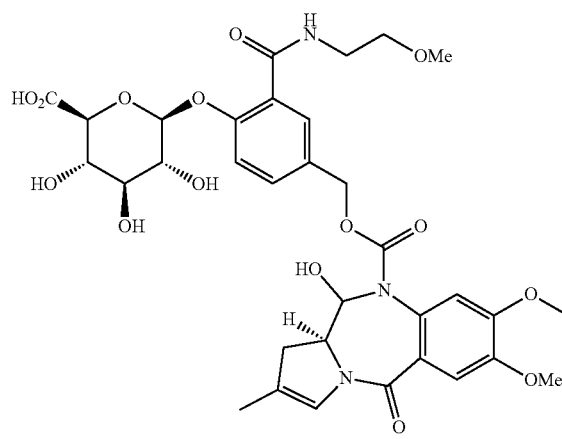
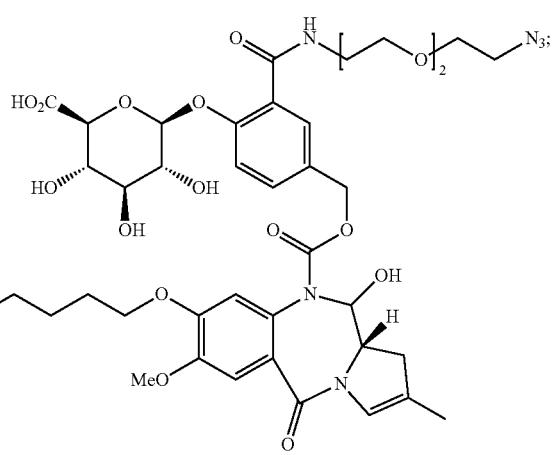

53 54
-continued
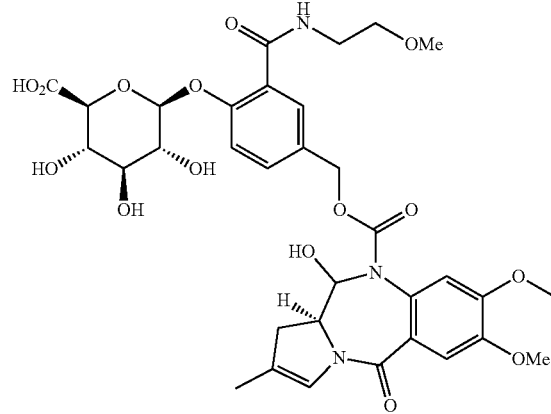
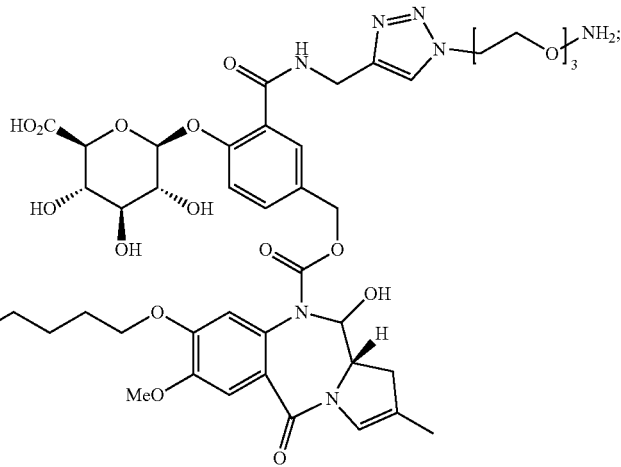
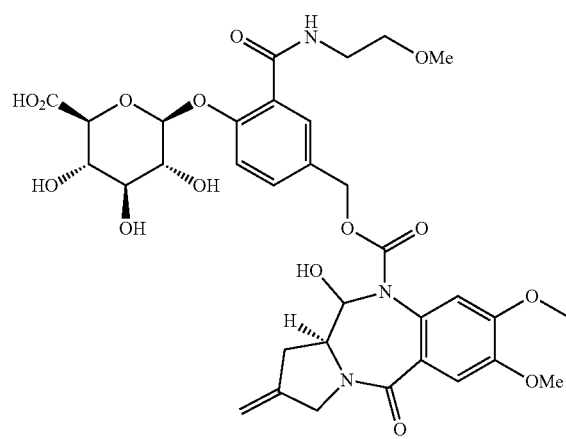
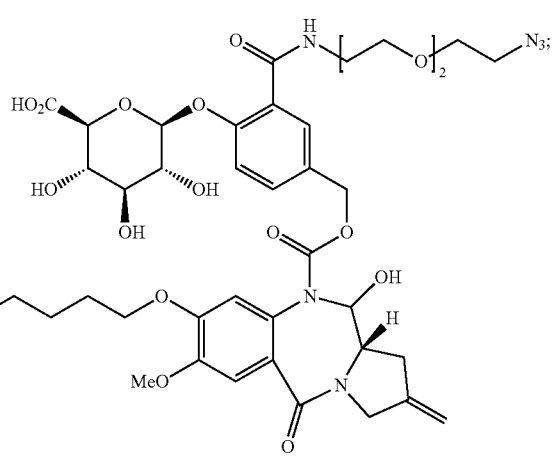
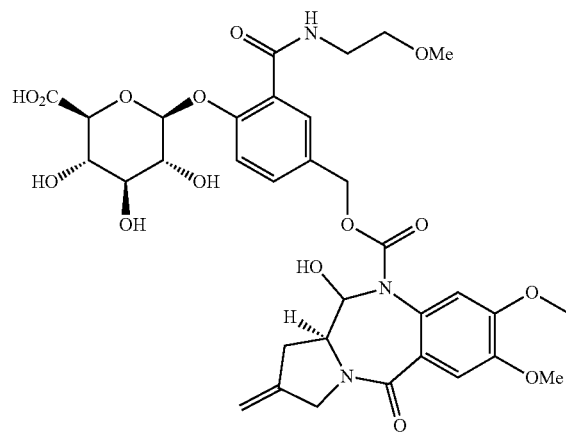
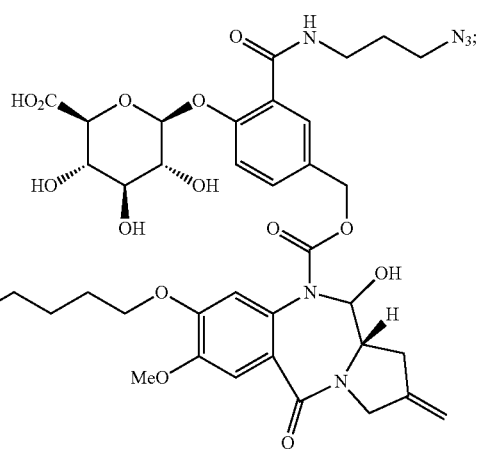

-continued
55
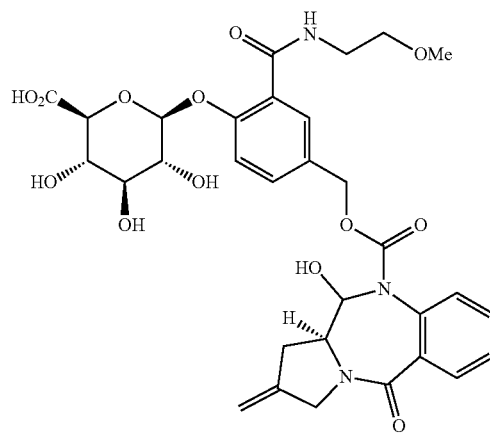
56
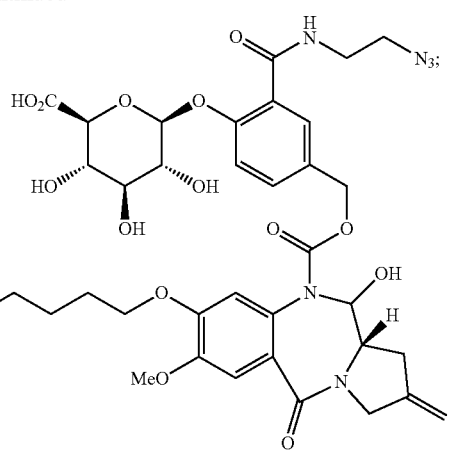
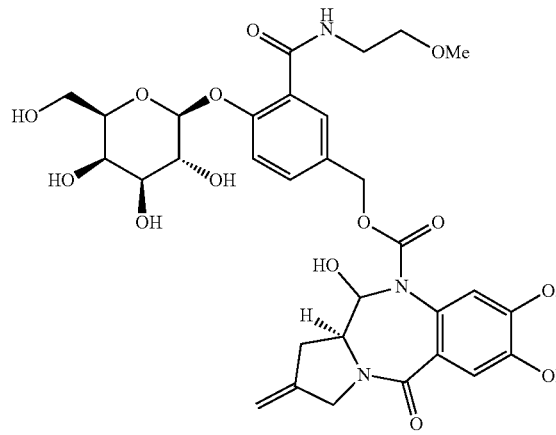
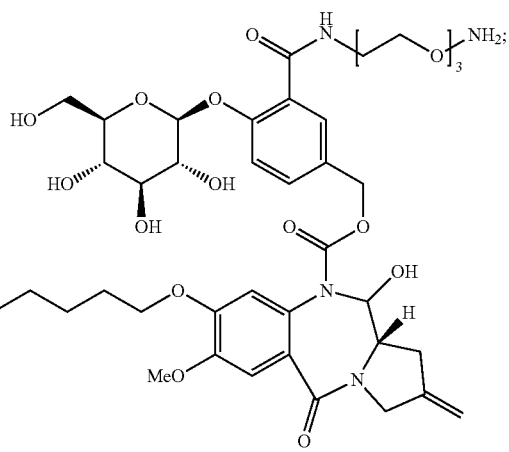
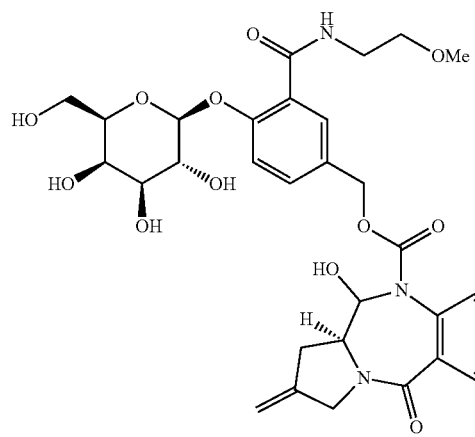
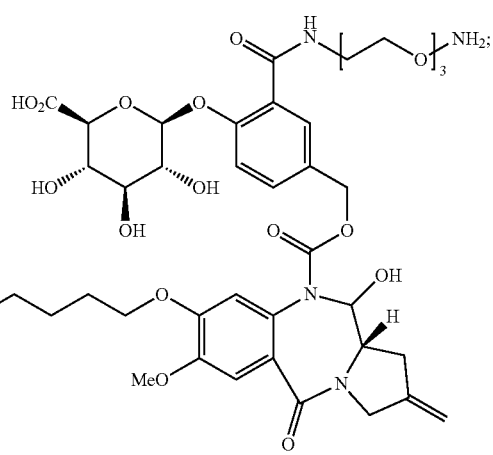

57 58
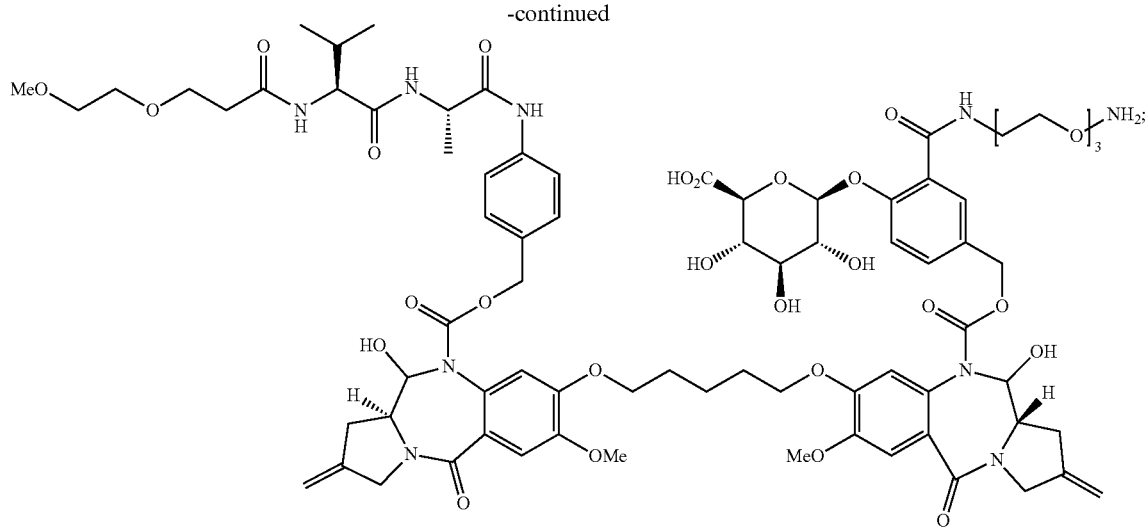
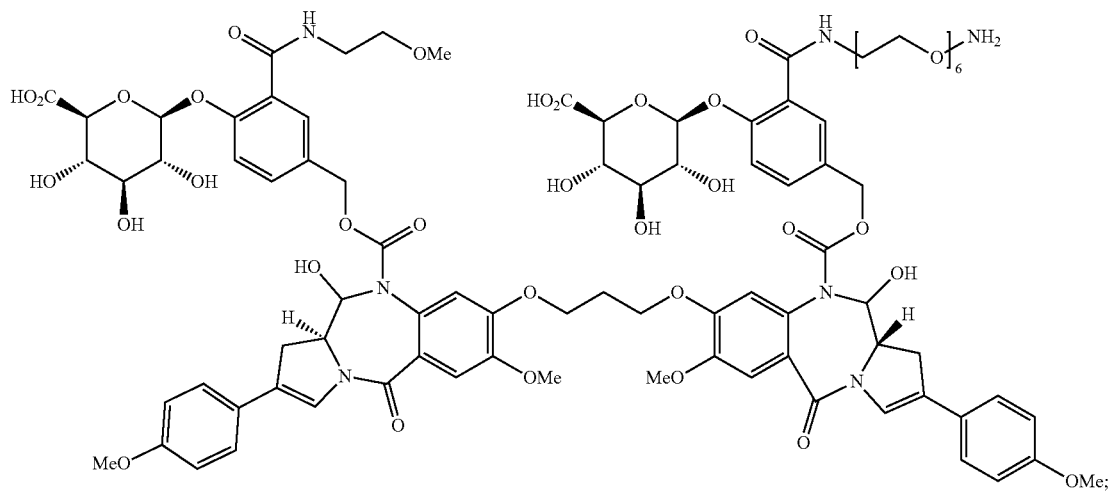
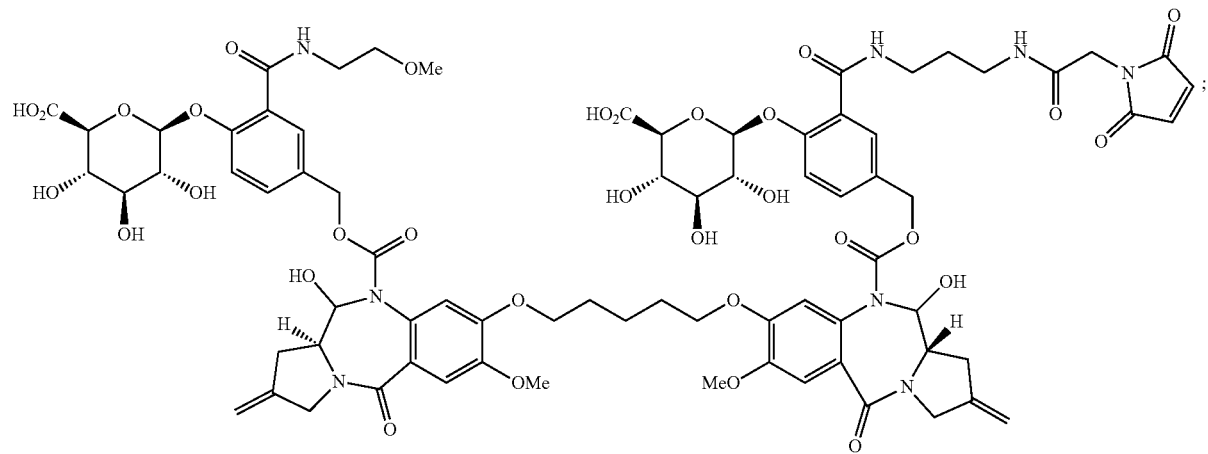

59
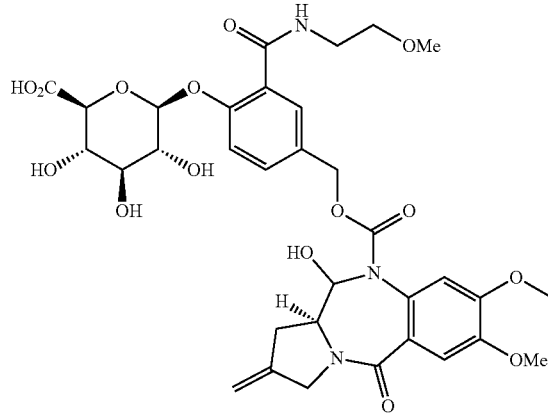
60
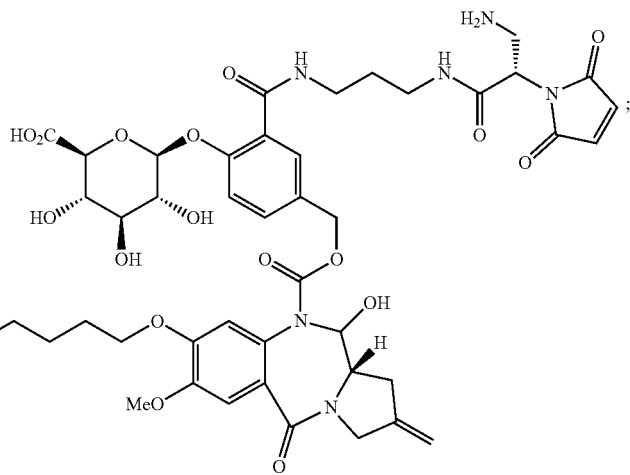
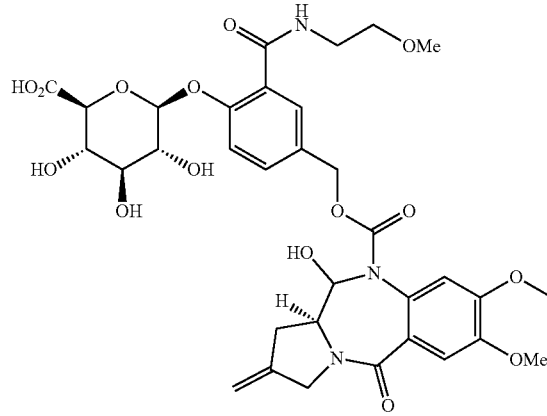
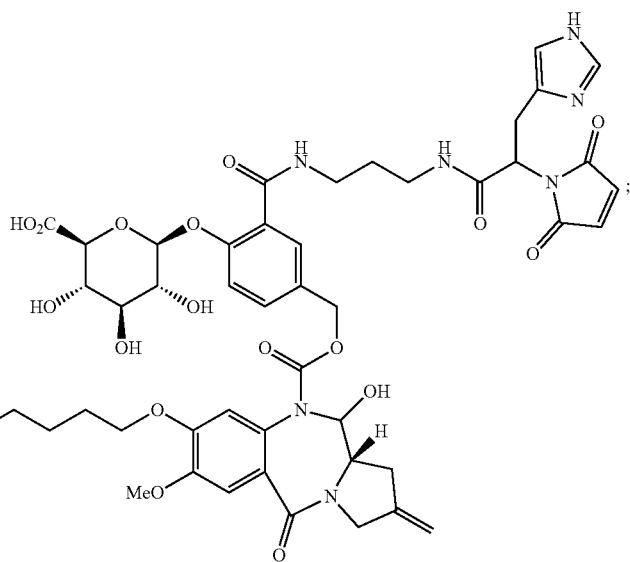
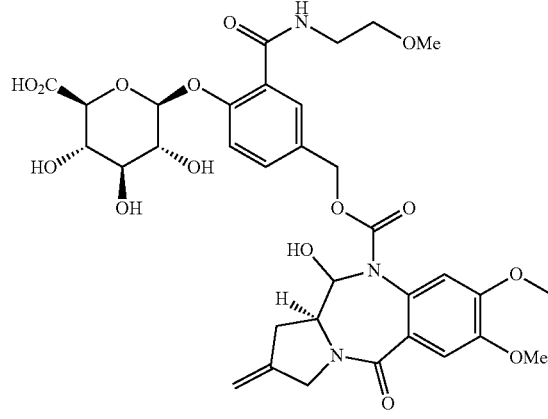
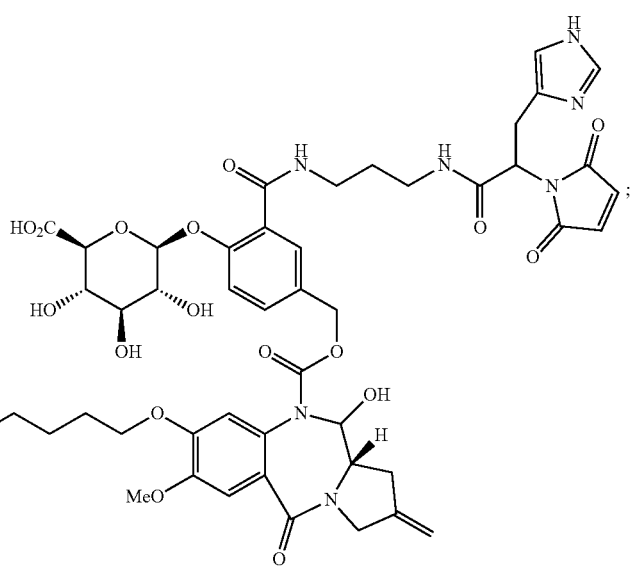

61    62
-continued
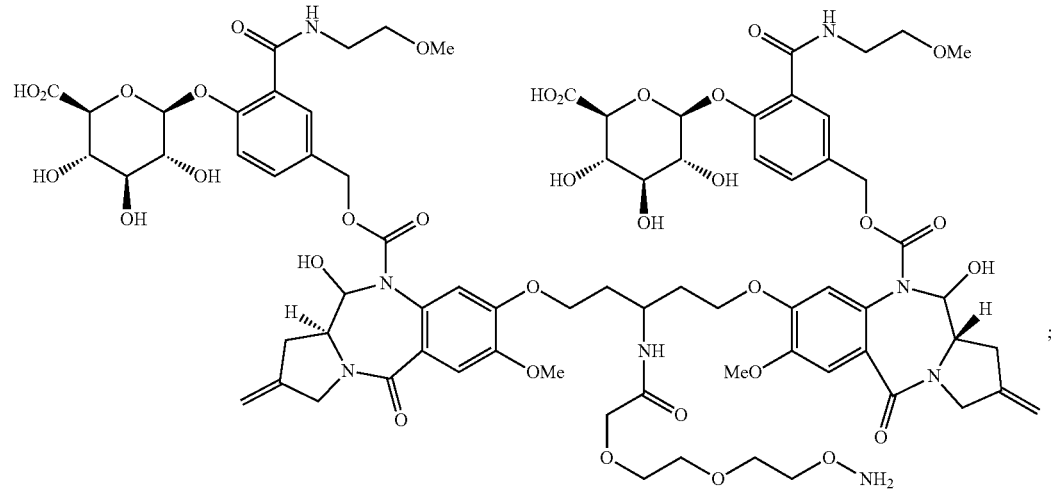
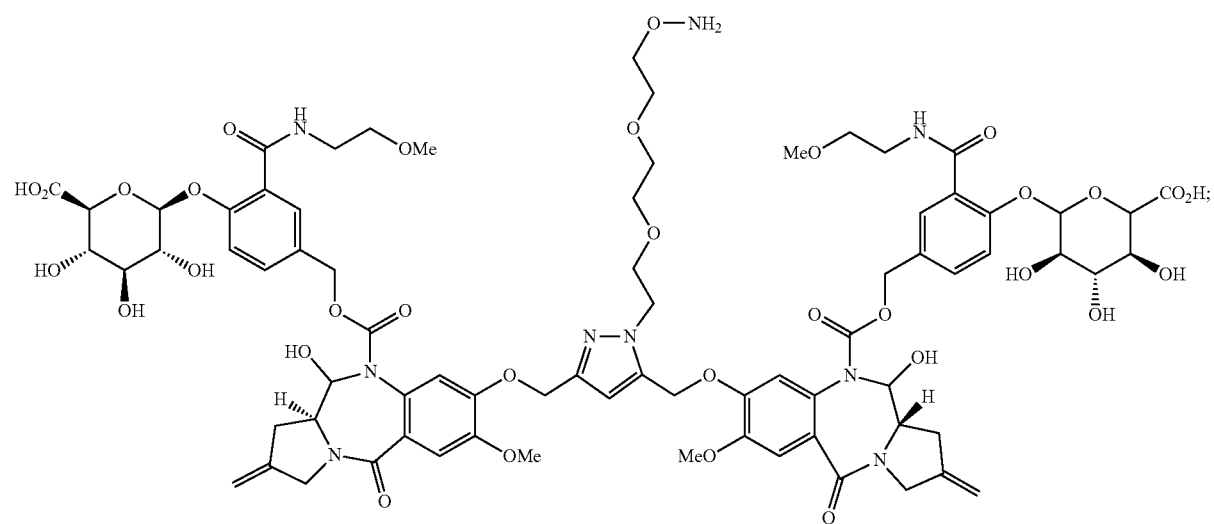
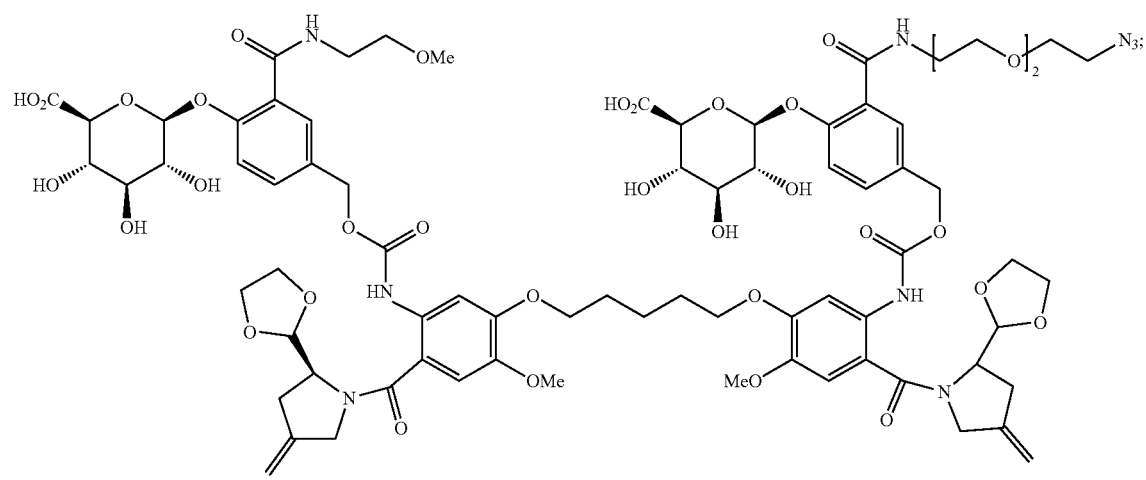

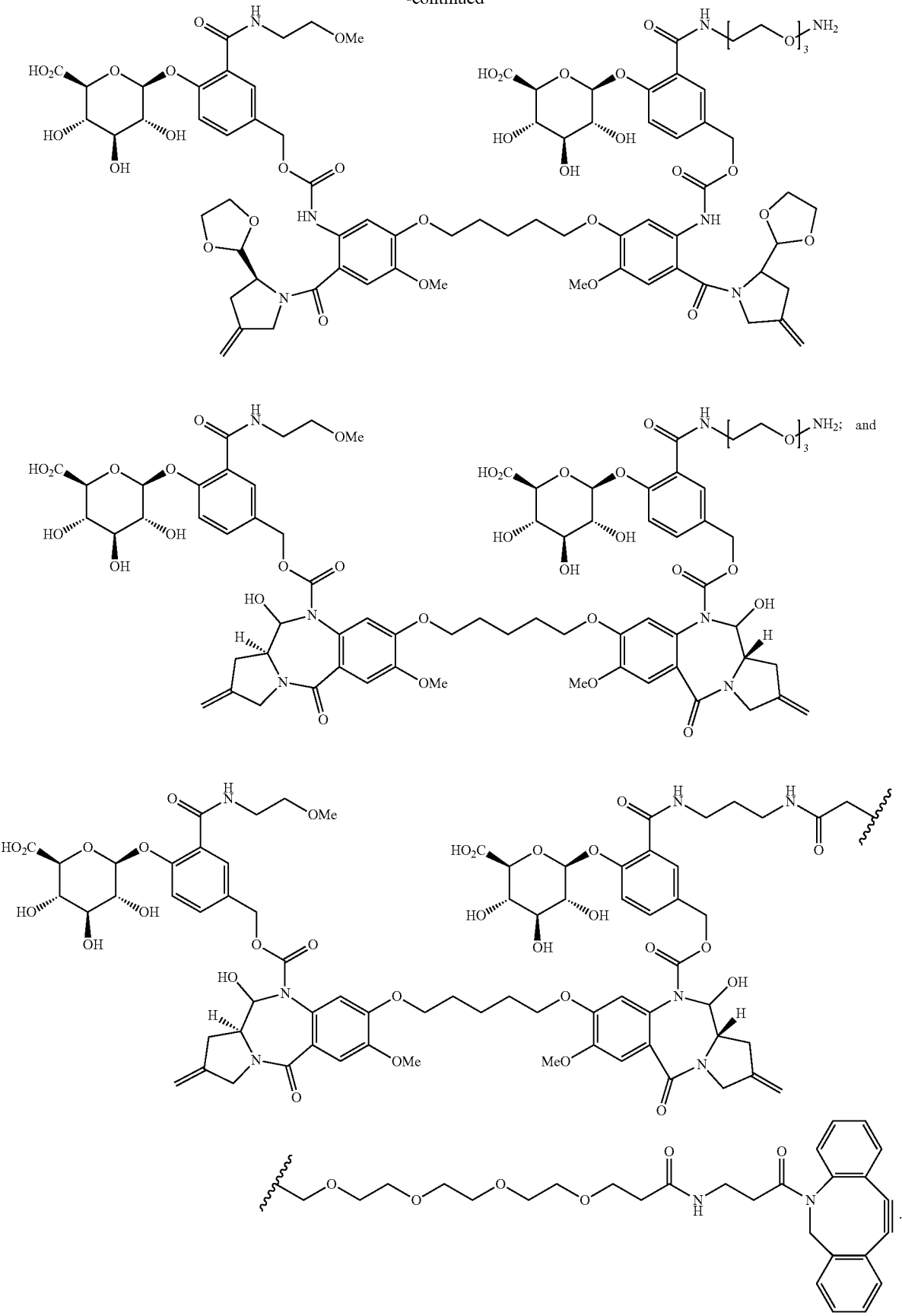

In another aspect, the present invention provides, in relation to the preparation of a drug for prevention or treatment of illnesses associated with over-expression of ROR1, a use for the antibody-drug conjugate according to the present invention, or a pharmaceutically acceptable salt or solvate thereof.

Here, an illness associated with over-expression of ROR1 is cancer, examples of which are, but not limited to: chronic lymphocytic leukemia (CLL), B-cell leukemia, lymphoma, acute myeloid leukemia (AML), Burkitt lymphoma, mantle cell lymphoma (MCL), acute lymphoblastic leukemia (ALL), Diffuse large B-cell lymphoma (DLBCL), follicular lymphoma (FL) and marginal zone lymphoma (MZL), breast cancer, renal cancer, ovarian cancer, gastric cancer, liver cancer, lung cancer, colorectal cancer, pancreatic cancer, skin cancer, bladder cancer, testicular cancer, uterine cancer, prostate cancer, non-small cell lung cancer (NSCLC), neuroblastoma, brain cancer, colon cancer, squamous cell carcinoma, melanoma, myeloma, cervical cancer, thyroid cancer, head and neck cancer and adrenal cancer.

In another aspect, the present invention provides a pharmaceutical composition for prevention or treatment of illness associated with over-expression of ROR1, the composition comprising the antibody-drug conjugate according to the present invention or a pharmaceutically acceptable salt or solvate thereof.

Further, a pharmaceutically efficacious amount of chemotherapeutic agent, for example at least one type of therapeutic co-agent, and pharmaceutically acceptable excipients may additionally be included.

In some embodiments, the therapeutic co-agent may be used with agents exhibiting preventive, improving or therapeutic effects against illnesses associated with over-expression of ROR1, agents which are able to reduce the adverse effects which appear upon administration of therapeutic agents for illnesses associated with over-expression of ROR1, or agents which exhibit an immune-boosting effect, but agents with which the therapeutic co-agent are not limited to the foregoing. This means that the therapeutic co-agent may be used in combination with any medicine which exhibits therapeutically useful effects, further improves the stability of pyrrolobenzodiazepine, reduces the adverse effects which may manifest upon administration of pyrrolobenzodiazepine, or boosts immunity to maximize therapeutic effect when applied in the form of a compound drug with pyrrolobenzodiazepine.

In another aspect of the present invention, the present invention provides a method for treating illness associated with over-expression of ROR1 in a subject having an illness associated with over-expression of ROR1, the method comprising a step of administering a subject with the antibody-drug conjugate according to the present invention or pharmaceutically acceptable salt or solvate thereof in an effective dose for treating illness associated with over-expression with ROR1, and a method of administering [the antibody-drug conjugate according to the present invention or pharmaceutically acceptable salt or solvate thereof] by mixing with one or more anti-proliferative, cytostatic or cytotoxic substances.

In one aspect of the present invention, a method for treating cancer, the method comprises a step of administering the above pharmaceutical composition to a patient, is provided.

The antibody-drug conjugate according to the present invention is suitable for use in providing an active agent, specifically pyrrolobenzodiazepine, to a target position on a target object. The antibody-drug conjugate according to the present invention discharges active pyrrolobenzodiazepine that does not have any linkers, and does not contain any modification which can impact the reactivity of the pyrrolobenzodiazepine compound.

Antibody-drug conjugates described herein, by including an antibody as described above, is able to effectively, specifically and selectively deliver a drug to cells expressing ROR1. By having an antibody stably bonded to a drug to maintain in-vivo stability while exhibiting the intended cytotoxicity, and in particular being more stable in the serum and stable in circulation, and employing linker technology which includes a self-immolative group which allows a drug to be easily released within a cancer cell to maximize efficacy, these conjugates exhibit a benefit of providing a drug-linker-ligand system which allows a drug and/or toxin to safely reach a target cell and effectively exhibit efficacy while having greatly reduced toxicity.

BRIEF DESCRIPTION OF THE DRAWINGS

In FIG. 10, whether or not cell death occurred was analyzed using a single mechanism of action where possible. It was found in the results of treating a cell line expressing ROR1 with an anti-ROR1 antibody according to the present invention that the antibody formed a multimer and was able to induce cell death. As for the 2A2 antibody used as a reference group, it was found that cell death was not induced even in cases where a multimer was formed.

Figure 1:
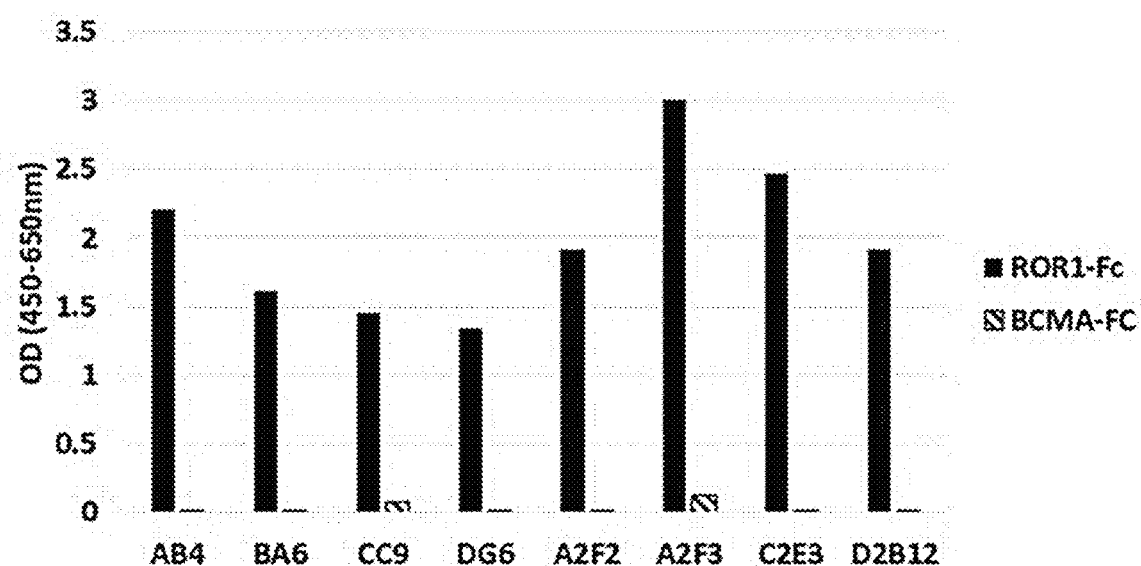
FIG. 1 shows results of analyzing (ELISA) the binding capacity of an anti-ROR1 monoclonal phage antibody prepared according to one example of the present invention to ROR1 antigen. It is shown that the respective anti-ROR1 monoclonal antibodies specifically bind to extracellular domain ROR1 antigen. BCMA-Fc is a negative control group, and it is shown that the respective anti-ROR1 monoclonal antibodies specifically bind only to ROR1 antigen, and do not bind to the BCMA protein or the Fc used as a tag.

The present invention is based on the development of antibodies able to specifically bind to ROR1.

The titles used under this section are used for convenience in stating the specification, and the present invention is not limited thereto.

Unless otherwise defined. In the present disclosure, scientific and technical terms used in the present invention shall be defined as ordinarily understood by a skilled person of the present technical field. Further, unless specifically required in context, singular expressions include plural expressions, and plural expressions include singular expressions.

DEFINITIONS

The following definitions apply in the present specification:

In the present specification, "conjugates" refers to cell binding agents that are covalently linked to one or more molecules of a cytotoxic compound. Here, "cell binding agent" is a molecule having affinity for a biological target, for example, a ligand, protein, antibody, specifically a monoclonal antibody, protein or antibody fragment, and the binding agent serves to direct the biologically active compound to the biological target. In some embodiments, the conjugate may be designed to target tumor cells through cell surface antigens. The antigen may be a cell surface antigen that is overexpressed or expressed in an abnormal cell type. Specifically, the target antigen may be expressed only on proliferative cells (e.g., tumor cells). Target antigens may be selected based on different expression, usually between proliferative and normal tissues. In the present disclosure, a ligand is bonded to a linker.

In the present disclosure, a "variant" of a polypeptide such as an antigen-binding fragment, protein or antibody is a polypeptide where, compared to another polypeptide sequence, insertion, deletion, addition and/or substitution has occurred in at least one amino acid residue, including fused polypeptides. Further, protein variants include those which have been modified by proteolytic cleavage, phosphorylation or other post-translational modification, but maintain the biological activity of the antibody disclosed, for example binding and specificity to ROR1. The variant may be approximately 99%, 98%, 97%, 96%, 95%, 94%, 93%, 92%, 91%, 90%, 89%, 88%, 87%, 86%, 85%, 84%, 83%, 82%, 81% or 80% identical to the sequence of the antibody or antigen-binding fragment thereof disclosed in the present invention. Percent identity (%) or homology may be calculated with reference to the following.

In one example, percent identity of peptide sequences can be calculated, for example, as 100×[(identical positions)/min($TG_A$, $TG_B$)], where $TG_A$ and $TG_B$ are the sum of the number of residues and internal gap positions in peptide sequences A and B in the alignment that minimizes $TG_A$ and $TG_B$. (Russell et al., *J. Mol Biol.*, 244: 332-350 (1994)).

In the present disclosure, conservative amino acid substitution refers to a substitution which does not significantly impact the activity or antigenicity of the polypeptide. A polypeptide may include one or more conservative substitutions. Non-limiting examples are disclosed in Table 3 below.

In the present disclosure, a "derivative" of a polypeptide refers to a polypeptide wherein at least one residue has been chemically modified through conjugation with another chemical moiety, and is different from an insertion, deletion, addition or substitution variant.

In the present disclosure, the term "found in nature" used in relation to polypeptide, nucleic acid and host cells, etc. means that the materials exist naturally.

The ROR1 (Receptor Tyrosine Kinase-Like Orphan Receptor) recognized by the antibody according the present invention refers to a transmembrane protein of the RTK (Receptor Tyrosine Kinase) family. In one example, the extracellular domain is recognized in particular. The ROR1 recognized by the antibody according to the present invention may be an extracellular domain which exists on the cell membrane or does not exist on the cell membrane. The human protein of ROR1 is comprised of 937 amino acids, where the amino acid sequence is NCBI Reference Sequence ID: NP_005003.2 and the nucleic acid sequence is NM_005012.3. Unless clear from the context used. In the present disclosure, ROR1 designates hROR1, but the antibody according to the present invention also has mouse ROR1-specific binding capacity. The Mouse ROR1 amino acid is GenBank: BAA75480.1.

In the present disclosure, "identity" means sequence similarity of two or more polypeptides or two or more polynucleotides, as determined by aligning and comparing two or more polypeptides or two or more polynucleotide sequences. Such intersequence identity is generally expressed as "percent identity", which means the same amino acid or nucleotide ratio between molecules being compared and is calculated based on the smallest molecule of the molecules being compared. Methods that can be used to align nucleic acids or polypeptides to calculate multimolecular identity are known in the art.

In the present disclosure, "affinity" or ["affinity"] is the strength of interaction between an antibody or its antigen-binding fragment and an antigen, and it is determined by properties of the antigen such as size, shape and/or charge of antigen, and CDR sequences of the antibody or antigen-binding fragment. The methods for determining the affinity are known in the art, and the following may be used as references.

The antibody or its antigen-binding fragment is called "specifically binding" to its target such as an antigen, when a dissociation constant ($K_D$) is $<10^{-6}$M. The antibody specifically binds to a target with "high affinity" when $K_D$ is $<1\times^{-8}$M.

As used in the present disclosure, "antigen-binding fragment" of a chain (heavy chain or light chain) of an antibody or immunoglobulin includes a part of an antibody which lacks some amino acids compared to a full-length chain, but can specifically bind to an antigen. This fragment can be considered as having biological activity, in that it can specifically bind to a target antigen, or can compete with other antibodies or an antigen binding fragment to bind to a specific epitope. In some embodiments, this fragment comprises at least one CDR present in a full-length light chain or heavy chain, and in some examples, it includes a short-chain heavy chain and/or light chain, or part thereof. This biological active fragment may be produced by a recombinant DNA technique or may be produced, for example, by cutting an intact antibody enzymatically or chemically. An immunologically functional immunoglobulin fragment includes Fab, Fab, F(ab)2, scFab, dsFv, Fv, scFV, scFV-Fc, diabody, minibody, scAb, and dAb, but not limited thereto, and may be derived from any mammal, including, but not limited to, human, mouse, rat, camelid or rabbit. The functional parts of antibodies such as the one or more CDRs disclosed in the present invention may be linked with a secondary protein or a small molecular compound by a covalent bond, and thereby used as a targeted therapeutic agent for a specific target.

In the present disclosure, "Fc" region comprises two heavy chain fragments comprising CH2 and CH3 domains of an antibody. These 2 heavy chain fragments are combined each other by hydrophobic interaction of two or more of disulfide bonds and a CH3 domain.

In the present disclosure, "Fab fragment" consists of 1 light chain and 1 heavy chain comprising a variable region and $CH_1$ only. The heavy chain of a Fab molecule cannot form a disulfide bond with another heavy chain molecule. In an scFab, two molecules of Fab are linked by a flexible linker.

In the present disclosure, "Fab' fragment" includes a Fab fragment and additionally a region between CH1 and CH2 domains of a heavy chain. A disulfide bond may form between two heavy chains of Fab' fragments of two molecules, forming a $F(ab')_2$ molecule.

In the present disclosure, as aforementioned, "$F(ab')_2$ fragment" comprises two light chains and two heavy chains comprising a variable region CH1 and part of a constant region between the CH1 and CH2 domains, with an interchain disulfide bond formed between the two heavy chains. Accordingly, a $F(ab')_2$ fragment consists of two Fab' fragments, and the two Fab' fragments are joined to each other by the disulfide bond between them.

In the present disclosure, "Fv region" is a fragment of an antibody which comprises each variable region of a heavy chain and a light chain, but does not comprise constant regions. In an sdFV, a heavy chain and a light chain are linked by a disulfide bond. In an scFc, the Fv is linked by a flexible linker. In an scFv-Fc, an Fc is linked to an scFV. In a minibody, CH3 is linked to an scFV. A diabody comprises the scFVs of two molecules.

In the present disclosure, "single chain Fv" or "scFv" antibody fragment includes the VH and VL domains of an antibody, these domains existing within a single polypeptide chain. An Fv polypeptide may additionally comprise a polypeptide linker between a Vh domain which enables the scFv to form the target structure for antigen binding, and a VL domain.

In the present disclosure, "short-chain antibody (scAb)" is a single polypeptide chain comprising one light chain constant region or one constant region of a heavy chain, wherein heavy chain and light chain variable regions are linked by a flexible linker. A reference for a short-chain antibody may be found in U.S. Pat. No. 5,260,203, disclosed in the present invention by reference.

In the present disclosure, "domain antibody (dAb)" is an immunologically functional immunoglobulin fragment comprising only a variable region of a heavy chain or a variable region of a light chain. In one embodiment, two or more VH regions are linked by a covalent bond by a peptide linker, to form a bivalent domain antibody. Two VH regions of this bivalent domain antibody may target the same or different antigen.

In the present disclosure, "complementarity determining region" (CDR; that is, CDR1, CDR2 and CDR3) denotes amino acid residues of the variable domain of an antibody, which are necessary for binding to antigen. Each variable domain typically has three CDR domains, identified as CDR1, CDR2 and CDR3.

In the present disclosure, "framework region" (FR) refers to variable domain residues other than the CDR residues. Each variable domain typically has four FRs, identified as FR1, FR2, FR3 and FR4.

In the present disclosure, "bivalent antigen-binding protein" or "bivalent antibody" comprises 2 antigen-binding sites. The two antigen-binding sites included in a bivalent antibody may have the same antigen specificity, or the antibody may be a dual-specific antibody where the antigen-biding sites bind to different antigens.

In the present disclosure, "multi-specific antigen-binding protein" or "multi-specific antibody" targets two or more of antigens or epitopes.

In the present disclosure, "linker" refers to a compound which covalently bonds a cytotoxic compound to a ligand or antibody. In some embodiments, the linker disclosed in PCT/US2016/063564 and PCT/US2016/063595 may be used, both of which are hereby incorporated by reference herein in their entireties, and particularly for the linkers disclosed therein.

In the present disclosure, "non-substituted or substituted" is used to refer to a group which may be non-substituted or substituted; "substituted" refers to a group having at least one substituent group; and "substituent group" refers to a chemical part covalently bonded to or joined with a parent group. It is understood that substituents and substitution patterns on the compounds of the present invention can be selected by one of ordinary skilled person in the art to result in chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. For example, the substituent may be, but is not limited to, hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. In certain embodiments, groups (e.g., alkyl, cycloalkyl, heteroaryl, heterocyclyl, or aryl groups) referred to in the structural formulae herein are optionally substituted, i.e., are non-substituted or substituted. In certain embodiments, groups (e.g., alkyl, cycloalkyl, heteroaryl, heterocyclyl, or aryl groups) referred to in the structural formulae herein are unsubstituted.

As used herein, the terms "optionally substituted" or "non-substituted or substituted" refer to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or $CH_2$—OP(O)(O-alkyl)$_2$. Preferably, "optionally substituted" or "non-substituted or substituted" refer to the replacement of one to four hydrogen radicals in a given structure with the substituents mentioned above. More preferably, one to three hydrogen radicals are replaced by the substituents as mentioned above. It is understood that the substituent can be further substituted.

In the present disclosure, "halo" refers to fluorine, chlorine, bromine or iodine, etc.

In certain embodiments of the present disclosure, "alkyl" is a monovalent moiety obtained by removing a hydrogen atom from a carbon atom of an aliphatic or alicyclic, saturated or unsaturated (unsaturated, fully unsaturated) hydrocarbon compound. Examples of saturated alkyls include methyl, ethyl, Butyl, n-pentyl (amyl), n-hexyl, n-heptyl and the like, saturated cyclic alkyl groups such as methyl, ethyl, Isopropyl, isobutyl, sec-butyl, tert-butyl, isopentyl and neopentyl, etc.

In other embodiments of the present disclosure, the term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

In both of the above embodiments and throughout the specification, examples, and claims, "alkyl" is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

In the present disclosure, "alkoxy" refers to —OR where R is an alkyl group, and examples include methoxy, ethoxy, n-propoxy, isopropoxy, n-butoxy, sec-butoxy, isobutoxy and tert-butoxy, etc.

In the present disclosure, "alkenyl" is an alkyl having at least one carbon-carbon double bond. Examples of unsaturated alkenyl groups are ethenyl (vinyl, —CH=$CH_2$), 1-propenyl (—CH=$CHCH_3$), 2-propenyl, isopropenyl, butenyl, pentenyl and hexenyl, etc.

In the present disclosure, "alkynyl" is an alkyl group having at least one carbon-carbon triple bond, and examples of unsaturated alkynyl group include ethynyl and 2-propynyl, etc.

In the present disclosure, "carboxy" refers to —C(=O)OH.

In the present disclosure, "formyl" refers to —C(=O)H.

In the certain embodiments of the present disclosure, "aryl" refers to a monovalent moiety obtained by removing a hydrogen atom from an aromatic ring atom of an aromatic compound. For example, "$C_{5-7}$ aryl" is a moiety having from 5 to 7 ring atoms, which is a monovalent moiety obtained by removing a hydrogen atom from the aromatic ring atoms of an aromatic compound, and "$C_{5-10}$ aryl" is a moiety having from 5 to 10 ring atoms, which is a monovalent moiety obtained by removing a hydrogen atom from the aromatic ring atoms of an aromatic compound. Here, the prefixes ($C_{5-7}$, $C_{5-10}$, etc.) refer to the number of ring atoms or a range for the number of ring atoms, regardless of whether they are carbon atoms or hetero atoms. For example, "$C_{5-6}$ aryl" relates to an aryl group having 5 or 6 ring atoms. Here, the ring atoms may be all carbon atoms as in a "carboaryl group". Examples of a carboaryl group include, but are not limited to, those derived from benzene, naphthalene, azulene, anthracene, phenanthrene, naphthacene and pyrene. Examples of aryl groups that include a fused ring wherein at least one is an aromatic ring include, but are not limited to, groups derived from indane, indene, isoindene, tetralin, acenaphthene, fluorene, phenalene, acesphenanthrene and aseantrene. Alternatively, the ring atoms may contain one or more heteroatoms as in a "heteroaryl group".

In other embodiments of the present disclosure, "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

In the present disclosure, "heteroaryl" refers to aryl containing one or more heteroatoms, such as pyridine, pyrimidine, benzothiophene, furyl, dioxolanyl, pyrrolyl, oxazolyl, pyridyl, pyridazinyl, More specifically benzofuran, isobenzofuran, indole, isoindole, indolizine, indolin, isoindoline, purine (adenine or guanine), benzimidazole, indazole, benzoxazole, benzisoxazole, benzodioxole, benzofuran, benzotriazole, benzothiofuran, benzothiazole, $C_9$ having two fused rings derived from benzothiazole, chromene, iso-chromene, chroman, iso-chroman, benzodioxane, quinoline, isoquinoline, quinolizine, benzoxazine, benzodiazine, pyridopyridine, quinoxaline, quinazoline, cinnoline, phthalazine, naphthyridine, $C_{10}$ having two fused rings derived from pteridin, $C_{11}$ having two fused rings derived from benzodiazepine, carbazole, dibenzofuran, dibenzothiophene, carboline, pyrimidine, $C_{13}$ having three fused rings derived from pyridoindole, acridine, xanthene, thioxanthene, phenoxathiine, phenazine, phenoxazine, phenothiazine, thianthrene, phenanthridine, phenanthroline, and $C_{14}$ having three fused rings derived from phenazine.

In the present disclosure, "cycloalkyl" refers to an alkyl group which is a cycloalkyl group, and relates to a monovalent moiety obtained by removing a hydrogen atom from an alicyclic ring atom of a cyclic hydrocarbon compound. Examples of cycloalkyl groups include, but are not limited to, those derived from:

Saturated single ring hydrocarbon compounds, such as: cyclopropane, cyclobutane, cyclopentane, cyclohexane, cycloheptane, methylcyclopropane, dimethylcyclopropane, methylcyclobutane, dimethylcyclobutane, methylcyclopentane, dimethylcyclopentane and methylcyclohexane; or Unsaturated single ring hydrocarbon compounds, such as: cyclopropene, cyclobutene, cyclopentene, cyclohexene, methylcyclopropene, dimethylcyclopropene, methylcyclobutene, dimethylcyclobutene, methylcyclopentene, dimethylcyclopentene and methylcyclohexene; and saturated heterocyclic hydrocarbon compounds: norcaran, norphenen, and norbornene.

In the present disclosure, "heterocyclyl" refers to a monovalent moiety obtained by removing a hydrogen atom from a ring atom of a heterocyclic compound.

In the present disclosure, the prefixes (e.g., $C_{1-12}$, $C_{3-8}$, etc.) refer to the number of ring atoms or a range for the number of ring atoms, regardless of whether they are carbon atoms or hetero atoms. For example, the term "$C_{3-6}$ heterocyclyl" used in the present specification relates to a heterocyclyl group having 3 to 6 ring atoms.

Examples of single ring heterocyclyl groups include, but are not limited to, those derived from:

1N: aziridine, azetidine, pyrrolidine, pyrroline, 2H- or 3H-pyrrole, piperidine, dihydropyridine, tetrahydropyridine, azepine;

2N: imidazolidine, pyrazolidine, imidazoline, pyrazoline, piperazine;

1O: oxirane, oxetane, oxolane, oxol, oxane, dihydropyran, pyran, oxepine;

2O: dioxolane, dioxane and dioxepane;

3O: trioxane;

1N1O: tetrahydrooxazole, dihydrooxazole, tetrahydroisoxazole, dihydroisoxazole, morpholine, tetrahydrooxazine, dihydrooxazine, 1S: thiirane, thietane, thiolane, thiane, thiepane;

1N1S: thiazoline, thiazolidine, thiomorpholine;

2N1O: oxadiazine;

1O1S: oxathiol, oxathiane; and

1N1O1S: oxathiazine

In the present disclosure, "prodrug" refers to compounds which, under in vivo physiological conditions (e.g. enzymatic oxidation, reduction and/or hydrolysis), may, by action of enzyme or gastric acid, be converted directly or indirectly into a pyrrolobenzodiazepine drug.

In the present disclosure, "pharmaceutically acceptable salt" may be an acid addition salt formed by pharmaceutically acceptable free acid, where the free acid is an organic acid or an inorganic acid.

The organic acids include, but are not limited to, citric, acetic, lactic, tartaric, maleic, fumaric, formic, propionic, oxalic, trifluoroacetic, benzoic, gluconic, methane sulfonic, glycolic, succinic, glutamic and aspartic acid. Also, the inorganic acids include, but are not limited to, hydrochloric acid, bromic acid, sulfuric acid and phosphoric acid.

For example, if the compound has a functional group which is an anion or may be an inion (e.g. —COOH may be —COO—), a suitable cation may be used for forming a salt. Examples of suitable inorganic cations include, but are not limited to, $Na^+$ and $K^+$, alkaline earth cations such as $Ca^{2+}$ and $Mg^{2+}$ and other cations such as $Al^{3+}$ Examples of suitable organic cations include, but are not limited to, ammonium ion (i.e., $NH_4\pm$) and substituted ammonium ions (e.g. $NH_3R^+$, $NH_2R_2^+$, $NHR_3^+$, $NR_4^+$).

Some examples of suitable substituted ammonium ions are derived from the following: ethylamine, diethylamine, dicyclohexylamine, triethylamine, butylamine, ethylenediamine, ethanolamine, diethanolamine, piperazine, benzylamine, phenylbenzylamine, choline, meglumine and tromethamine, as well as amino acids such as lysine and arginine. An example of a typical quaternary ammonium ion is $N(CH_3)^{4+}$.

If the compound has a functional group which may be a cation or a cation (e.g., —$NH_2$ may be —$NH_3^+$), a salt may be formed with a suitable anion. Examples of suitable inorganic anions include, but are not limited to, those derived from the following inorganic acids: hydrochloric acid, hydrobromic acid, hydroiodic acid, sulfuric acid, sulfuric acid, nitric acid, nitrous acid, phosphoric acid and phosphorous acid.

Examples of suitable organic anions include, but are not limited to, those derived from organic acids such as: 2-acetoxybenzoic acid, acetic acid, ascorbic acid, aspartic acid, benzoic acid, camphorsulfonic acid, cinnamic acid, citric acid, disulfonic acid, ethanesulfonic acid, fumaric acid, glutaronic acid, gluconic acid, glutamic acid, glycolic acid, hydroxymaleic acid, hydroxynaphthalenecarboxylic acid, isethionic acid, lactic acid, But are not limited to, malic acid, methanesulfonic acid, mucilous acid, oleic acid, oxalic acid, palmitic acid, pamic acid, pantothenic acid, phenylacetic acid, phenylsulfonic acid, propionic acid, pyruvic acid, salicylic acid, stearic acid, succinic acid, sulfanilic acid and tartaric acid, etc. Examples of suitable multimeric organic anions include, but are not limited to, those derived from the following multimeric acids: tannic acid, carboxymethylcellulose, etc.

In the present disclosure, "solvate" refers to a molecular complex between a compound according to the present invention and solvent molecules, examples of which include but are not limited to water, isopropanol, ethanol, methanol, dimethylsulfoxide, ethyl acetate, acetic acid, ethanolamine or the compound according to the present invention bonded to a mixed solvent thereof.

It may be convenient or desirable to prepare, purify and/or handle solvates corresponding to active compounds. In the present specification, the term "solvate" is used in its conventional sense to refer to solutes (e.g., active compounds and salts of active compounds) and complexes of solvents. When the solvent is water, the solvate may conveniently be referred to as a hydrate, such as monohydrate, dihydrate or trihydrate, etc.

In the present disclosure, "effective dose" or "effective therapeutic dose" refers to a dose necessary to achieve the target therapeutic effect (with respect to administration dose, administration period and means). An effective dose is a minimum amount of activating agent necessary to give an object a minimum therapeutic benefit, and is less than a toxic dose. For example, the administration dose may be in a range of approximately 100 ng to approximately 100 mg/kg per patient, more typically in a range of approximately 1 µg/kg to approximately 10 mg/kg. In a case where the activating compound is a salt, ester, amide or prodrug, etc., the administration dose is calculated based on the parent compound, and therefore the actual mass used increases proportionally. The pyrrolobenzodiazepine compound according to the present invention may be formulated to include 0.1 mg to 3000 mg, 1 mg to 2000 mg, or 10 mg to 1000 mg active ingredient per unit dosage form, but is not limited thereto.

The active ingredient may be administered to obtain a peak plasma concentration of active compound of approximately 0.05 µM to 100 µM, 1 µM to 50 µM, or 5 µM to 30 µM. For example, a solution of 0.1 w/v % to 5 w/v % active ingredient in saline solution, arbitrarily, may be administered by intravenous injection.

The concentration of an active compound in a pharmaceutical composition may be determined by the absorption, inactivation and excretion rate of the drug, and other factors known to those skilled in the art. The administration dose may differ according to the severity of the symptoms or illness. Further, the dose and method of administration for a given patient may be adjusted according to the professional judgment of the administration supervisor, giving general consideration to the degree of symptoms/illness of the patient, necessity, age, and reactivity to the drug, etc., and the range of concentrations stated in the present invention are only exemplary, and are not intended to limit the present invention to the examples presented of the composition claimed. Further, the active ingredient may be administered in one administration, or smaller doses may be administered over multiple administrations.

Antibody or Antigen-Binding Fragment

The present invention discloses an antibody which binds specifically to the extracellular domain of ROR1 protein. As disclosed in the present disclosure, the antibody according to the present invention is a polypeptide comprising six complementarity-determining area or region (CDR).

In some examples, the CDR is included in a "framework" region, and the framework orients the CDR(s) so that the CDR(s) may have the appropriate antigen-binding properties.

The antibody according to the present invention specifically binds to the extracellular domain of human and mouse-derived ROR1, and can specifically bind to extracellular domain in isolated form, or to the extracellular domain of ROR1 expressed at the cell surface.

The antibody disclosed in the present invention binds to ROR1, specifically human ROR1 and mouse ROR1. The antibody disclosed in the present disclosure, able to specifically bind to human or mouse-derived ROR1 extracellular domain or to ROR1 expressed at the cell surface, can be useful in targeted treatment of cancer targeting ROR1. For example, the antibody according to the present invention maybe bonded to an anti-cancer medicine and used for treatment of specific cancers.

Further, as the antibody binds to mouse ROR1, on-target tox can be verified through mouse testing, and in vivo efficacy can be verified through a syngeneic model using a mouse cancer cell line overexpressing mouse ROR1. As such, the antibody can be useful in development of various drugs associated with ROR1.

The antibody may include, but not limited to, a monoclonal antibody, dual-specific antibody, double antibody, multi-specific antibody, multiple antibody, minibody, domain antibody, antibody mimetic (or synthetic antibody), chimeric antibody or antibody fusion (or antibody conjugate) and fragment thereof, and includes various forms of antibodies disclosed herein.

In some embodiments, the antibody fragment of the antibody disclosed in the present invention may include Fab, Fab', F(ab')$_2$, scFab, Fv, dsFv, scFV, scFV-Fc, minibody, diabody, scAb or dAb.

In some embodiments, the antibody disclosed in the present invention may consist of a polypeptide of only light chains or only heavy chains comprising the variable regions disclosed in Table 2a and Table 2b.

One antibody disclosed in the present invention may share a specific region or sequence with another antibody disclosed in the present invention. In some embodiments, it may share a constant region of the antibody or antigen-binding fragment. In some embodiments, it may share an Fc region. In some embodiments, it may share a frame of a variable region.

In some embodiments, the antibody has a typical structure of an antibody found in nature. Camelid animals produce an antibody consisting of a single heavy chain, but the structural unit of this antibody commonly comprises a tetrameric polypeptide, where the tetramer comprises a pair of two polypeptide chain bodies consisting of different 2 polypeptide chains. In a typical antibody, the one pair of polypeptide chain body comprises one full-length light chain (approximately 25 kDa) and one full-length heavy chain (approximately 50 to 70 kDa). Each chain shows a characteristic folding pattern, and consists of several immunoglobulin domains, consisting of about 90 to 110 amino acids. These domains are basic units making up an antibody polypeptide. The amino-terminal part of each chain typically comprises a part called a variable region or V region that recognizes an antigen. The carboxy-terminal part is conserved evolutionarily more so than the amino-terminal, and includes a part called a constant region or C region. The human light chain is commonly classified as a kappa (κ) or lambda (λ) light chain, and these comprise one variable region and one constant region, respectively.

A heavy chain is typically classified as a mu (μ), delta (δ), gamma (γ), alpha (α) or epsilon (ε) chain, and these are defined as IgM, IgD, IgG, IgA and IgE isotypes, respectively. IgG has a multiplicity of subtypes, including but not limited to IgG1, IgG2, IgG3 and IgG4. IgM subtypes include IgM and IgM2. IgA subtypes include IgA1 and IgA2. In humans, IgA and IgD isotypes comprise 4 heavy chains and 4 light chains;

IgG and IgE isotypes comprise 2 heavy chains and 2 light chains, and the IgM isotype comprises 5 heavy chains and 5 light chains. The heavy chain constant region typically includes at least one domain exhibiting an effector function. The number of heavy chain constant region domains varies depending on the isotype. An IgG heavy chain, for example, comprises 3 C region domains known as CH1, CH2 and CH3, respectively. The antibody disclosed in the present invention may be any one of these isotypes and subtypes. In some embodiments, the antibody is an IgG1, IgG2a, IgG2b, IgG3 or IgG4 subtype. In some embodiments, the antibody of the present invention is an IgG1- or IgG2-type. In a further embodiment, the antibody of the present invention is an IgG1-type.

The heavy chain variable region and light chain variable region according to the present invention may be linked to at least a part of a human constant region. The selection of a constant region may be determined in part by whether or not antibody-dependent cell-mediated cytotoxicity, antibody-dependent cell phagocytosis, and/or complement-dependent cytotoxicity is required. For example, human isotypes IgG land IgG3 have complement-dependent cytotoxicity and human isotypes IgG2 and IgG4 do not have this cytotoxicity. In addition, human IgG land IgG3 induce a cell-mediated effector function stronger than that of human IgG2 and IgG4. The light chain constant region may be lambda or kappa.

In some embodiments, the antibody may be a human antibody, and the heavy chain constant region may be an IgG1-, IgG2-IgG3- or IgG4-type. In some embodiments, the antibody of the present invention is an IgG1- or IgG2-type.

In some embodiments, the antibody is a human antibody, and recognizes mouse ROR1 specifically.

In a full-length light chain and heavy chain, a variable region and a constant region are linked by a region "J" that is about 12 or more amino acids in length, and the heavy chain comprises a "D" region of about 10 or more amino acids. For example, see Fundamental Immunology, 2nd ed., Ch. 7 (Paul, W., ed.) 1989, New York: Raven Press. Typically, a variable region of a light chain/heavy chain pair of an antibody forms an antigen-binding site.

A variable region of an immunoglobulin chain generally has the same overall structure, and comprises a comparatively conserved framework region (FR) connected by 3 hypervariable regions called "complementarity determining sites or regions or domains" or CDRs (Complementarity Determining Region). The CDR of a variable region derived from each chain comprising a heavy chain/light chain pair is typically arranged by a framework region to form a structure specifically binding to a specific epitope of a target protein (ROR1). These factors of naturally occurring light chain and heavy chain regions are typically comprised from the N-terminal to the C-terminal in the following order: FR1, CDR1, FR2, CDR2, FR3, CDR3 and FR4. The position of amino acid sequences corresponding to each variable region may be determined by Kabat. The CDRs determined by each definition, when compared against each other, may be subsets which overlap or where one includes another. However, in the present disclosure, all CDRs to be defined by each of the above methods are included in the scope of the invention. Those skilled in the art will be readily able to easily select CDR sequences according to the definitions above, given a variable region sequence of an antibody.

CDR sequences which may be included in heavy chain and light chain variable regions of the antibody or antigen-binding fragment according to some embodiments of the present invention are disclosed in Table 1a to Table 1f, respectively.

TABLE 1a

Heavy Chain CDR1

| Sequence | SEQ ID NO |
|---|---|
| SYDMS | 1 |
| DYYMS | 2 |
| NYDMS | 3 |
| NYAMS | 4 |
| DYDMA | 5 |

TABLE 1b

Heavy Chain CDR2

| Sequence | SEQ ID NO |
|---|---|
| WISPDSGSIYYADSVKG | 6 |
| SISPDGSNTYYADSVKG | 7 |
| WISPGGGSKYYADSVKG | 8 |
| AIYHSGSSKYYADSVKG | 9 |
| GISHGSGNKYYADSVKG | 10 |
| SISHNSGSTYYADSVKG | 11 |
| VISPDGGSIYYADSVKG | 12 |
| SISPSSGSSIYYADSVKG | 13 |
| SISPDASNTYYADSVKG | 96 |

TABLE 1c

CDR3 of VH

| Sequence | SEQ ID NO |
| --- | --- |
| PTGRFDY | 14 |
| NLRAFDY | 15 |
| VNGRFDY | 16 |
| GGNGAWDTGFDY | 17 |
| RLSLRRRPSYYSDNAMDV | 18 |
| FISARKSLGRSYSNGMDV | 19 |
| DVVECNMNPCSYDNAMDV | 20 |
| APGWCQAPSCYYDNAMDV | 21 |
| GGNAAWDTGFDY | 97 |

TABLE 1d

Light Chain CDR1

| Sequence | SEQ ID NO |
| --- | --- |
| SGSSSNIGNNNVN | 22 |
| SGSSSNIGSNTVY | 23 |
| SGSSSNIGNNNVS | 24 |
| SGSSSNIGSNDVS | 25 |
| TGSSSNIGNNAVN | 26 |
| TGSSSNIGSNDVT | 27 |
| SGSSSNIGSNYVS | 28 |
| SGSSSNIGNNDVS | 29 |

TABLE 1e

Light Chain CDR2

| Sequence | SEQ ID NO |
| --- | --- |
| YDNXRPS | 30 |
| ANSQRPS | 31 |
| ADSHRPS | 32 |
| YDNNRPS | 33 |
| YDSNRPS | 34 |
| ADSKRPS | 35 |
| DDSHRPS | 36 |
| DDSQRPS | 37 |

TABLE 1f

Light chain CDR3

| Sequence | SEQ ID NO |
| --- | --- |
| GTWDASLSGYV | 38 |
| GSWDYSLSGYV | 39 |
| ATWDYSLSGYV | 40 |
| GAWDDSLSGYV | 41 |
| GAWDDSLSGYV | 41 |
| GTWDYSLSGYV | 42 |

In some embodiments of the present invention, the heavy chain and light chain variable region sequences of the antibody or antigen-binding fragment comprising the above light chain and heavy chain CDR sequences are disclosed in Table 2a and Table 2b below, respectively.

TABLE 2a

| Heavy Chain Variable Region (VH) Sequence | SEQ ID NO |
| --- | --- |
| EVQLLESGGGLVQPGGSLRLSCAASGFTFSSYDMSWVRQAPGKGLEWVSWISPDSGSIYYADSVKGRFTISRDNSKNTLYLQMNSLRAEDTAVYYCARPTGRFDYWSQGTLVTVSS | 43 |
| EVQLLESGGGLVQPGGSLRLSCAASGFTFSDYYMSWVRQAPSKGLEWVSSISPDGSNTYYADSVKGRFTISRDNSKNTLYLQMNSLRAEDTAVYYCAKNLRAFDYWGQGTLVTVSS | 44 |
| EVQLLESGGGLVQPGGSLRLSCAASGFTFSSYDMSWVRQAPGKGLEWVSWISPGGGSKYTADSVKGRFTISRDNSKNTLYLQMNSLRAEDTAVYYCVARVSGRFDYWGQGTLVTVSS | 45 |
| EVQLLESGGGLVQPGGSLRLSCAASGFTFSNYDMSWVRQAPGKGLEWVSAIYHSGSSKYYADSVKGRFTISRDNSKNTLYLQMNSLRAEDTAVYYCARGGNGAWDTGFDYWGQGTLVTVSS | 46 |
| EVQLLESGGGLVQPGGSLRLSCAASGFTFSSYDMSWVRQAPGKGLEWVSGISHGSGNKYYADSVKGRFTISRDNSKNTLYLQMNSLRAEDTAVYYCAKRLSLRRRPSYYSDNAMDVWGQGTLVTVSS | 47 |
| EVQLLESGGGLVQPGGSLRLSCAASGFTFSNYAMSWVRQAPGKGLEWVSSISHNSGSTYYADSVKGRFTISRDNSKNTLYLQMNSLRAEDTAVYYCAKFISARKSLGRSYSNGMDVWGQGTLVTVSS | 48 |
| EVQLLESGGGLVQPGGSLRLSCAASGFTFSDYDMSWVRQAPGKGLEWVSVISPDGGSIYYADSVKGRFTISRDNSKNTLYLQMNSLRAEDTAVYYCARDVVECNMNPCSYDNAMDVWGQGTLVTVSS | 49 |

TABLE 2a-continued

| Heavy Chain Variable Region (VH) Sequence | SEQ ID NO |
|---|---|
| EVQLLESGGGLVQPGGSLRLSCAASGFTFSNYDMSWVRQAPGKGLEWVS SISPSSGSSIYYADSVKGRFTISRDNSKNTLYLQMNSLRAEDTAVYYCAKA PGWCQAPSCYYDNAMDVWGQGTLVTVSS | 50 |
| EVQLLESGGGLVQPGGSLRLSCAASGFTFSDYYMSWVRQAPSGKGLEWVS SISPDASNTYYADSVKGRFTISRDNSKNTLYLQMNSLRAEDTAVYYCAKN LRAFDYWGQGTLVTVSS | 98 |
| EVQLLESGGGLVQPGGSLRLSCAASGFTFSNYDMSWVRQAPGKGLEWVS AIYHSGSSKYYADSVKGRFTISRDNSKNTLYLQMNSLRAEDTAVYYCAR GGNAAWDTGFDYWGQGTLVTVSS | 99 |

TABLE 2b

| Light Chain Variable Region (VL) Sequence | SEQ ID NO |
|---|---|
| QSVLTQPPSASSTPGQRVTISCSGSSSNIGNNNVNWYQQLPSTAPKILIYY DNKRPSSVPDRESGSKSGTSASLAISGLRSEDEADYYCGTWDASLSGYVF GGGTKLTVLG | 51 |
| QSVLTQPPPASGTPGQRVTISCSGSSSNIGSNTVYWYQQLPGTAPKLLIYA NSQRPSGVPDRFSGSKSGTSASLAISGLRSEDEADYYCGSWDYSLSGYVF GGGTKLTVLG | 52 |
| QSVLTQPPSASGTPGQRVTISCSSSSSNIGNNNVSWYQQLPGTAPKLLIYA DSHRPSGVPDRFSGSKSGTSASLAISGLRSEDEADYYCATWDYSLSGYVF GGGTKLTVLG | 53 |
| QSVLTQPPSASGTPGQRVTISCSGSSSNIGSNDVSWYQQLPGTAPKLLIYY DNNRPSGVPDRFSGSKSGTSASLAISGLRSEDEADYYCGAWDDSLSGYVF GGGTKLTVLG | 54 |
| QSVLTQPPSASGTPGQRVTISCTGSSSNIGNNAVNWYQQLPGTAPKLLIYY DSNRPSGVPDRFSGSKSGTSASLAISGLRSEDEADYYCGAWDDSLSGYVF GGGTKLTVLG | 55 |
| QSVLTQPPSASGTPGQRVTISCTGSSSNIGSNDVTWYQQLPGTAPKLLIYA DSKRPSGVPDRFSGSKSGTSASLAISGLRSEDEADYYCGTWDYSLSGYVF GGGTKLTVLG | 56 |
| QSVLTQPPSASGTPGQRVTLSCSSSSSNIGSNYVSWYQQLPGTAPKLLIYD DSHRPSGVPDRFSGSKSGTSASLAISGLRSEDEADYYCGAWDDSLSGYVF GGGTKLTVLG | 57 |
| QSVLTQPPSASGTPGQRVTISCSGSSSNIGNNDVSWYQQLPGTAPKLLIYD DSQRPSGVPDRESGSKSGTSASLAISGLRSEDEADYYCGAWDDSLSGYVF GGGTKLTVLG | 58 |

In some embodiments, the CDRs of the respective light chain variable regions and the CDRs of the respective heavy chain variable regions disclosed in Table 1a through Table 1f above may be combined freely.

In some embodiments, the heavy chain and light chain variable regions disclosed in Table 2a and Table 2b may be combined freely for preparation of various forms of antibody, and for example, a single antibody such as ScFV or a domain antibody or full-length antibody may be formed.

Each of the heavy chain and light chain variable regions disclosed in the present invention may bind to various target heavy chain and light chain constant regions to form heavy chains and light chains, respectively, of an intact antibody. Further, the respective heavy chain and light chain sequences bonded to constant regions may further be combined to form an intact antibody structure.

Any variable region of a heavy chain or light chain of the antibody according to the present invention may be linked to at least part of a constant region. The constant region may be selected according to whether antibody-dependent cell-mediated cytotoxicity, antibody-dependent cell phagocytosis and/or complement-dependent cytotoxicity, etc. is required.

Whichever is appropriate of the above constant regions may be used depending on the objective, for example human or mouse-derived constant region. In some embodiments, a human heavy chain constant region IgG1 is used, represented by SEQ ID No. 91. In some embodiments, a human lambda region represented by SEQ ID No. 93 is used as a light chain constant region.

Any variable region disclosed in the present invention may bind to a constant region to form heavy chain and light chain sequences. In some embodiments, a heavy chain variable region disclosed in the present invention may be linked to a human IgG1 constant region, represented by SEQ ID NO. 59 to 66, 100 and 101. In some embodiments, the light chain variable region disclosed in the present invention may be linked to a human lambda constant region, and these are represented respectively by SEQ ID No. 67 through 74. The light chain and heavy chain according to the present invention may be combined in a variety of combinations to form intact antibodies comprising two light chains and two heavy chains.

However, these constant region sequences which may be combined with variable regions disclosed in the present invention are intended to be exemplary, and those skilled in the art shall be able to know that other variable regions, including IgG1 heavy chain constant regions, IgG3 or IgG4 heavy chain constant regions, any kappa or lambda light chain constant region, or other variable regions modified to give target characteristics such as stability, expression, manufacturability or otherwise may be used.

The present invention also includes one or more nucleic acid sequences having substantial sequence identity to one or more nucleic acid sequences disclosed in the present invention. Substantial identity means that the antibody or antigen-binding fragment encoded by the nucleic acid maintains the effect disclosed. In the present disclosure, even with sequence variation. In some embodiments, the sequence has about 90%, 95%, or 99% identity to the heavy chain variable regions disclosed in Table 2a. In some embodiments, the sequence has about 90%, 95%, or 99% identity to the light chain variable regions disclosed in Table 2b. For example, in the case of variant showing 90%, 95%, or 99% identity to the antibody or antigen-binding fragment disclosed. In the present disclosure, the variation occurs at the framework of the variable region, rather than at the CDRs.

In some embodiments, the nucleic acid coding the antibody disclosed in the present invention or a fragment thereof is a nucleic acid which codes the CDRs disclosed. In the present disclosure, a variable region including the CDRs, and a whole length antibody including the variable region and a constant region. Upon determining the amino acid sequence, the nucleic acid sequence may be readily determined using known reverse transcription programs and with consideration for codon usage, etc. An example of a nucleic acid sequence for a heavy chain constant region coding human IgG1 may be represented by SEQ ID No. 92. An example of a nucleic acid sequence for a light chain constant region coding human lambda may be represented by SEQ ID No. 94 or 95. Examples of nucleic acid sequence for a whole-length heavy chain including the above constant region nucleic acid may be represented by SEQ ID NO. 75 through 82, 102 and 103 (heavy chain including human IgG1 constant region), and examples of nucleic acid sequence for a whole-length light chain may be SEQ ID No. 83 through 90 (light chain including human lambda constant region).

Further, nucleic acid sequences coding the CDR sequences of Table 1a through Table 1f, and the variable regions of Table 2a and Table 2b, are included. These nucleic acids are included in the nucleic acid sequences coding the whole-length antibody disclosed in the above, and are not indicated separately. Those skilled in the art will be able to, based on the protein sequences of the CDRs and variable regions disclosed. In the present disclosure, readily identify from among SEQ ID No. 75 through 90 the nucleic acid sequences which code the same.

The present invention further includes at least one nucleic acid sequence which has substantial sequence identity with at least one nucleic acid disclosed in the present invention. Substantial identity means that the antibody or antigen-binding fragment encoded by the nucleic acid maintains the effect disclosed. In the present disclosure, even in cases where nucleic acid variation causes conservative substitution or amino acid variation in which the variation of nucleic acid is not accompanied by amino acid substitution.

Specificity and Affinity of Antibody to Antigen

The antibody or antigen-binding fragment according to the present invention has specificity in particular to the ECD of ROR1 antigen, and affinity appropriate for use as an antibody therapeutic or diagnostic agent. In one embodiment, according to Table 6, the affinity to an aggregate is $KD<1.0\times10^{-9}$ M; and in another embodiment, $KD\leq1.0\times10^{-10}$ M. The antibody or antigen-binding fragment according to the present invention having such affinity has the advantage of being administrable in loser doses compared to antibodies having lower affinity, for example $10^{-8}$ M or $10^{-9}$ M. Whereas antibodies are not limited to those described in the foregoing, [those described] have a large clinical advantage as sufficient efficacy can be achieved through more convenient methods of administration, such as subcutaneous injection.

Variable Region of Antibody

The present invention includes the variable regions of the heavy chains and light chains disclosed in Table 2a and Table 2b above. Further, the present invention includes an antibody including an immunological functional fragment, a derivative, a mutant protein and a variant of the light chain and heavy chain variable regions (and corresponding nucleic acid sequence). An antibody wherein the variable regions of heavy chains and light chains according to the present invention are combined in various ways may be expressed as "VHx/VLy", where "x" is the heavy chain variable region SEQ ID NO., and "y" corresponds to the light chain. In one example, the variable region may include the following combinations: VH43/VL51, VH43/VL52, VH43/VL53, VH43/VL54, VH43/VL55, VH43/VL56, VH43/VL57, VH43/VL58, VH44/VL51, VH44/VL52, VH44/VL53, VH44/VL54, VH44/VL55, VH44/VL56, VH44/VL57, VH44/VL58, VH45/VL51, VH45/VL52, VH45/VL53, VH45/VL54, VH45/VL55, VH45/VL56, VH45/VL57, VH45/VL58, VH46/VL51, VH46/VL52, VH46/VL53, VH46/VL54, VH46/VL55, VH46/VL56, VH46/VL57, VH46/VL58, VH47/VL51, VH47/VL52, VH47/VL53, VH47/VL54, VH47/VL55, VH47/VL56, VH47/VL57, VH47/VL58, VH48/VL51, VH48/VL52, VH48/VL53, VH48/VL54, VH48/VL55, VH48/VL56, VH48/VL57, VH48/VL58, VH49/VL51, VH49/VL52, VH49/VL53, VH49/VL54, VH49/VL55, VH49/VL56, VH49/VL57, VH49/VL58, VH50/VL51, VH50/VL52, VH50/VL53, VH50/VL54, VH50/VL55, VH50/VL56, VH50/VL57, VH50/VL58, VH98/VL51, VH98/VL52, VH98/VL53, VH98/VL54, VH98/VL55, VH98/VL56, VH98/VL57, VH98/VL58, VH99/VL51, VH99/VL52, VH99/VL53, VH99/VL54, VH99/VL55, VH99/VL56, VH99/VL57, or VH99/VL58.

Various Other Forms of Antibody

The antibody disclosed in the present invention is also a variant of the antibody disclosed in the present invention. For example, a part of an antigen comprises conservative amino acid substitution in one or more of the residues of the heavy chains, light chains, variable regions or CDR sequences disclosed in the above. A conservative amino acid substitution refers to a substitution which does not substantially affect the activity of a polypeptide or its antigenicity. In some embodiments, a conservative amino acid substitution refers to a substitution with another residue falling in the same category in the following amino acid categorization. Naturally occurring amino acids can be categorized as follows, based on common properties of side chain properties: 1) hydrophobic: norleucine, Met, Ala, Val, Leu, Ile; 2) neutral, hydrophilic: Cys, Ser, Thr, Asn, Gln; 3) acidic: Asp, Glu; 4) basic: His, Lys, Arg; 5) residue affecting a chain direction: Gly, Pro; and 6) aromatic: Trp, Tyr, Phe. The conservative amino acid substitution may also comprise a non-naturally-occurring amino acid residue such as a peptide mimetic, and this residue is typically introduced by chemical synthesis, not a cell.

Non-limiting examples of conservative amino acid substitution are shown in, and are not limited to, Table 3.

TABLE 3

Conservative amino acid substitution

| original residue | Exemplary subsititution |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Non-conservative substitution includes substitution with a residue which belongs to other categories in the above categorization. Such substitution may be adopted into a region of an antibody which is homologous to a human antibody, or a non-homologous region of the same.

Preparation of Antibody

In the present disclosure, non-human antibody may be derived from, for example, any antibody-producing animal, for example, mouse, rat, rat, rabbit, goat, donkey or non-human primates (for example monkeys such as the cynomolgus monkey or rhesus macaque) or apes (for example, chimpanzees). Non-human antibody can be produced by immunizing animals using methods known to the art. The antibody may be polyclonal or monoclonal, or may be synthesized within a cell host through expression of recombinant DNA. Fully human antibody may be produced by administering antigen to a transformed animal including a human immunoglobulin gene locus, or by treating a phage display library expressing a human antibody repertoire with antigen, then selecting the target antibody.

A monoclonal antibody (mAb) may be produced using conventional monoclonal antibody methods, for example the standard somatic hybridization method in literature (See: Kohler and Milstein, 1975, Nature 256:495).

The single chain antibody disclosed in the present invention may be produced using an amino acid bridge (short peptide linker) to link heavy chain and light chain variable domain (Fv region) fragments. The single-chain antibody disclosed in the present invention includes scFv including combinations of heavy chain and light chain variable region domains listed in Table 1a through Table 1f, or the CDRs disclosed in Table 1a through Table 1f, but is not limited thereto.

Also, the antibody disclosed in the present invention may be modified to a different subtype antibody through subtype switching. Accordingly, an IgG antibody may, for example, be derived from an IgM antibody, and the reverse is also possible.

Accordingly, included among the antibodies disclosed in the present invention are, for example, the variable domain combination antibody according to the present invention, switched to the target isotype (for example, IgA, IgG1, IgG2, IgG3, IgG4, IgE and IgD).

Method for Expressing Antibody

The present invention further relates to an expression systems and constructs in the form of plasmids, expression vectors, and transcription or expression cassettes including at least one polynucleotide described in the above; a host cell comprising such expression systems or constructs; and a method for producing antibody using the expression systems or host cells.

The antibody disclosed in the present invention may be expressed in a hybridoma cell line or a cell line other than a hybridoma. Expression constructs coding the antibody may be used to transform mammalian, insect or microbial host cells. Constructs such as plasmids may be prepared, as described in the foregoing, any of various known methods for introducing polynucleotide into a host cell. The specific method may vary according to the type of host cell. Methods for introducing a heterogeneous polynucleotide into a mammalian cell are widely known to the art, and include, and are not limited to, for example, dextran-mediated transfer, calcium phosphate precipitation, polybrene-mediated transfer, protoplast fusion, electrophoresis, capsulation of transferred polynucleotide using liposome, mixing of nucleic acid and positively charged lipid, and direct microinjection of DNA into the nucleus.

Use of Human ROR1 Antibody for Therapeutic and Treatment Purposes

In cancers, ROR1 is associated with unfavorable prognosis of cancer patients, and is reported to also affect metastasis. ROR1 is overexpressed not only in hematologic malignancy such as B-cell leukemia, lymphoma, acute myeloid leukemia (AML), Burkitt lymphoma, chronic lymphocytic leukemia (CLL), mantle cell lymphoma (MCL), acute lymphoblastic leukemia (ALL), Diffuse large B-cell lymphoma (DLBCL), follicular lymphoma (FL) and marginal zone lymphoma (MZL), etc. but also solid cancer including breast cancer, renal cancer, ovarian cancer, gastric cancer, liver cancer, lung cancer, colorectal cancer, pancreatic cancer, skin cancer, bladder cancer, testicular cancer, uterine cancer, prostate cancer, non-small cell lung cancer (NSCLC), neuroblastoma, brain cancer, colon cancer, squamous cell carcinoma, melanoma, myeloma, cervical cancer, thyroid cancer, head and neck cancer and adrenal cancer, etc. For anti-cancer antibody therapy, for example, ROR1 antibody may, as described. In the present disclosure, be used in the form of the antibody alone or in a form bonded to various cytotoxic agents to remove cancer cells which overexpress ROR1. Accordingly, antibody binding to ROR1 may be used alone or as bonded to anti-cancer chemotherapeutic agents, cytotoxic agents or radioactive materials, or may be embodied as a cytotherapeutic agent such as CAR-T cells for example, to target an anti-cancer target, and thereby used as a targeted therapeutic agent which guides a therapeutic agent derived from the antibody disclosed in the present invention to a cell expressing ROR1.

Method of Treatment: Pharmaceutical Formulation and Administration Pathway

A treatment method using an antibody, an antibody drug conjugate, or a pharmaceutically acceptable salt or solvate thereof is also provided. In certain embodiments, the antibody, antibody drug conjugate, or a pharmaceutically acceptable salt or solvate thereof is provided to a patient. The antibody, antibody drug conjugate, or a pharmaceutically acceptable salt or solvate thereof binds to human ROR1 expressed on the surface of cancer cells, thereby suppressing metastasis of cancer cells. In some embodiments, the antibody in a form bonded to a cytotoxic agent binds to human ROR1 expressed on the surface of cancer cells, specifically delivering the cytotoxic agent to cancer cells to induce cell death of the cancer cells. In some embodiments, the antibody in a form of an antibody specific to the same or a different target binds to human ROR1 expressed on the surface of cancer cells, thereby increasing the specificity of a multi-specific antibody to cancer cells or inducing the connection of cancer cells to other types of cell such as immune cells, and inducing death of cancer cells. In certain embodiments, the antibody is expressed on the surface of cytotherapeutic agents such as CAR-T cells, binding to human ROR1 and thereby specifically delivering the cytotherapeutic agent to the cancer cells to induce their death.

A pharmaceutical composition comprising a therapeutically effective dose of the antibody drug conjugate and a pharmaceutically acceptable diluent, carrier, solubilizer, emulsifier, preservative and/or supplement is also provided. In addition, for example, a method for treating a cancer patient by administering such a pharmaceutical composition is included. The term "patient" includes a human patient.

The pharmaceutical composition may comprise pharmaceutically acceptable carriers. Here, carriers refer to excipients, diluents or adjuvants. The carrier may be selected from a group comprised of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, saline, PBS and other buffer solutions, methylhydroxybenzoate, propylhydroxybenzoate, talc, magnesium stearate and mineral oil. The composition may include fillers, anticoagulants, lubricants, wetting agents, flavoring agents, emulsifiers, preservatives, or combinations thereof.

The pharmaceutical composition may be formulated as any dosage form according to known methods. The composition may be formulated into formulations for oral administration (for example, powders, tablets, capsules, syrups, pills or granules) or non-oral administration (for example, injections). Further, the composition may be prepared as a systemic or local formulation.

The pharmaceutical composition may comprise the antibody conjugate, an antigen-binding fragment thereof, anti-cancer agents, or combinations of these in effective amounts. The term "effective amount" refers to an amount sufficient to exhibit preventive or therapeutic effects when administered to an individual requiring prevention or treatment. The effective amount may be appropriately selected by a PHOSITA depending on the cell or individual, and may be determined based on elements including severity of illness, patient age, body weight, health, gender, sensitivity to drugs, duration of administration, administration pathway, excretion ratio, duration of therapy, and drugs mixed with the composition or used concomitantly therewith, and other elements well known to the field of medicine. The effective amount may be approximately 0.1 $\mu g$ to approximately 2 g per [unit missing] of the pharmaceutical composition.

The administration dose of the pharmaceutical composition may be, for example, 10 $\mu g$/kg to approximately 30 mg/kg for an adult, selectively 0.1 mg/kg to approximately 30 mg/kg, or alternatively 0.3 mg/kg to approximately 20 mg/kg. The administration may be performed once a day, multiple times a day, or once per week to four weeks, or one two twelve times per year.

In the following, preferred embodiments are presented to aid understanding of the present invention. However, the following embodiments are provided to facilitate understanding of the present invention, and the present invention is not limited to these embodiments.

Embodiment 1: Preparation of ROR1 Antibody

Embodiment 1-1: Antigen

As the antigen, an ROR1 ECD-Fc type protein wherein Fc is connected to the C-terminal of the extracellular domain (ECD) of human ROR1 was used.

Specifically, to prepare the antigen, a residue including the extracellular domain of ROR1 and corresponding to amino acid 1 through amino acid 406 of the ROR1 amino acid sequence represented by NCBI reference number NP_0050032 was used. As for the gene coding the extracellular domain of the ROR1, cDNA from Origene was purchased and used (Origene, RC214967). In addition, to purify the ROR1 extracellular domain thereafter, a gene coding human IgG1-derived Fc protein was synthesized and linked to the 3' terminal of the gene coding the ROR1 extracellular domain (hereinafter referred to as 'ROR1-Fc'). By introducing the gene into a pcDNA3.1 vector, a vector which codes ROR1-Fc nucleic acid in a mammalian cell line was obtained.

The expression vector was transiently transfected into HEK 293E cells to express ROR1-Fc by culturing in DMEM-/F12 medium at 8% CO2 and 37° C., and collecting the medium every 72 hours. Protein A affinity chromatography was used to purify the Fc-ROR1 ECD protein.

Embodiment 1-2: Selection of Antibody Through Phage Library Screening

Preparation of Library Phage

*Escherichia coli* $2\times10^{10}$ with a human-derived single-chain variable fragment (scFv) library (Yang et. Al., 2009 Mol. Cells 27: 225) gene with binding potential to various antigens was cultured for 2 to 3 hours at 37° C. (OD600=0.5~0.7) in medium containing 2×YT (Amresco, J902-500G), carbenicillin (Duchefa, C01090025) 100 $\mu g/m\ell$ and 2% glucose (sigma, G7021), then infected with helper phage and cultured for 16 hours at 30° C. in a 2×YT medium [2×YT, carbenicillin, 70 $\mu g/m\ell$ kanamycin (Duchefa, K0126), 1 mM IPGTG (Duchefa, I1401)] to induce phage packaging. Thereafter, the cultured cells were centrifuged (6000 rpm, 15 minutes, 4° C.), and then 4% PEG8000 (sigma, P2139) and 3% NaCl (Samchun, S2097) was added to the supernatant and dissolved thoroughly and reacted for 1 hour in ice. After centrifuging once again (8000 rpm, 20 minutes, 4° C.), PBS (Phosphate buffered saline, Gibco 10010-023) was added to the pellet to create a suspension, which was again centrifuged (12000 rpm, 10 minutes, 4° C.). The supernatant containing library phage was placed in a new tube, and kept at 4° C. until use.

Panning Through Phage Display

To screen antibodies binding to human ROR1 protein, the ROR1-Fc protein prepared in Embodiment 1-1 was used to carry out panning a total of three times as explained in the following.

Specifically, in an immunotube (maxisorp 444202), ROR1-Fc at a concentration of 10 $\mu g/m\ell$ and a negative control-Fc (BCMA-Fc) were added to PBS. Protein was allowed to be adsorbed on the surface of the immunotube over night at 4° C., after which a 3% BSA (bovine serum albumin) solution was added to the immunotube to protect surfaces on which the ROR1-Fc had not been adsorbed. The immunotube was emptied, and 10¹² CFU antibody phage library dispersed in 3% BSA solution was placed in the immunotube where the control Fc protein is adsorbed, then allowed to react for 1 hour at room temperature (negative selection). Thereafter, the phages which did not bind to the negative control Fc were recovered and bonded to the immunotube to which ROR1-Fc had been adsorbed. The non-specifically bound phages were removed by washing 5 to 30 times using PBS-T solution (Phosphate buffered saline-0.05% Tween 20), then the remaining antigen-specific phage antibodies were recovered using 100 mM triethylamine solution. The recovered phages were neutralized with 1M Tris buffer (pH 7.4). ER2537 E. Coli was infected for 1 hour at 37° C., and the infected E. Coli was plated on 2×YT agar medium and cultured overnight at 37° C. The next day, the cultured E. Coli was suspended in 4 mℓ of 2×YT carbenicillin culture, and 15% glycerol was added. Some was stored at −80° C., and the rest was used to prepare phages for the next experiment. This process was repeated a total of three times to amplify and concentrate the ROR1 antigen-specific phage pool.

Monoclonal Phage Antibody Screening (Single Clone Screening)

The following experiment was performed to select a monoclonal antibody that specifically binds to ROR1 from the phage pool obtained through panning.

To isolate the monoclones from the concentrated pool, the phage pool was plated in LB-tetracycline/carbenicillin agar medium and cultured to obtain a single colony. Monoclones were then inoculated into 96 deep well plates containing 400 µℓ of 2×YT-tetracycline/carbenicillin medium per well and grown overnight, then 10 µℓ of the culture was added to a new 96 deep well plate containing 390 µℓ of 2×YT-tetracycline/carbenicillin and incubated at 37° C. for 4 hours. 1 mM IPTG was added to the culture solution and incubated overnight at 30° C. The culture solution cultured overnight was centrifuged to obtain the supernatant.

Thereafter, the ELISA method was used as follows to select clones expressing monoclonal soluble scFv binding to ROR1-Fc antigen (Steinberger Rader and Barbas III 2000 Phage display vectors In: Phage Display Laboratory Manual 1sted Cold Spring Harbor Laboratory Press NY USA pp 119-1112). Specifically, 100 ng per well of recombinant human ROR1-Fc prepared in Embodiment 1-1 or FBMA-Fc was placed in a 96-well microtiter plate (Nunc-Immuno Plate, NUNC, USA), which was coated overnight at 4° C. BCMA-Fc is the protein used as a negative control, a recombinant protein where the extracellular domain of human BCMA protein is linked to human Fc. 200 µL each of 3% BSA was placed in each well, and blocked for 2 hours at 37° C.

The monoclonal phage supernatant was prepared by mixing 1:1 with 3% BSA, and 100 µL each of this mixture was loaded into the wells and reacted for 2 hours at 37° C. After washing 5 times with 300 µL PBST, anti-HA HRP binding antibody was added, reacted for 1 hour at 37° C., then washed 5 times with PBST. 100 µL TMB (Tetramethylbenzidine, Sigma, T0440) was added for color development, and then 50 µL 1N H2SO4 was added to stop the reaction. Absorbance was measured at 450 nm and 650 nm, and clones where the absorbance at 450 nm and 650 nm was 10 or higher when coated with 1 µg/mL ROR1 were screened (FIG. 1)

Figure 2:
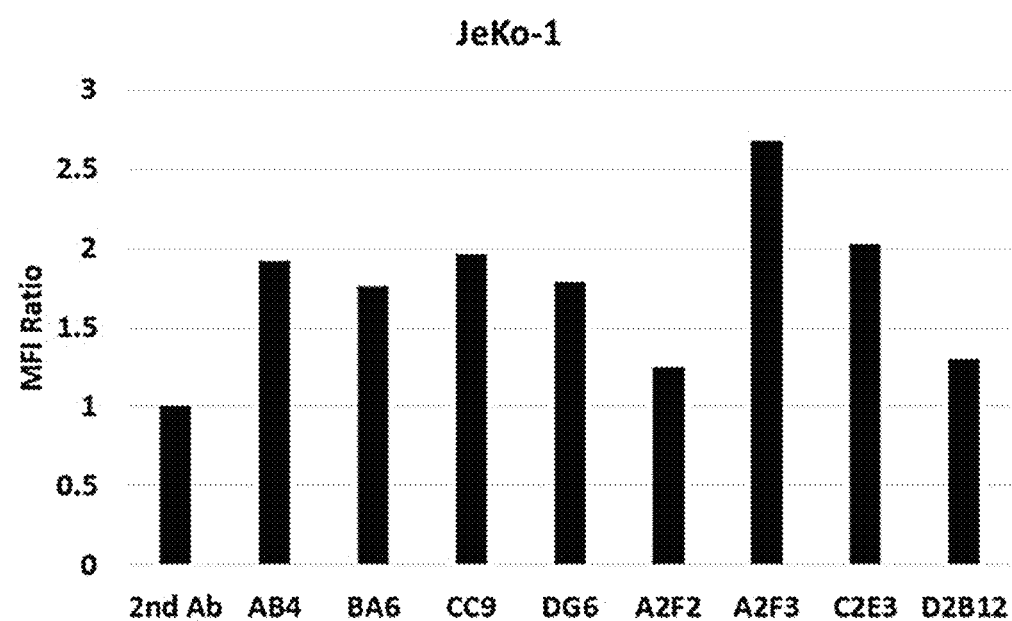
FIG. 2 shows results of measuring (FACS) the binding capacity of an anti-ROR1 monoclonal phage antibody according to one example of the present invention to cell surface-expressed ROR1 antigen, and a JeKo-1 cell line was used as the cell expressing ROR1 on the cell surface. It is shown that each anti-ROR1 monoclonal antibody binds specifically to the ROR1 expressed on the cell surface.

Next, flow cytometry was used to screen clones binding to cell lines expressing ROR1. Specifically, 100 µℓ of the monoclonal scFv supernatant was reacted with a cell line (JeKo-1) overexpressing ROR1, then washed two times with PBS. After reacting with anti-HA-FITC antibody (Sigma, H7411) at 4° C. for 30 minutes, and washing twice with PBS then suspending in 200 µℓ PBS, a FACSCalibur flow cytometer (BD Bioscience) was used to screen clones binding to the JeKo-1 cell line (FIG. 2)

This this process, 10 antibody clones (AB4, A2F2, A2F3, BA6, CC9, C2E3, DG6, D2B12, A2F2 M1 and BA6 M1) binding to recombinant human ROR1 protein and cell lines expressing ROR1 were screened. The amino acid sequence and CDR sequence of the heavy chain variable region and light chain variable region of each of these antibodies are as shown in the following tables.

TABLE 4a

| | CDR Sequence of Heavy Chain Variable (VH) | | | | | | |
|---|---|---|---|---|---|---|---|
| | CDR1 | | CDR2 | | CDR3 | | VH |
| Clone | Sequence | SEQ ID NO | Sequence | SEQ ID NO | Sequence | SEQ ID NO | SEQ ID NO |
| AB4 | SYDMS | 1 | WISPDSGSIYYADSVKG | 6 | PIGRFDY | 14 | 43 |
| A2F2 | DYYMS | 2 | SISPDGSNTYYADSVKG | 7 | NLRAFDY | 15 | 44 |
| A2F3 | SYDMS | 1 | WISPGGGSKYYADSVKG | 8 | VNGRFDY | 16 | 45 |
| BA6 | NYDMS | 3 | AIYHSGSSKYYADSVKG | 9 | GGNGAWDTGFDY | 17 | 46 |
| CC9 | SYDMS | 1 | GISHGSGNKYYADSVKG | 10 | RLSLRRRPSYYSDNAMDV | 18 | 47 |
| C2E3 | NYAMS | 4 | SISHNSGSTYYADSVKG | 11 | FISARKSLGRSYSNGMDV | 19 | 48 |
| DG6 | SYSMS | 5 | VISPDGGSIYYADSVKG | 12 | DVVECNMNPCSYDNAMDV | 20 | 49 |

TABLE 4a-continued

CDR Sequence of Heavy Chain Variable (VH)

| Clone | CDR1 Sequence | SEQ ID NO | CDR2 Sequence | SEQ ID NO | CDR3 Sequence | SEQ ID NO | VH SEQ ID NO |
|---|---|---|---|---|---|---|---|
| D2B12 | NYDMS | 3 | SISPSSGSSIYYADSVKG | 13 | APGWCQAPSCYYDNAMDV | 21 | 50 |
| A2F2 M1 | DYYMS | 2 | SISPDASNTYYADSVKG | 96 | NLRAFDY | 15 | 98 |
| BA6 M1 | NYDMS | 3 | AIYHSGSSKYYADSVKG | 9 | GGNAAWDTGFDY | 97 | 99 |

TABLE 4b

CDR Sequence of Light Chain Variable (VL)

| Clone | CDR1 Sequence | SEQ ID NO | CDR2 Sequence | SEQ ID NO | CDR3 Sequence | SEQ ID NO | VL SEQ ID NO |
|---|---|---|---|---|---|---|---|
| AB4 | SGSSSNIGNNNVN | 22 | YDNKRPS | 30 | GTWDASLSGYV | 38 | 51 |
| A2F2 | SGSSSNIGSNTVY | 23 | ANSQRPS | 31 | GSWDYSLSGYV | 39 | 52 |
| A2F3 | SGSSSNIGNNNVS | 24 | ADSHRPS | 32 | ATWDYSLSGYV | 40 | 53 |
| BA6 | SGSSSNIGSNDVS | 25 | YDNNRPS | 33 | GAWDDSLSGYV | 41 | 54 |
| CC9 | TGSSSNIGNNAVN | 26 | YDSNRPS | 34 | GAWDDSLSGYV | 41 | 55 |
| C2E3 | TGSSSNIGSNDVT | 27 | ADSKRPS | 35 | GTWDYSLSGYV | 42 | 56 |
| DG6 | SGSSSNICSNYVS | 28 | DDSHRPS | 36 | GAWDDSLSGYV | 41 | 57 |
| D2B12 | SGSSSNIGNNDVS | 29 | DDSQRPS | 37 | GAWDDSLSGYV | 41 | 58 |
| A2F2 M1 | SGSSSNIGSNTVY | 23 | ANSQRPS | 31 | GSWDYSLSGYV | 39 | 52 |
| BA6 M1 | SGSSSNIGSNDVS | 25 | YDNNRPS | 33 | GSWDYSLSGYV | 41 | 54 |

The nucleic acid sequence encoding the variable region and CDR sequences is included as part of the nucleic acid sequence encoding the following full length heavy chains and light chains, in the order of AB4, A2F2, A2F3, BA6, CC9, C2E3, DG6, D2B12, A2F2 M1 and BA6 M1: SEQ ID NO. 75 (Heavy chain) and 83 (light chain); SEQ ID NOs. 76 (heavy chain) and 84 (light chain); SEQ ID NOs. 77 (heavy chain) and 85 (light chain); SEQ ID NOs. 78 (heavy chain) and 86 (light chain); SEQ ID NOs. 79 (heavy chain) and 87 (light chain); SEQ ID NOs. 80 (heavy chain) and 88 (light chain); SEQ ID NOs. 81 (heavy chain) and 89 (light chain); SEQ ID NOs. 82 (heavy chain) and 90 (light chain); SEQ ID NOs: 102 (heavy chain) and 84 (light chain); SEQ ID NO: 103 (heavy chain) and 86 (light chain). The nucleic acid sequence encoding the constant region in the nucleic acid sequence is SEQ ID NO. 92 (heavy chain), and SEQ ID NO. 94 (light chain) or 95 (light chain).

Embodiment 2: Conversion of Anti-ROR1 scFV into Full IgG Form, and Production of the Same Embodiment 2-1: Cloning of Anti-ROR1 scFV into Full IgG Form To convert the sequences of each of the ROR1-specific monoclonal phage antibodies obtained in Embodiment 1 to full IgG form, nucleic acids encoding the heavy chain and light chain variable regions of the respective clones obtained in Embodiment 1 were synthesized (Genotech, South Korea). After synthesizing genes encoding the heavy chain and light chain constant regions (SEQ ID No. 91 and 93, respectively) of the human IgG1 subtypes, the genes were connected with nucleic acid encoding the respective heavy chain and light chain variable regions. The nucleic acids encoding the light chains and heavy chains of the respective antibodies were respectively cloned into pcDNA3.1-based expression vectors, obtaining vectors encoding antibody nucleic acids in CHO—S mammalian cell lines.

As for the reference group, a chimera antibody where human IgG1 is bonded to the variable region of the conventional anti-ROR1 antibody 2A2 (U.S. Pat. No. 9,316, 646) was used.

The antibodies according to the present invention in IgG form are disclosed with the following heavy and light chain full-length sequences, in the order of AB4, A2F2, A2F3, BA6, CC9, C2E3, DG6, D2B12 A2F2 M1 and BA6 M1 SEQ ID NOs. 59 (heavy chain) and 67 (light chain); SEQ ID NOs. 60 (heavy chain) and 68 (light chain); SEQ ID NOs. 61 (heavy chain) and 69 (light chain); SEQ ID NOs. 62 (heavy chain) and 70 (light chain); SEQ ID NOs. 63 (heavy chain) and 71 (light chain); SEQ ID NOs. 64 (heavy chain) and 72 (light chain); SEQ ID NOs. 65 (heavy chain) and 73 (light chain); SEQ ID NOs. 66 (heavy chain) and 74 (light chain) SEQ ID NOs: 100 (heavy chain) and 68 (light chain); SEQ ID NOs: 101 (heavy chain) and 70 (light chain).

Embodiment 2-2: Expression of Anti-ROR1 IgG Antibodies

CHO—S cells were adjusted to a concentration of 1.5× 106 cells/ml in CD-CHO (Gibco, 10743) medium, then cultured for 1 day at 37° C. and 8% CO2. On the day of DNA transfection, the cells, which had grown to 2.5 to 3×106 cells/ml, were prepared to a concentration of 2.1×106 cells/ml using a CD-CHO medium containing 1% DMSO and then cultured for 3 hours at 37° C. and 8% CO2. After centrifuging for 15 minutes at 3000 rpm, the supernatant was removed, and re-suspended in RPMI 1640 medium containing 25% FBS. Thereafter, vectors expressing the heavy chain and light chain of Embodiment 2-1 were diluted in Opti-MEM medium at a rate of 1 μg per ml medium, and PEI (Polysciences, 23966, stock concentration: 1 mg/ml) was diluted at a rate of 8 μg per ml culture medium.

The vector and PEI mixture was fixed at room temperature for 10 minutes, then placed in a flask containing cells prepared as described above. After culturing for 4 hours at 5% CO2, 37° C. and 100 rpm, CD-CHO of the same volume as the culture was added, followed by culturing for 4 days at 8% CO2, 37° C. and 110 rpm.

Embodiment 2-3: Isolation and Purification of Anti-ROR1 IgG Antibodies

Equilibrium buffer solution (50 mM Tris-HCl, pH7.5, 100 mM NaCl) was brought to equilibrium by passing through a Mab selectsure (GE healthcare, 5 mL), the culture solution of Embodiment 3-2 was passed through a column (Mab selectsure (GE healthcare, 5 mL) so that the expressed antibody would bind to the column Thereafter, after eluting with 50 mM Na-citrate (pH 3.4) and 100 mM NaCl solution, 1M Tris-HCl (pH 9.0) was used to neutralize and achieve a final pH of 7.2. The buffer solution was exchanged with PBS (phosphate buffered saline, pH 7.4).

Embodiment 3: Analysis of Binding Specificity of Anti-ROR1 IgG Antibody to ROR1

Embodiment 3-1: Analysis of Binding Capacity (ELISA) of Anti-ROR1 IgG Antibody to ROR1 Antigen (Extracellular Domain)

The specific binding capacities of the IgG antibodies of the respective clones prepared and screened in Embodiment 2 to antigen were analyzed as follows.

Anti-ROR1 antibody—antigen binding affinity was assessed using an ELISA-based solution binding assay. Specifically, a 96-well microtiter plate (Nunc-Immuno Plates), NUNC) was coated for 16 hours at 4° C. with the ROR1 protein described below at a concentration of 1 μg/ml in PBS solution, and non-specific binding sites were blocked for 2 hours with 3% BSA (bovine serum albumin). Here, the ROR1 protein used was, in the case of human ROR1, the ROR1-Fc or recombinant human ROR1-His (Sino Biological, 13968-H08H) of Embodiment 1. The ROR1-His used in ELISA, as stated in the above sentence, was a protein from the Sino Biological company (13968-H08H), and the ROR1-His of Embodiment 1 or recombinant mouse ROR1 protein was used (Acrobiosystems, RO1-M5221-100 μg )

Subsequently, the anti-ROR1 antibodies prepared in Embodiment 3 were added at the concentrations stated in FIG. 2 to a 96-well microtiter plate, and binding capacity was analyzed using ELISA as follows. Specifically, after incubating for 2 hours, the plate was washed 5 times with PBS containing 0.05% Tween 20, then HRP-conjugated Fab multiclonal antibody reagent (Perce, 31414) was diluted to 1:10,000 and placed in the washed microtiter plate. After reacting for 1 hour at 37° C., the ROR1 antibodies bonded to the plate were detected. After the reaction, color development was performed using TMB (Tetramethylbenzidine, Sigma, T0440). The enzymatic reaction was stopped using 0.5 mol/L sulfuric acid, and absorbance at 450 nm and 650 nm was measured (450 nm-650 nm) using a micro plate reader (Molecular Device)

Figure 3A:
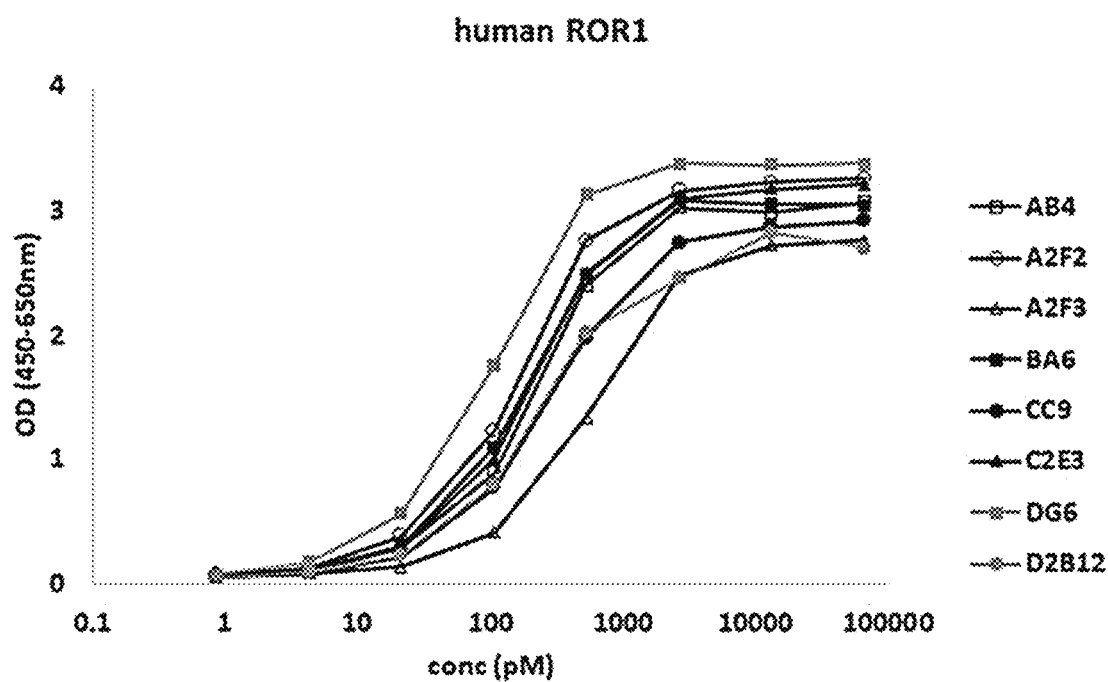
FIGS. 3A & B show the results of analyzing (ELISA) the binding capacity of an anti-ROR1 IgG antibody prepared according to an example of the present invention to human ROR1 antigen. It is shown that the respective antibodies bind to human ROR1 antigen in a concentration-dependent manner. The results show that binding capacity to ROR1 is maintained even after a monoclonal phage antibody is changed to an IgG form.
Figure 3B:
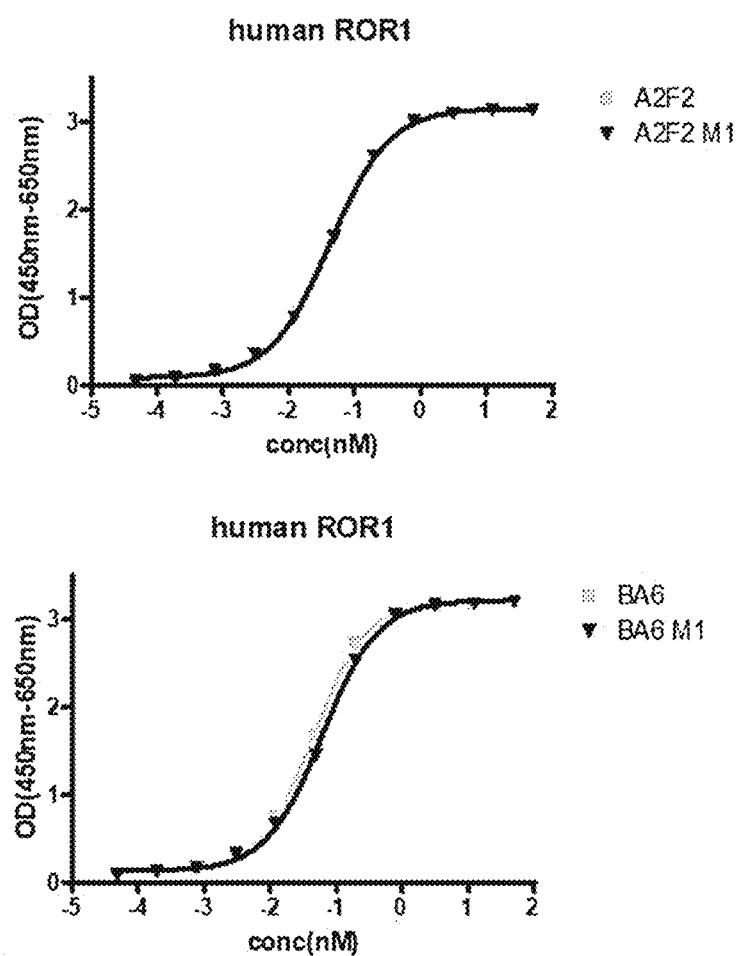
Figure 4:
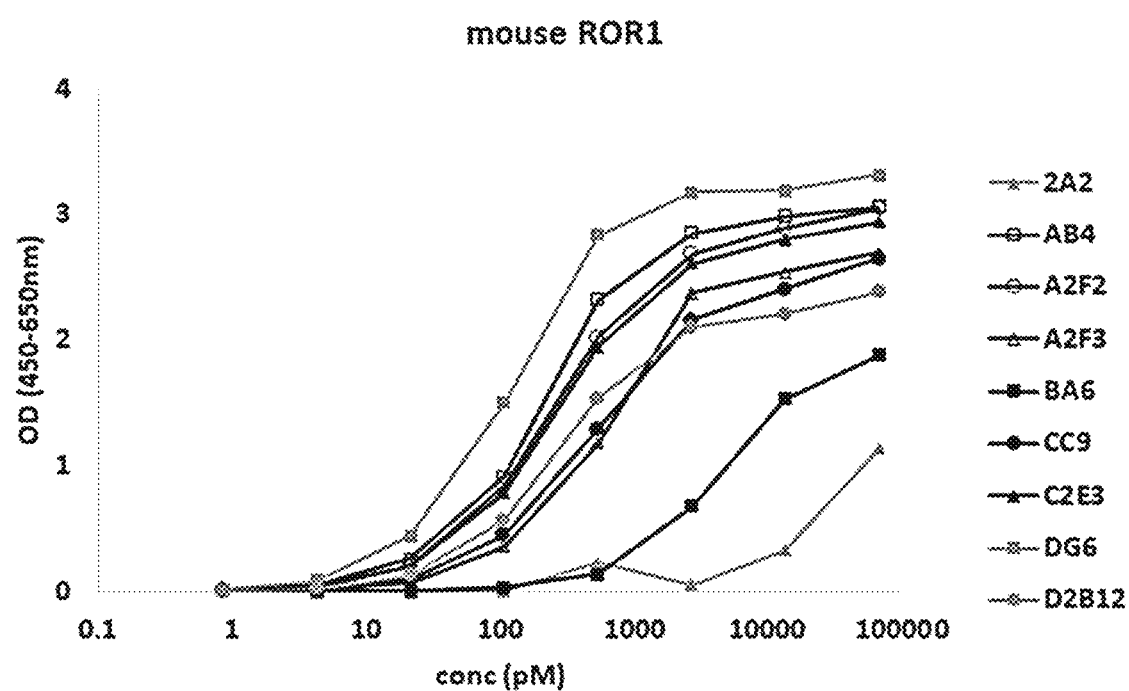
FIG. 4 shows results of analyzing (ELISA) the binding capacity of an anti-ROR1 IgG antibody prepared according to one example of the present invention to mouse ROR1 antigen. It is shown that each antibody binds to mouse ROR1 antigen in a concentration-dependent manner. Through this experiment, it was confirmed that the anti-ROR1 antibody of the present invention has cross-reactivity with mouse ROR1. As for the 2A2 antibody used as a reference group, it was found that whereas it had cross-reactivity with mouse ROR1, the degree of binding was relatively weak compared to the anti-ROR1 antibody of the present invention.

The results are shown in FIG. 3a, FIG. 3b and FIG. 4, and it was confirmed that the anti-ROR1 antibody of the present invention binds to human ROR1 and mouse ROR1 in a concentration-dependent manner. Further when comparing the cross-reactivity to mouse ROR1 protein, the ROR1 antibody according to the present invention was found to have superior binding capacity compared to the 2A2 antibody used as a reference group.

Embodiment 3-2: Measuring the Specific Binding Capacity of Anti-ROR1 IgG Antibody to Cell Surface-Expressed ROR1 Antigen (FACS)

It is critical for an antibody to a certain antigen to be used in vivo as a therapeutic antibody, for example, that it binds to antigens expressed at the cell surface. Some antigens will bind to purified antigen, but will not bind to cell surface-expressed antigen. In such cases, even in the antibody is administered in vivo, it cannot bind to antigen, meaning that the antibody is unable to bind to cells expressing the antigen and that a therapeutic antibody, etc. is unable to exhibit in vivo activity.

Accordingly, FACS analysis was carried out to confirm that the anti-ROR1 antibody of the present invention binds to cell surface-expressed ROR1.

For this experiment, using cell lines (FIG. 5 and FIG. 7, respectively) transiently (CHO-human ROR1, CHO-human ROR2, CHO-mouse ROR1) or stably (MC38-human ROR1) transfected with ROR1 gene to achieve artificial over-expression of ROR1 protein, an ROR1-expressing cell line (JeKo-1, Mino) (FIG. 6), a non ROR1-expressing cell line (MCF7) (FIG. 6) and a FACSCalibur (BD Biosciences) device was used to measure the degree to which anti-ROR1 antibody and ROR1 were bound, as follows. MCF7 is a negative control which does not express ROR1, and CHO-human ROR2 is a negative control expressing human ROR2. JeKo-1, Mino, CHO-human ROR1, CHO-mouse ROR1 and MC38-human ROR1 are all cell lines which express human ROR1 or mouse ROR1.

Specifically, after dissociating each cell line and washing in PBS, the number of cells was counted and adjusted to $2 \times 10^5$ cells/200 µℓ PBS. Then the respective ROR1 monoclonal antibodies prepared in Embodiment 3 were diluted 5 times from 10 µg /mL or 10 µg /mL, then reacted for 1 hour at 4° C. After the reaction, the cells were washed in PBS, then FITC-marked constant region (Fc) specific antibody (Goat anti-human IgG FITC conjugate, Fc specific, Sigma, F9512, concentration 20 mg/ml) was suspended in 2 µℓ /1× $10^5$ cells/200 µℓ PBS and reacted for 1 hour at 4° C. As for identification of the degree of expression of the transiently over-expressed human ROR1, human ROR2 and mouse ROR1, a commercially available FACS analysis antibody (anti-ROR1: R&D Systems, FAB 2000G, anti-ROR2: R&D, FAB20641P) was used. After reacting the cells were washed in PBS and analyzed using a FACSCalibur device. The negative control (2nd Ab) was only treated with FITC-marked constant region (Fc) specific antibody. The shifted readings for the respective experimental groups treated with ROR1 monoclonal antibody were compared against the shifted reading for the control group (MFI Ratio: MFI of anti-ROR1/MFI of 2nd Ab).

Figure 5:
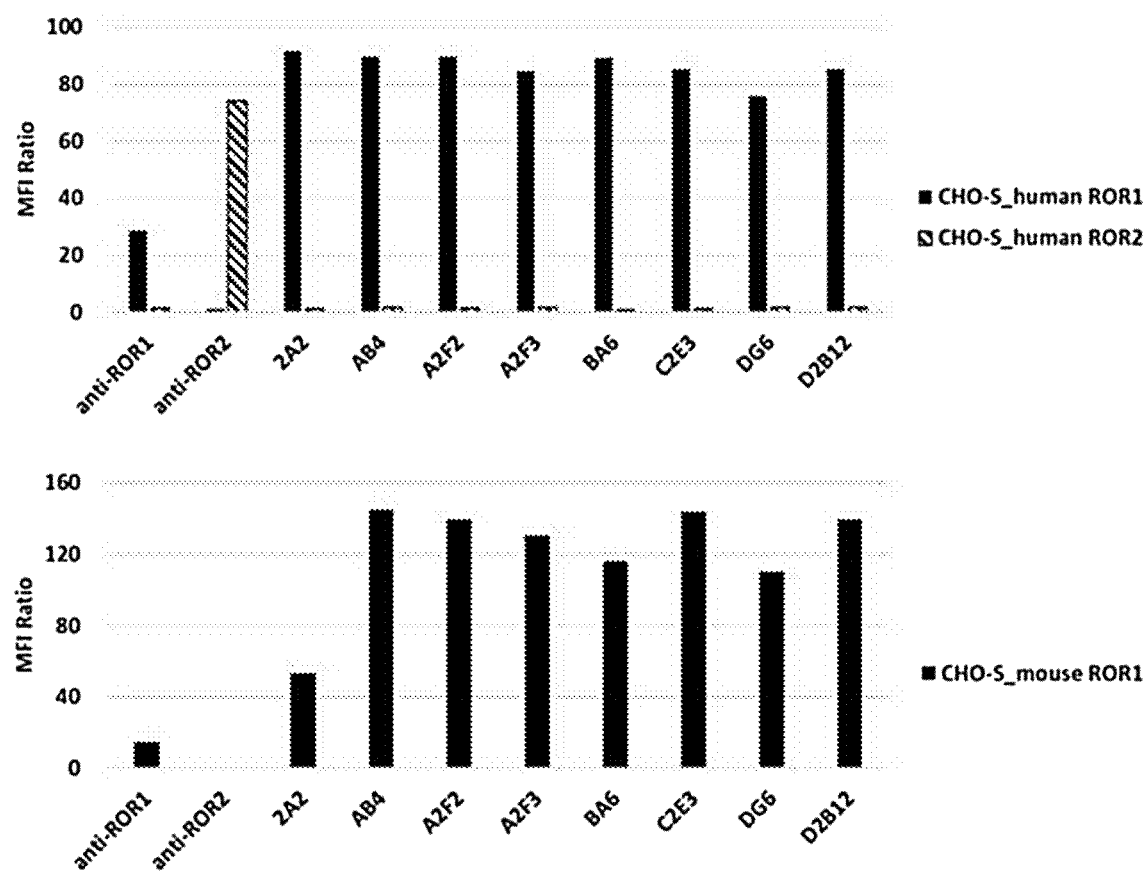
FIG. 5 shows results of measuring (FACS) the binding capacity of an anti-ROR1 antibody prepared according to one example of the present invention to cell surface-expressed ROR1 antigen, where human ROR1 is artificially over-expressed in the CHO-human ROR1 cell line, human ROR2 is over-expressed in CHO-human ROR2, and mouse ROR1 is over-expressed in CHO-mouse ROR1. It was shown that the respective antibodies specifically bind to human ROR1 expressed on the cell surface, and not to the family protein human ROR2. Further, by confirming binding to a cell line wherein mouse ROR1 was artificially overexpressed, it was confirmed that the anti-ROR1 antibody of the present invention has inter-species cross-reactivity to mouse ROR1. As for the 2A2 antibody used as a reference group, it was found that whereas it had cross-reactivity with mouse ROR1, the degree of binding was relatively weak compared to the anti-ROR1 antibody of the present invention.
Figure 6:
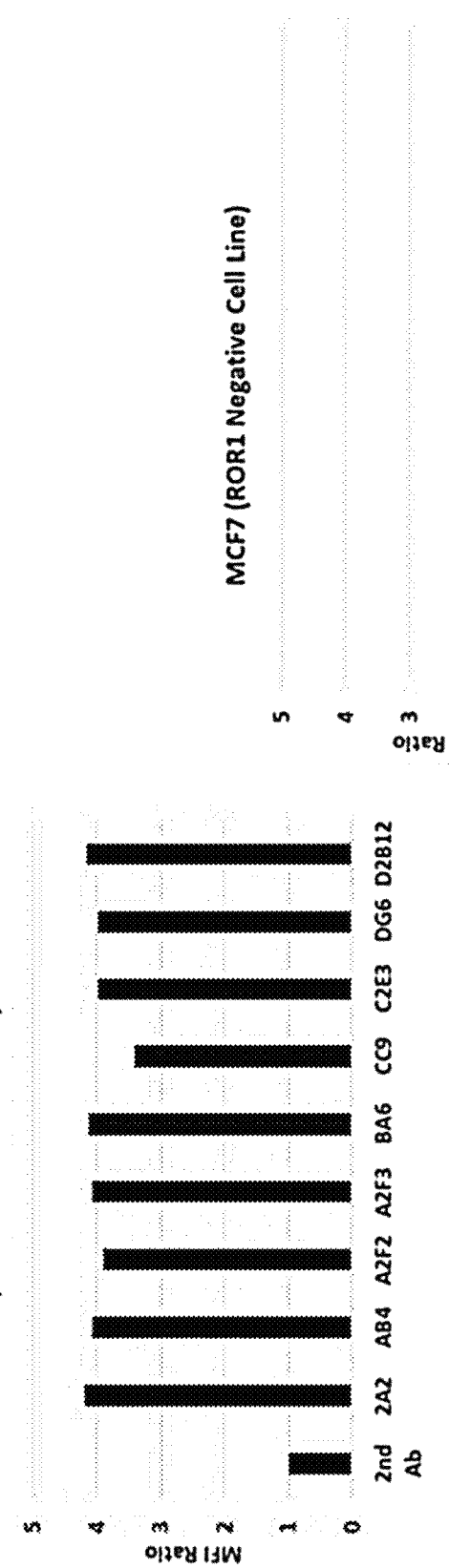
FIG. 6 shows results of measuring (FACS) the binding capacity of an anti-ROR1 antibody prepared according to one example of the present invention to cell surface-expressed ROR1 antigen, using the JeKo-1 and Mino cell lines as the ROR1 expression positive cell lines and the MCF7 cell line as the ROR1 negative cell line. The respective antibodies were found to specifically bind to ROR1 expressed on the cell surface, and not to bind to MCF7, a cell line which does not express ROR1.
Figure 6:
Figures 7, 8:
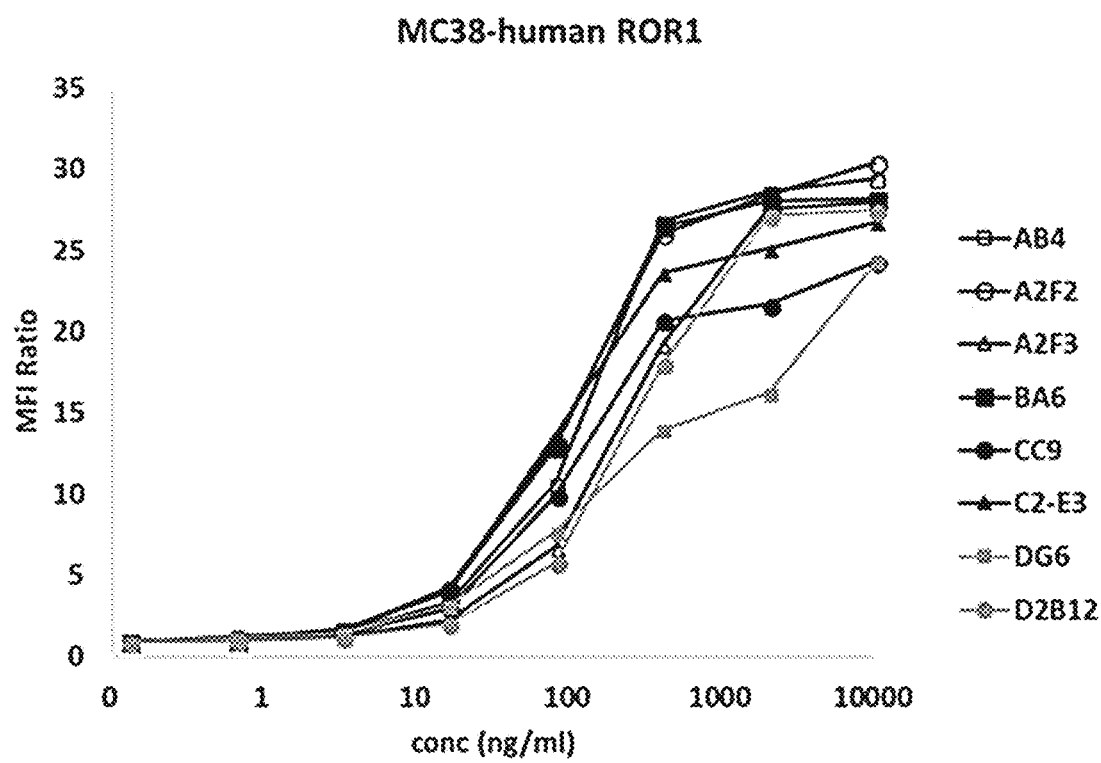
FIG. 7 shows results of measuring (FACS) the binding capacity of an anti-ROR1 antibody prepared according to one example of the present invention to cell surface-expressed ROR1 antigen. An MC38 human ROR1 cell line, where human ROR1 was artificially over-expressed on the mouse colon cancer cell line MC38, was used. The respective antibodies were found to bind to the cell line with human ROR1 over-expression in a concentration-dependent manner.
FIG. 8 shows results of measuring (FACS) the binding capacity of an anti-ROR1 antibody prepared according to one example of the present invention to cell surface-expressed ROR1 antigen in various cancer cell lines.

The results are represented in FIG. 5, FIG. 6 and FIG. 7. In the results, it was found that the anti-ROR1 antibody of the present invention binds specifically and in a concentration-dependent manner to human ROR1 (FIG. 6) which is originally expressed in cells, and the extracellular domain of human ROR1 (FIG. 5 and FIG. 7) artificially over-expressed in cells.

Further, it was confirmed that it does not bind to the family protein human ROR2, and that it has inter-species cross-reactivity with to mouse ROR1 (FIG. 5). When comparing cross-reactivity to cell surface-expressed mouse ROR1, it was confirmed that the ROR1 antibody of the present invention has a superior degree of binding than the 2A2 antibody used as a reference group (FIG. 5).

Embodiment 3-3: Measuring the Binding Ability of Anti-ROR1 IgG Antibody to Cell Surface-Expressed ROR1 Antigen in Various Cancers (FACS)

Subsequently, FACS analysis was performed to verify that the anti-ROR1 antibody of the present invention binds to cell surface-expressed ROR1 in various types of cancer cell lines. ROR1 is expressed in a variety of cancer cells, including not only blood cancers such as B-cell leukemia, lymphoma, acute myeloid leukemia (AML), Burkitt lymphoma, mantle cell lymphoma (MCL), acute lymphoblastic leukemia (ALL), chronic lymphocytic leukemia (CLL), Diffuse large B-cell lymphoma (DLBCL), follicular lymphoma (FL) and marginal zone lymphoma (MZL), etc. but also solid cancers including breast cancer, renal cancer, ovarian cancer, gastric cancer, liver cancer, lung cancer, colorectal cancer, pancreatic cancer, skin cancer, bladder cancer, testicular cancer, uterine cancer, prostate cancer, non-small cell lung cancer (NSCLC), neuroblastoma, brain cancer, colon cancer, squamous cell carcinoma, melanoma, myeloma, cervical cancer, thyroid cancer, head and neck cancer and adrenal cancer, etc.

For this experiment, the following various cancer cell lines were used: AGS (ATCC CRL1739™, human gastric adenocarcinoma), NCI-N87 (ATCC CRL-5822™, human gastric carcinoma), MKN-28 (KCLB 80102, human gastric adenocarcinoma), SNU-1750 (KCLB 01750, human gastric adenocarcinoma), SNU-16 (ATCC CRL5974™, human gastric carcinoma), HCC1187 (ATCC CRL-2322™, human breast cancer TNM stage IIA grade 3), MDA-MB-231 ATCC HTB-26™, human breast cancer), MDA-MB-468 (ATCC HTB-132™, human breast cancer), HCC70 (ATCC CRL2315™, human breast cancer TNM stage IIIA, grade 3), HCC1143 (ATCC CRL-2321™, TNM stage IIA, grade3, primary ductal carcinoma), BT20 (ATCC HTB-19™ human breast cancer), HCC1806 (ATCC CRL2335™, human breast cancer TNM stage IIB grade 2), HCC1937 (ATCC CRL2336™, TNM stage IIB, grade3, primary ductal carcinoma), BT474 (ATCC HTB-20™, ductal carcinoma), MCF7 (ATCC HTB-22™, breast cancer metastatic site), H460 (ATCC HTB-177™, large cell lung cancer), A549 (ATCC CCL-185™, lung carcinoma), NCI-H1975 (ATCC CRL-5908™, non-small cell lung cancer), H1437 (ATCC CRL5872™, stage 1, adenocarcinoma nonsmall cell lung cancer), Calu-6 (ATCC HTB-56™, anaplastic lung carcinoma), HCT116 (ATCC-CCL247™, colorectal carcinoma), DLD-1 (ATCC CCL-221™, Dukes' type C, colorectal adenocarcinoma), HT29 (ATCC HTB-38™, colorectal adenocarcinoma), 697 (DSMZACC 42, acute myeloblastic leukemia), Kasumi-2 (ATCC CRL-2724™, acute myeloblastic leukemia), Mino (ATCC CRL3000™, Mantle Cell Lymphoma), JeKo-1 (ATCC CRL3006™, Mantle Cell Lymphoma), Jurkat (ATCC TIB-152™, acute Tcell leukemia). FACS analysis (FACSCalibur, BD Biosciences) was used to analyze the binding of the anti-ROR1 antibody of the present invention to ROR1 in the above cell lines.

Specifically, the respective cell lines were dissociated and washed in PBS, then the numbers of cells were counted and adjusted to $2 \times 10^5$ cells/200 µℓ PBS. Then, they were treated with 10 µg /mL of the antibody of clone name C2E3 of the ROR1 monoclonal antibodies prepared in Embodiment 3, and reacted for 1 hour at 4° C. After the reaction, the cells were washed in PBS, then FITC-marked constant region (Fc) specific antibody (Goat anti-human IgG FITC conjugate, Fc specific, Sigma, F9512, concentration 20 mg/ml) was suspended in 2 µℓ /1×$10^5$ cells/200 µℓ PBS and reacted for 1 hour at 4° C. After reacting, the cells were washed with PBS and analyzed with the FACSCalibur equipment. The negative control was only treated with FITC-marked constant region (Fc) specific antibody. To compare the degree of ROR1 expression among the respective cancer cell lines, the quotient of dividing the shifted readings for the experimental group treated with the ROR1 monoclonal antibody (C2E3) of the present invention by the shifted readings for the control group (MFI Ratio: MFI of anti-ROR1/MFI or 2nd Ab) is indicated.

The results are shown in FIG. 8. The anti-ROR1 antibody of the present invention was confirmed to bind to ROR1 expressed in various cancer cell lines derived from gastric cancer, breast cancer, lung cancer, colon cancer, acute lymphocytic leukemia (ALL), and mantle cell lymphoma (MCL).

Embodiment 4: Measuring the Affinity of Anti-ROR1 IgG Antibody to ROR1

A 96-well black microplate (greiner bio one) was mounted on a biosensor tray case, and 200 µℓ 10×KB or DW was added to each of 8 wells. Then Anti Penta His biosensors or 8 AR2G biosensors (ForteBio, USA) were inserted to hydrate for 10 minutes. 600 µℓ of the assay samples were diluted 2-fold or 3-fold to the appropriate assay concentrations, using 1×KB or 10×KB to 30 to 0.021 nM. To immobilize the antigen, recombinant human ROR1-His (Sino Biological, 13968-H08H) was diluted to 1 µg/ML with 10×KB or Sodium Acetate pH5 buffer. Immobilization was fixed at a threshold of 0.3 nm in the loading step. The association assay was carried out for 3 to 10 minutes, and the dissociation assay was carried out for 20 minutes. According to the Octet program template, the buffer was placed in a new 96-well black microplate according to order. As Baseline1, 200 µℓ 10×KB or DW was placed. Then 200 µℓ each of 1 µℓ/mL of the antigen to be loaded, the ROR1-HIS protein, was added. As Baseline2, 200 µℓ 10×KB or 1×KB was placed. Then to each well 30 to 0.021 nM of the diluted antibody and 200 µℓ each of 10×KB buffer or 1×KB corresponding to a reference blank was added. The temperature of the test plate was fixed at 30° C. After all of the samples were introduced, the equipment was started, and after the assay was completed, results were uploaded to the Octet Analysis 90 software, with KD values analyzed through 1:1 fitting. The results are shown in Table 6 below. By obtaining KD values through the Octet assay method, it was confirmed that the anti-ROR1 antibody had strong binding potential to ROR1 antigen.

TABLE 6

Measuring affinity of anti-ROR1 IgG antibody to ROR1

| NO | Clone | KD (M) | kon(1/Msec) | koff(1/sec) | Chi | R^2 |
|---|---|---|---|---|---|---|
| 1 | AB4 | 6.39E-11 | 1.81E+06 | 1.16E-04 | 0.016 | 0.996 |
| 2 | A2F2 | 7.73E-11 | 1.53E+06 | 1.19E-04 | 0.106 | 0.997 |
| 3 | A2F3 | 2.40E-11 | 1.38E+06 | 3.31E-05 | 0.131 | 0.992 |
| 4 | BA6 | 9.37E-11 | 2.47E+06 | 2.31E-04 | 0.138 | 0.993 |
| 5 | C2E3 | 4.24E-11 | 5.46E+06 | 2.31E-03 | 0.176 | 0.966 |
| 6 | CC9 | 7.54E-10 | 7.31E+06 | 5.51E-04 | 0.200 | 0.992 |
| 7 | DG6 | 1.52E-10 | 2.23E+06 | 3.38E-04 | 0.506 | 0.964 |
| 8 | D2B12 | 8.03E-10 | 4.50E+05 | 3.61E-04 | 0.341 | 0.952 |

Embodiment 5: Analyzing the Cancer Growth Suppression Efficacy of Anti-ROR1 IgG Antibody in Mouse Tumor Xenograft Model Human cancer xenograft mice were prepared by transplanting $1 \times 10^7$ cells/head of the ROR1-expressing human mantle cell lymphoma cell line JeKo-1 to severe combined immunodeficiency mice (SCID). After xenograft, when tumor size reached 170 mm³ on average (Day 1), the mice were divided into groups, and 5 types of anti-ROR-1 antibody were peritoneally injected into the mice using a 1 mL syringe twice a week at 10 mg/kg for a total of 5 administrations (Days 1, 4, 7, 10 and 14). The negative control group was peritoneally administered 10 mg/kg each of human IgG1 (InVivoPlus human IgG1 isotype control, BioXCell, BP0297) having a structure similar to that of ROR-1 antibody twice a week for a total of 5 administrations. The size of the tumors grafted to the mice and the weight of the mice were measured immediately before initial administration (Day 1), immediately before administration on each administration date thereafter, and at two days after final administration (Day 16).

Figure 9A:
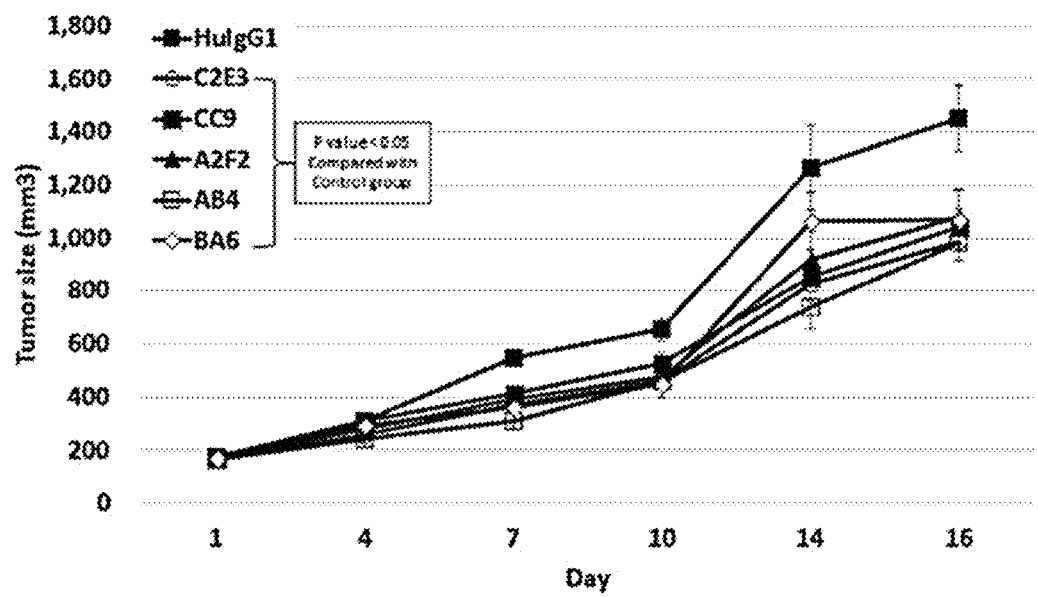
FIGS. 9A & B show the results of analyzing the cancer suppression efficacy of an anti-ROR1 antibody according to one example of the present invention in a mouse tumor xenograft model.
Figure 9B:
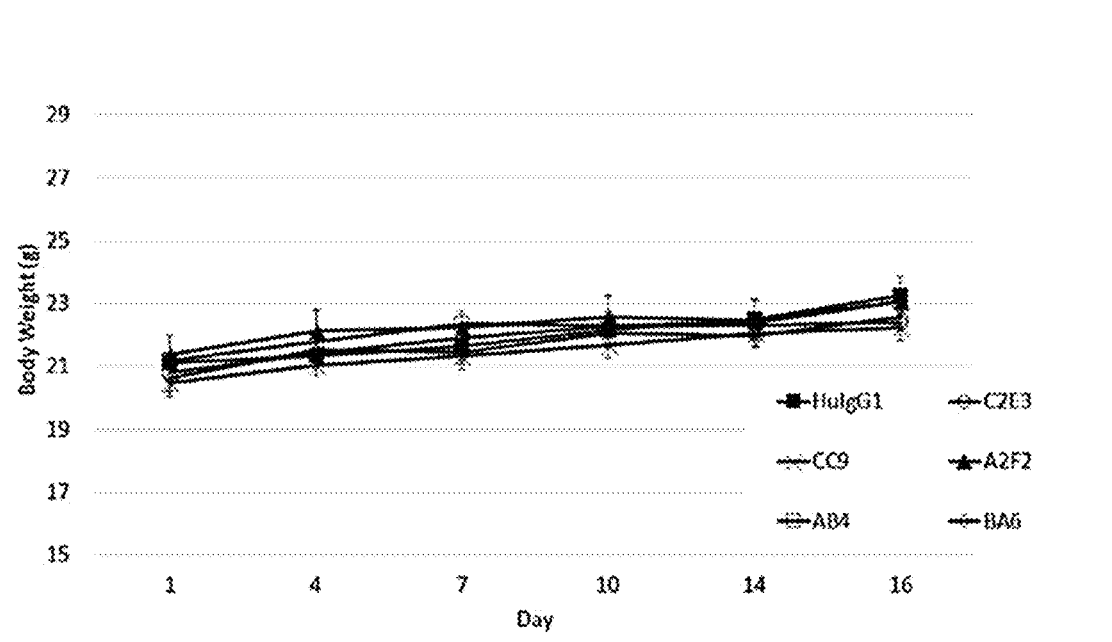

The results are presented in FIG. 9a and FIG. 9b. The anti-ROR-1 antibodies according to the present invention suppressed growth of cancer, and the % tumor growth inhibition (% TGI) of the [antibody according to] the present invention compared to the human IgG1 antibody (HuIgG1) negative control was of Day 16 when the experiment ended was C2E3 360%, A2F2 289%, AB4 361%, BA6 317%, and CC9 294%. The anti-ROR1 antibodies according to the present invention were found to have a statistically significant difference compared to the HuIgG-administered group (one-way ANOVA, P value <0.05) (FIG. 9a) Results of body weight measurement (FIG. 9b) did not reveal a significant difference between the administration groups. As stated in Embodiments 3-1 and 3-2, the anti-ROR1 antibodies of the present invention have cross-reactivity to mouse ROR1 antigen. Accordingly, the anti-ROR1 antibodies of the present invention administered can bind to human ROR1 expressed by the xenografted human mantle cell lymphoma cell line JeKo-1, as well as to the mouse ROR1 expressed by the mouse itself. Measuring body weight indicated similar increasing trends in body weight between the negative control group (HuIgG1) and the anti-ROR1 antibodies of the present invention, and this can be said to indicate that administration of the anti-ROR1 antibodies of the present invention does not induce toxicity. These results indicate that the antibodies according to the present invention may be useful as cancer therapeutic agents.

In the mouse tumor xenograft model, all 5 ROR1 antibodies of the present invention were found to suppress growth of cancer. Of these, some antibodies (C2E3 and AB4), as shown in Embodiment 6 and FIG. 10 below, were found to be able to induce auto-active cell death of ROR1-overexpressing cancer cell lines when multimerized by anti-human Fc antibody. However, various cancer inhibition mechanisms are possible, such as inducing auto-active cell death, inhibiting division and growth of cancer cells, suppressing tumor angiogenesis, and activation of immune cells. As such, the results of FIG. 10 below indicate that each of the anti-ROR1 antibodies according to the present invention are able to suppress cancer growth in vivo through different action mechanisms.

Embodiment 6: Analysis of Anti-ROR1 IgG Antibodies' Ability to Induce Auto-Active Cell Death To analyze the possible mechanisms of the antibodies according to the present invention exhibiting tumor suppression capacity as shown in Embodiment 5, their ability to induce cell death was analyzed.

To this end, the ROR1 over-expressing cell line JeKo-1 was centrifuged to remove the serum-containing medium. After washing once with PBS, 5×106 cells were seeded in each well of a 6-well plate using serum-free RPMI1640 medium. 100 µg/mL of the anti-ROR1 antibody according to the present invention and 300 μg/ml of anti-human Fc antibody (Thermo Fisher, 31125) were placed at a 1:1 ratio in an equivalent tube, an reacted for 10 minutes at room temperature so that the anti-ROR1 antibody was cross-linked by the anti-human Fc antibody. 150 μℓ each of the mixtures was placed in the wells containing 15 ml medium so that the final amount of antibody treated was 10 μℓ/mL for ROR1 antibody, and 30 μℓ/mL for anti-human Fc antibody, then reacted by culturing for 24 hours at 5% $CO_2$ and 37° C.

Next, to confirm whether or not whether or not the ROR1 antibody alone and the cross-linked anti-ROR1 antibody had the capacity to induce auto-active cell death, the cells of each well were collected and washed once with PBS. Thereafter, each group was reacted with the auto-active cell death marker Annexin V and the cell death marker PI, and the degree to which the groups were dyed was observed through FACS analysis.

Figure 10:
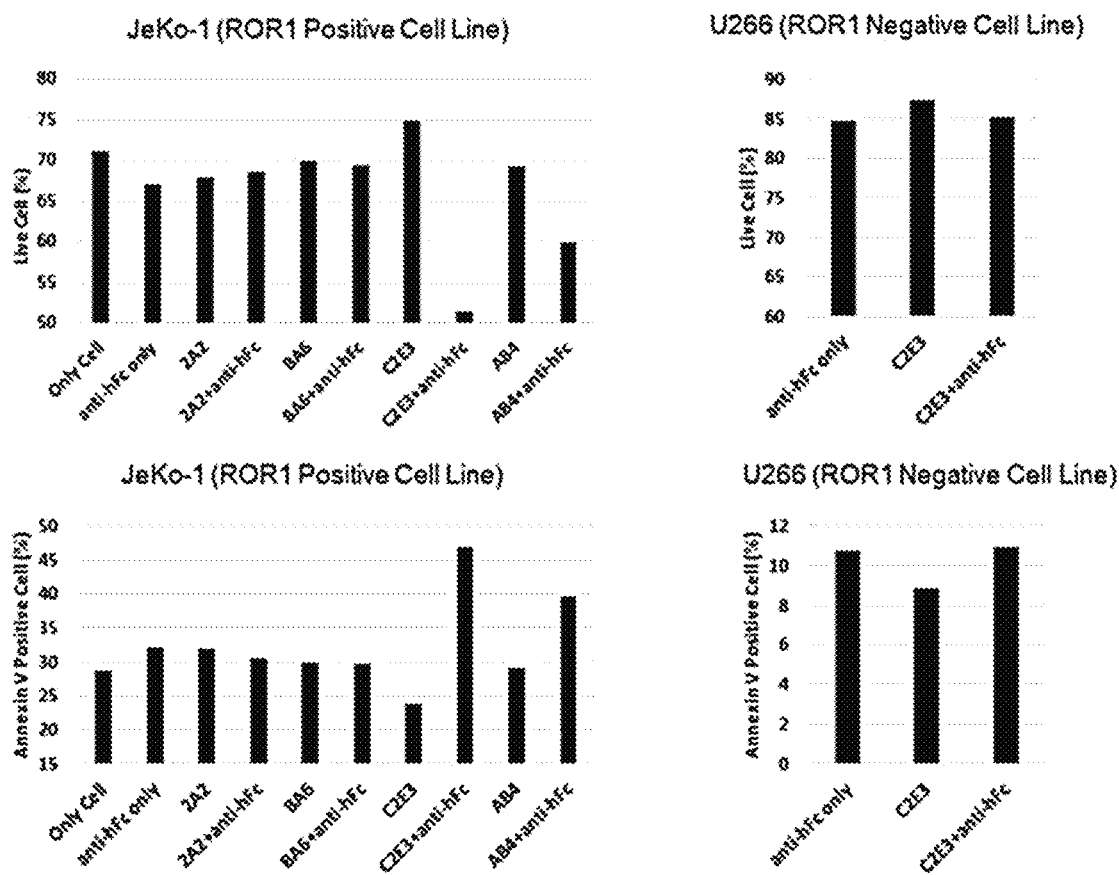
FIG. 10 shows results of analyzing the mechanism of action of an anti-ROR1 antibody prepared according to one example of the present invention. Suppression of cancer growth by the antibody may manifest in the form of, for example, inducing autophagic cell death, suppression cancer cell division, suppressing tumor angiogenesis, and/or immune cell activation, and identical or different mechanisms of action may be exhibited according to the antibody.

The results are shown in FIG. 10. In the results of the experiment, no auto-active cell death was observed for the group treated with anti-ROR1 antibody alone, but in the case of some anti-ROR1 antibody clones (C2E3 and AB4) cross-linked by anti-human Fc, the degree of dyeing by Annexin V and PI was increased over the control group. In particular, in terms of dyeing by the auto-active cell death marker Annexin V, there was a 23% increase for the C2E3 clone and a 10% increase for the AB4 clone over the control. To see if such capacity to induce auto-active cell death is a reaction specific to ROR1, the same method was carried out on the ROR1 non-expressing cell line U266 using the C2E3 clone to examine the degree of dyeing by Annexin V and PI. It was confirmed that the ROR1 non-expressing cell line U266 was not able to induce auto-active cell death, proving that the capacity of the one cross-linked anti-ROR1 antibody to induce auto-active cell death was an ROR1-specific reaction. Antibodies are able to form multimers in vivo by binding with Fc gamma receptors through their Fc regions, and therefore the formation of anti-ROR1 antibody multimer using anti-human Fc antibody can be said to represent conditions similar to in vivo phenomena. The above analysis results relate to a single mechanism, signifying that the anti-ROR1 antibody according to the present invention may induce auto-active cell death in ROR1 over-expressing cancer cell lines.

It should be noted that induction of auto-active cell death of cancer cell lines through multimerization of ROR1 antibody is not a phenomenon observed in all types of ROR 1 antibody. For example, in the case of the BA6 clone among the ROR1 antibodies of the present invention and the 2A2 antibody used as a reference group, these did not induce auto-active cell death of ROR1 over-expressing cancer cell lines even when multimerized by anti-human Fc antibody. This signifies that the ROR1 antibodies according to the present invention have cancer cell suppression capacity through different action mechanisms. This difference may be due to differences in epitopes to which the respective ROR1 antibodies bind, but this theory is not the sole explanation thereof.

Embodiment 7: Preparation of Compounds 1, 2, 3 and 4

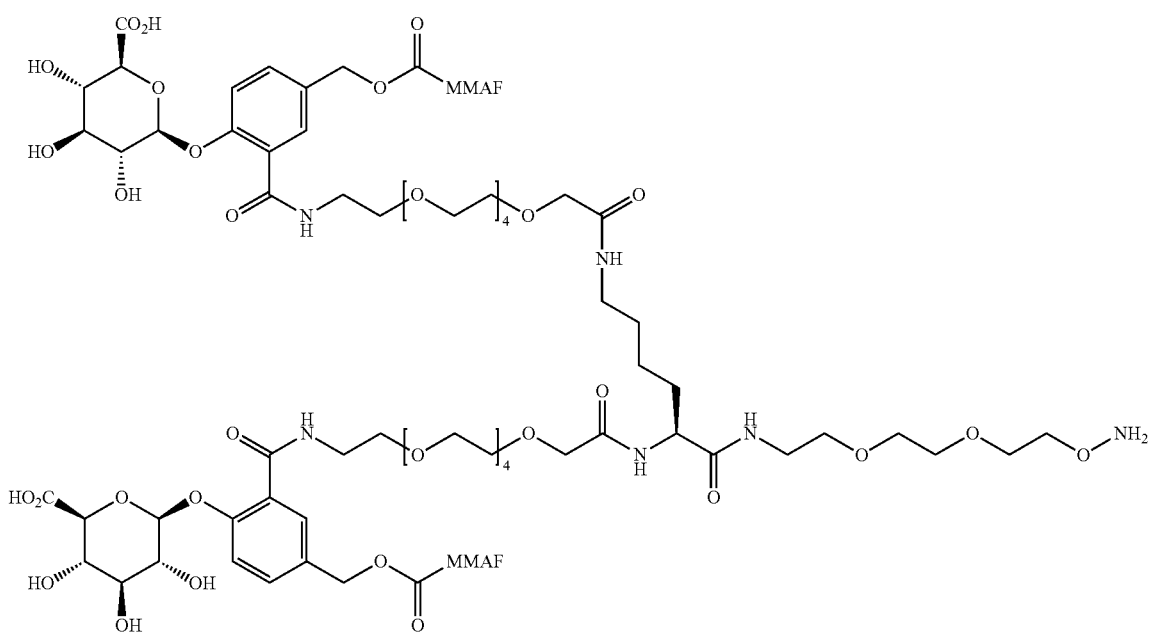

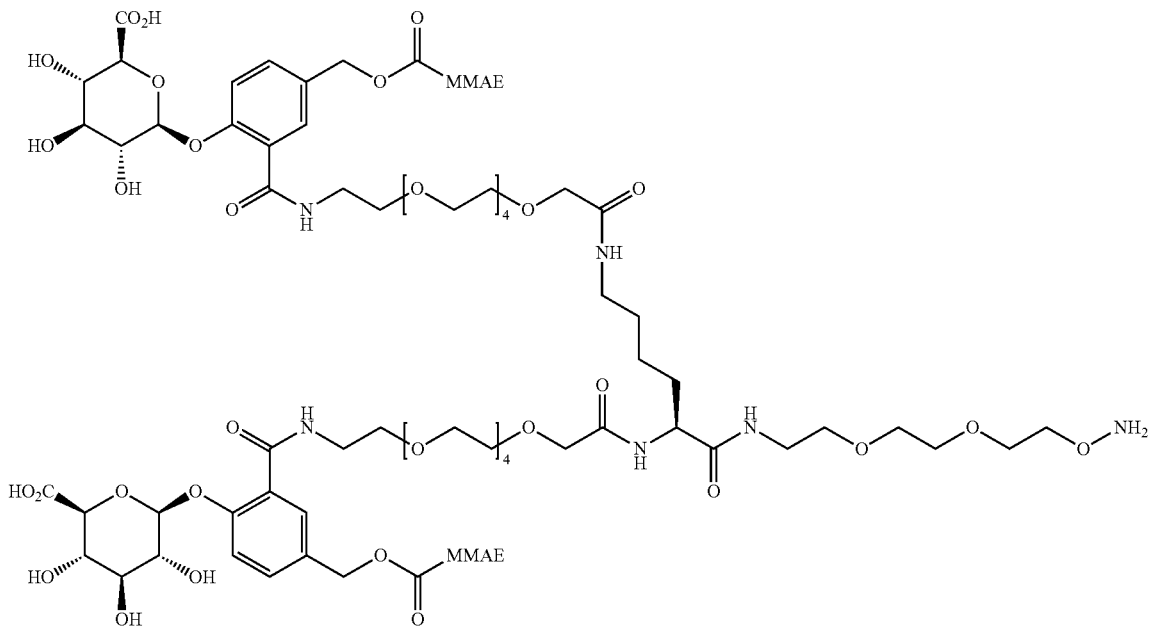
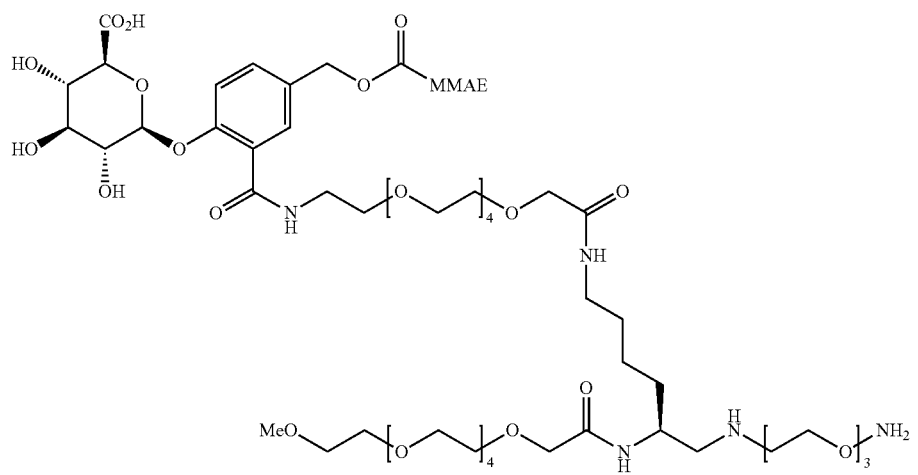

-continued
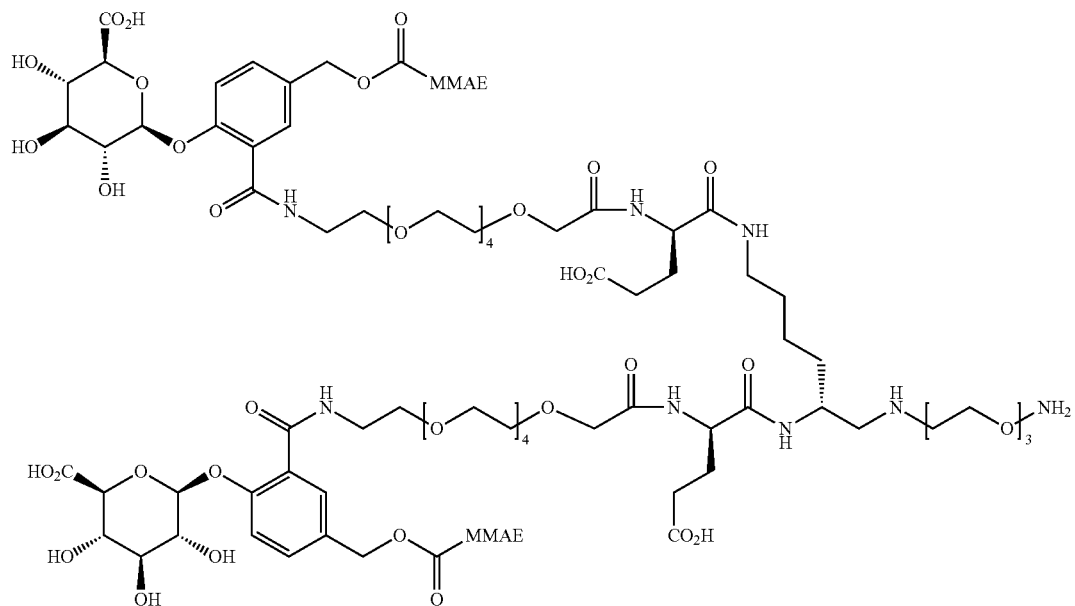
4
Compounds 1, 2 3 and 4 above were prepared using the method stated in Patent WO 2017-089895.
In Compounds 1, 2, 3 and 4 above, the structures of MMAE or MMAF are as follow:
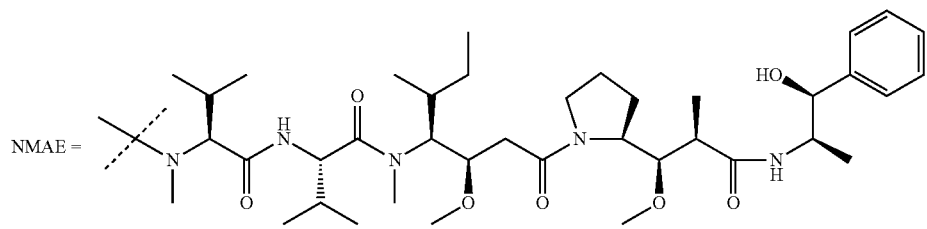
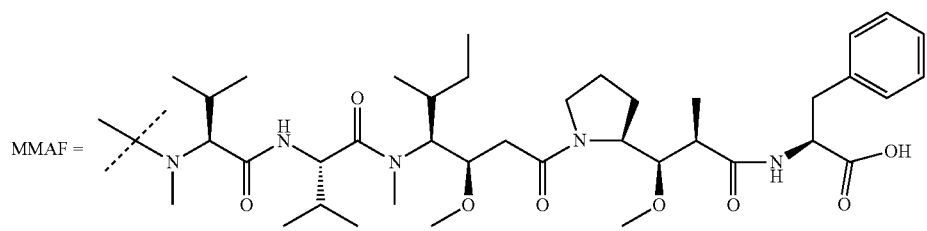

Embodiment 8: Preparation of Compounds 5, 6 and 7
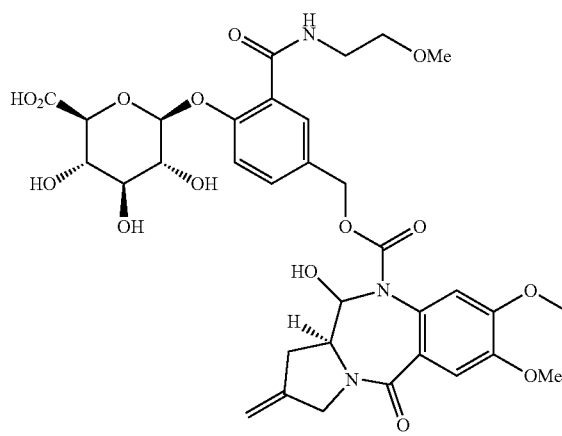
5
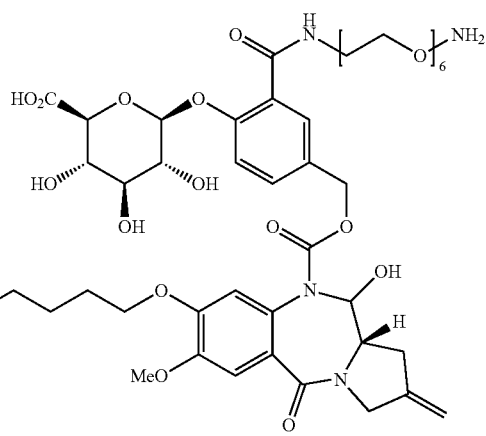
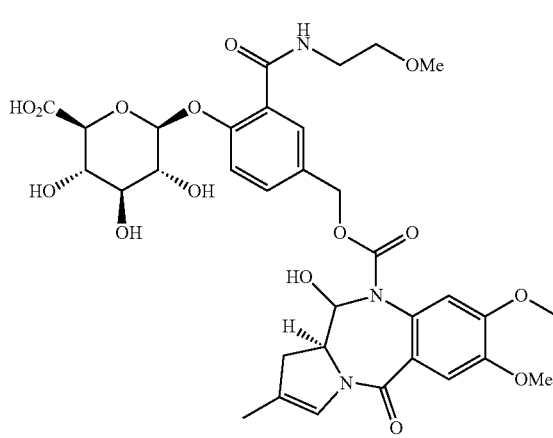
6
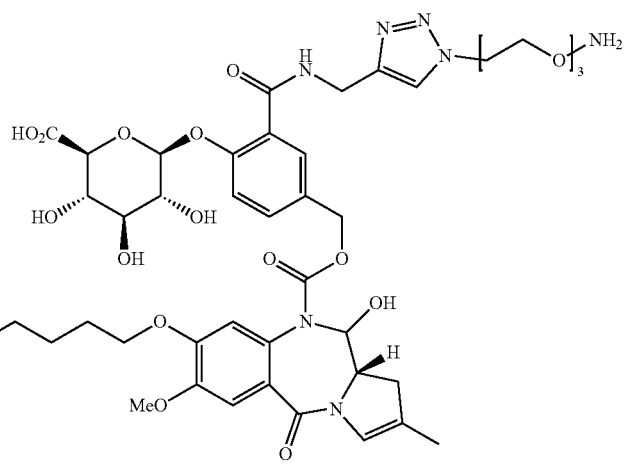
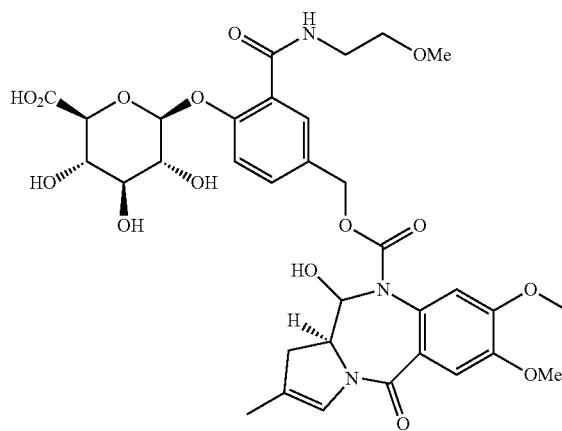
7
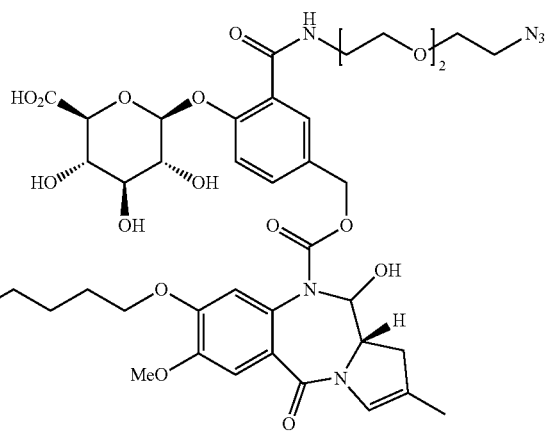

Compounds 5, 6 and 7 above were prepared using the method stated in Korean Patent Application No. 10-2018-0036895.

Embodiment 9: Preparation of ADC

ADC was prepared through the following two steps, and the LCB14-0511 and LCB14-0606 used commonly were prepared using the method stated in Korean Laid-open Patent No. 10-2014-0035393.

The structural formulae of LCB14-0511 and LCB14-0606 are as follow:

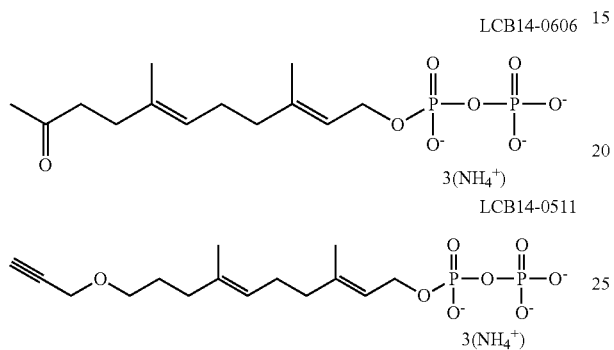

Step 1: Preparation of Prenylated Antibody

A prenylation reaction mixture of an ROR1 monoclonal antibody (C2E3) of the present invention was prepared and reacted for 16 hours at 30° C. The reaction mixture was comprised of 24 μM antibody, 200 nM FTase (Calbiochem #344145) and buffer solution (50 mM Tris-HCl (pH 7.4), 5 mM MgCl2, 10 μM ZnCl2, 0.144 mM DTT) containing 0.144 mM LCB14-0511 or LCB14-0606. After the reaction was completed, the prenylated antibody was desalted using a G25 Sepharose column (AKTA purifier, GE healthcare) equilibrated with PBS buffer solution.

As the reference group antibody, a chimera antibody (2A2) where human IgG1 is bonded to the variable region of an existing anti-ROR1 antibody 2A2 (U.S. Pat. No. 9,316,646) was used.

Step 2: Method of Drug-Conjugation

<Conjugation by Oxime Bond Formation>

The mixture for oxime bond-forming reaction between prenylated antibody and linker-drug was prepared by mixing 100 mM Na-acetate buffer solution pH 5.2, 10% DMSO, 20 μM antibody and 200 μM linker-drug (in, house, compounds 1, 2, 3, 4, 5 and 7 from Embodiments 7 and 8), and stirred lightly at 30° C. After reacting for 6 or 24 hours, an FPLC (AKTA purifier, GE healthcare) process was carried out to remove the surplus small compounds used. The protein fraction was collected and concentrated.

<Conjugation by Click Reaction>

The mixture for oxime bond-forming reaction between prenylated antibody and linker-drug was prepared by mixing 10% DMSO, 20 μM antibody and 200 μM linker-drug (in, house, compound 6 from Embodiment 8), 1 mM copper (II) sulfate pentahydrate, 2 mM (BimC4A)3 (Sigma-Aldrich 696854), 10 mM sodium ascorbate and 10 mM aminoguanidine hydrochloride, reacted for 3 hours at 25° C., then treated with 20 mM EDTA and reacted for 30 minutes. After reacting, an FPLC (AKTA purifier, GE healthcare) process was carried out to remove the surplus small compounds used. The protein fraction was collected and concentrated.

TABLE 7

List of ADCs prepared

| ADCs | Antibody | Prenylation group | Toxin |
|---|---|---|---|
| ADC1 | C2E3 | LCB14-0000 | Compound 1 |
| ADC2 | | | Compound 2 |
| ADC3 | | | Compound 3 |
| ADC4 | | | Compound 4 |
| ADC5 | | | Compound 5 |
| ADC6 | | | Compound 6 |
| ADC7 | | LCB14-0511 | Compound 7 |
| ADC8 | 2A2 | LCB14-0606 | Compound 1 |
| ADC9 | | | Compound 2 |
| ADC10 | | | Compound 3 |

Embodiment 10: Assessing ADC Properties

Using the ADCs prepared in Embodiment 9, the properties of the ADCs according to the present invention were analyzed.

For this purpose, hydrophobic interaction chromatography-high-performance liquid chromatography (HIC-HPLC) analysis was carried out. The ADCs were subjected to hydrophobic interaction chromatography-high-performance liquid chromatography using a phenyl-5PW column (7.5×75 mm, 10 μm, Tosoh Bioscience, USA). 50 mM potassium phosphate buffer solution (pH 7.0) containing 1.5M ammonium sulfate was used as buffer solution A, and 50 mM potassium phosphate buffer solution (pH 7.0) containing 30% acetonitrile was used as buffer solution B, and 70% A and 30% B were stabilized as an initial condition. Using a 70% A/30% B v. 10% A/90% B linear gradient, elution was performed for the next 25 minutes, with 5 minutes additional elution at 10% A/90% B. Flow rate and temperature were set to 1.0 mℓ/min and 25° C., respectively. This was followed by detection at both 254 and 280 mm ROR1 antibody was used, and prenylated ROR1 antibody was used as a reference group.

In addition, size exclusion chromatography-high-performance liquid chromatography (SEC-HPLC) analysis was carried out. Size exclusion chromatography-high-performance liquid chromatography was carried out on the ADCs using an SWXL guard column (6.0×40 mm, Tosoh Bioscience, USA) and a G3000SWxl column (7.8×300 mm, 5 μm, Tosoh Bioscience, USA). Using 200 mM potassium phosphate buffer solution (pH 7.0) containing 250 mM phosphate chloride and 15% isopropyl alcohol as the mobile phase, analysis was carried out for 30 minutes under conditions of 0.5 mℓ/min flow rate and 25° C. This was followed by detection at both 254 and 280 mm ROR1 antibody was used, and prenylated ROR1 antibody was used as a reference group.

Figure 11A:
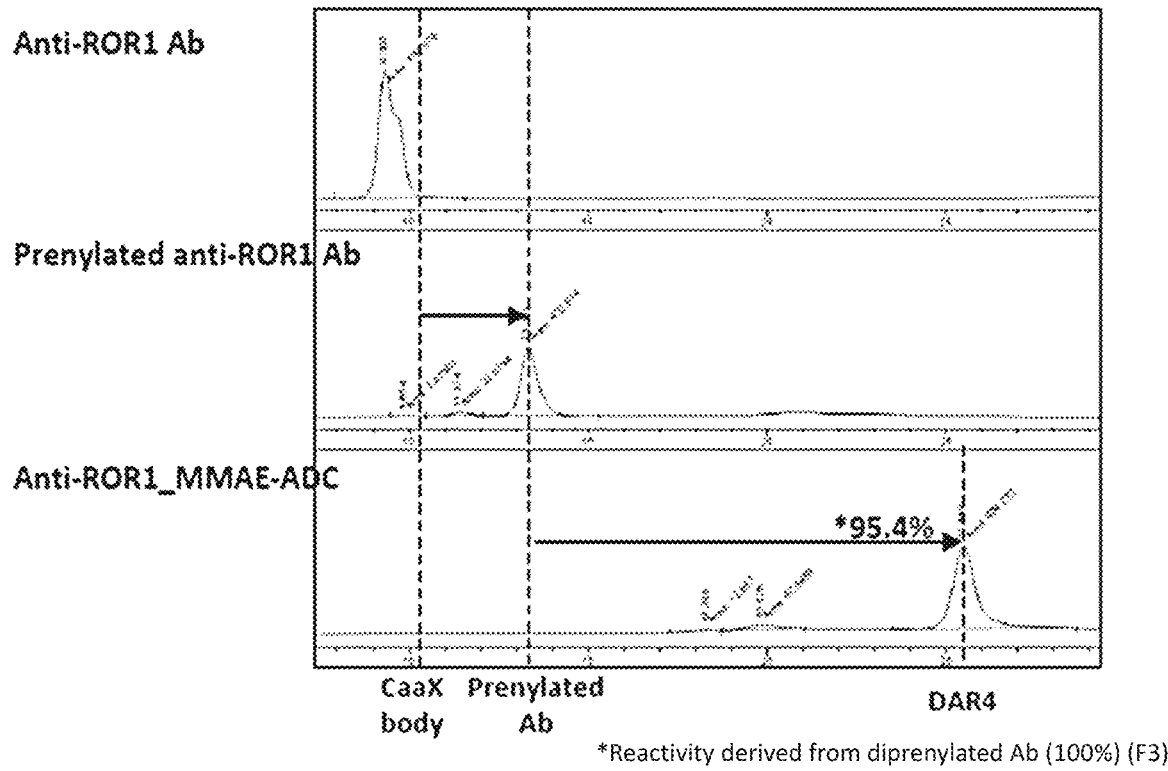
FIG. 11*a* is a drawing showing the characteristics of an anti-ROR1 antibody-MMAE conjugate (DAR4) prepared according to one example of the present invention.
Figure 11A:
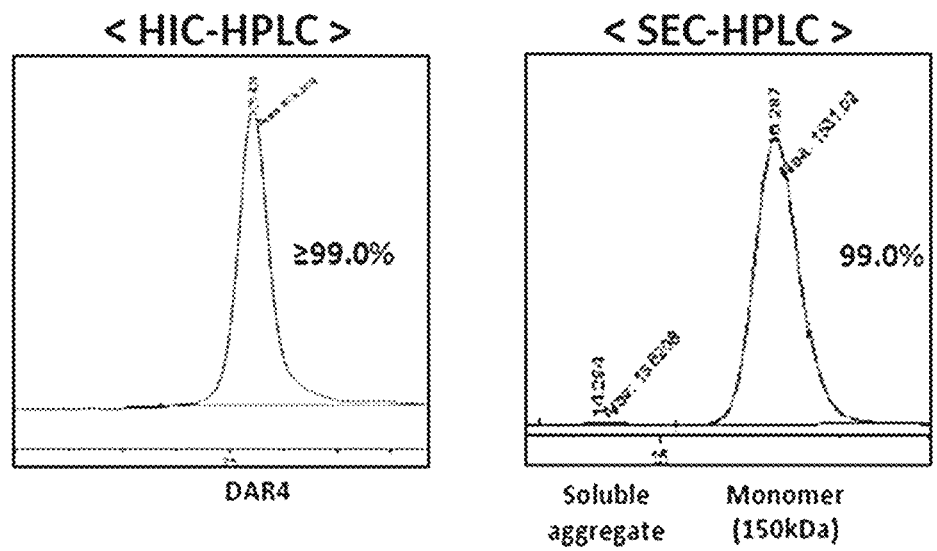
Figure 11B:
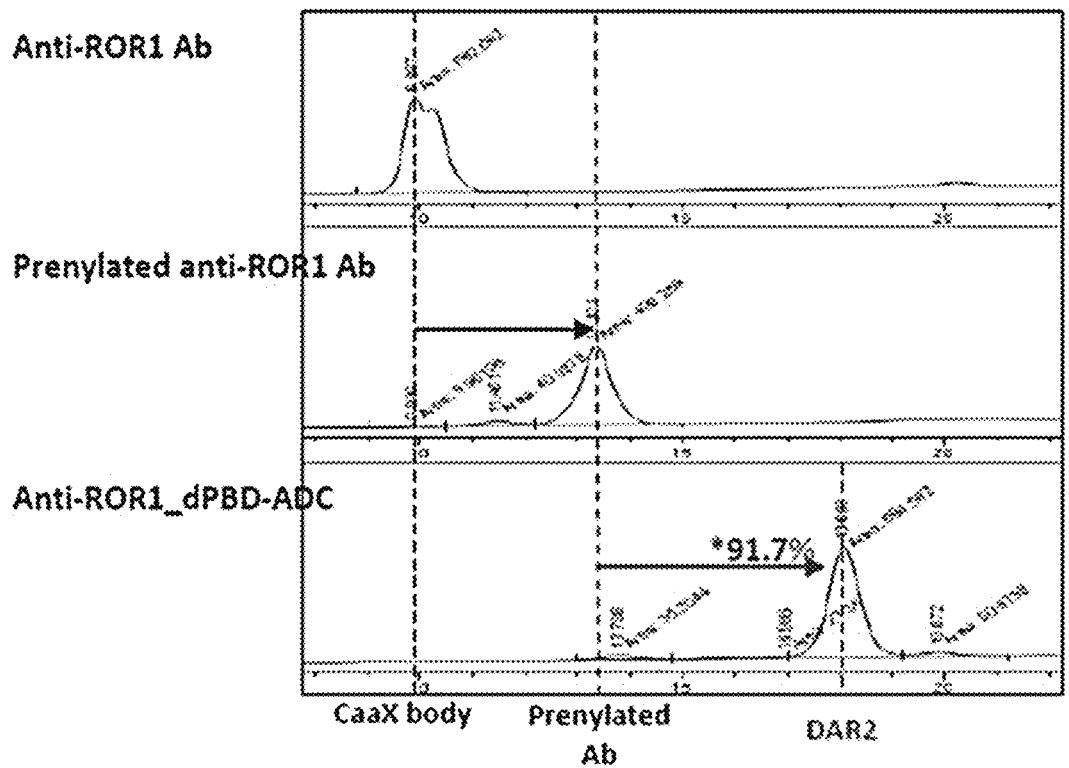
FIG. 11*b* is a drawing showing the characteristics of an anti-ROR1 antibody-dPBD conjugate (DAR2) prepared according to one example of the present invention.
Figure 11B:
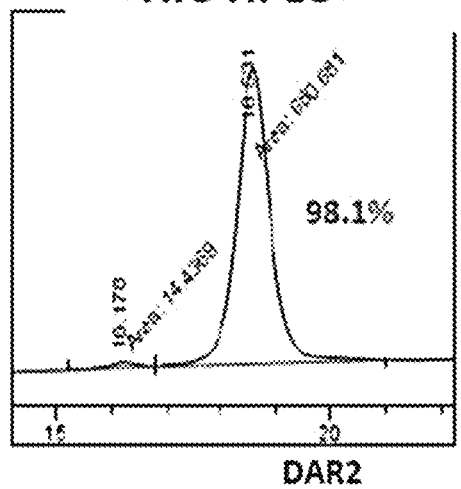
Figure 11B:
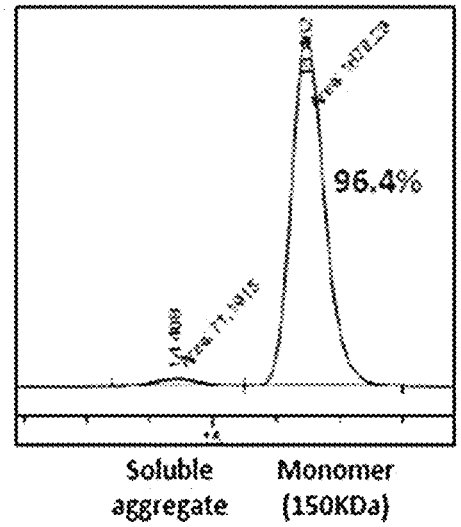

The results of analyzing properties of ADC2 and ADC5 among the ADCs prepared in Embodiment 9 are represented in FIG. 11a and FIG. 11b.

Embodiment 11: In Vitro Cytotoxicity Assessment

The cancer cell line cell proliferation inhibition activity of the ADCs prepared in Embodiment 9 was measured.

For this purpose, commercially available cancer cell lines were used (Mino, Jeko-1, REC-1, H2228, NCIN87, HCC1806, MDA-MB-231, MCF-7 and Daudi cell lines). In a 96-well plate, each well was seeded with 4,000 to 5,000 of the respective cancer cell lines. After culturing for 24 hours, they were treated with the ADCs in Table 8 at a concentration of 0.0015 to 10.0 nM (serially diluted threefold). 72 hours later, the number of live cells was measured using WST-8 (Dojindo Molecular Technology Inc.) dye.

The results are stated in Table 8 below. In cancer cell lines over-expressing ROR1, the anti-ROR1 monoclonal antibodies of the present invention were confirmed to have far superior cytotoxicity than the ADCs (ADC 8, 9 and 10) conjugated with conventional anti-ROR1 antibody. Further, it was confirmed that pyrrolobenzodiazepine based ADCs exhibited strong cytotoxicity compared to auristatin-based ADCs.

TABLE 8

Cytoxicity comparison of ADC specimens

|  | Jeko-1 | MDA-MB-231 | H2228 | HCC1806 | MCF-7 |
|---|---|---|---|---|---|
| Ag level (MIF fold) | 13 | 11.2 | 9.4 | 2.7 | 1 |
| Test sample |  | IC$_{50}$ [pM] |  |  |  |
| ADC1 | 2,067 | n.d. | n.d. | n.d. | — |
| ADC8 | n.d. | n.d | n.d. | — | — |
| ADC2 | 2,909 | 10,276 | 11,587 | 15,526 | 12,567 |
| ADC9 | 7,259 | 17,806 | 19,500 | 23,583 | 32,049 |
| ADC5 | 247 | 243 | n.d. | 5,092 | — |
| ADC10 | 481 | ~1,000 | n.d. | 23,430 | — |

*n.d: Cytotoxicity observed as concentration increases, but cells did not completely die at maximum concentration, and IC50 value could not be found.
*—: Exhibited weak or no cytotoxicity at maximum concentration.
*N/A: no data Embodiment 12: Analysis of In Vivo Cancer Growth Suppression Efficacy Embodiment 12-1: Analysis of Cancer Growth Suppression Efficacy by ADC in Mouse Model Grafted with ROR1-Expressing Breast Cancer Cell Line $1 \times 10^7$ cells/head of human ROR-1 expressing breast cancer cell line MDA-MB-468 were grafted to female Balb/C nude mice to prepare human cancer grafted mice. After grafting, the mice were grouped when tumor size reached 166 mm$^3$ on average (Day 1), and 1 mg/kg of ADCS prepared in Embodiment 9 was intravenously injected into the mice. In the control group, 10 ml/kg PBS was intravenously injected into the mice.

The size of the tumors grafted into the mice and the body weight of the mice were measured immediately before first administration (Day 1), and at regular intervals for 56 days thereafter.

Also, $1 \times 10^7$ cells/head of human ROR-1 expressing breast cancer cell line MDA-MB-231 were grafted to severe combined immunodeficient (SCID) mice to prepare human cancer grafted mice. After grafting, the mice were grouped when tumor size reached 110 mm$^3$ on average (Day 1), and 0.5, 1.0 or 2.0 mg/kg of ADCS prepared in Embodiment 9 was intravenously injected into the mice once, or 0.33 mg/kg ADCS was intravenously injected twice weekly a total of three times (Days 1, 7 and 14). In the control group, 10 ml/kg PBS was intravenously injected into the mice. The size of the tumors grafted into the mice and the body weight of the mice were measured immediately before first administration (Day 1), and at regular intervals for 22 days thereafter.

Also, $1 \times 10^7$ cells/head of human ROR-1 expressing breast cancer cell line HCC1187 were grafted to severe combined immunodeficient (SCID) mice to prepare human cancer grafted mice. After grafting, the mice were grouped when tumor size reached 110 mm$^3$ on average (Day 1), and 1.25 or 0.31 mg/kg of ADCS prepared in Embodiment 9 was intravenously injected into the mice once, or 3.75 mg/kg ADC2 was intravenously injected once. In the control group, 10 ml/kg PBS was intravenously injected into the mice. The size of the tumors grafted into the mice and the body weight of the mice were measured immediately before first administration (Day 1), and at regular intervals for 41 days thereafter.

Figure 12:
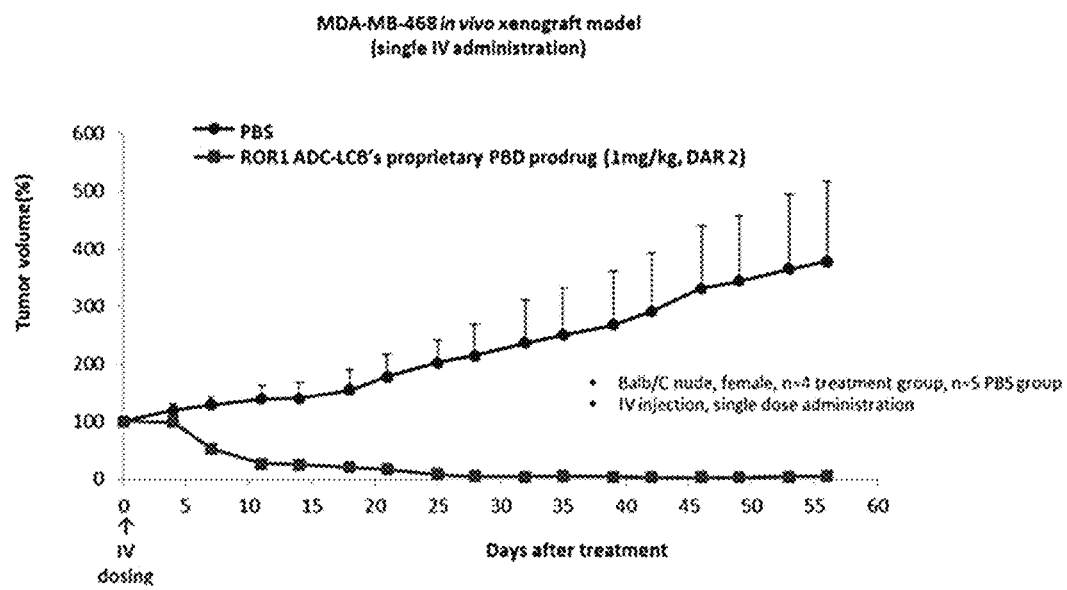
FIG. 12 shows results of analyzing the cancer suppression efficacy of an anti-ROR1 antibody-dPBD conjugate (DAR2) prepared according to one example of the present invention in an MDA-MB-468 breast cancer cell line transplanted mouse model. It is shown that the anti-ROR1 antibody-dPBD conjugate (DAR2) according to the present invention is effective in carcinoma elimination in an ROR1-expressing breast cancer cell line transplanted mouse model.
Figure 13:
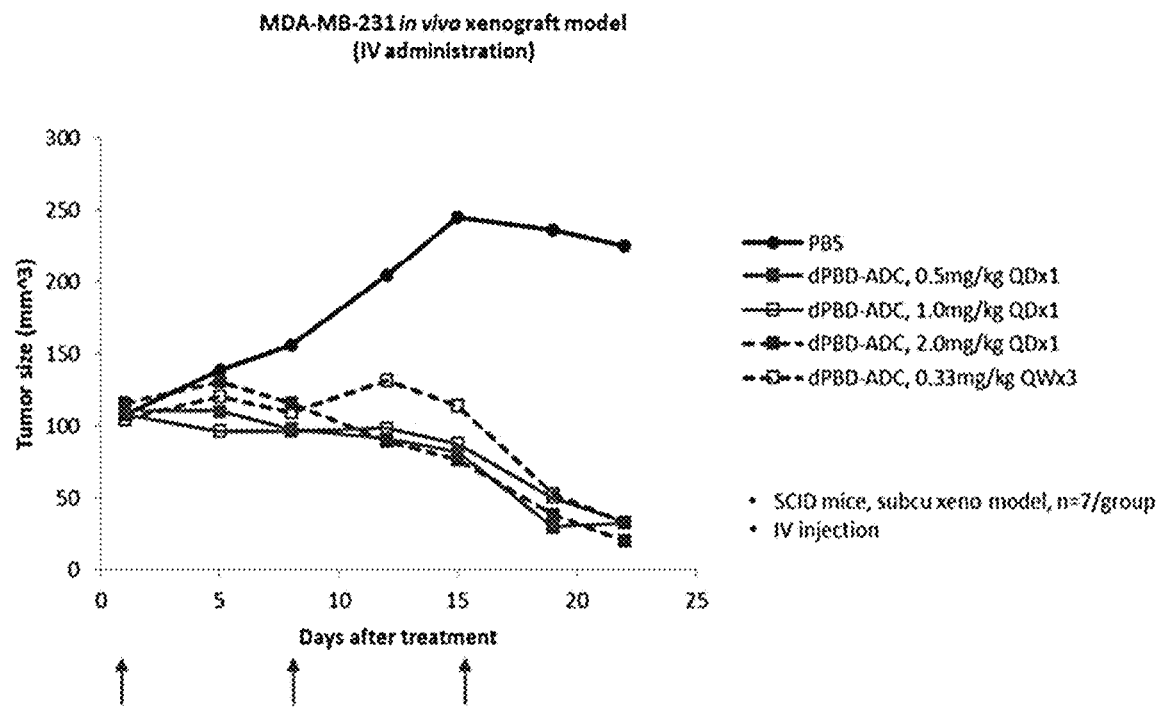
FIG. 13 shows results of analyzing the cancer suppression efficacy of an anti-ROR1 antibody-dPBD conjugate (DAR2) prepared according to one example of the present invention in an MDA-MB-231 breast cancer cell line transplanted mouse model. It is shown that the anti-ROR1 antibody-dPBD conjugate (DAR2) according to the present invention is effective in carcinoma elimination in an ROR1-expressing breast cancer cell line transplanted mouse model.
Figure 14:
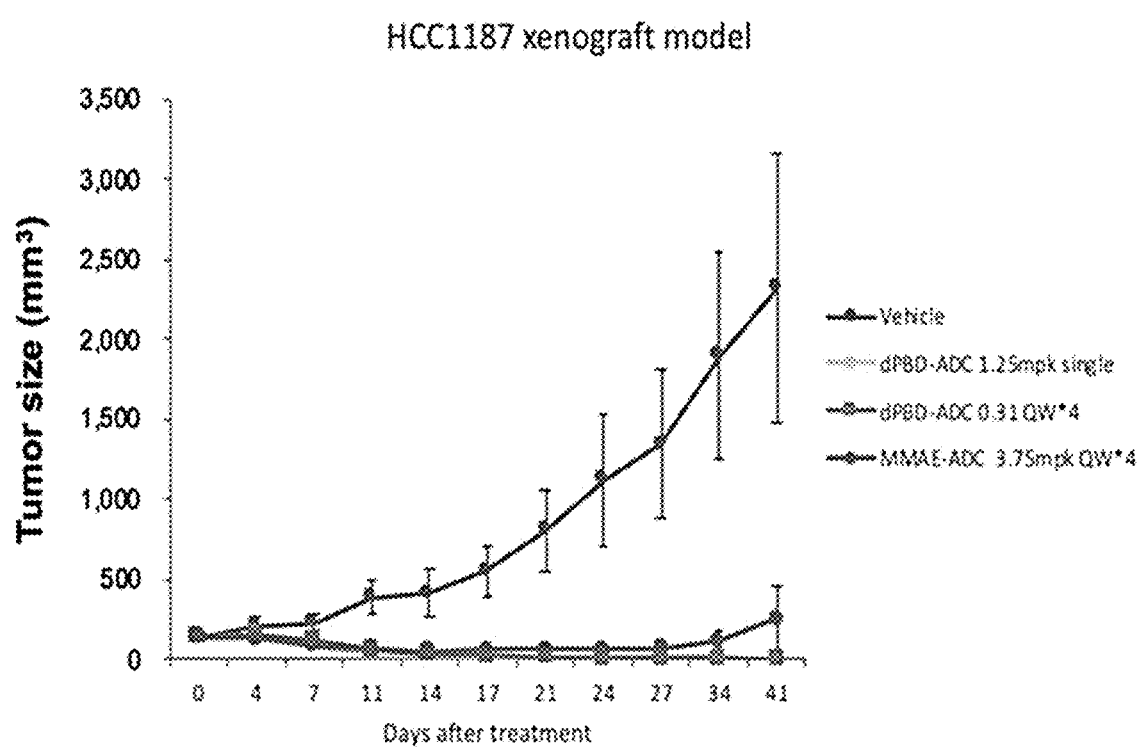
FIG. 14 shows results of analyzing the cancer suppression efficacy of an anti-ROR1 antibody-dPBD conjugate (DAR2) prepared according to one example of the present invention in an HCC1187 lung cancer cell line transplanted mouse model. It is shown that the anti-ROR1 antibody-dPBD conjugate (DAR2) according to the present invention is effective in carcinoma elimination in an ROR1-expressing lung cancer cell line transplanted mouse model.

The results are stated in FIG. 12, FIG. 13 and FIG. 14. It was confirmed that the ADCs of the present invention suppress growth of cancer in ROR1-expressing breast cancer cell line-grafted mouse models.

Embodiment 12-2: Analysis of Cancer Growth Suppression Efficacy by ADC in Mouse Model Grafted with ROR1-Expressing Breast Cancer Cell Line $1 \times 10^7$ cells/head of human ROR-1 expressing lung cancer cell line Calu-3 were grafted to female Balb/C nude mice to prepare human cancer grafted mice. After grafting, the mice were grouped when tumor size reached 184 mm$^3$ on average (Day 1), and 3 mg/kg of ADC2 prepared in Embodiment 9 was intravenously injected into the mice once, or 0.25 or 1.0 mg/kg ADCS prepared in Embodiment 9 was intravenously injected once. In the control group, 10 ml/kg PBS was intravenously injected into the mice. The size of the tumors grafted into the mice and the body weight of the mice were measured immediately before first administration (Day 1), and at regular intervals for 35 days thereafter.

Figure 15:
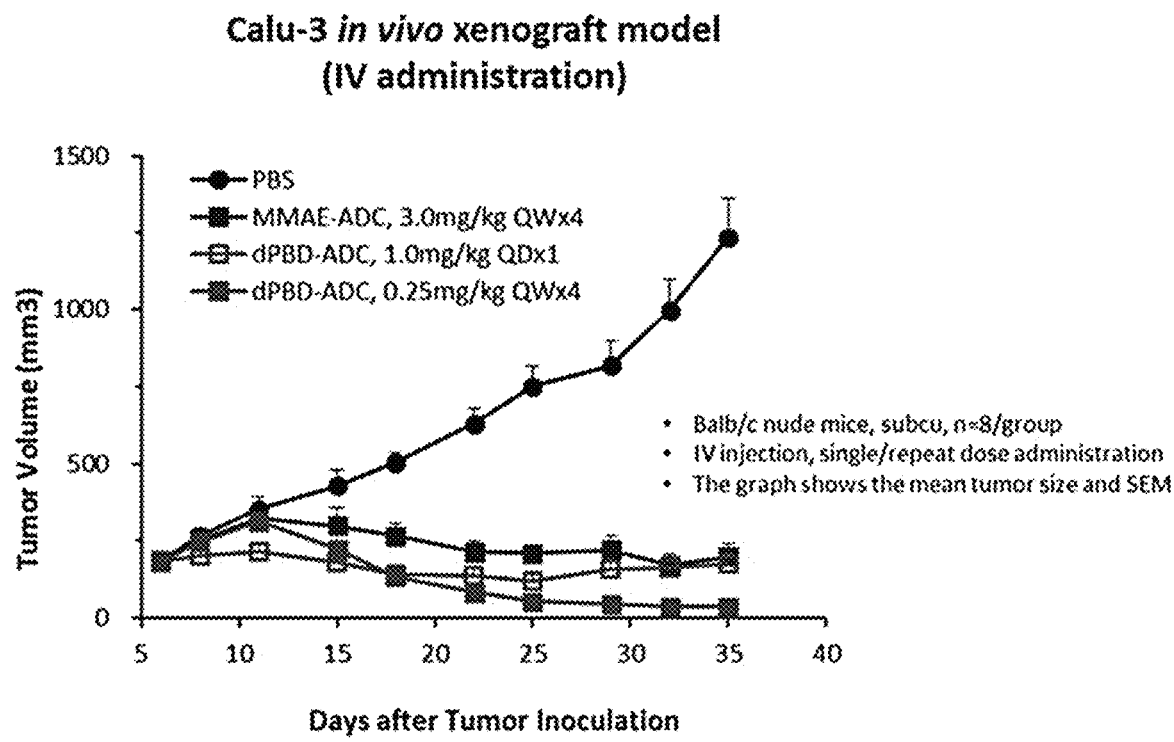
FIG. 15 shows results of analyzing the cancer suppression efficacy of an anti-ROR1 antibody-dPBD conjugate (DAR2) and anti-ROR1 antibody-MMAE conjugate (DAR4) prepared according to one example of the present invention in a Calu-3 breast cancer cell line transplanted mouse model. It is shown that the anti-ROR1 antibody-dPBD conjugate (DAR2) and anti-ROR1 antibody-MMAE conjugate (DAR4) according to the present invention are effective in carcinoma elimination in an ROR1-expressing breast cancer cell line transplanted mouse model.

The results are stated in FIG. 15. It was confirmed that the ADCs of the present invention suppress growth of cancer in ROR1-expressing lung cancer cell line-grafted mouse models.

Embodiment 12-3: Analysis of Cancer Growth Suppression Efficacy by ADC in Mouse Model Grafted with ROR1-Expressing Mantle Cell Lymphoma Cell Line $1 \times 10^7$ cells/head of human ROR-1 expressing human mantle cell lymphoma cell line Jeko-1 were grafted to severe combined immunodeficient (SCID) mice to prepare human cancer grafted mice. After grafting, the mice were grouped when tumor size reached 110 mm$^3$ on average (Day 1), and 3 mg/kg of ADC2 prepared in Embodiment 9 was intravenously injected into the mice once, or 0.25 or 1.0 mg/kg ADCS prepared in Embodiment 9 was intravenously injected once. In the control group, 10 ml/kg PBS was intravenously injected into the mice. The size of the tumors grafted into the mice and the body weight of the mice were measured immediately before first administration (Day 1), and at regular intervals for 33 days thereafter.

Figure 16:
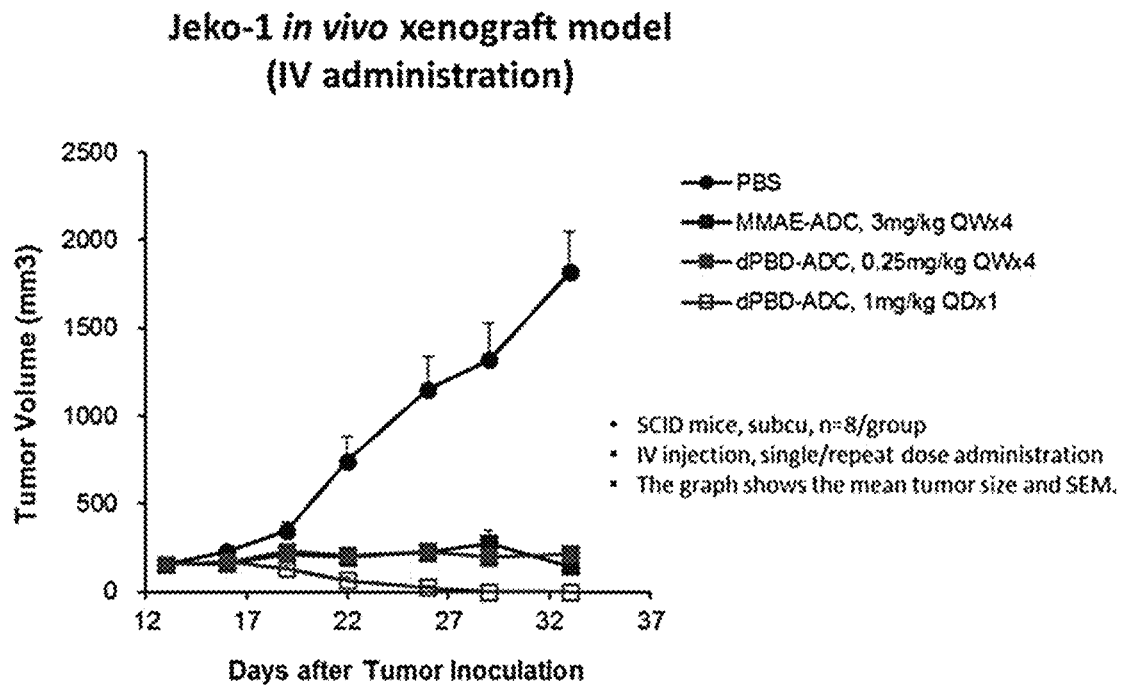
FIG. 16 shows results of comparing the cancer suppression efficacy of anti-ROR1 anti-drug conjugates according to the present invention in a Jeko-1 mantle cell lymphoma cell line transplanted mouse model.

The results are stated in FIG. 16. It was confirmed that the ADCs of the present invention suppress growth of cancer in ROR1-expressing mantle cell lymphoma cell line-grafted mouse models.

Embodiment 12-4: Comparison of Cancer Growth Suppression Efficacy Among ADCs in Mouse Model Grafted with ROR1-Expressing Mantle Cell Lymphoma Cell Line Cancer growth suppression efficacy depending on the antibodies and drugs comprising the ADCs was compared.

For this purpose, 1×10⁷ cells/head of human ROR-1 expressing human mantle cell lymphoma cell line Calu-3 were grafted to severe combined immunodeficient (SCID) mice to prepare human cancer grafted mice. After grafting, the mice were grouped when tumor size reached 110 mm³ on average (Day 1), and 1 mg/kg or 4 mg/kg of ADC2 (C2 MMAE)) or ADC9 (2A2 MMAE) prepared in Embodiment 9 was intravenously injected into the mice once, or 0.25 or 1.0 mg/kg of ADC5 (dPBD-ADC) or ADC10 (2A2 dPBD) prepared in Embodiment 9 was intravenously injected once. In the control group, 10 ml/kg PBS was intravenously injected into the mice. The size of the tumors grafted into the mice and the body weight of the mice were measured immediately before first administration (Day 1), and at regular intervals for 37 days thereafter.

Figure 17:
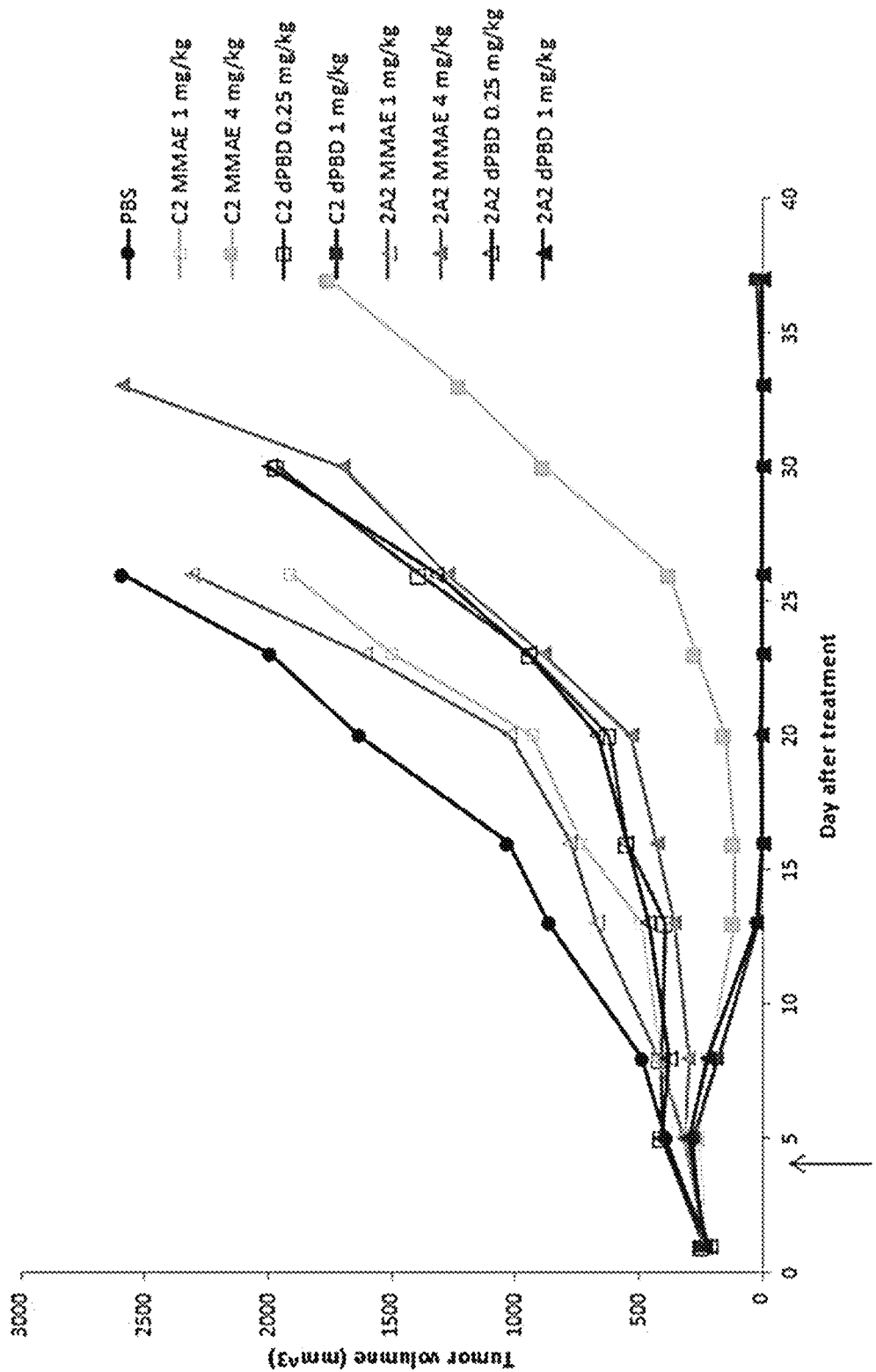
FIG. 17 shows results of the anti-ROR1 antibody-dPBD conjugate (DAR2) and anti-ROR1 antibody-MMAE conjugate (DAR4) according to the present invention. It is shown that the anti-ROR1 antibody-dPBD conjugate (DAR2) and anti-ROR1 antibody-MMAE conjugate (DAR4) according to the present invention are effective in carcinoma elimination in an ROR1-expressing mantle cell lymphoma cell line transplanted mouse model.

The results are stated in FIG. 17. The ADCs conjugated with the anti-ROR1 monoclonal antibodies of the present invention were confirmed to have superior cancer growth suppression efficacy than the ADCs (ADC 9 and 10) conjugated with conventional anti-ROR1 antibody. Further, it was confirmed that pyrrolobenzodiazepine based ADCs exhibited stronger cancer growth suppression than auristatin-based ADCs.

---

What is claimed:

1. An antibody conjugate comprising General Formula I, or a pharmaceutically acceptable salt thereof:

Ab-(X)y    [General Formula I]

wherein:
Ab is an anti-ROR1 antibody, or an antigen-binding fragment thereof,
the antibody or antigen-binding fragment thereof comprises a variable heavy chain complementarity determining region 1 (CDRH1), a variable heavy chain complementarity determining region 2 (CDRH2), a variable heavy chain complementarity determining region 3 (CDRH3), a variable light chain complementarity determining region 1 (CDRL1), a variable light chain complementarity determining region 2 (CDRL2), and a variable light chain complementarity determining region 3 (CDRL3); wherein, (a) CDRH1, CDRH2 and CDRH3 comprise the amino acid sequence of SEQ ID NOs. 1, 6 and 14, respectively, and CDRL1, CDRL2 and CDRL3 comprise the amino acid sequence of SEQ ID NOs. 22, 30 and 38, respectively;

(b) CDRH1, CDRH2 and CDRH3 comprise the amino acid sequence of SEQ ID NOs. 2, 7 and 15, respectively, and CDRL1, CDRL2 and CDRL3 comprise the amino acid sequence of SEQ ID NOs. 23, 31 and 39, respectively;

(c) CDRH1, CDRH2 and CDRH3 comprise the amino acid sequence of SEQ ID NOs. 1, 8 and 16, respectively, and CDRL1, CDRL2 and CDRL3 comprise the amino acid sequence of SEQ ID NOs. 24, 32 and 40, respectively;

(d) CDRH1, CDRH2 and CDRH3 comprise the amino acid sequence of SEQ ID NOs. 3, 9 and 17, respectively, and CDRL1, CDRL2 and CDRL3 comprise the amino acid sequence of SEQ ID NOs. 25, 33 and 41, respectively;
(e) CDRH1, CDRH2 and CDRH3 comprise the amino acid sequence of SEQ ID NOs. 1, 10 and 18, respectively, and CDRL1, CDRL2 and CDRL3 comprise the amino acid sequence of SEQ ID NOs. 26, 34 and 41, respectively;
(f) CDRH1, CDRH2 and CDRH3 comprise the amino acid sequence of SEQ ID NOs. 4, 11 and 19, respectively, and CDRL1, CDRL2 and CDRL3 comprise the amino acid sequence of SEQ ID NOs. 27, 35 and 42, respectively;
(g) CDRH1, CDRH2 and CDRH3 comprise the amino acid sequence of SEQ ID NOs 5, 12 and 20, respectively, and CDRL1, CDRL2 and CDRL3 comprise the amino acid sequence of SEQ ID NOs 28, 36 and 41, respectively;
(h) CDRH1, CDRH2 and CDRH3 comprise the amino acid sequence of SEQ ID NOs. 3, 13 and 21, respectively, and CDRL1, CDRL2 and CDRL3 comprise the amino acid sequence of SEQ ID NOs. 29, 37 and 41, respectively;
(i) CDRH1, CDRH2 and CDRH3 comprise the amino acid sequence of SEQ ID NOs. 2, 96 and 15, respectively, and CDRL1, CDRL2 and CDRL3 comprise the amino acid sequence of SEQ ID NOs. 23, 31 and 39, respectively; or
(i) CDRH1, CDRH2 and CDRH3 comprise the amino acid sequence of SEQ ID NOs. 3, 9 and 97, respectively, and CDRL1, CDRL2 and CDRL3 comprise the amino acid sequence of SEQ ID NOs. 25, 33 and 41, respectively
each X is independently selected from a moiety that comprises at least one active agent and a linker, wherein the linker couples Ab to the at least one active agent;
wherein the linker links Ab and the at least one active agent; and
y is an integer from 1 to 20.

2. The antibody conjugate of claim 1, wherein the antibody comprises a heavy chain variable region comprising:
the amino acid sequence of any one of SEQ ID NOs. 43-50, 98 and 99;
at least 90% sequence identity to the amino acid sequence of any one of SEQ ID NOs 43-50, 98 and 99, or;
at least 95% sequence identity to the amino acid sequence of any one of SEQ ID NOs 43-50, 98 and 99,
or a pharmaceutically acceptable salt thereof.

3. The antibody conjugate of claim 1, wherein the antibody comprises a light chain variable region comprising:
the amino acid sequence of any one of SEQ ID NOs 51-58;
at least 90% sequence identity to the amino acid sequence of any one of SEQ ID NOs 51-58; or
at least 95% sequence identity to the amino acid sequence of any one of SEQ ID NOs 51-58,
or a pharmaceutically acceptable salt thereof.

4. The antibody conjugate of claim 1, wherein the antibody comprises a combination of heavy chain and light chain variable regions comprising the amino acid sequence of: SEQ ID NOs. 43 and 51, respectively; SEQ ID NOs. 44 and 52, respectively; SEQ ID NOs. 45 and 53, respectively; SEQ ID NOs. 46 and 54, respectively; SEQ ID NOs. 47 and 55, respectively; SEQ ID NOs. 48 and 56, respectively; SEQ ID NOs. 49 and 57, respectively; SEQ ID NOs. 50 and 58, respectively; SEQ ID NOs. 98 and 52, respectively; or SEQ ID NOs. 99 and 54, respectively.

5. The antibody conjugate of claim 1, wherein the antibody comprises a combination of heavy chain and light chain comprising the amino acid sequence of: SEQ ID NOs. 59 and 67, respectively; SEQ ID NO 60 and 68, respectively; SEQ ID NO 61 and 69, respectively; SEQ ID NO 62 and 70, respectively; SEQ ID NO 63 and 71, respectively; SEQ ID NO 64 and 72, respectively; SEQ ID NO 65 and 73, respectively; or SEQ ID NO 66 and 74, respectively.

6. The antibody conjugate of claim 1, wherein the antibody is a monocloncal antibody, a domain antibody (dAb), a single chain antibody (scab), a Fab fragment, a Fab' fragment, a F(ab')2 fragment, an scFab fragment, an Fv fragment, a dsFv fragment, a single chain variable fragment (scFv), an ScFv-Fc fragment, a single domain heavy chain antibody, a single domain light chain antibody, a variant antibody, a multimeric antibody, a minibody, a diabody, a bispecific antibody or a multispecific antibody.

7. The antibody conjugate of claim 1, wherein the antibody is a rabbit, mouse, chimeric, humanized, or fully human monoclonal antibody.

8. The antibody conjugate of claim 1, wherein the linker between the antibody and the active agent comprises a cleavable bond.

9. The antibody conjugate of claim 1, wherein the antibody drug conjugate has a structure represented by General Formula II:

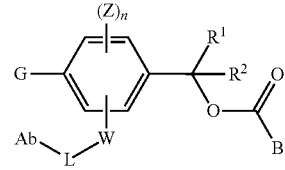

[General Formula II]

or a pharmaceutically acceptable salt thereof, wherein
G is a glucuronic acid moiety or

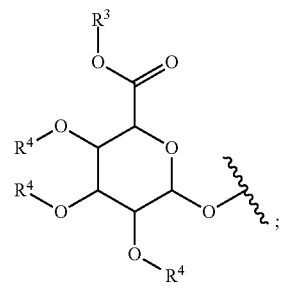

$R^3$ is a hydrogen or carboxyl protecting group;
each of the $R^4$ are independently a hydrogen or hydroxyl protecting group;
B is an active agent;
$R^1$ and $R^2$ are each independently hydrogen, $C_1$-$C_8$ alkyl or $C_3$-$C_8$ cycloalkyl;
W is —C(O)—, —C(O)NR'—, —C(O)O—, SO$_2$NR'—, —P(O)R"NR'—, —SONR'— or —PO$_2$NR'—; wherein the C, S or P is directly bound to the phenyl ring;
R' and R" are each independently hydrogen, $C_1$-$C_8$ alkyl, $C_3$-$C_8$ cycloalkyl, $C_1$-$C_8$ alkoxy, $C_1$-$C_8$ alkylthio, mono-or di- $C_1$-$C_8$ alkylamino, $C_3$-$C_{20}$ heteroaryl or $C_6$-$C_{20}$ aryl;

each Z is independently $C_1$-$C_8$ alkyl, halogen, cyano or nitro;
n is an integer of 0 to 3;
the bond overlaid with the wavy line represents a connection to the antibody, and
L is a linker comprising:
A) a $C_1$-$C_{50}$ alkylene or 1-50 atom heteroalkylene and:
(i) comprises at least one unsaturated bond;
(ii) is substituted by a bivalent substituent where 2 atoms in L are the same as in a substituent, this completing a heteroarylene; or
(iii) is substituted with $C_{1-20}$ alkyl; or
B) at least one isoprenyl group of General Formula III below:

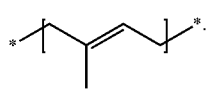
[General Formula III]

10. The antibody conjugate of claim 9, wherein W is —C(O)—, —C(O)NR'— or —C(O)O—.

11. The antibody conjugate of claim 9, wherein L further comprises a hydrophilic amino acid.

12. The antibody conjugate of claim 11, wherein the hydrophilic amino acid is selected from arginine, aspartate, asparagine, glutamate, glutamine, histidine, lysine, ornithine, proline, serine and threonine.

13. The antibody conjugate of claim 11, wherein L further comprises 2 to 20 amino acids.

14. The antibody conjugate of claim 9, wherein L comprises at least one isoprenyl unit represented by General Formula III:

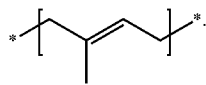
[General Formula III]

15. The antibody conjugate of claim 9, wherein L comprises a 3 to 50 heteroalkylene comprising an oxime, wherein the oxygen atom of the oxime is on the side of L linked to W and the carbon atom of the oxime is on the side of L linked to Ab; or wherein the carbon atom of the oxime is on the side of L linked to W and the oxygen atom of the oxime is on the side of L linked to Ab.

16. The antibody conjugate of claim 9, wherein L further comprises a connecting unit represented by General Formula VIII or General Formula IX:

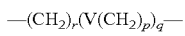   [General Formula VIII]

   [General Formula IX]

wherein
V is a single bond, —O—, —S—, —$NR^{21}$—, —C(O)$NR^{22}$—, $NR^{23}$C(O)—, $NR^{24}SO_2$—, or —$SO_2NR^{25}$—;
X is —O—, $C_1$-$C_8$ alkylene or —$NR^{21}$—;
$R^{21}$ to $R^{25}$ are, independently and respectively hydrogen, ($C_1$-$C_6$) alkyl, ($C_1$-$C_6$) alkyl ($C_6$-$C_{20}$) aryl, or ($C_1$-$C_6$) alkyl ($C_3$-$C_{20}$) heteroaryl;
r is an integer of 0 to 10;
p is an integer of 0 to 10;
q is an integer of 1 to 20; and
w is an integer of 1 to 20.

17. The antibody conjugate of claim 16, wherein V is —O—.

18. The antibody conjugate of claim 16, wherein X is —O—.

19. The antibody conjugate of claim 9, wherein L further comprises a binding unit formed by a 1,3-dipolar cycloaddition reaction, hetero-diels reaction, nucleophilic substitution reaction, nonaldol type carbonyl reaction, additions to carbon-carbon multiple bond, oxidation reaction or click reaction.

20. The antibody conjugate of claim 9, wherein L further comprises a binding unit represented by General Formula IV, V, VI or VII:

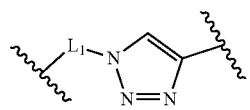
[General Formula IV]

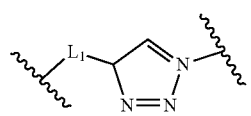
[General Formula V]

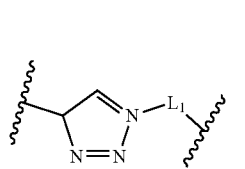
[General Formula VI]

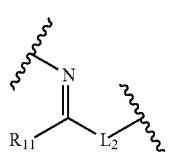
[General Formula VII]

wherein
$L^1$ is a single bond or an alkylene of $C_1$-$C_{30}$;
$L^2$ is an alkylene having 1 to 30 carbon atoms; and
$R^{11}$ is a hydrogen or an alkyl of $C_1$-$C_{10}$.

21. The antibody conjugate of claim 20, wherein L comprises

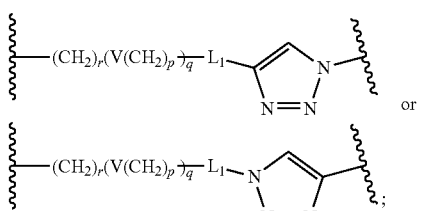

wherein
V is a single bond, —O—, —S—, —$NR^{21}$—, —C(O)$NR^{22}$—, $NR^{23}$C(O)—, $NR^{24}SO_2$—, or —$SO_2NR^{25}$—;

$R^{21}$ to $R^{25}$ are, independently and respectively hydrogen, $C_1$-$C_6$ alkyl, $C_1$-$C_6$ alkyl $C_6$-$C_{20}$ aryl, or $C_1$-$C_6$ alkyl $C_3$-$C_{20}$ heteroaryl;

r is an integer of 1 to 10;
p is an integer of 0 to 10;
q is an integer of 1 to 20; and
$L^1$ is a single bond.

22. The antibody conjugate of claim 9, wherein L further comprises one or more branched linkers covalently coupled to Ab, wherein
    i) each branched linker comprises a branching unit (BR) covalently coupled to Ab by a primary linker (PL);
    ii) each branched linker comprises a first branch (B1), in which a first active agent is covalently coupled to the branching unit by a secondary linker (SL) and a cleavage group (CG); and
    iii) each branched linker further comprises a second branch (B2), in which either a) a second active agent is covalently coupled to the branching unit by a secondary linker (SL) and a cleavage group (CG) or b) a polyethylene glycol moiety is covalently coupled to the branching unit,
    wherein each cleavage group can be hydrolyzed to release the active agent from the antibody-drug conjugate.

23. The antibody conjugate of claim 22, wherein the branching unit is represented by:

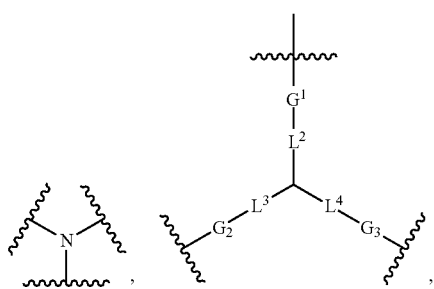

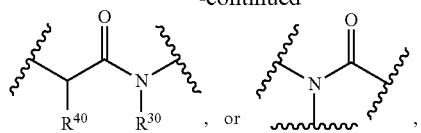

$L^2$, $L^3$ and $L^4$ are each independently a bond or —$C_nH_{2n}$—;

n is an integer of 1 to 30;

$G^1$, $G^2$ and $G^3$ are each independently, a bond,

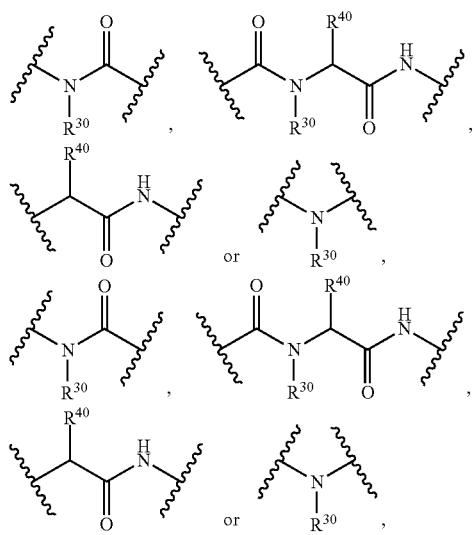

$R^{30}$ is hydrogen or $C_{1-30}$ alkyl;
$R^{40}$ is hydrogen or $L_4$—$COOR_{50}$ and
$R^{50}$ is hydrogen or $C_{1-30}$ alkyl.

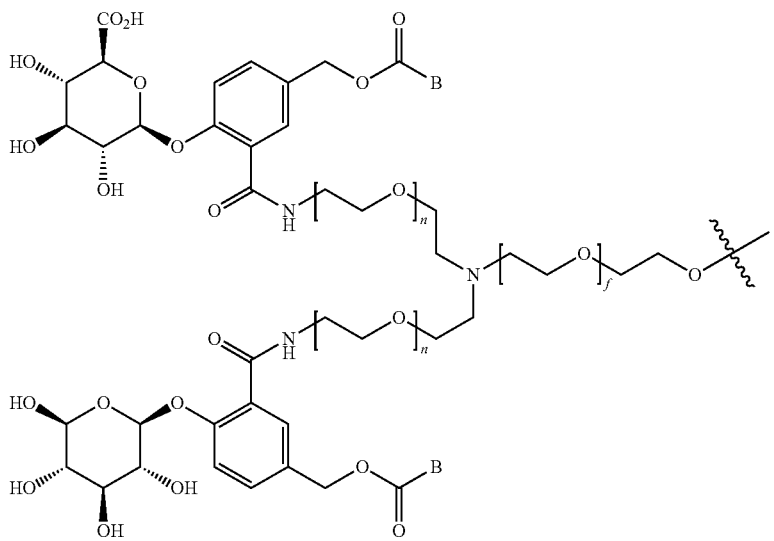

24. The antibody conjugate of claim 9, wherein the antibody conjugate comprises a structure represented by:
  wherein
  each B is independently an active agent;
  each n is independently an integer of 0 to 30; and
  f is an integer of 0 to 30.
25. The antibody conjugate of claim 1, wherein the conjugate is represented by:
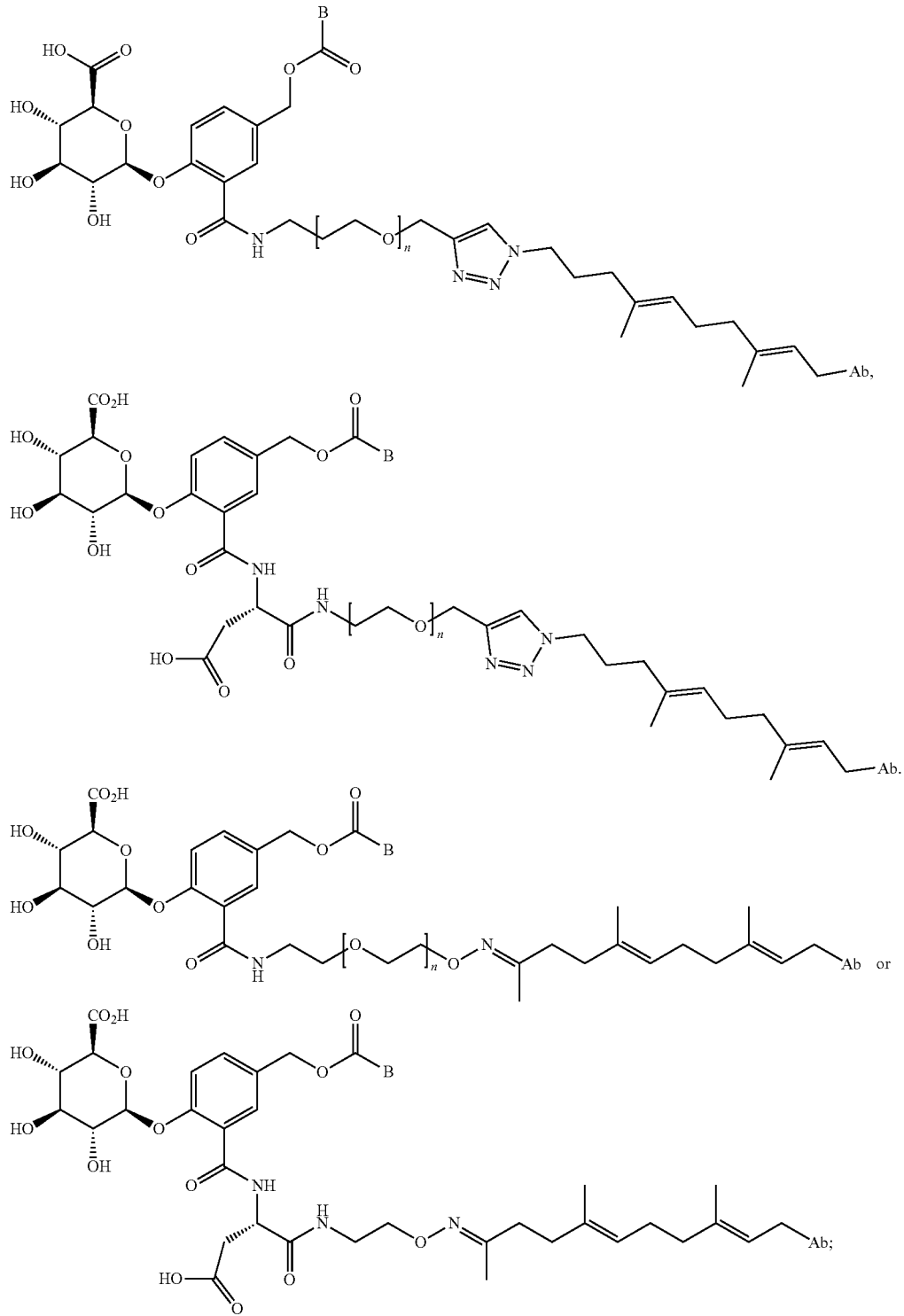

or a pharmaceutically acceptable salt thereof, wherein Ab is an anti-ROR1 antibody; B is an active agent and; n is an integer of 1 to 20.

26. The antibody conjugate of claim 1, wherein the active agent is an immunoregulatory compound, anti-cancer agent, antiviral, antibacterial, antifungal, antiparasitic or a combination of thereof.

27. The antibody conjugate of claim 1, wherein:
Ab is an anti-ROR1 antibody;
the active agent is a pyrrolobenzodiazepine dimer; and
y is an integer of 1 to 20.

28. The antibody conjugate of claim 27, wherein the pyrrolobenzodiazepine dimer is represented by General Formula X or General Formula XI below:

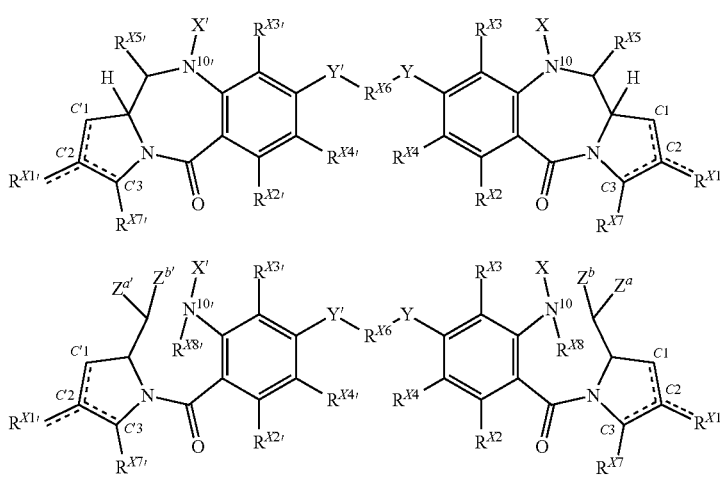

[General Formula X]

[General Formula XI]

wherein:
a dotted line represents an optional double bond as permitted by valency;
X and X' are, respectively and independently, —C(O)O*, —S(O)O—*, —C(O) —*, —C(O)NR$^X$—*, —S(O)$_2$NR$^X$—*, —P(O)R'NR$^X$—*, —S(O)NR$^X$—*, or —PO$_2$NR$^X$—*;
R$^{X1}$ and R$^{X1'}$ are independently selected from H, OH, =O, =CH$_2$ CN, R$^m$, OR$^m$, =CH—R$^{m'}$, =C(R$^{m'}$)$_2$, OSO$_2$—R$^m$, CO$_2$R$^m$, COR$^m$, halo and dihalo;
R$^{m'}$ is selected from R$^m$, CO$_2$R$^m$, COR$^m$, CHO, CO$_2$H and halo;
each R$^m$ is independently selected from of C$_{1-12}$ alkyl, C$_{2-12}$ alkenyl, C$_{2-12}$ alkynyl, C$_{5-20}$ aryl, C$_{5-20}$ heteroaryl, C$_{3-6}$ cycloalkyl, 3-7 membered heterocyclyl, 3-7 membered heterocycloalkyl and 5 to 7 heteroaryl; further wherein R$^m$ is optionally substituted with C$_{1-12}$ alkyl, C$_{2-12}$ alkenyl, C$_{2-12}$ alkynyl, C$_{5-20}$ aryl, C$_{5-20}$ heteroaryl, C$_{3-6}$ cycloalkyl, 3-7 membered heterocyclyl, 3-7 membered heterocycloalkyl or 5 to 7 heteroaryl;
R$^{X2}$, R$^{X2'}$, R$^{X3}$, R$^{X3'}$, R$^{X5}$ and R$^{X5'}$ are independently selected from H, R$^m$, OH, OR$^m$, SH, SR$^m$, NH$_2$, NHR$^m$, NR$^m{}_2$, NO$_2$, Me$_3$Sn and halo;
R$^{X4}$ and R$^{X4'}$ are independently selected from H, R$^m$, OH, OR$^m$, SH, SR$^m$, NH$_2$, NHR$^m$, NR$^m{}_2$, NO$_2$, Me$_3$Sn, halo, C$_{1-6}$ alkyl C$_{1-6}$ alkoxy, C$_{2-6}$ alkenyl, C$_{2-6}$ alkynyl, C$_{3-6}$ cycloalkyl, 3-7 membered heterocycloalkyl, C$_{5-12}$ aryl, 5 to 7 heteroaryl, —CN, —NCO, —OR$^n$, —OC(O)R$^n$, —OC(O)NR"R"', —OS(O)R", —OS(O)$_2$R", —SR", —S(O)R", —S(O)$_2$R", —S(O)NR"R"', —S(O)$_2$NR"R"', —OS(O)NR"R"', —OS(O)$_2$NR"R"', —NR"R"', —NR"C(O)R°, —NR"C(O)OR°, NR°C(O)NR°R°', —NR"S(O)R°, —NR"S(O)$_2$R°, —NR"S(O)NR°R°', —NR"S(O)$_2$NR°R°' —C(O)R", —C(O)OR" and —C(O)NR"R"';
each R$^X$ is independently selected from H, OH, N$_3$, CN, NO$_2$, SH, NH$_2$, ONH$_2$, NHNH$_2$, halo, C$_{1-8}$ alkyl, C$_{3-8}$ cycloalkyl, C$_{1-8}$ alkoxy, C$_{1-8}$ alkylthio, C$_{3-20}$ heteroaryl, C$_{5-20}$ aryl and mono- or di-C$_{1-8}$ alkylamino;
Y and Y' are each independently selected from O, S and N(H);
each R$^{x6}$ is independently selected from C$_{3-12}$ alkylene, C$_{3-12}$ alkenylene, or C$_{3-12}$ heteroalkylene;
R$^{X7}$ and R$^{X7'}$ are independently selected from H, C$_{1-6}$ alkyl, C$_{2-6}$ alkenyl, C$_{2-6}$ alkynyl, C$_{3-6}$ cycloalkyl, 3-7 membered heterocycloalkyl, C$_{6-10}$ aryl, 5 to 7 heteroaryl, —OR$^r$, —OC(O)R$^r$, —OC(O)NR'R", —OS(O)R$^r$, —OS(O)$_2$R$^r$, —SR$^r$, —S(O)R$^r$, —S(O)$_2$R$^r$, —S(O)NR'R", —S(O)$_2$NR'R", —OS(O)NR'R", —OS(O)$_2$NR'R", —NR'R", —NR'C(O)R$^s$, —NR'C(O)OR$^s$, —NR'C(O)NR$^s$R$^{s'}$, —NR'S(O)R$^s$, —NR'S(O)$_2$R$^s$, —NR'S(O)NR$^s$R$^{s'}$, —NR'S(O)$_2$NR$^s$R$^s$, —C(O)R$^r$, —C(O)OR$^s$ or —C(O)NR'R";
each R'R", R$^s$ and R$^{s'}$ is independently selected from H, C$_{1-7}$ alkyl, C$_{2-7}$ alkenyl, C$_{2-7}$ alkynyl, C$_{3-13}$ cycloalkyl, 3-7 membered heterocycloalkyl, C$_{5-10}$ aryl and 5 to 7 heteroaryl;
each R$^{X8}$ and R$^{X8'}$ is independently selected from H, C$_{1-6}$ alkyl, C$_{2-6}$ alkenyl, C$_{2-6}$ alkynyl, C$_{3-6}$ heteroalkyl, 3-7 membered heterocycloalkyl, C$_{5-10}$ aryl, 5 to 7 heteroaryl, —S(O)R$^m$, —S(O)$_2$R$^m$, —S(O)NR$^m$R$^{m'}$, —S(O)$_2$NR$^m$R$^{m'}$, —NR$^m$R$^{m'}$, —NR$^m$C(O)R$^m$, NR$^m$C(O)OR$^n$, —NR$^m$C(O)NR$^m$R$^n$, —NR$^m$S(O)R$^n$, —NR$^m$S(O)$_2$R$^n$, —NR$^m$S(O)NR$^n$R$^{n'}$, —NR$^m$S(O)$_2$NR$^n$R$^{n'}$, —C(O)R$^m$, —C(O)OR$^m$ and —C(O)NR$^m$R$^{m'}$;
Z$^a$ is selected from OR$^{X12a}$, NR$^{X12a}$R$^{X12a}$, or SR$^{X12a}$;
Z$^b$ is selected from OR$^{X13a}$, NR$^{X13a}$R$^{X14a}$, or SR$^{X13a}$;
Z$^{a'}$ is selected from OR$^{X12a}$, NR$^{X12a}$R$^{X12a}$, or SR$^{X12a}$;
Z$^{b'}$ is selected from OR$^{X13a'}$, NR$^{X13a'}$R$^{X14a'}$, or SR$_{X13a}$;
each R$^{X12a}$, R$^{X12a'}$, and R$^{x13a'}$ is independently selected from H, C$_{1-6}$ alkyl, C$_{2-6}$ alkenyl, C$_{2-6}$ alkynyl, C$_{3-6}$ cycloalkyl, 3 to 7 membered heterocycloalkyl, C$_{5-10}$ aryl, 5 to 7 heteroaryl, —C(O)R$^{X15a}$, —C(O)OR$^{X15a}$ and —C(O)NR$^{X15a}$R$^{X15a'}$;

each $R^{X15a}$ and $R^{x15a'}$ is independently selected from $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3-7 membered heterocyclyl, 3-7 membered heterocycloalkyl, and 5 to 7 heteroaryl;

each $R^{X13a}$ and $R^{X14a}$ is independently H or alkyl; or $R^{X13a}$ and $R^{X14a}$, together with the atom to which it is connected, form 3-7 membered heterocyclyl, form 3-7 membered heterocycloalkyl, or form 3-7 membered heteroaryl, and the $R^{X13a'}$ and $R^{X14a'}$ arbitrarily bind to the atoms to which they are attached to form 3-7 membered heterocyclyl, 3-7 membered heterocycloalkyl, or 3-7 membered heteroaryl; and each of $R^n$, $R^{n'}$, $R^o$, and $R^{o'}$ is independently selected from H, $C_{1-7}$ alkyl, $C_{2-7}$ alkenyl, $C_{2-7}$ alkynyl, $C_{3-13}$ cycloalkyl, 3-7 membered heterocycloalkyl, $C_{5-10}$ aryl, and 5 to 7 heteroaryl.

29. The antibody conjugate of claim 28, wherein $R^{X1}$ and $R^{X1'}$ are both $R^m$; and $R^m$ is $C_{1-6}$ alkyl, $C_{2-6}$ alkenyl, $C_{5-7}$ aryl, or $C_{3-6}$ heteroaryl.

30. The antibody conjugate of claim 28, wherein each of $R^{X2}$, $R^{X2'}$, $R^{X3}$, $R^{X3'}$, $R^{X5}$ and $R^{X5'}$, are independently selected from H or OH.

31. The antibody conjugate of claim 28, wherein $R^{X4}$ and $R^{X4'}$ are both $C_{1-6}$ alkoxy.

32. The antibody conjugate of claim 28, wherein Y and Y' are O.

33. The antibody conjugate of claim 28, wherein:
$R^{x6}$ is $C_{3-12}$ alkylene, $C_{3-12}$ alkenylene or $C_{3-12}$ heteroalkylene, where $R^{x6}$ is substituted with —$NH_2$, —$NHR^m$, —$NHC(O)R^m$, —$NHC(O)CH_2$—$[OCH_2CH_2]_n$—$R^{XX}$, or —$[CH_2CH_2O]^n$—$R^{XX}$;
$R^{XX}$ is H, OH, $N_3$, CN, $NO_2$, SH, $NH_2$, $ONH_2$, $NHNH_2$, halo, $C_{1-8}$ alkyl, $C_{3-8}$ cycloalkyl, $C_{1-8}$ alkoxy, $C_{1-8}$ alkylthio, $C_{3-20}$ heteroaryl, $C_{5-20}$ aryl or mono- or di-$C_{1-8}$ alkyl amino; and
n is an integer of 1 through 6.

34. The antibody conjugate of claim 1, wherein the conjugate has a structure represented by General Formula XII or General Formula XIII;

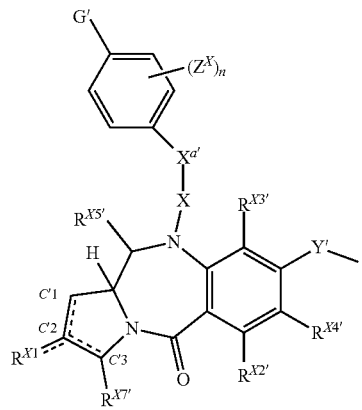

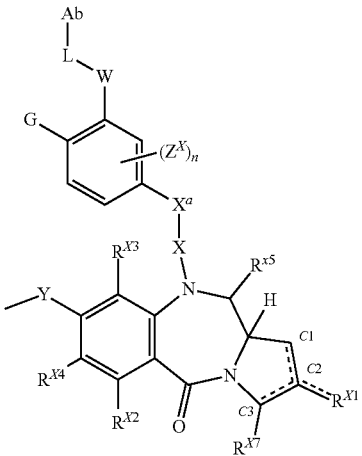

[General Formula XII]

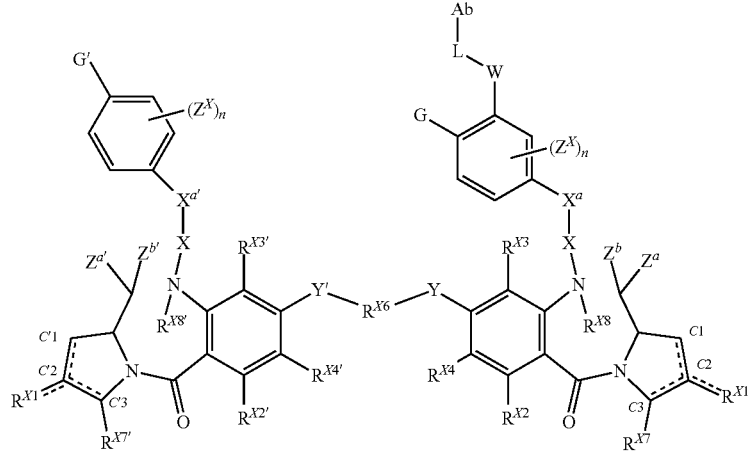

[General Formula XIII]

wherein a dotted line represents an optional double bond as permitted by valency;

W is —C(O)—, —C(O)NR'—, —C(O)O—, SO$_2$NR'—, —P(O)R''NR'—, —SONR'— or —PO$_2$NR'—; wherein the C, S or P is directly bound to the phenyl ring;

$R^{X1}$ and $R^{X1'}$ are independently selected from H, OH, =O, =CH$_2$ CN, R''', OR''', =CH—R''', =C(R''')$_2$, OSO$_2$—R''', CO$_2$R''', COR''', halo and dihalo;

R''' is selected from R''', CO$_2$R''', COR''', CHO, CO$_2$H and halo;

each R''' is independently selected from of C$_{1-12}$ alkyl, C$_{2-12}$ alkenyl, C$_{2-12}$ alkynyl, C$_{5-20}$ aryl, C$_{5-20}$ heteroaryl, C$_{3-6}$ cycloalkyl, 3-7 membered heterocyclyl, 3-7 membered heterocycloalkyl and 5 to 7 heteroaryl; or R''' is X or X;

$R^{X2}$, $R^{X2'}$, $R^{X3}$, $R^{X3'}$, $R^{X5}$ and $R^{X5'}$ are independently selected from H, R''', OH, OR''', SH, SR''', NH$_2$, NHR''', NR'''$_2$, NO$_2$, Me$_3$Sn and halo;

$R^{X4}$ and $R^{X4'}$ are independently selected from H, R''', OH, OR''', SH, SR''', NH$_2$, NHR''', NR'''$_2$, NO$_2$, Me$_3$Sn, halo, C$_{1-6}$ alkyl C$_{1-6}$ alkoxy, C$_{2-6}$ alkenyl, C$_{2-6}$ alkynyl, C$_{3-6}$ cycloalkyl, 3-7 membered heterocycloalkyl, C$_{5-12}$ aryl, 5 to 7 heteroaryl, —CN, —NCO, —OR$_n$, —OC(O)R'', —OC(O)NR''R''', —OS(O)R'', —OS(O)$_2$R'', —SR'', —S(O)R'', —S(O)$_2$R'', —S(O)NR''R''', —S(O)$_2$NR''R''', —OS(O)NR''R''', —OS(O)$_2$NR''R''', —NR''R''', —NR''C(O)R$^o$, —NR''C(O)OR$^o$, —NR$^o$C(O)NR$^o$R$^{o'}$, —NR''S(O)R$^o$, —NR''S(O)$_2$R$^o$, —NR''S(O)NR$^o$R$^{o'}$, —NR''S(O)$_2$NR$^o$R$^{o'}$—C(O)R'', —C(O)OR'' and —C(O)NR''R''';

X and X' are each independently selected from C$_{1-8}$ alkyl, C$_{3-8}$ cycloalkyl, C$_{1-8}$ alkoxy, C$_{1-8}$ alkylthio, C$_{3-20}$ heteroaryl, C$_{5-20}$ aryl or C$_{1-8}$ alkylamino;

Y and Y' are each independently selected from O, S and N(H);

each $R^{x6}$ is independently selected from C$_{3-12}$ alkylene, C$_{3-12}$ alkenylene, or C$_{3-12}$ heteroalkylene;

$R^{X7}$ and $R^{X7'}$ are independently selected from H, C$_{1-6}$ alkyl, C$_{2-6}$ alkenyl, C$_{2-6}$ alkynyl, C$_{3-6}$ cycloalkyl, 3-7 membered heterocycloalkyl, C$_{6-10}$ aryl, 5 to 7 heteroaryl, —OR$^r$, —OC(O)R$^r$, —OC(O)NR'R'', —OS(O)R$^r$, —OS(O)$_2$R$^r$, —SR$^r$, —S(O)R$^r$, —S(O)$_2$R$^r$, —S(O)NR'R'', —S(O)$_2$NR'R'', —OS(O)NR'R'', —OS(O)$_2$NR'R'', —NR'R'', —NR'C(O)R$^s$, —NR'C(O)OR$^s$, —NR'C(O)NR$^s$R$^{s'}$, —NR'S(O)R$^s$, —NR'S(O)$_2$R$^s$, —NR'S(O)NR$^s$R$^{s'}$, —NR'S(O)$_2$NR$^s$R$^{s'}$, —C(O)R$^r$, —C(O)OR$^s$ or —C(O)NR'R'';

each R$^r$, R$^{r'}$, R$^s$ and R$^{s'}$ is independently selected from H, C$_{1-7}$ alkyl, C$_{2-7}$ alkenyl, C$_{2-7}$ alkynyl, C$_{3-13}$ cycloalkyl, 3-7 membered heterocycloalkyl, C$_{5-10}$ aryl and 5 to 7 heteroaryl;

each $R^{X8}$ and $R^{X8'}$ is independently selected from H, C$_{1-6}$ alkyl, C$_{2-6}$ alkenyl, C$_{2-6}$ alkynyl, C$_{3-6}$ heteroalkyl, 3-7 membered heterocycloalkyl, C$_{5-10}$ aryl, 5 to 7 heteroaryl, —S(O)R''', —S(O)$_2$R''', —S(O)NR'''R'''', —S(O)$_2$NR'''R'''', —NR'''R'''', —NR'''C(O)R''', NR'''C(O)OR'', —NR'''C(O)NR''R''', —NR'''S(O)R'', —NR'''S(O)$_2$R'', —NR'''S(O)NR''R''', —NR'''S(O)$_2$NR''R''', —C(O)R''', —C(O)OR''' and —C(O)NR'''R'''';

$Z^a$ is selected from OR$^{X12a}$, NR$^{X12a}$R$^{X12a}$, or SR$^{X12a}$;

$Z^b$ is selected from OR$^{X13a}$, NR$^{X13a}$R$^{X14a}$, or SR$^{X13a}$;

$Z^{a'}$ is selected from OR$^{X12a}$, NR$^{X12a}$R$^{X12a}$, or SR$^{X12a}$;

$Z^{b'}$ is selected from OR$^{X13a'}$, NR$^{X13a'}$R$^{X14a'}$, or SR$^{X13a'}$;

each R$^{X12a}$, R$^{X12a'}$, and R$^{x13a'}$ is independently selected from H, C$_{1-6}$ alkyl, C$_{2-6}$ alkenyl, C$_{2-6}$ alkynyl, C$_{3-6}$ cycloalkyl, 3 to 7 membered heterocycloalkyl, C$_{5-10}$ aryl, 5 to 7 heteroaryl, —C(O)R$^{X15a}$, —C(O)OR$^{X15a}$ and —C(O)NR$^{X15a}$R$^{X15a'}$;

each R$^{X15a}$ and R$^{X15a'}$ is independently selected from C$_{1-12}$ alkyl, C$_{2-12}$ alkenyl, C$_{2-12}$ alkynyl, C$_{5-20}$ aryl, C$_{5-20}$ heteroaryl, C$_{3-6}$ cycloalkyl, 3-7 membered heterocyclyl, 3-7 membered heterocycloalkyl, and 5 to 7 heteroaryl;

each R$^{X13a}$ and R$^{X14a}$ is independently H or alkyl; or R$^{X13a}$ and R$^{X14a}$, together with the atom to which it is connected, form 3-7 membered heterocyclyl, form 3-7 membered heterocycloalkyl, or form 3-7 membered heteroaryl, and the R$^{X13a'}$ and R$^{X14a'}$ arbitrarily bind to the atoms to which they are attached to form 3-7 membered heterocyclyl, 3-7 membered heterocycloalkyl, or 3-7 membered heteroaryl; and each of R'', R''', R$^o$, and R$^{o'}$ is independently selected from H, C$_{1-7}$ alkyl, C$_{2-7}$ alkenyl, C$_{2-7}$ alkynyl, C$_{3-13}$ cycloalkyl, 3-7 membered heterocycloalkyl, C$_{5-10}$ aryl, and 5 to 7 heteroaryl G and G' are each independently a glucuronic acid moiety or

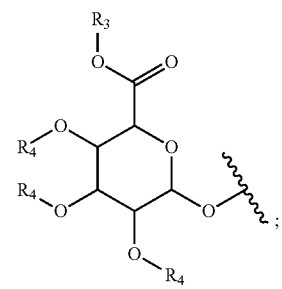

$R^3$ is a hydrogen or carboxyl protecting group;

each of the $R^4$ are independently a hydrogen or hydroxyl protecting group;

the bond overlaid with the wavy line represents a connection to the antibody;

L is a linker comprising:

A) a C$_1$-C$_{50}$ alkylene or 1-50 atom heteroalkylene and:

(i) comprises at least one unsaturated bond;

(ii) is substituted by a bivalent substituent where 2 atoms in L are the same as in a substituent, this completing a heteroarylene; or (iii) is substituted by C$_{1-20}$ alkyl; or B) at least one isoprenyl group of General Formula III below:

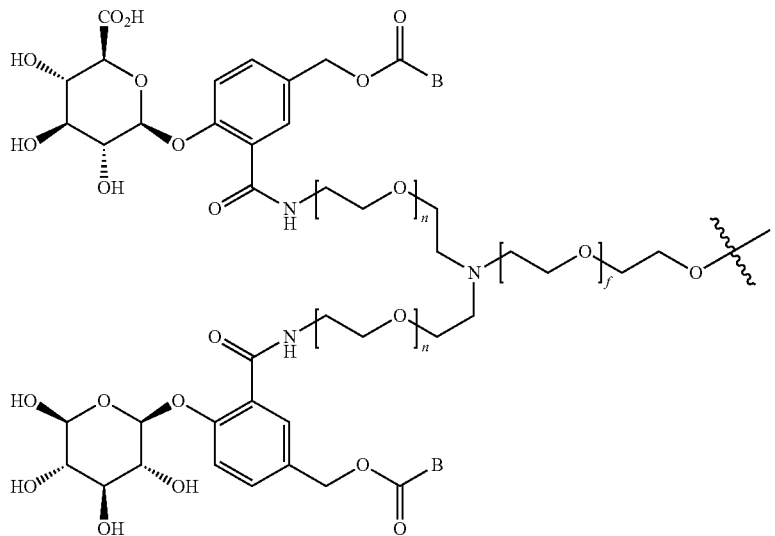

$X^a$ and $X^{a'}$ are each independently a bond or $C_{1-6}$ alkylene;

$Z^{X'}$ and $Z^X$ are each independently selected from hydrogen, $C_{1-8}$ alkyl, halogen, cyano, nitro, and $—(CH_2)_m—OCH_3$;

each $R^{80}$, $R^{90}$ and $R^{100}$ is independently selected from hydrogen, $C_{1-8}$ alkyl, $C_{2-6}$ alkenyl, $C_{1-6}$ alkoxy, an alkoxyalkyl and $—(CH_2CH_2O)_m—(CH_2)_{m2}CH_3$;

n is 0 to 3; and m is 0 to 12 and m2 is an integer of 1 to 12.

35. The antibody conjugate of claim 34, wherein the conjugate comprises a structure represented by:

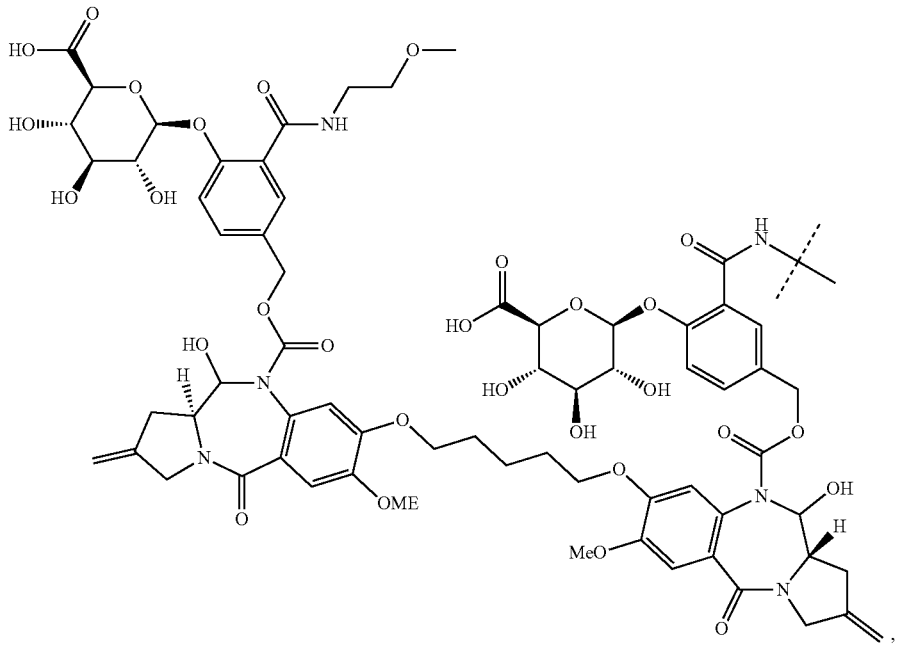

223
224
-continued
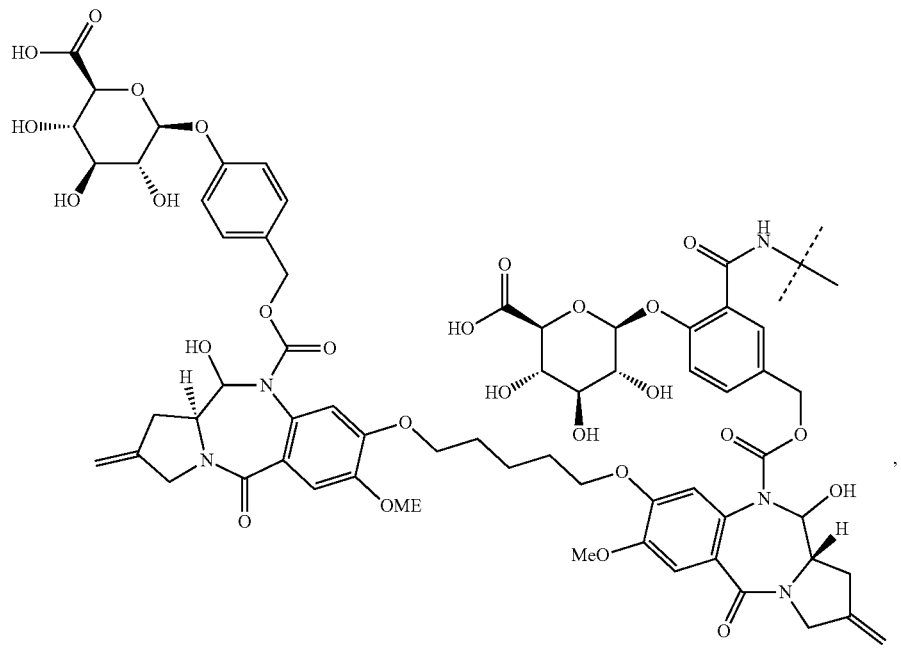
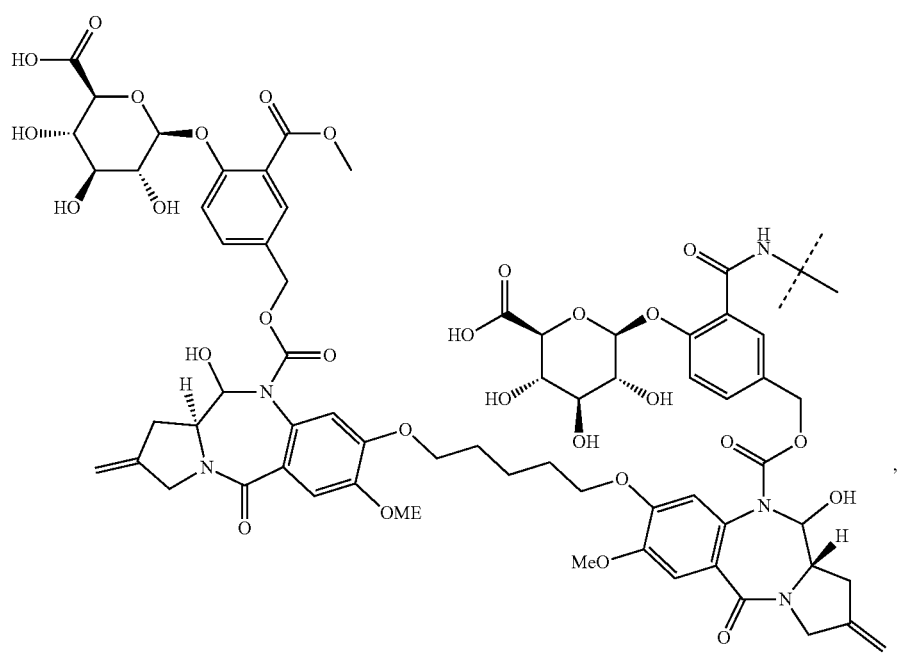

225
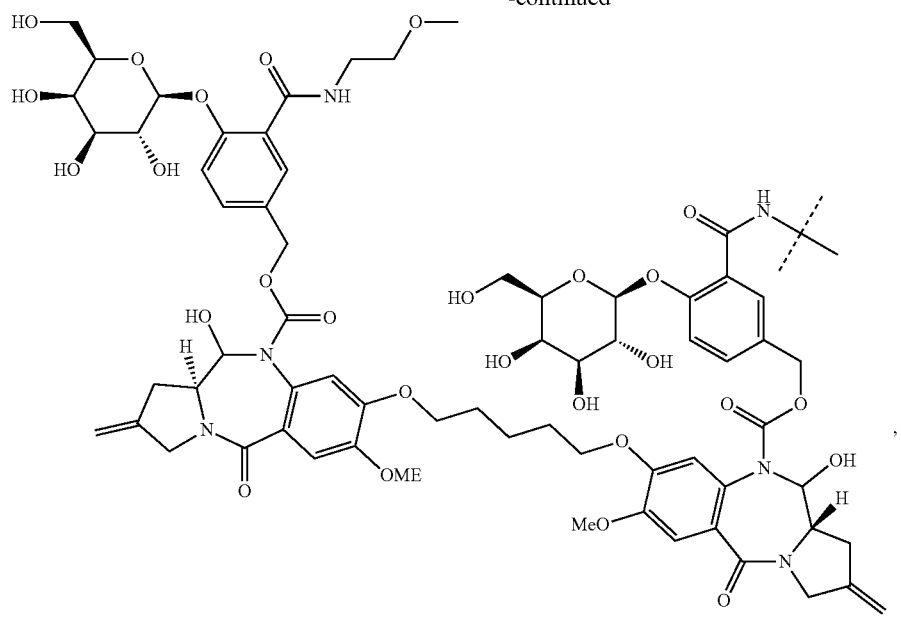
226
-continued
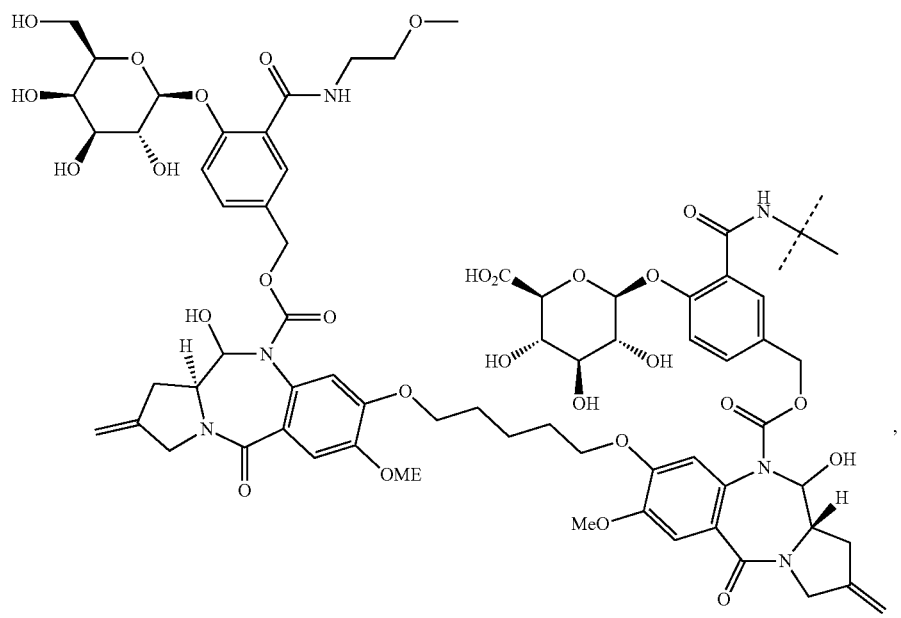

227                                    228
-continued
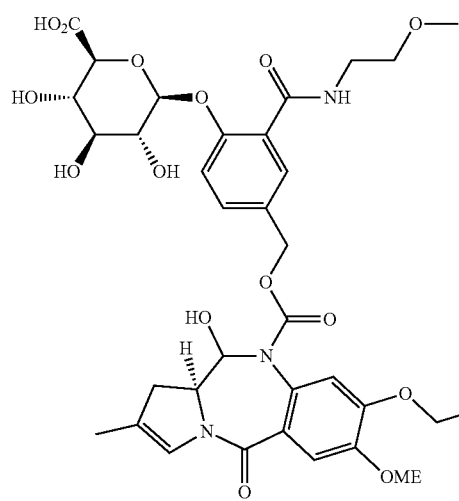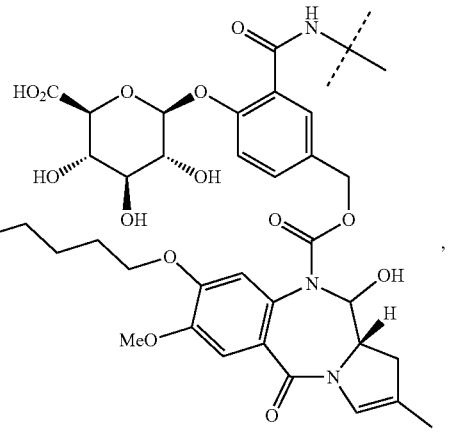
,
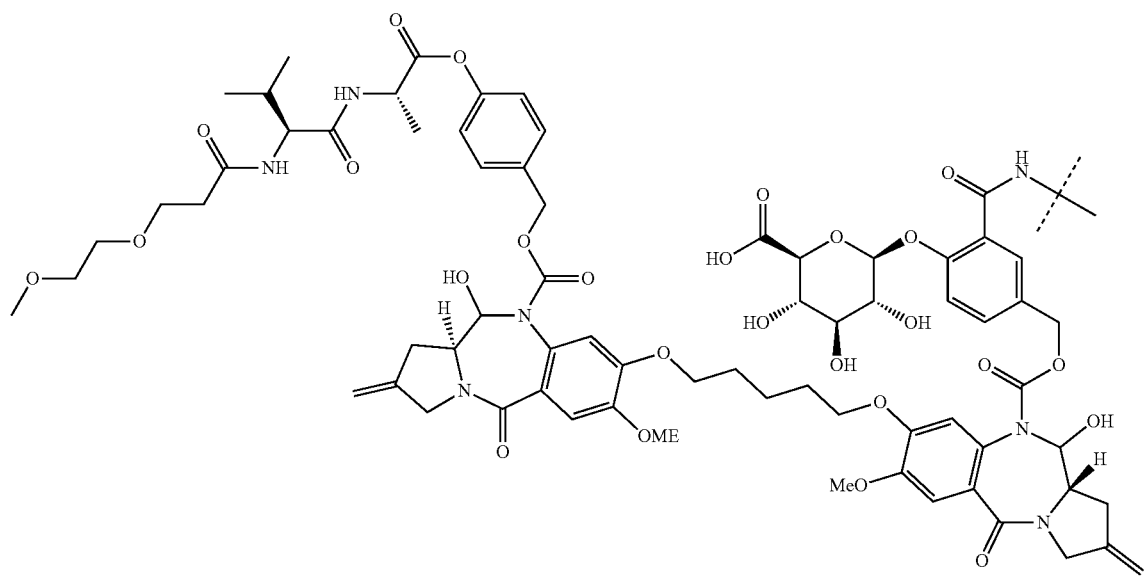

229
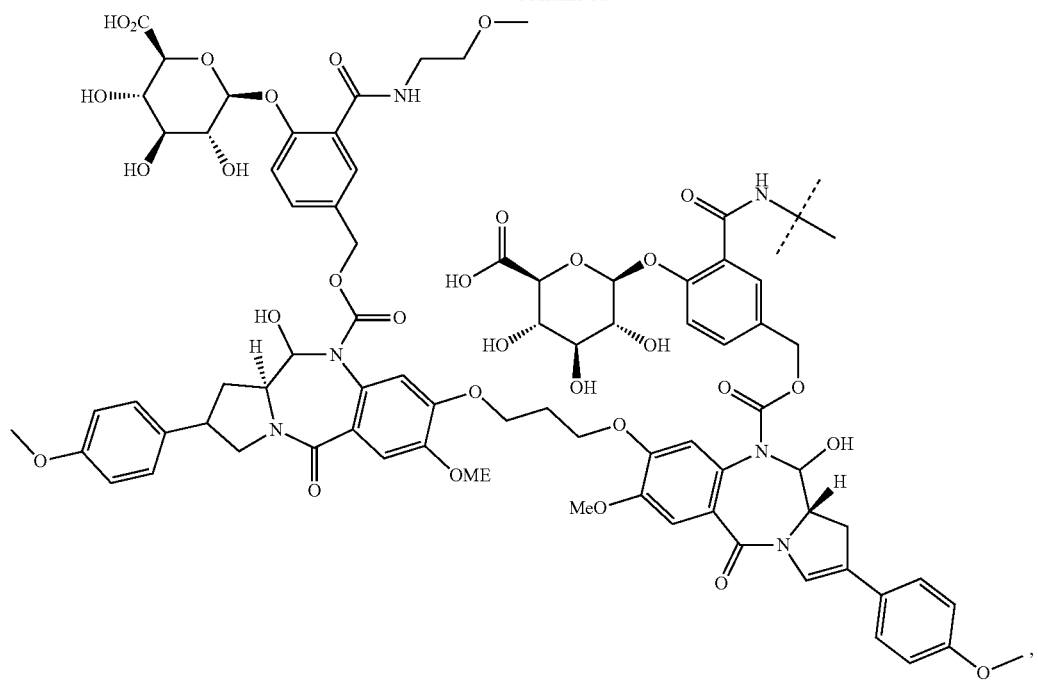
-continued
230
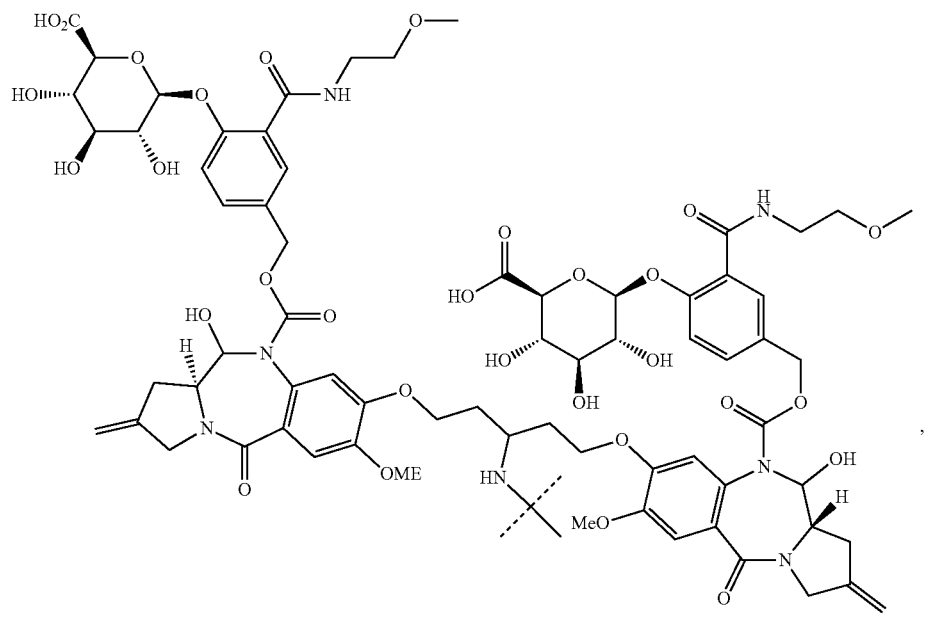

-continued

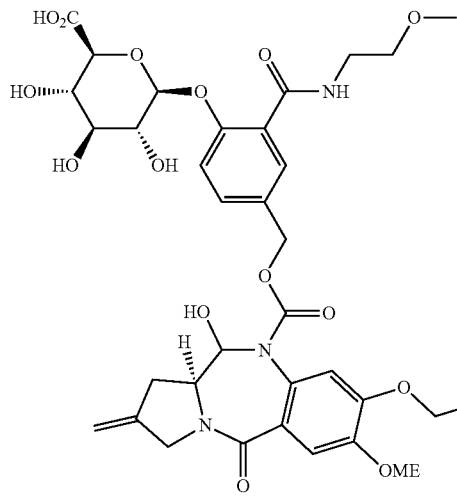

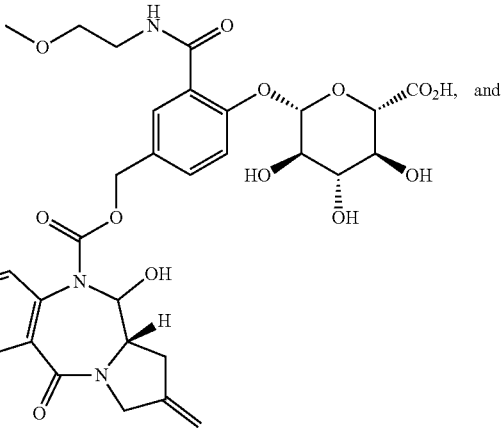

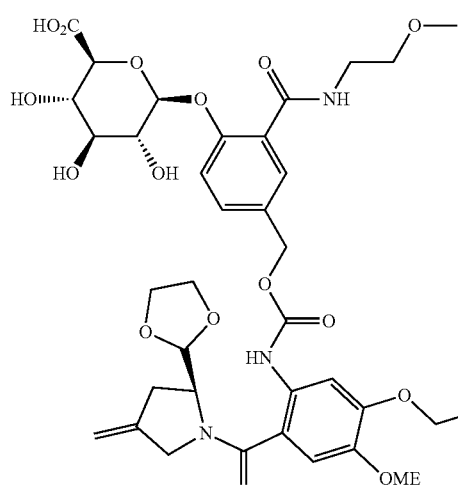

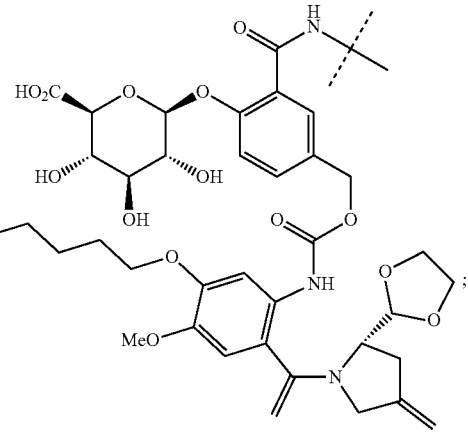

or a pharmaceutically acceptable salt thereof; and the bond overlaid with a dashed line represents a connection point to L.

36. A pharmaceutical composition comprising an antibody drug conjugate of claim 1 and a pharmaceutically acceptable excipient.

37. A method of treating a disease or disorder associated with the over-expression of ROR1 in a subject, comprising administering an antibody drug conjugate of claim 1 or a pharmaceutically acceptable salt thereof to the subject.

38. A method of treating cancer in a subject, comprising administering an antibody drug conjugate claim 1 or a pharmaceutically acceptable salt thereof to the subject.

* * * * *